US012286640B2

(12) United States Patent
Stevens

(10) Patent No.: US 12,286,640 B2
(45) Date of Patent: *Apr. 29, 2025

(54) MODIFIED STRAINS FOR IMPROVED SECRETION OF RECOMBINANT PROTEINS

(71) Applicant: BOLT THREADS, INC., Emeryville, CA (US)

(72) Inventor: Thomas Stevens, Emeryville, CA (US)

(73) Assignee: BOLT THREADS, INC., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/178,275

(22) Filed: Mar. 3, 2023

(65) Prior Publication Data

US 2023/0407340 A1 Dec. 21, 2023

Related U.S. Application Data

(63) Continuation of application No. 16/415,605, filed on May 17, 2019, now Pat. No. 11,634,729.

(60) Provisional application No. 62/673,001, filed on May 17, 2018.

(51) Int. Cl.
  *C12N 15/90* (2006.01)
  *C07K 16/14* (2006.01)
  *C12N 15/62* (2006.01)

(52) U.S. Cl.
  CPC ............ *C12N 15/905* (2013.01); *C07K 16/14* (2013.01); *C12N 15/625* (2013.01)

(58) Field of Classification Search
  None
  See application file for complete search history.

(56) References Cited

U.S. PATENT DOCUMENTS

| 6,228,590 | B1 * | 5/2001 | Baker | C12N 15/1034 |
|---|---|---|---|---|
| | | | | 435/254.11 |
| 2011/0021378 | A1 | 1/2011 | Callewaert et al. | |
| 2017/0029827 | A1 | 2/2017 | Gasser et al. | |
| 2018/0079788 | A1 * | 3/2018 | Achmüller | C12N 15/81 |

FOREIGN PATENT DOCUMENTS

| WO | WO-2010099195 | A1 | | 9/2010 | |
| WO | WO-2010135678 | A1 * | 11/2010 | ........... C07K 14/395 |
| WO | WO-2015/042164 | A2 | | 3/2015 | |
| WO | WO-2019/070246 | A1 | | 4/2019 | |

OTHER PUBLICATIONS

Accession XM_002491310, 2017. Komagataella phaffii GS115 Non-essential subunit of Sec63 complex (Sec63p, Sec62p, Sec66p and Sec72p) (PAS_chr2-1_0448), partial mRNA (Year: 2017).*

Feldhiem et al. Sec72p Contributes to the Selective Recognition of Signal Peptides by the Secretory I lypeptide Transl ation Complex 1994, The Journal of Cell Biology, vol. 126, No. 4, 935-943 (Year: 1994).*
Schutter et al. Genome sequence of the recombinant protein production host Pichia pastoris. 2009. Nature Biotechnology vol. 27 No. 6 (Year: 2009).*
J.L. Cereghino, J.M. Cregg. Heterologous protein expression in the methylotrophic yeast Pichia pastorisFEMS Microbiology Reviews 24 (2000) 45-66 (Year: 2000).*
Delic et al. Engineering of Protein Folding and Secretion—Strategies to Overcome Bottlenecks for Efficient Production of Recombinant Proteins. 2014. Antioxidants & Redox Signaling vol. 21, No. 3 (Year: 2014).*
GenBank: ADO95142.1. alpha-mating factor secretion signal peptide/hemagglutinin fusion protein. 2012. Accession ADO95142 (Year: 2012).*
Jiang et al. An interaction between the SRP receptor and the translocon is critical during cotranslational protein translocation. 2008. The Journal of Cell Biology, vol. 180, No. 6, 1149-1161 (Year: 2008).*
Accession XM_002491310, Komagataella phaffil GS115 Non-essential subunit of Sec63 complex (Sec63p, Sec62p, Sec66p and Sec72p) PAS_chr2-1_0448), partial mRNA (2017).
Ast et al., "A network of cytosolic factors targets SRP-independent proteins to the endoplasmic reticulum", Cell, vol. 152, No. 5, pp. 1134-1145 (Feb. 2013).
Cereghino and Cregg, "Heterologous protein expression in the methylotrophic yeast Pichia pastoris," FEMS Microbiology Reviews, 24:45-66 (2000).
Delic et al., "The secretory pathway: exploring yeast diversity", FEMS Microbiol. Rev., vol. 37, No. 6, pp. 872-914 (Nov. 2013).
Delic et al., "Engineering of protein folding and secretion—strategies to overcome bottlenecks for efficient production of recombinant proteins," Antioxidants & Redox Signaling, vol. 21, No. 3 (2014).
Fahnestock et al., "Production of synthetic spider dragline silk protein in Pichia pastoris," Applied Microbiology and Biotechnology, 47(1):33-39 (1997).
Fahnstock et al., "Microbial production of spider silk proteins", Reviews in Molecular Biotechnology, 74:105-119 (2000).
Feldhiem et al., "Sec 72p Contributes to the selective recognition of signal peptides by the Secretory I lypeptide Translation Complex", The Journal of Cell Biology, vol. 126, No. 4, pp. 935-943 (1994).
Finke et al., "A second trimeric complex containing homologs of the Sec61p complex functions in protein transport across the ER membrane of S. cerevisiae", EMBO J., vol. 15, No. 7, pp. 1482-1494 (1996).
GenBank: ADO95142.1. Alpha-mating factor secretion signal peptide/hemagglutinin fusion protein, Accession ADO95142 (2012).

(Continued)

*Primary Examiner* — Celine X Qian
*Assistant Examiner* — Tiffany Nicole Grooms
(74) *Attorney, Agent, or Firm* — MARSHALL, GERSTEIN & BORUN LLP

(57) ABSTRACT

Disclosed herein are modified strains for improving secretion of recombinantly expressed products secreted from a host organism with improved growth and productivity characteristics, as well as methods of using the modified strains.

20 Claims, 16 Drawing Sheets

Specification includes a Sequence Listing.

(56) References Cited

OTHER PUBLICATIONS

Harty et al., "Analysis of Sec61p and Ssh1p interactions in the ER membrane using the split-ubiquitin system", BMC Cell Biol., vol. 14, No. 14, pp. 1-12 (2013).
Jan et al., "Principles of ER cotranslational translocation revealed by proximity-specific ribosome profiling", Science, vol. 346, No. 6210 (Nov. 7, 2014).
Ji Hai-bing et al., "Gene cloning, expression and enzymatic properties of carboxypeptidase Y from Actinomyces elegans", Modern Food Science and Technology, 33(1):80-86 (2017).
Jiang et al., "An interaction between the SRP receptor and the translocon is critical during cotranslational protein translocation", The Journal of Cell Biology, vol. 180, No. 6, pp. 1149-1161 (2008).
PCT International Search Report and Written Opinion App. PCT/US19/32879 Sep. 20, 2019.
Schutter et al., "Genome sequence of the recombinant protein production host Pichia pastoris", Nature Biotechnology, vol. 27, No. 6 (2009).
Supplementary European Application No. 19804157.6, European Search Report and Opinion, mailed Feb. 23, 2022.
Uniprot Accession C4QVV4. C4QVV4_KOMG. online) Nov. 22, 2017 [retrieved Aug. 29, 2019]. Available on the internet: < www.uniprot.org/uniprot/C4VV4.txt?version=55>.
UniprotKB Accession C4R0Q1. C4ROQ1_KOMPG (online) Nov. 22, 2017 [retrieved Aug. 29, 2019] Available on the internet <www.uniprot.org/uniprot/C4ROQ1.txt?version=54>.
UniprotKB Accession F2QQ76. F2QQ76_KOMPC. (on line) Nov. 22, 2017 [retrieved Aug. 29, 2019]. Available on the internet: < www.uniprot.org/uniprot/F2QQ76.txt?version=40>.
UniProtKB/Swiss-Prot P01149 (2008).
UniProtKB/Swiss-Prot P07267 (2009).
Whittall et al., "Host systems for the production of recombinant spider silk," Trends in Biotechnology, 39(6):560-573 (2021).
Wittke et al., "Recognition of a subset of signal sequences by Ssh1p, a Sec61p-related protein in the membrane of endoplasmic reticulum of yeast *Sacchromyces cerevisiae*", Mol. Biol. Cell., vol. 13, No. 7, pp. 2223-2232 (Jul. 2002).

\* cited by examiner

| Complex Membership | | | S. cerevisiae | P. pastoris | % ID (blastp) |
|---|---|---|---|---|---|
| SEC (heptameric) | SEC61 (trimeric) | SSH1 (trimeric) | SSH1 | PAS_chr1-4_0629 | 39% |
| | | | SSS1 | PAS_chr1-1_0023 | 52% |
| | | | SBH2* | PAS_chr2-2_0210 | 57% |
| | | | SEC61 | PAS_chr1-3_0202 | 70% |
| | SEC63 complex | | SEC62 | PAS_chr3_1014 | 35% |
| | | | SEC63 | PAS_chr4_0395 | 38% |
| | | | SEC66 | PAS_chr2-1_0433 | 41% |
| | | | SEC72 | PAS_chr2-1_0448 | 29% |

FIG. 1

Homology Arm Insertion into Nourseothricin Marker Plasmid

MODIFIED STRAINS FOR IMPROVED SECRETION OF RECOMBINANT PROTEINS

CROSS-REFERENCE TO RELATED APPLICATIONS

This application is a continuation of U.S. patent application Ser. No. 16/415,605, filed May 17, 2019, which claims the benefit of U.S. Provisional Patent Application No. 62/673,001, filed May 17, 2018, the contents of each of which are incorporated by reference in its entirety.

INCORPORATION BY REFERENCE OF MATERIAL SUBMITTED ELECTRONICALLY

A sequence listing, which is a part of the present disclosure, is submitted concurrently with the specification as an XML file. The name of the file containing the sequence listing is "50019A_SubSeqlisting.xml." The sequence listing was created on Jul. 11, 2023, and is 311,089 bytes in size. The subject matter of the sequence listing is incorporated by reference herein in its entirety.

FIELD OF THE INVENTION

The present disclosure relates to methods of strain optimization to enhance secretion of proteins or metabolites from cells. The present disclosure also relates to compositions resulting from those methods. In particular, the disclosure relates to yeast cells selected or genetically engineered to enhance secretion of recombinant proteins expressed by the yeast cells, while minimizing or improving growth yields, and to methods of cultivating yeast cells for the production of useful compounds.

BACKGROUND OF THE INVENTION

The methylotrophic yeast *Pichia pastoris* is widely used in the production of recombinant proteins. *P. pastoris* grows to high cell density, provides tightly controlled methanol-inducible trans gene expression and is capable of secreting recombinant proteins into a defined media.

However, much of the expressed recombinant protein remains located intracellularly, which can make collection difficult and can negatively impact cell growth and longevity. Furthermore, recombinantly expressed proteins may be degraded in the cell before they are secreted, resulting in a mixture of proteins that includes fragments of recombinantly expressed proteins and a decreased yield of full-length recombinant proteins. What is needed, therefore, are tools and engineered strains to enhance secretion in *P. pastoris*, while mitigating any loss of or improving recombinant protein productivity, including maintaining growth characteristics, as many modifications can negatively impact the natural functioning of the cell.

What is needed, therefore, are modified organisms and methods of using these organisms to produce and secrete recombinant proteins while minimizing any negative effect on cell growth and productivity.

SUMMARY OF THE INVENTION

In some embodiments, provided herein is A *Pichia pastoris* microorganism, in which the activity of SEC72 has been eliminated or the sec72 gene has been deleted, and wherein said microorganism expresses a recombinant protein. In some embodiments, the microorganism further compres a recombinantly expressed SSH1 translocon complex.

In some embodiments, the SEC72 comprises a polypeptide sequence at least 95% identical to SEQ ID NO: 1. In some embodiments, the SEC72 comprises SEQ ID NO: 1. In some embodiments, the SEC72 is encoded by a sec72 gene. In some embodiments, the sec72 gene comprises a polynucleotide sequence at least 95% identical to SEQ ID NO: 2. In some embodiments, the sec72 gene comprises at least 15, 20, 25, 30, 40, or 50 contiguous nucleotides of SEQ ID NO: 2. In some embodiments, the sec72 gene comprises SEQ ID NO: 2. In some embodiments, the sec72 gene is at locus PAS_chr2-1_0448 of said microorganism.

In some embodiments, the SSH1 translocon complex comprises a first polypeptide sequence at least 95% identical to SEQ ID NO: 4, a second polypeptide sequence at least 95% identical to SEQ ID NO: 6, and a third polypeptide sequence at least 95% identical to SEQ ID NO: 8. In some embodiments, the SSH1 translocon complex comprises a first polypeptide comprising SEQ ID NO: 4, a second polypeptide comprising SEQ ID NO: 6, and a third polypeptide comprising SEQ ID NO: 8.

In some embodiments, the microorganism further comprises a recombinantly expressed translocon complex. In some embodiments, the translocon complex is expressed from a recombinant SSH1 gene, a recombinant SSS1 gene, and a recombinant SBH2 gene.

In some embodiments, the SSH1 gene comprises SEQ ID NO: 3. In some embodiments, the SSH1 gene comprises a polynucleotide sequence at least 95% identical to SEQ ID NO: 3. In some embodiments, the SSH1 gene comprises at least 15, 20, 25, 30, 40, or 50 contiguous nucleotides of SEQ ID NO: 3.

In some embodiments, the SSS1 gene comprises SEQ ID NO: 5. In some embodiments, the SSS1 gene comprises a polynucleotide sequence at least 95% identical to SEQ ID NO: 5. In some embodiments, the SSS1 gene comprises at least 15, 20, 25, 30, 40, or 50 contiguous nucleotides of SEQ ID NO: 5.

In some embodiments, the SBH2 gene comprises SEQ ID NO: 7. In some embodiments, the SBH2 gene comprises a polynucleotide sequence at least 95% identical to SEQ ID NO: 7. In some embodiments, the SBH2 gene comprises at least 15, 20, 25, 30, 40, or 50 contiguous nucleotides of SEQ ID NO: 7.

In some embodiments, expression of said recombinant SSH1 gene to increase levels of said SSH1 translocon in said microorganism above that expressed by the native organism improves the growth rate and/or fermentation performance of said microorganism.

In some embodiments, the translocon complex comprises an SSH1 protein, an SSS1 protein, and an SBH2 protein. In some embodiments, the SSH1 protein comprises a polypeptide sequence at least 95% identical to SEQ ID NO: 4. In some embodiments, the SSH1 protein comprises SEQ ID NO: 4. In some embodiments, the SSS1 protein comprises a polypeptide sequence at least 95% identical to SEQ ID NO: 6. In some embodiments, the SSS1 protein comprises SEQ ID NO: 6. In some embodiments, the SBH2 protein comprises a polypeptide sequence at least 95% identical to SEQ ID NO: 8. In some embodiments, the SBH2 protein comprises SEQ ID NO: 8.

In some embodiments, the activity of a YPS1-1 protease and a YPS1-2 protease in said microorganism has been attenuated or eliminated.

In some embodiments, the YPS1-1 protease comprises a polypeptide sequence at least 95% identical to SEQ ID NO:

10. In some embodiments, the YPS1-1 protease comprises SEQ ID NO: 10. In some embodiments, the YPS1-1 protease is encoded by a YPS1-1 gene. In some embodiments, the YPS1-1 gene comprises a polynucleotide sequence at least 95% identical to SEQ ID NO: 9. In some embodiments, the YPS1-1 gene comprises at least 15, 20, 25, 30, 40, or 50 contiguous nucleotides of SEQ ID NO: 9. In some embodiments, the YPS1-1 gene comprises SEQ ID NO: 9. In some embodiments, the YPS1-1 gene is at locus PAS_chr4_0584 of said microorganism.

In some embodiments, the YPS1-2 protease comprises a polypeptide sequence at least 95% identical to SEQ ID NO: 12. In some embodiments, the YPS1-2 protease comprises SEQ ID NO: 12. In some embodiments, the YPS1-2 protease is encoded by a YPS1-2 gene. In some embodiments, the YPS1-2 gene comprises a polynucleotide sequence at least 95% identical to SEQ ID NO: 11. In some embodiments, the YPS1-2 gene comprises at least 15, 20, 25, 30, 40, or 50 contiguous nucleotides of SEQ ID NO: 11. In some embodiments, the YPS1-2 gene comprises SEQ ID NO: 11. In some embodiments, the YPS1-2 gene is at locus PAS_chr3_1157 of said microorganism.

In some embodiments, the YPS1-1 gene or said YPS1-2 gene, or both, of said microorganism has been mutated or knocked out. In some embodiments, the activity of one or more additional proteases of said microorganism has been attenuated or eliminated.

In some embodiments, the recombinant protein expressed by said microorganism comprises at least one block polypeptide sequence from a silk protein. In some embodiments, the recombinant protein comprises a silk-like polypeptide. In some embodiments, the silk-like polypeptide comprises one or more repeat sequences $\{GGY\text{-}[GPG\text{-}X_1]_{n1}\text{-}GPS\text{-}(A)_{n2}\}_{n3}$, wherein $X1$=SGGQQ or GAGQQ or GQGPY or AGQQ or SQ; n1 is from 4 to 8; n2 is from 6 to 20; and n3 is from 2 to 20. In some embodiments, the silk-like polypeptide comprises comprises a polypeptide sequence encoded by SEQ ID NO: 21.

In some embodiments, the recombinant protein comprises a secretion signal peptide. In some embodiments, the secretion signal peptide is selected from the group consisting of: a PEP4 signal sequence, a CPY+4 signal sequence, a DAP2 signal sequence, and a MFα1 signal sequence. In some embodiments, the secretion signal peptide is selected from the group consisting of: SEQ ID NO: 84, SEQ ID NO: 86, SEQ ID NO: 88, and SEQ ID NO: 90.

Also provided herein, according to some embodiments, is a *Pichia pastoris* microorganism, wherein the activity of SEC72 of said microorganism has been eliminated or an sec72 gene comprising SEQ ID NO: 1 has been knocked out, wherein the microorganism comprises a recombinantly expressed SSH1 gene comprising SEQ ID NO: 3, a recombinantly expressed SSS1 gene comprising SEQ ID NO: 5, and a recombinantly expressed SBH2 gene comprising SEQ ID NO: 7, and wherein said microorganism comprises a silk-like polypeptide comprising a polypeptide sequence encoded by SEQ ID NO: 21.

Also provided herein, according to some embodiments, is a cell culture comprising a recombinant microorganism described herein.

Also provided, herein, according to some embodiments, is a cell culture comprising a recombinant microorganism as described herein, wherein said cell culture has an improved strain growth rate and fermentation performance under standard cell culture conditions as compared to a cell culture that does not comprise a recombinantly expressed SSH1 translocon complex.

Also provided, herein, according to some embodiments, is a cell culture comprising a recombinant microorganism as described herein, wherein said cell culture has an improved yield or specific productivity of said recombinant protein under standard cell culture conditions as compared to a cell culture of otherwise identical microorgansims that comprises a functional sec72 gene and does not comprise a recombinantly expressed SSH1 translocon complex, wherein each microorganism has the same number of copies of recombinant silk polypeptide genes.

Also provided herein, according to some embodiments, is a method of producing a recombinant protein, the method comprising: culturing the recombinant microorganism described herein in a culture medium under conditions suitable for expression of the recombinantly expressed protein; and isolating the recombinant protein from the microorganism or the culture medium.

In some embodiments, the recombinant protein is secreted from said microorganism, and isolating said recombinant protein comprises collecting a culture medium comprising said secreted recombinant protein.

In some embodiments, the microorganism has an increased yield or specific productivity of said recombinant protein as compared to an otherwise identical microorganism wherein said sec72 gene is not deleted.

In some embodiments, the microorganism has an increased yield or specific productivity of said recombinant protein as compared to an otherwise identical microorganism not comprising said recombinantly expressed SSH1 translocon complex, and wherein said sec72 gene is not deleted.

Also provided herein, according to some embodiments, is a method of modifying *Pichia pastoris* to improve the secretion of a recombinantly expressed protein, said method comprising knocking out a gene encoding an SEC72 protein. In some embodiments, the method of modifying *Pichia pastoris* to improve the secretion of a recombinantly expressed protein further comprises transforming said *Pichia pastoris* with a vector comprising genes encoding a recombinantly expressed SSH1 translocon complex.

In some embodiments, the recombinantly expressed protein comprises a silk-like polypeptide. In some embodiments, the silk-like polypeptide comprises one or more repeat sequences $\{GGY\text{-}[GPG\text{-}X_1]_{n1}\text{-}GPS\text{-}(A)_{n2}\}_{n3}$, wherein $X_1$=SGGQQ or GAGQQ or GQGPY or AGQQ or SQ; n1 is from 4 to 8; n2 is from 6 to 20; and n3 is from 2 to 20. In some embodiments, the recombinantly expressed protein comprises a polypeptide sequence encoded by SEQ ID NO: 21.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 1 depicts groupings of genes in secretion complexes SEC, SEC61, SEC63, and SSH1. Also shown is a value of the homology between *S. cerevisiae* and *P. pastoris* translocon complex proteins.

DETAILED DESCRIPTION

Figure 2:
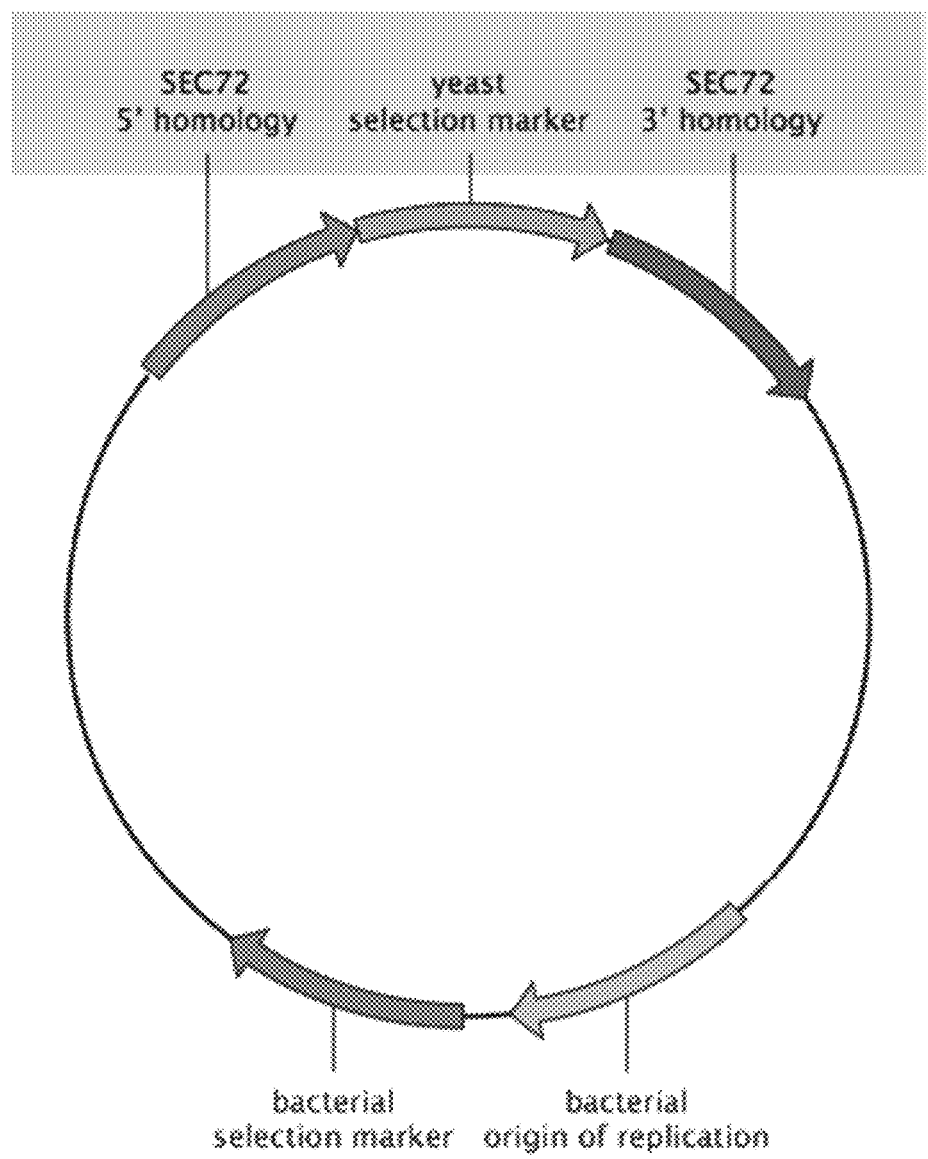
FIG. 2 is a plasmid map of a vector for SEC72 deletion comprising a yeast selection marker flanked by SEC72 homology arms.

The details of various embodiments of the invention are set forth in the description below. Other features, objects, and advantages of the invention will be apparent from the description and the drawings, and from the claims.

Definitions

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. The terms "a" and "an" includes plural references unless the context dictates otherwise. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

An endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 75%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique*, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

The term "deletion" as used herein refers to the removal of one or more nucleotides from a nucleic acid molecule or one or more amino acids from a protein, the regions on either side being joined together.

The term "knock-out" as used herein is intended to refer to a gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "regulatory element" refers to any element which affects transcription or translation of a nucleic acid molecule. These include, by way of example but not limitation: regulatory proteins (e.g., transcription factors), chaperones, signaling proteins, RNAi molecules, antisense RNA molecules, microRNAs and RNA aptamers. Regulatory elements may be endogenous to the host organism. Regulatory elements may also be exogenous to the host organism. Regulatory elements may be synthetically generated regulatory elements.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. Promoters may be endogenous to the host organism. Promoters may also be exogenous to the host organism. Promoters may be synthetically generated regulatory elements.

Promoters useful for expressing the recombinant genes described herein include both constitutive and inducible/repressible promoters. Where multiple recombinant genes are expressed in an engineered organism of the invention, the different genes can be controlled by different promoters or by identical promoters in separate operons, or the expression of two or more genes may be controlled by a single promoter as part of an operon.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "wild-type" (i.e., "WT") as used herein refers to a comparative strain lacking the modification being discussed. It does not refer to the native, unmodified strain, but rather to a strain lacking a selected modification. For example, when comparing two versions of a recombinant strain modified to express a recombinant silk polypeptide, where one is a sec72 KO, the KO strain may be referred to as the Δsec72 strain, while the other version is referred to as "WT."

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is sometimes also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A useful algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

Throughout this specification and claims, the word "comprise" or variations such as "comprises" or "comprising," will be understood to imply the inclusion of a stated integer or group of integers but not the exclusion of any other integer or group of integers.

Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Overview

Provided herein are recombinant strains and methods of improving secretion and productivity of recombinantly expressed proteins in yeast strains (e.g., *P. pastoris*).

Proteins destined for secretion must first cross the membrane of the endoplasmic reticulum (ER translocation). Multiple targeting pathways recruit elongating ribosomes or fully translated proteins to the ER membrane, which polypeptide chains enter via pore-forming protein complexes called translocons. Yeasts including *S. cerevisiae* and *P. pastoris* express two translocons, the SEC61 and SSH1 complexes. Each consists of a core trimeric complex, but the SEC61 translocon also associates with the tetrameric SEC63 complex. FIG. 1 shows the protein subunits contained within each of these translocon complexes.

SEC72 encodes a nonessential member of the SEC63 complex, but deletion of SEC72 (Δsec72) results in the accumulation of some secretory precursors. Surprisingly, herein we show that Δsec72 strains have improved secretion of recombinant silk polypeptides.

In some embodiments, the strains are modified to delete the sec72 gene (SEQ ID NO: 1). As we describe and shown herein, the deletion of sec72, which expresses SEC72 (SEQ ID NO: 2), an accessory factor for translocating proteins into the ER for secretion, unexpectedly assists silk secretion in bench-scale block model assays (up to +75%). This remained true across expression levels, signal sequences, and different silks.

In some embodiments, deletion of sec72 is effected using a plasmid having a 5' homology arm to sec72 and a 3' homology arm to sec72 flanking a yeast selection marker, e.g., as shown in FIG. 2. The Δsec72 deletion elicited transcriptional adaptation that could indirectly assist secretion. Sequences of the sec72 gene and the SEC72 protein are provided in Table 1.

TABLE 1 sec72 open reading frame and SEC72 protein sequences

| Description | SEQ ID NO: | Sequence |
| --- | --- | --- |
| sec72 (PAS_chr2-1_0448) ORF sequence (5' to 3') | 1 | atgctaccatttcgtacgacgtgagctcaaagaaactgaaagtcaca ggtgactacgcagacttagaatatgacatacagcagctgaacaccttg agcggagagatcctggccaataaagcagatgttccttctccaccaagt aaggagtcgtttgacaagaaattgtcccacatggctcagaaattacac gagtcggctgtatccaacataaagacaggcaagtatcctgaggctatc aaattgttgacgacgggtcttgaaatggttaacagaaggcccaagtac gagagttttcagatgacgttgagtgaaatgacgatctttattgtcact agagctgacgcttacatgatgaatggagactttgaaggggcattcaat gatgcagatttactggtaacgctcctgccatccattccagataattac attagaagaggggtagcccttttcaagatggggagatacgttgatgca aaaaacaattttgagagaggactttcatttgacccagataatgcaaaa ttgaagaaggagttagattttgtgctgaagaagatcgacgaggagaat ggagagttatag |
| SEC72 (PAS_chr2-1_0448) Protein Sequence | 2 | MLPFSYDVSSKKLKVTGDYADLEYDIQQLNTLSGEILANKADVPSPPS KESFDKKLSHMAQKLHESAVSNIKTGKYPEAIKLLTTGLEMVNRRPKY ESFQMTLSEMTIFIVTRADAYMMNGDFEGAFNDADLLVTLLPSIPDNY IRRGVALFKMGRYVDAKNNFERGLSFDPDNAKLKKELDFVLKKIDEEN GEL |

In some observed cases, the sec72 deletion slowed strain growth, and fermentation production screens of Δsec72 strains struggled with glucose accumulation. Thus, also provided herein, according to some embodiments, are strains recombinantly overexpressing proteins that comprise the SSH1 translocon complex. As shown herein, overexpression of the SSH1 translocon complex in Δsec72 strains improved the strain growth rate and fermentation performance, while maintaining improved secretion. Runs of this combined deletion-overexpression strain with only 4 copies of of recombinant silk-like block polypeptide expressing genes (i.e., 18B) showed similar titers and improved specific productivity (+18%) over a strain with 6 copies of silk-like block polypeptide expressing genes (i.e., 18B).

Figure 3:
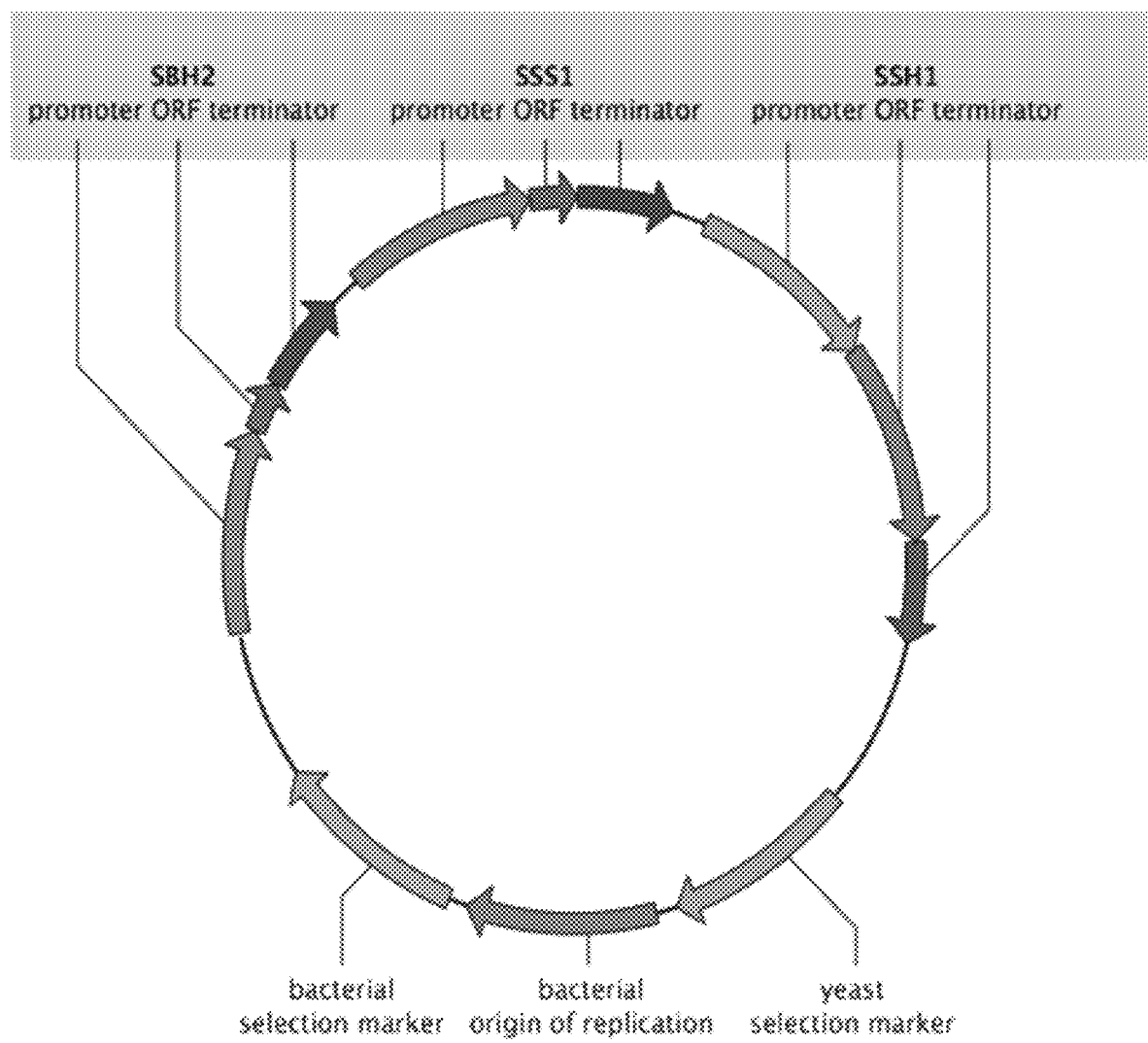
FIG. 3 is a plasmid map of a vector for overexpression of genes encoding proteins comprising the SSH1 complex. It includes a promoter, an open reading frame (ORF), and a terminator for SBH2, SSS1, and SSH1, as well as a yeast selection marker.

In some embodiments, the SSH1 translocon complex is overexpressed in host cells by inserting a plasmid comprising genes encoding recombinant SBH2, SSS1, and SSH1 (FIG. 3). Sequences for these genes and the expressed protein can be found in Table 2.

TABLE 2

Open reading frame and protein sequences for subunits of the SSH1 translocon complex.

| Description | SEQ ID NO: | Sequence |
|---|---|---|
| SSH1 (PAS_chr1-4_0629) ORF sequence | 3 | atggcggggttgcgttttttagacattgcaagaccatttgtcagctgg atcccggaagttgaacttccttatgaaaactgggggttcgatgaaaag ctgatttactcattttttcactgctgccatctatttgattctgtccctg cctatatacggtgtcaaatcctctgaagtcgtggacccagttccccat ttgcgttctgccttagggagtgagaagggaacattgctggagcttggg ttactgcctgtgattacttcggcatttatcttgcagttgttggctggt tggaaagttttcaaagtaaactttgatctggttagtgacagaatattg ttccaaactttgcaaaagatcacttcagtcgttatcagcatcgtatat gctgttcttctcacatttttgtgactactttactccaggtgtgtccact gataacgtcttgtggtcccaattctgatcatcttacagatagtggtg gtcaacttcttggttactctactcgttgaagtcattgacaaggattac ggattttcttcaggagctctattgttgcttgcggtttattccgccacc aacttcgttttttggcacgattggtcttagcaccgtcaacacctccaga tcgaacgaatctattggtgctctgattcaattattccgcaatttgagc tctaaaccaattggtgttgccatatatgactccttcttcagagtaaac cttcctaacttgactcaattttatctggggattgccattatttgtgtt tgtctgttcttgaataatgcaagatacgaagtaccaattaagccaaac aaggttcgtgccatggcctcagcttacccaatcaagctacttttcaat ggttctttgccacttctgtacacgtggactgtgctgtacaacttgaac cttattggttttctttgtcttcaagcttaccaacttttctcttttaggg aacttcaaagtggacccattcggcaacaactactacgaaattacatct ggactgctgtatttattgactcctactttcaacgctgaagctggactt ttacccaatgttgctaagccatttgttttcattgccttctatgttggt gttagcactttctttgctagatcgtggtccaacattaacgggtcgtca ggcaaggacattgccaagttttttcaaggctcaaggaatctcattgtta ggaaaaagagatgcctctgtgtctaaagagtttaacaccctagttcct gttgcttctgcctctggagctttcctattgtcttttccagttgccgtc gctgagttattgggtggctctggtgttccaacctctatcggaatcggt cttttgagtggttttggctattttggaaactgttttgcaagaatggcaa cagtctggaggtgcctcacagttctcccaatacttccagacttcttag |
| SSH1 (PAS_chr1-4_0629) Protein Sequence | 4 | MAGLRFLDIARPFVSWIPEVELPYENWGFDEKLIYSFFTAAIYLILSL PIYGVKSSEVVDPVPHLRSALGSEKGTLLELGLLPVITSAFILQLLAG WKVFKVNFDLVSDRILFQTLQKITSVVISIVYAVLLTFCDYFTPGVST DNVLWSQFLIILQIVVVNFLVTLLVEVIDKDYGFSSGALLLLAVYSAT NFVFGTIGLSTVNTSRSNESIGALIQLFRNLSSKPIGVAIYDSFFRVN LPNLTQFYLGIAIICVCLFLNNARYEVPIKPNKVRAMASAYPIKLLFN GSLPLLYTWTVLYNLNLIGFFVFKLTNFSLLGNFKVDPFGNNYYEITS GLLYLLTPTFNAEAGLLPNVAKPFVFIAFYVGVSTFFARSWSNINGSS GKDIAKFFKAQGISLLGKRDASVSKEFNTLVPVASASGAFLLSFPVAV AELLGGSGVPTSIGIGLLSGLAILETVLQEWQQSGGASQFSQYFQTS |
| SSS1 (PAS_chr1-1_0023) ORF sequence | 5 | atgtcccaaaaagtcaccgacgtccctctggaatttgttaaggaaggt tccaaattcatctctaaatgtactaaaccctctcagaaggagtactta aagatagtaagagctgttggagttgggttttaatgatgggcgtggtt ggttacgttgtcaagctcattcatattccaatcagatatttgattgtt taa |
| SSS1 (PAS_chr1-1_0023) Protein Sequence | 6 | MSQKVTDVPLEFVKEGSKFISKCTKPSQKEYLKIVRAVGVGFLMMGVV GYVVKLIHIPIRYLIV |
| SBH2 (PAS_chr2-2_0210) ORF sequence | 7 | atggtaagtgtccagtttgatgagtgcagaatggttccaagtttttaga ccagttactaataatatttaaagtctacagcaattccaggaggacagagaa cgttagctaaaagaagagcagcaaacttggataagaaacaggatgaac caacctccgccagatctgccggtgctggaggttcttcgtctaccatgc taaagttgtacacagacgaggcccaaggtttgaaagttgatccttttaa ttgttcttgttcttgctgttggtttcatttcagtgtcattggtttgc acgttgttgctaagctgacaggaaagttgatcaactaa |

TABLE 2-continued

Open reading frame and protein sequences for subunits
of the SSH1 translocon complex.

| Description | SEQ ID NO: | Sequence |
| --- | --- | --- |
| SBH2 (PAS_chr2-2_0210) Protein Sequence | 8 | MSTAIPGGQRTLAKRRAANLDKKQDEPTSARSAGAGGSSSTMLKLYTD EAQGLKVDPLIVLVLAVGFIFSVIGLHVVAKLTGKLIN |

Protease Knock-Outs

In some embodiments, to attenuate a protease activity in *Pichia pastoris*, the genes encoding these enzymes are inactivated or mutated to reduce or eliminate activity. This can be done through mutations or insertions into the gene itself of through modification of a gene regulatory element. This can be achieved through standard yeast genetics techniques. Examples of such techniques include gene replacement through double homologous recombination, in which homologous regions flanking the gene to be inactivated are cloned in a vector flanking a selectable maker gene (such as an antibiotic resistance gene or a gene complementing an auxotrophy of the yeast strain). In some embodiments, the Nourseothricin selection plasmid shown in FIG. 4A can be used as a base plasmid, and homology arms (HA) flanking resistance cassettes (FIG. 4B and FIG. 4C) can be used, where the homology arms specifically target the desired protease to be knocked out. Description of protease knock-outs and methods of modifying host cells to inhibit recombinant protein degradation are provided in U.S. application Ser. No. 15/724,196 and PCT Application No. PCT/US2017/054997, each of which are incorporated herein by reference in its entirety.

Alternatively, the homologous regions can be PCR-amplified and linked through overlapping PCR to the selectable marker gene. Subsequently, such DNA fragments are transformed into *Pichia pastoris* through methods known in the art, e.g., electroporation. Transformants that then grow under selective conditions are analyzed for the gene disruption event through standard techniques, e.g. PCR on genomic DNA or Southern blot. In an alternative experiment, gene inactivation can be achieved through single homologous recombination, in which case, e.g. the 5' end of the gene's ORF is cloned on a promoterless vector also containing a selectable marker gene. Upon linearization of such vector through digestion with a restriction enzyme only cutting the vector in the target-gene homologous fragment, such vector is transformed into *Pichia pastoris*. Integration at the target gene site is confirmed through PCR on genomic DNA or Southern blot. In this way, a duplication of the gene fragment cloned on the vector is achieved in the genome, resulting in two copies of the target gene locus: a first copy in which the ORF is incomplete, thus resulting in the expression (if at all) of a shortened, inactive protein, and a second copy which has no promoter to drive transcription.

Alternatively, transposon mutagenesis is used to inactivate the target gene. A library of such mutants can be screened through PCR for insertion events in the target gene.

The functional phenotype (i.e., deficiencies) of an engineered/knockout strain can be assessed using techniques known in the art. For example, a deficiency of an engineered strain in protease activity can be ascertained using any of a variety of methods known in the art, such as an assay of hydrolytic activity of chromogenic protease substrates, band shifts of substrate proteins for the selected protease, among others.

Attenuation of a protease activity described herein can be achieved through mechanisms other than a knockout mutation. For example, a desired protease can be attenuated via amino acid sequence changes by altering the nucleic acid sequence, placing the gene under the control of a less active promoter, down-regulation, expressing interfering RNA, ribozymes or antisense sequences that target the gene of interest, or through any other technique known in the art. In preferred strains, the protease activity of proteases encoded at PAS_chr4_0584 (YPS1-1) and PAS_chr3_1157 (YPS1-2) (e.g., polypeptides comprising SEQ ID NO: 10 and 12) is attenuated by any of the methods described above. In some aspects, the invention is directed to methylotrophic yeast strains, especially *Pichia pastoris* strains, wherein a YPS1-1 and a YPS1-2 gene (e.g., as set forth in SEQ ID NO: 9 and SEQ ID NO: 11) have been inactivated. In some embodiments, additional protease encoding genes may also be knocked-out in accordance with the methods provided herein to further reduce protease activity of a desired protein product expressed by the strain.

TABLE 3

Open reading frame nucleotide sequence and polypeptide sequence for
proteases targeted for deletion in *P. pastoris*

| Description | SEQ ID NO: | Sequence |
| --- | --- | --- |
| PAS_chr4_0584 (YPS1-1) ORF sequence (5' to 3') | 9 | atgttgaaggatcagttcttgttatgggttgctttgatagcgagcgtaccggtttc cggcgtgatggcagctcctagcgagtccgggcataacacggttgaaaaacgagatg ccaaaaacgttgttggcgttcaacagttggacttcagcgttctgaggggtgattcc ttcgaaagtgcctcttcagagaacgtgcctcggcttgtgaggagagatgacacgct agaagctgagctaatcaaccagcaatcattctacttgtcacgactgaaagttggat cacatcaagcggatattggaatcctagtggacacaggatcctctgatttatggta atggactcggtaaacccatactgcagtagccgttcccgcgtgaagagagatataca cgatgagaagatcgccgaatgggatcccatcaatctcaagaaaaatgaaacttctc agaataaaaatttttgggattggctcgttggaactagcactagttctccttccacc gccacggcaactggtagtggtagtggtagtggtagtggtagtggtagtggtagtgc tgccacagccgtatcggtaagttctgcacaggcaacattggattgctctacgtatg gaacgtttgatcacgctgattcctcgacgttccatgacaataatacagacttttc |

TABLE 3-continued

Open reading frame nucleotide sequence and polypeptide sequence for proteases targeted for deletion in *P. pastoris*

| Description | SEQ ID NO: | Sequence |
|---|---|---|
| | | atctcatacgctgataccacttttgcttcaggaatctggggttatgacgacgtcat tatcgacggcatagaggtgaaagaactttccttcgccgttgcagacatgaccaatt cctctattggtgtgttaggtattggactgaaaggcctagaatccacatatgctagt gcatcttcggtcagtgaaatgtatcagtatgacaatttgccagccaagatggtcac cgatgggttgatcaacaaaaatgcatactccttgtacttgaactccaaggacgcct caagtggttccatcctctttggaggtgtggatcatgaaaaatattcgggacaattg ttgacagttccagtcatcaacacactcgcttccagtggttacagagaggcaattcg tttacaaattactttaaatgaatagatgtgaaaaaggttctgaccagggaactc ttttacaagggagatttgctgcattattggactctggagctacgctaacgtatgct ccttcttctgttttaaattcaattggccggaacctgggcggtcctatgattcgtc aagacaagcttataccattcgttgtgtttctgcatcagataccacttctctggtat tcaattttgggggtgctacagtggaagtttccctgtacgatctacagattgcaaca tattacaccggggggaagtgccacgcaatgtcttattggaatattcagctctggaag tgatgagtttgtgctcggtgatacctcttgaggtcagcctacgtggtttacgatc ttgatgggcttgaagtgtcgcttgcccaagccaacttcaacgaaaccgattctgat gttgaggctattacctccagtgtaccttccgctactcgtgcatccggatacagttc tacatggtctggttctgccagcggtacagtttacacttcggttcagatggaatccg gtgctgcttccagctccaactcttctggatcgaatatgggttcctcttcctcatcg tcctcttcatcgtcctcgacttccagtggagacgaagaaggagggagctccgccaa cagggtccccttcagctaccttctctctgtttggtagttattctcggcgtgtgta tagtatag |
| PAS_chr4_0584 (YPS1-4) Polypeptide Sequence | 10 | MLKDQFLLWV ALIASVPVSG VMAAPSESGH NTVEKRDAKN VVGVQQLDFS VLRGDSFESA SSENVPRLVR RDDTLEAELI NQQSFYLSRL KVGSHQADIG ILVDTGSSDL WVMDSVNPYC SSRSRVKRDI HDEKIAEWDP INLKKNETSQ NKNFWDWLVG TSTSSPSTAT ATGSGSGSGS GSGSGSAATA VSVSSAQATL DCSTYGTFDH ADSSTFHDNN TDFFISYADT TFASGIWGYD DVIIDGIEVK ELSFAVADMT NSSIGVLGIG LKGLESTYAS ASSVSEMYQY DNLPAKMVTD GLINKNAYSL YLNSKDASSG SILFGGVDHE KYSGQLLTVP VINTLASSGY REAIRLQITL NGIDVKKGSD QGTLLQGRFA ALLDSGATLT YAPSSVLNSI GRNLGGSYDS SRQAYTIRCV SASDTTSLVF NFGGATVEVS LYDLQIATYY TGGSATQCLI GIFSSGSDEF VLGDTFLRSA YVVYDLDGLE VSLAQANFNE TDSDVEAITS SVPSATRASG YSSTWSGSAS GTVYTSVQME SGAASSSNSS GSNMGSSSSS SSSSSSTSSG DEEGGSSANR VPFSYLSLCL VVILGVCIV |
| PAS_chr3_1157 (YPS1-2) ORF sequence (5' to 3') | 11 | atgatcatcaaccacttggtattgacagccctcagcattgcactagcaagtgcgca actccaatcgccttcaaggctaacaagttgccattcaaaaagtttatcattccaa cgacccaaaggaccgtttaattaagagagatgactacgagtccctcgacttgagac acatcggagtcttgtacactcagagatccaaattggatctgacgaaactgaaatt gaggtcattgtcgacactggttctgccgacttgtgggtcatcgattccgacgctgc cgtctgtgagttatcctacgatgagattgaggccaatagcttttcctcggcttctg ccaaattcatggacaagatagcctcctccatcacaagagctcctggatgggctgagt gagtttggatttgctctcgatggtgaaatttctcaataccttagccgataaatctgg acgtgtttcgaaaagagaggaaaatcaacaagatttcaacattaaccgtgacgagc ctgtgtgtgaacagtttggttccttcgattctagttcttccgacactttccaaagc aacaattcagcttttggtattgcttaccttgatggaaccactgctaacggaacttg ggtcagggacacagtccgcatcggcgacttttgccatcagccaacagagttttgcct tagtcaacatcacagataactacatgggaatcttgggtctcggtcctgctacccaa caaaccaccaatagtaacccaattgcagcaaacagatttacttatgatggtgttgt ggattcattgcggtcccaaggatttatcaattcagcatcgttttctgttacttgt ctccagatgaagataacgagcacgacgaattcagcgacggagaaattttatttggt gctattgatagggcaagatagacgggccatttagacttttcccatatgtcaatcc ttacaaaccagtttaccccgatcaatatacttcctacgttacagtgtccacaattg cggtgtcttcgtcagatgaaactctcattattgaaagacgtcctcgtttggcatta atcgatacaggtgccaccttctcctatttgccaacctacccattgattcgtttagc gttttccatccatggaggctttgaatatgtttctcaattgggactatttgtcattc gtacaagttctctgtctgttgctagaaataaggtgattgagttcaagtttggtgaa gacgttgtgatccaatcccagtttctgatcatctattggacgtctcaggcctttt tactgatggccaacaatactccgcattaactgtacgtgaaagtcttgacggactttt ccattctaggtgatacattcatcaaatcggcctacttattctttgacaatgaaaac agccagctgggtattggtcagatcaacgtcactgatgacgaggatattgaggtggt cggtgatttcactattgaacgagacccagcctactcctctacttggtctagcgatt tacctcatgaaacacccactagggctttgagtactgcttcaggggggaggccttggt accggaataaacacggccacaagtcgtgcaagttctcgttccacatctggctctac ttcacgaacttcttctacatctggctctgcttctggtacttcttcaggtgcatctt ctgctactcaaaatgacgaaacatccactgatcttggagctccagctgcatcttta agtgcaacgccatgtcttttttgccatcttgctgctcatgttgtag |
| PAS_chr3_1157 (YPS1-2) Polypeptide Sequence | 12 | MIINHLVLTA LSIALANDYE SLDLRHIGVL YTAEIQIGSD ETEIEVIVDT GSADLWVIDS DAAVCELSYD EIEANSFSSA SAKFMDKIAP PSQELLDGLS EFGFALDGEI SQYLADKSGR VSKREENQQD FNINRDEPVC EQFGSFDSSS SDTFQSNNSA FGIAYLDGTT ANGTWVRDTV RIGDFAISQQ SFALVNITDN YMGILGLGPA TQQTTNSNPI AANRFTYDGV VDSLRSQGFI NSASFSVYLS PDEDNEHDEF SDGEILFGAI DRAKIDGPFR LFPYVNPYKP VYPDQYTSYV TVSTIAVSSS DETLIIERRP RLALIDTGAT FSYLPTYPLI RLAFSIHGGF |

TABLE 3-continued

Open reading frame nucleotide sequence and polypeptide sequence for
proteases targeted for deletion in *P. pastoris*

| Description | SEQ ID NO: | Sequence |
|---|---|---|
| | | EYVSQLGLFV IRTSSLSVAR NKVIEFKFGE DVVIQSPVSD HLLDVSGLFT
DGQQYSALTV RESLDGLSIL GDTFIKSAYL FFDNENSQLG IGQINVTDDE
DIEVVGDFTI ERDPAYSSTW SSDLPHETPT RALSTASGGG LGTGINTATS
RASSRSTSGS TSRTSSTSGS ASGTSSGASS ATQNDETSTD LGAPAASLSA
TPCLFAILLL ML |

Production of Recombinant Strains

Provided herein are methods of transforming a strain to reduce activity, e.g., using vectors to deliver recombinant genes or to knock-out or otherwise attenuate endogenous genes as desired. These vectors can take the form of a vector backbone containing a replication origin and a selection marker (typically antibiotic resistance, although many other methods are possible), or a linear fragment that enables incorporation into the target cell's chromosome. The vectors should correspond to the organism and insertion method chosen.

Once the elements of a vector are selected, construction of the vector can be performed in many different ways. In an embodiment, a DNA synthesis service or a method to individually make every vector may be used.

Once the DNA for each vector (including the additional elements required for insertion and operation) is acquired, it must be assembled. There are many possible assembly methods including (but not limited to) restriction enzyme cloning, blunt-end ligation, and overlap assembly [see, e.g., Gibson, D. G., et al., Enzymatic assembly of DNA molecules up to several hundred kilobases. Nature methods, 6(5), 343-345 (2009), and GeneArt Kit (http://tools.invitrogen.com/content/sfs/manuals/geneart_seamless_cloning_and_assembly_man.pdf)]. Overlap assembly provides a method to ensure all of the elements get assembled in the correct position and do not introduce any undesired sequences.

The vectors generated above can be inserted into target cells using standard molecular biology techniques, e.g., molecular cloning. In an embodiment, the target cells are already engineered or selected such that they already contain the genes required to make the desired product, although this may also be done during or after further vector insertion.

Depending on the organism and library element type (plasmid or genomic insertion), several known methods of inserting the vector comprising DNA to incorporate into the cells may be used. These may include, for example, transformation of microorganisms able to take up and replicate DNA from the local environment, transformation by electroporation or chemical means, transduction with a virus or phage, mating of two or more cells, or conjugation from a different cell.

Several methods are known in the art to introduce recombinant DNA in bacterial cells that include but are not limited to transformation, transduction, and electroporation, see Sambrook, et al., Molecular Cloning: A Laboratory Manual (1989), Second Edition, Cold Spring Harbor Press, Plainview, N.Y. Non-limiting examples of commercial kits and bacterial host cells for transformation include NovaBlue Singles™ (EMD Chemicals Inc., NJ, USA), Max Efficiency® DH5α™, One Shot® BL21 (DE3) *E. coli* cells, One Shot @BL21 (DE3) pLys *E. coli* cells (Invitrogen Corp., Carlsbad, Calif., USA), XL1-Blue competent cells (Stratagene, CA, USA). Non limiting examples of commercial kits and bacterial host cells for electroporation include Zappers™ electrocompetent cells (EMD Chemicals Inc., NJ, USA), XL1-Blue Electroporation-competent cells (Stratagene, CA, USA), ElectroMAX™ *A. tumefaciens* LBA4404 Cells (Invitrogen Corp., Carlsbad, Calif., USA).

Several methods are known in the art to introduce recombinant nucleic acid in eukaryotic cells. Exemplary methods include transfection, electroporation, liposome mediated delivery of nucleic acid, microinjection into to the host cell, see Sambrook, et al., Molecular Cloning: A Laboratory Manual (1989), Second Edition, Cold Spring Harbor Press, Plainview, N.Y. Non-limiting examples of commercial kits and reagents for transfection of recombinant nucleic acid to eukaryotic cell include Lipofectamine™ 2000, Optifect™ Reagent, Calcium Phosphate Transfection Kit (Invitrogen Corp., Carlsbad, Calif., USA), GeneJammer® Transfection Reagent, LipoTAXI® Transfection Reagent (Stratagene, CA, USA). Alternatively, recombinant nucleic acid may be introduced into insect cells (e.g. sf9, sf21, High Five™) by using baculo viral vectors.

Transformed cells are isolated so that each clone can be tested separately. In an embodiment, this is done by spreading the culture on one or more plates of culture media containing a selective agent (or lack of one) that will ensure that only transformed cells survive and reproduce. This specific agent may be an antibiotic (if the library contains an antibiotic resistance marker), a missing metabolite (for auxotroph complementation), or other means of selection. The cells are grown into individual colonies, each of which contains a single clone.

Colonies are screened for desired production of a protein, metabolite, or other product, for reduction in protease activity, for growth, or for increase in secretion activity. In an embodiment, screening identifies recombinant cells having the highest (or high enough) product production titer or efficiency. This includes a decreased proportion of degradation products or an increased total amount of desired polypeptides secreted from a cell and collected from a cell culture.

This assay can be performed by growing individual clones, one per well, in multi-well culture plates. Once the cells have reached an appropriate biomass density, they are induced with methanol. After a period of time, typically 24-72 hours of induction, the cultures are harvested by spinning in a centrifuge to pellet the cells and removing the supernatant. The supernatant from each culture can then be tested for to determine whether desired secretion amounts have been achieved.

Silk Sequences

In some embodiments, the modified strains described herein recombinantly express a silk-like polypeptide sequence. In some embodiments, the silk-like polypeptide sequences are 1) block copolymer polypeptide compositions generated by mixing and matching repeat domains derived from silk polypeptide sequences and/or 2) recombinant expression of block copolymer polypeptides having sufficiently large size (approximately 40 kDa) to form useful fibers by secretion from an industrially scalable microorganism. Large (approximately 40 kDa to approximately 100 kDa) block copolymer polypeptides engineered from silk repeat domain fragments, including sequences from almost all published amino acid sequences of spider silk polypeptides, can be expressed in the modified microorganisms described herein. In some embodiments, silk polypeptide sequences are matched and designed to produce highly expressed and secreted polypeptides capable of fiber formation. In some embodiments, knock-out of protease genes or reduction of protease activity in the host modified strain reduces degradation of the silk like polypeptides. In some embodiments, knock-out of sec72 and overexpression of an SSH1 translocon complex improves secretion while mitigating defects in growth, maintaining, or improving growth of the strain.

Provided herein, in several embodiments, are compositions for expression and secretion of block copolymers engineered from a combinatorial mix of silk polypeptide domains across the silk polypeptide sequence space, wherein the block copolymers have minimal degradation. In some embodiments provided herein are methods of secreting block copolymers in scalable organisms (e.g., yeast, fungi, and gram positive bacteria) with minimal degradation. In some embodiments, the block copolymer polypeptide comprises 0 or more N-terminal domains (NTD), 1 or more repeat domains (REP), and 0 or more C-terminal domains (CTD). In some aspects of the embodiment, the block copolymer polypeptide is >100 amino acids of a single polypeptide chain. In some embodiments, the block copolymer polypeptide comprises a domain that is at least 80%, 81%, 82%, 83%, 84%, 85%, 86%, 87%, 88%, 89%, 90%, 91%, 92%, 93%, 94%, 95%, 96%, 97%, 98%, or 99% identical to a sequence of a block copolymer polypeptide as disclosed in International Publication No. WO/2015/042164, "Methods and Compositions for Synthesizing Improved Silk Fibers," incorporated by reference in its entirety.

Several types of native spider silks have been identified. The mechanical properties of each natively spun silk type are believed to be closely connected to the molecular composition of that silk. See, e.g., Garb, J. E., et al., Untangling spider silk evolution with spidroin terminal domains, *BMC Evol. Biol.,* 10:243 (2010); Bittencourt, D., et al., Protein families, natural history and biotechnological aspects of spider silk, *Genet. Mol. Res.,* 11:3 (2012); Rising, A., et al., Spider silk proteins: recent advances in recombinant production, structure-function relationships and biomedical applications, *Cell. Mol. Life Sci.,* 68:2, pg. 169-184 (2011); and Humenik, M., et al., Spider silk: understanding the structure-function relationship of a natural fiber, *Prog. Mol. Biol. Transl. Sci.,* 103, pg. 131-85 (2011). For example:

Aciniform (AcSp) silks tend to have high toughness, a result of moderately high strength coupled with moderately high extensibility. AcSp silks are characterized by large block ("ensemble repeat") sizes that often incorporate motifs of poly serine and GPX. Tubuliform (TuSp or Cylindrical) silks tend to have large diameters, with modest strength and high extensibility. TuSp silks are characterized by their poly serine and poly threonine content, and short tracts of poly alanine. Major Ampullate (MaSp) silks tend to have high strength and modest extensibility. MaSp silks can be one of two subtypes: MaSp1 and MaSp2. MaSp1 silks are generally less extensible than MaSp2 silks, and are characterized by poly alanine, GX, and GGX motifs. MaSp2 silks are characterized by poly alanine, GGX, and GPX motifs. Minor Ampullate (MiSp) silks tend to have modest strength and modest extensibility. MiSp silks are characterized by GGX, GA, and poly A motifs, and often contain spacer elements of approximately 100 amino acids. Flagelliform (Flag) silks tend to have very high extensibility and modest strength. Flag silks are usually characterized by GPG, GGX, and short spacer motifs.

The properties of each silk type can vary from species to species, and spiders leading distinct lifestyles (e.g. sedentary web spinners vs. vagabond hunters) or that are evolutionarily older may produce silks that differ in properties from the above descriptions (for descriptions of spider diversity and classification, see Hormiga, G., and Griswold, C. E., Systematics, phylogeny, and evolution of orb-weaving spiders, Annu. Rev. Entomol. 59, pg. 487-512 (2014); and Blackedge, T. A. et al., Reconstructing web evolution and spider diversification in the molecular era, *Proc. Natl. Acad. Sci. U.S.A.,* 106:13, pg. 5229-5234 (2009)). However, synthetic block copolymer polypeptides having sequence similarity and/or amino acid composition similarity to the repeat domains of native silk proteins can be used to manufacture on commercial scales consistent silk-like fibers that recapitulate the properties of corresponding natural silk fibers.

In some embodiments, a list of putative silk sequences can be compiled by searching GenBank for relevant terms, e.g. "spidroin" "fibroin" "MaSp", and those sequences can be pooled with additional sequences obtained through independent sequencing efforts. Sequences are then translated into amino acids, filtered for duplicate entries, and manually split into domains (NTD, REP, CTD). In some embodiments, candidate amino acid sequences are reverse translated into a DNA sequence optimized for expression in *Pichia* (*Komagataella*) *pastoris*. The DNA sequences are each cloned into an expression vector and transformed into *Pichia* (*Komagataella*) *pastoris*. In some embodiments, various silk domains demonstrating successful expression and secretion are subsequently assembled in combinatorial fashion to build silk molecules capable of fiber formation.

Silk polypeptides are characteristically composed of a repeat domain (REP) flanked by non-repetitive regions (e.g., C-terminal and N-terminal domains). In an embodiment, both the C-terminal and N-terminal domains are between 75-350 amino acids in length. The repeat domain exhibits a hierarchical architecture. The repeat domain comprises a series of blocks (also called repeat units). The blocks are repeated, sometimes perfectly and sometimes imperfectly (making up a quasi-repeat domain), throughout the silk repeat domain. The length and composition of blocks varies among different silk types and across different species. Table 1 lists examples of block sequences from selected species and silk types, with further examples presented in Rising, A. et al., Spider silk proteins: recent advances in recombinant production, structure-function relationships and biomedical applications, *Cell Mol. Life Sci.,* 68:2, pg 169-184 (2011); and Gatesy, J. et al., Extreme diversity, conservation, and convergence of spider silk fibroin sequences, *Science,* 291: 5513, pg. 2603-2605 (2001). In some cases, blocks may be arranged in a regular pattern, forming larger macro-repeats that appear multiple times (usually 2-8) in the repeat domain of the silk sequence. Repeated blocks inside a repeat domain or macro-repeat, and repeated macro-repeats within the repeat domain, may be separated by spacing elements. In some embodiments, block sequences comprise a glycine rich region followed by a polyA region. In some embodiments, short (~1-10) amino acid motifs appear multiple times inside of blocks. For the purpose of this invention, blocks from different natural silk polypeptides can be selected without reference to circular permutation (i.e., identified blocks that are otherwise similar between silk polypeptides may not align due to circular permutation). Thus, for example, a "block" of SGAGG (SEQ ID NO: 23) is, for the purposes of the present invention, the same as GSGAG (SEQ ID NO: 24) and the same as GGSGA (SEQ ID NO: 25); they are all just circular permutations of each other. The particular permutation selected for a given silk sequence can be dictated by convenience (usually starting with a G) more than anything else. Silk sequences obtained from the NCBI database can be partitioned into blocks and non-repetitive regions.

TABLE 4

Samples of Block Sequences

| Species | Silk Type | Representative Block Amino Acid Sequence |
|---|---|---|
| Aliatypus gulosus | Fibroin 1 | GAASSSSTIITTKSASASAAADASAAATASAASRSSANAAASAFAQS<br>FSSILLESGYFCSIFGSSISSSYAAAIASAASRAAAESNGYTTHAYA<br>CAKAVASAVERVTSGADAYAYAQAISDAISHALLYTGRLNTANANSL<br>ASAFAYAFANAAAQASASSASAGAASASGAASASGAGSAS<br>(SEQ ID NO: 26) |
| Plectreurys tristis | Fibroin 1 | GAGAGAGAGAGAGAGAGSGASTSVSTSSSSGSGAGAGAGSGAGSGAG<br>AGSGAGAGAGAGGAGAGFGSGLGLGYGVGLSSAQAQAQAQAAAQAQA<br>QAQAQAYAAAQAQAQAQAQAQ<br>(SEQ ID NO: 27) |
| Plectreurys tristis | Fibroin 4 | GAAQKQPSGESSVATASAAATSVTSGGAPVGKPGVPAPIFYPQGPLQ<br>QGPAPGPSNVQPGTSQQGPIGGVGGSNAFSSSFASALSLNRGFTEVI<br>SSASATAVASAFQKGLAPYGTAFALSAASAAADAYNSIGSGANAFAY<br>AQAFARVLYPLVQQYGLSSSAKASAFASAIASSFSSGTSGQGPSIGQ<br>QQPPVTISAASASAGASAAAVGGGQVGQGPYGGQQQSTAASASAAAA<br>TATS<br>(SEQ ID NO: 28) |
| Araneus gemmoides | TuSp | GNVGYQLGLKVANSLGLGNAQALASSLSQAVSAVGVGASSNAYANAV<br>SNAVGQVLAGQGILNAANAGSLASSFASALSSSAASVASQSASQSQA<br>ASQSQAAASAFRQAASQSASQSDSRAGSQSSTKTTSTSTSGSQADSR<br>SASSSASASAFAQQSSASLSSSSSFSSAFSSATSISAV<br>(SEQ ID NO: 29) |
| Argiope aurantia | TuSp | GSLASSFASALSASAASVASSAAAQAASQSQAAASAFSRAASQSASQ<br>SAARSGAQSISTTTTTSTAGSQAASQSASSAASQASASSFARASSAS<br>LAASSSFSSAFSSANSLSALGNVGYQLGFNVANNLGIGNAAGLGNAL<br>SQAVSSVGVGASSSTYANAVSNAVGQFLAGQGILNAANA<br>(SEQ ID NO: 30) |
| Deinopis spinosa | TuSp | GASASAYASAISNAVGPYLYGLGLFNQANAASFASSFASAVSSAVAS<br>ASASAASSAYAQSAAAQAQAASSAFSQAAAQSAAAASAGASAGAGAS<br>AGAGAVAGAGAVAGASAAAASQAAASSSASAVASAFAQSAS<br>YALASSSAFAMAFASATSAGYLGSLAYQLGLTTAYNLGLSNAQAFAS<br>TLSQAVTGVGL<br>(SEQ ID NO: 31) |
| Nephila clavipes | TuSp | GATAASYGNALSTAAAQFFATAGLLNAGNASALASSFARAFSASAES<br>QSFAQSQAFQQASAFQQAASRSASQSAAEAGSTSSSTTTTTSAARSQ<br>AASQSASSSYSSAFAQAASSSLATSSALSRAFSSVSSASAASSLAYS<br>IGLSAARSLGIADAAGLAGVLARAAGALGQ<br>(SEQ ID NO: 32) |
| Argiope trifasciata | Flag | GGAPGGGPGGAGPGGAGFGPGGGAGFGPGGGAGFGPGGAAGGPGGPG<br>GPGGPGGAGGYGPGGAGGYGPGGVGPGGAGGYGPGAGGYGPGGSGP<br>GGAGPGGAGGEGPVTVDVDVTVGPEGVGGGPGGAGPGGAGFGPGGGA<br>GFGPGGAPGAPGGPGGPGGPGGPGGPGGVGPGGAGGYGPGGAGGVGP<br>AGTGGFGPGGAGGFGPGGAGGFGPGGAGGFGPAGAGGYGPGGVGPGG<br>AGGFGPGGVGPGGSGPGGAGGEGPVTVDVDVSV<br>(SEQ ID NO: 33) |
| Nephila clavipes | Flag | GVSYGPGGAGGPYGPGGPYGPGGEGPGGAGGPYGPGGVGPGGSGPGG<br>YGPGGAGPGGYGPGGSGPGGYGPGGSGPGGYGPGGSGPGGYGPGGSG<br>PGGYGPGGYGPGGSGPGGSGPGGSGPGGYGPGGTGPGGSGPGGYGPG<br>GSGPGGSGPGGYGPGGSGPGGFGPGGSGPGGYGPGGSGPGGAGPGGV<br>GPGGFGPGGAGPGGAAPGGAGPGGAGPGGAGPGGAGPGGAGPGGAGP<br>GGAGGAGGAGGSGGAGGSGGTTIIEDLDITIDGADGPITISEELPIS<br>GAGGSGPGGAGPGGVGPGGSGPGGVGPGGSGPGGVGPGGSGPGGVGP<br>GGAGGPYGPGGSGPGGAGGAGGPGGAYGPGGSYGPGGSGPGGAGGP<br>YGPGGEGPGGAGGPYGPGGAGGPYGPGGAGGPYGPGGEGGPYGP<br>(SEQ ID NO: 34) |
| Latrodectus hesperus | AcSp | GINVDSDIGSVTSLILSGSTLQMTIPAGGDDLSGGYPGGFPAGAQPS<br>GGAPVDFGGPSAGGDVAAKLARSLASTLASSGVFRAAFNSRVSTPVA<br>VQLTDALVQKIASNLGLDYATASKLRKASQAVSKVRMGSDTNAYALA<br>ISSALAEVLSSSGKVADANINQIAPQLASGIVLGVSTTAPQFGVDLS<br>SINVNLDISNVARNMQASIQGGPAPITAEGPDFGAGYPGGAPTDLSG<br>LDMGAPSDGSRGGDATAKLLQALVPALLKSDVFRAIYKRGTRKQVVQ<br>YVTNSALQQAASSLGLDASTISQLQTKATQALSSVSADSDSTAYAKA<br>FGLAIAQVLGTSGQVNDANVNQIGAKLATGILRGSSAVAPRLGIDLS<br>(SEQ ID NO: 35) |
| Argiope trifasciata | AcSp | GAGYTGPSGPSTGPSGYPGPLGGGAPFGQSGFGGSAGPQGGFGATGG<br>ASAGLISRVANALANTSTLRTVLRTGVSQQIASSVVQRAAQSLASTL<br>GVDGNNLARFAVQAVSRLPAGSDTSAYAQAFSSALFNAGVLNASNID |

TABLE 4-continued

Samples of Block Sequences

| Species | Silk Type | Representative Block Amino Acid Sequence |
|---|---|---|
| | | TLGSRVLSALLNGVSSAAQGLGINVDSGSVQSDISSSSSFLSTSSSS<br>ASYSQASASSTS<br>(SEQ ID NO: 36) |
| Uloborus diversus | AcSp | GASAADIATAIAASVATSLQSNGVLTASNVSQLSNQLASYVSSGLSS<br>TASSLGIQLGASLGAGFGASAGLSASTDISSSVEATSASTLSSSASS<br>TSVVSSINAQLVPALAQTAVLNAAFSNINTQNAIRIAELLTQQVGRQ<br>YGLSGSDVATASSQIRSALYSVQQGSASSAYVSAIVGPLITALSSRG<br>VVNASNSSQIASSLATAILQFTANVAPQFGISIPTSAVQSDLSTISQ<br>SLTAISSQTSSSVDSSTSAFGGISGPSGPSPYGPQPSGPTFGPGPSL<br>SGLTGFTATFASSFKSTLASSTQFQLIAQSNLDVQTRSSLISKVLIN<br>ALSSLGISASVASSIAASSSQSLLSVSA<br>(SEQ ID NO: 37) |
| Euprosthenops australis | MaSp1 | GGQGGQGQGRYGQGAGSSAAAAAAAAAAAAA<br>(SEQ ID NO: 38) |
| Tetragnatha kauaiensis | MaSp1 | GGLGGGQGAGQGGQQGAGQGGYGSGLGGAGQGASAAAAAAAA<br>(SEQ ID NO: 39) |
| Argiope aurantia | MaSp2 | GGYGPGAGQQGPGSQGPGSGGQQGPGGLGPYGPSAAAAAAAA<br>(SEQ ID NO: 40) |
| Deinopis spinosa | MaSp2 | GPGGYGGPGQQGPGQGQYGPGTGQQGQGPSGQQGPAGAAAAAAAAA<br>(SEQ ID NO: 41) |
| Nephila clavata | MaSp2 | GPGGYGLGQQGPGQQGPGQQGPAGYGPSGLSGPGGAAAAAAA<br>(SEQ ID NO: 42) |

Fiber-forming block copolymer polypeptides from the blocks and/or macro-repeat domains, according to certain embodiments of the invention, is described in International Publication No. WO/2015/042164, incorporated by reference. Natural silk sequences obtained from a protein database such as GenBank or through de novo sequencing are broken up by domain (N-terminal domain, repeat domain, and C-terminal domain). The N-terminal domain and C-terminal domain sequences selected for the purpose of synthesis and assembly into fibers include natural amino acid sequence information and other modifications described herein. The repeat domain is decomposed into repeat sequences containing representative blocks, usually 1-8 depending upon the type of silk, that capture critical amino acid information while reducing the size of the DNA encoding the amino acids into a readily synthesizable fragment. In some embodiments, a properly formed block copolymer polypeptide comprises at least one repeat domain comprising at least 1 repeat sequence, and is optionally flanked by an N-terminal domain and/or a C-terminal domain.

In some embodiments, a repeat domain comprises at least one repeat sequence. In some embodiments, the repeat sequence is 150-300 amino acid residues. In some embodiments, the repeat sequence comprises a plurality of blocks. In some embodiments, the repeat sequence comprises a plurality of macro-repeats. In some embodiments, a block or a macro-repeat is split across multiple repeat sequences.

In some embodiments, the repeat sequence starts with a Glycine, and cannot end with phenylalanine (F), tyrosine (Y), tryptophan (W), cysteine (C), histidine (H), asparagine (N), methionine (M), or aspartic acid (D) to satisfy DNA assembly requirements. In some embodiments, some of the repeat sequences can be altered as compared to native sequences. In some embodiments, the repeat sequences can be altered such as by addition of a serine to the C terminus of the polypeptide (to avoid terminating in F, Y, W, C, H, N, M, or D). In some embodiments, the repeat sequence can be modified by filling in an incomplete block with homologous sequence from another block. In some embodiments, the repeat sequence can be modified by rearranging the order of blocks or macrorepeats.

In some embodiments, non-repetitive N- and C-terminal domains can be selected for synthesis. In some embodiments, N-terminal domains can be by removal of the leading signal sequence, e.g., as identified by SignalP (Peterson, T. N., et al., SignalP 4.0: discriminating signal peptides from transmembrane regions, Nat. Methods, 8:10, pg. 785-786 (2011).

In some embodiments, the N-terminal domain, repeat sequence, or C-terminal domain sequences can be derived from *Agelenopsis aperta, Aliatypus gulosus, Aphonopelma seemanni, Aptostichus* sp. AS217, *Aptostichus* sp. AS220, *Araneus diadematus, Araneus gemmoides, Araneus ventricosus, Argiope amoena, Argiope argentata, Argiope bruennichi, Argiope trifasciata, Atypoides riversi, Avicularia juruensis, Bothriocyrtum californicum, Deinopis Spinosa, Diguetia canities, Dolomedes tenebrosus, Euagrus chisoseus, Euprosthenops australis, Gasteracantha mammosa, Hypochilus thorelli, Kukulcania hibernalis, Latrodectus hesperus, Megahexura fulva, Metepeira grandiosa, Nephila antipodiana, Nephila clavata, Nephila clavipes, Nephila madagascariensis, Nephila pilipes, Nephilengys cruentata, Parawixia bistriata, Peucetia viridans, Plectreurys tristis, Poecilotheria regalis, Tetragnatha kauaiensis*, or *Uloborus diversus*.

Figure 5:
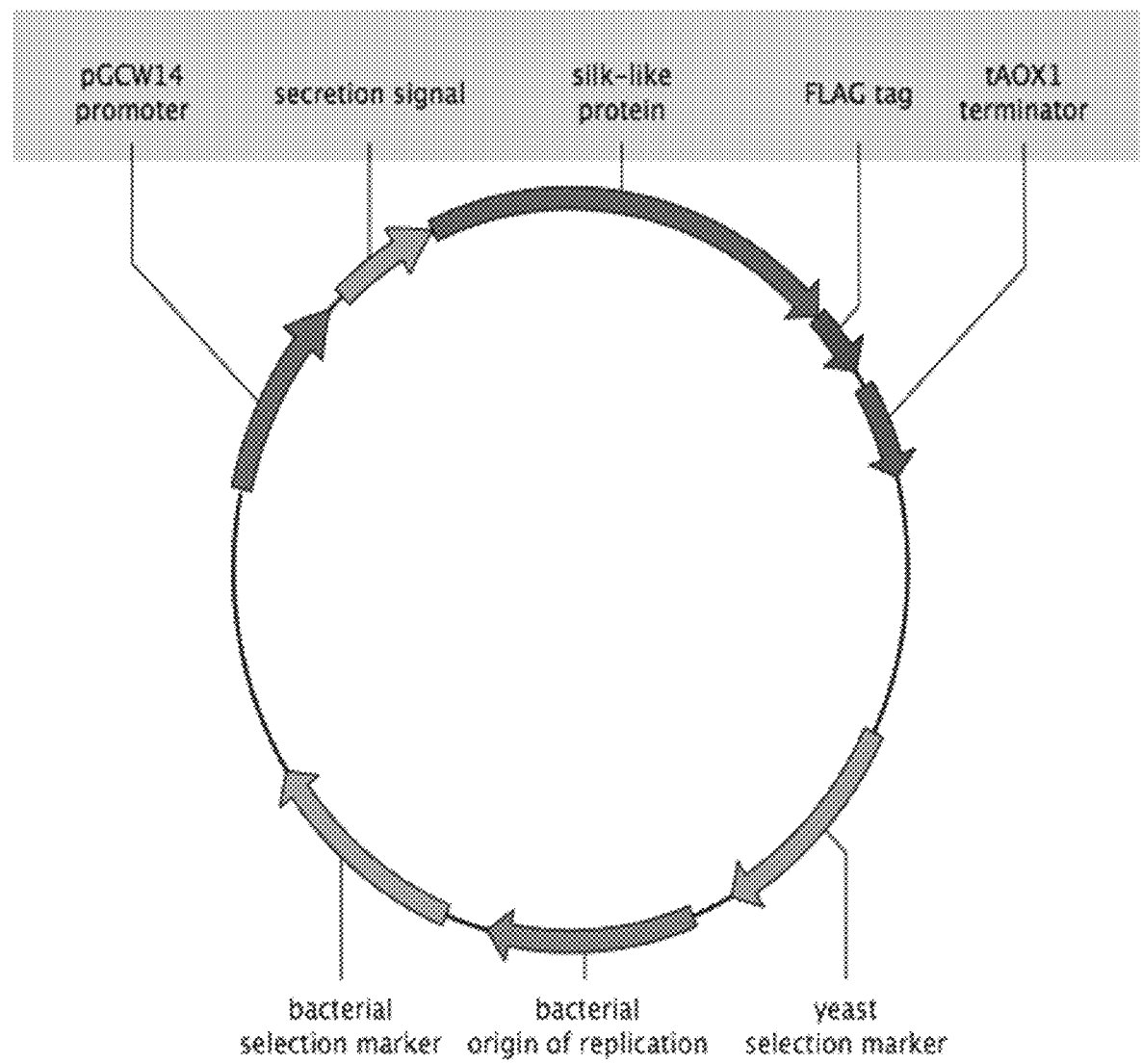
FIG. 5 is a plasmid map of a vector comprising an open reading frame (ORF) for expressing a silk-like polypeptide comprising a secretion signal and a FLAG tag. The ORF is operably linked to a pGCW14 promoter and a tAOX1 terminator. The vector also comprises selection markers to select successfully transformed cells.

In some embodiments, the silk polypeptide nucleotide coding sequence can be operatively linked to an alpha mating factor nucleotide coding sequence. In some embodiments, the silk polypeptide nucleotide coding sequence can be operatively linked to another endogenous or heterologous secretion signal coding sequence. In some embodiments, the silk polypeptide nucleotide coding sequence can be operatively linked to a 3×FLAG nucleotide coding sequence. In some embodiments, the silk polypeptide nucleotide coding sequence is operatively linked to other affinity tags such as 6-8 His residues. An example of a vector for delivering a silk polypeptide nucleotide coding sequence to a host cell is shown in FIG. 5, which depicts a plasmid map of a vector comprising an open reading frame (ORF) for expressing a silk-like polypeptide comprising a secretion signal and a FLAG tag. The ORF is operably linked to a pGCW14 promoter and a tAOX1 terminator. The vector also comprises selection markers to select successfully transformed cells.

In some embodiments, the silk polypeptide comprises a full length spider silk polypeptide. In some embodiments, the full length spider silk polypeptide is Major ampullate spidron 1 (MaSp1) or Major ampullate spidroin 2 (MaSp2).

Silk-Like Polypeptides

In some embodiments, the *P. pastoris* strains disclosed herein have been modified to express a silk-like polypeptide. Methods of manufacturing preferred embodiments of silk-like polypeptides are provided in WO 2015/042164, especially at Paragraphs 114-134, incorporated herein by reference. Disclosed therein are synthetic proteinaceous copolymers based on recombinant spider silk protein fragment sequences derived from MaSp2, such as from the species *Argiope bruennichi*. Silk-like polypeptides are described that include two to twenty repeat units, in which a molecular weight of each repeat unit is greater than about 20 kDa. Within each repeat unit of the copolymer are more than about 60 amino acid residues that are organized into a number of "quasi-repeat units." In some embodiments, the repeat unit of a polypeptide described in this disclosure has at least 95% sequence identity to a MaSp2 dragline silk protein sequence.

In some embodiments, each "repeat unit" of a silk-like polypeptide comprises from two to twenty "quasi-repeat" units (i.e., $n_3$ is from 2 to 20). Quasi-repeats do not have to be exact repeats. Each repeat can be made up of concatenated quasi-repeats. Equation 1 shows the composition of a repeat unit according the present disclosure and that incorporated by reference from WO 2015/042164. Each silk-like polypeptide can have one or more repeat units as defined by Equation 1.

(Equation 1)

(SEQ ID NO: 13)

$\{GGY\text{-}[GPG\text{-}X_1]_{n1}\text{-}GPS\text{-}(A)_{n2}\}_{n3}$.

The variable compositional element $X_1$ (termed a "motif") is according to any one of the following amino acid sequences shown in Equation 2 and $X_1$ varies randomly within each quasi-repeat unit.

(Equation 2)

(SEQ ID NO: 14)

$X_1$ = SGGQQ or (SEQ ID NO: 15)

GAGQQ or (SEQ ID NO: 16)

GQGPY or (SEQ ID NO: 17)

AGQQ or

SQ

Referring again to Equation 1, the compositional element of a quasi-repeat unit represented by "GGY-[GPG-$X_1$]$_{n1}$-GPS" (SEQ ID NO: 18) in Equation 1 is referred to a "first region." A quasi-repeat unit is formed, in part by repeating from 4 to 8 times the first region within the quasi-repeat unit. That is, the value of $n_1$ indicates the number of first region units that are repeated within a single quasi-repeat unit, the value of $n_1$ being any one of 4, 5, 6, 7 or 8. The compositional element represented by "(A)$_{n2}$" (SEQ ID NO: 19) (i.e., a polyA sequence) is referred to as a "second region" and is formed by repeating within each quasi-repeat unit the amino acid sequence "A" $n_2$ times (SEQ ID NO: 19). That is, the value of $n_2$ indicates the number of second region units that are repeated within a single quasi-repeat unit, the value of $n_2$ being any one of 6, 7, 8, 9, 10, 11, 12, 13, 14, 15, 16, 17, 18, 19, or 20. In some embodiments, the repeat unit of a polypeptide of this disclosure has at least 95% sequence identity to a sequence containing quasi-repeats described by Equations 1 and 2. In some embodiments, the repeat unit of a polypeptide of this disclosure has at least 80%, or at least 90%, or at least 95%, or at least 99% sequence identity to a sequence containing quasi-repeats described by Equations 1 and 2.

In additional embodiments, 3 "long" quasi repeats are followed by 3 "short" quasi-repeat units. Short quasi-repeat units are those in which $n_1$=4 or 5. Long quasi-repeat units are defined as those in which $n_1$=6, 7 or 8. In some embodiments, all of the short quasi-repeats have the same $X_1$ motifs in the same positions within each quasi-repeat unit of a repeat unit. In some embodiments, no more than 3 quasi-repeat units out of 6 share the same $X_1$ motifs.

In additional embodiments, a repeat unit is composed of quasi-repeat units that do not use the same $X_1$ more than two occurrences in a row within a repeat unit. In additional embodiments, a repeat unit is composed of quasi-repeat units where at least 1, 2, 3, 4, 5, 6, 7, 8, 9, 10, 11, 12, 13, 14, 15, 16, 17, 18, 19 or 20 of the quasi-repeats do not use the same $X_1$ more than 2 times in a single quasi-repeat unit of the repeat unit.

Thus, in some embodiments, provided herein are strains of yeast that recombinantly express silk-like polypeptides with a reduced degradation to increase the amount of full-length polypeptides present in the isolated product from a cell culture. In some embodiments, the strain expressing a silk-like polypeptide is a *P. pastoris* strain comprises a PAS_chr4_0584 knock-out and a PAS_chr3_1157 knock-out. In some embodiments, the strain expressing a silk-like polypeptide is a *P. pastoris* strain comprising an sec72 knock-out and/or an overexpressed SSH1 translocon complex.

TABLE 5

18B vector

| Description | SEQ ID NO: | 5' to 3' Sequence | | | | | |
|---|---|---|---|---|---|---|---|
| 18B silk-like | 20 | ggtggttacg | gtccaggcgc | tggtcaacaa | ggtccaggaa | gtggtggtca | acaaggacct 60 |
| polypeptide | | ggcggtcaag | gaccctacgg | tagtggccaa | caaggtccag | gtggagcagg | acagcagggt 120 |
| encoding | | ccgggaggcc | aaggacctta | cggaccaggt | gctgctgctg | ccgccgctgc | cgctgccgga 180 |
| sequence | | ggttacggtc | caggagccgg | acaacagggt | ccaggtggag | ctggacaaca | aggtccagga 240 |
| | | tcacaaggtc | ctggtggaca | aggtccatac | ggtcctggtg | ctggtcaaca | gggaccaggt 300 |

TABLE 5-continued 18B vector

| Description | SEQ ID NO: | 5' to 3' Sequence | |
|---|---|---|---|
| | | agtcaaggac ctggttcagg tggtcagcag ggtccaggag gacagggtcc ttacggccct | 360 |
| | | tctgccgctg cagcagcagc cgctgccgca ggaggatacg gacctggtgc tggacaacga | 420 |
| | | tctcaaggac caggaggaca aggtccttat ggacctggcg ctggccaaca aggacctggt | 480 |
| | | tctcagggtc caggttcagg aggccaacaa ggcccaggag gtcaaggacc atacggacca | 540 |
| | | tccgctgcgg cagctgcagc tgctgcaggt ggatatggcc caggagccgg acaacagggt | 600 |
| | | cctggttcac aaggtccagg atctggtggt caacagggac caggcggcca gggaccttat | 660 |
| | | ggtccaggag ccgctgcagc agcagcagct gttggaggtt acggccctgg tgccggtcaa | 720 |
| | | caaggcccag gatctcaggg tcctggatct ggaggacaac aaggtcctgg aggtcagggt | 780 |
| | | ccatacggac cttcagcagc agctgctgct gcagccgctg gtggttatgg acctggtgct | 840 |
| | | ggtcaacaag gaccgggttc tcagggtccg ggttcaggag gtcagcaggg ccctggtgga | 900 |
| | | caaggacctt atggacctag tgcggctgca gcagctgccg ccgcaggtgg ttacggtcca | 960 |
| | | ggcgctggtc aacaaggtcc aggaagtggt ggtcaacaag gacctggcgg tcaaggaccc | 1020 |
| | | tacggtagtg gccaacaagg tccaggtgga gcaggacagc agggtccggg aggccaagga | 1080 |
| | | ccttacggac caggtgctgc tgctgccgcc gctgccgctg ccggaggtta cggtccagga | 1140 |
| | | gccggacaac agggtccagg tggagctgga caacaaggtc caggatcaca aggtcctggt | 1200 |
| | | ggacaaggtc catacggtcc tggtgctggt caacagggac caggtagtca aggacctggt | 1260 |
| | | tcaggtggtc agcagggtcc aggaggacag ggtccttacg gcccttctgc cgctgcagca | 1320 |
| | | gcagccgctg ccgcaggagg atacggacct ggtgctggac aacgatctca aggaccagga | 1380 |
| | | ggacaaggtc cttatggacc tggcgctggc caacaaggac tggttctcaa gggtccaggt | 1440 |
| | | tcaggaggcc aacaaggccc aggaggtcaa ggaccatacg gaccatccgc tgcggcagct | 1500 |
| | | gcagctgctg caggtggata tggcccagga gccggacaac agggtcctgg ttcacaaggt | 1560 |
| | | ccaggatctg gtggtcaaca gggaccaggc ggccagggac cttatggtcc aggagccgct | 1620 |
| | | gcagcagcag cagctgttgg aggttacggc cctggtgccg gtcaacaagg cccaggatct | 1680 |
| | | cagggtcctg gatctggagg acaacaaggt cctggaggtc agggtccata cggaccttca | 1740 |
| | | gcagcagctg ctgctgcagc cgctggtggt tatggacctg gtgctggtca acaaggaccg | 1800 |
| | | ggttctcagg gtccgggttc aggaggtcag cagggccctg gtggacaagg acctatgga | 1860 |
| | | cctagtgcgg ctgcagcagc tgccgccgca ggtggttacg gtccaggcgc tggtcaacaa | 1920 |
| | | ggtccaggaa gtggtggtca acaaggacct ggcggtcaag gacctacgg tagtggccaa | 1980 |
| | | caaggtccag gtggagcagg acagcagggt ccggaggcc aaggaccta cggaccaggt | 2040 |
| | | gctgctgctg ccgccgctgc cgctgccgga ggttacggtc caggagccgg acaacagggt | 2100 |
| | | ccaggtggag ctggacaaca aggtccagga tcacaaggtc ctggtggaca aggtccatac | 2160 |
| | | ggtcctggtg ctggtcaaca gggaccaggt agtcaaggac ctggttcagg tggtcagcag | 2220 |
| | | ggtccaggag gacagggtcc ttacggccct tctgccgctg cagcagcagc cgctgccgca | 2280 |
| | | ggaggatacg gacctggtgc tggacaacga tctcaaggac caggaggaca aggtccttat | 2340 |
| | | ggacctggcg ctggccaaca aggacctggt tctcagggtc caggttcagg aggccaacaa | 2400 |
| | | ggcccaggag gtcaaggacc atacggacca tccgctgcgg cagctgcagc tgctgcaggt | 2460 |
| | | ggatatggcc caggagccgg acaacagggt cctggttcac aaggtccagg atctggtggt | 2520 |
| | | caacagggac caggcggcca gggaccttat ggtccaggag ccgctgcagc agcagcagct | 2580 |
| | | gttggaggtt acggccctgg tgccggtcaa caaggcccag gatctcaggg tcctggatct | 2640 |
| | | ggaggacaac aaggtcctgg aggtcagggt ccatacggac cttcagcagc agctgctgct | 2700 |
| | | gcagccgctg gtggttatgg acctggtgct ggtcaacaag gaccgggttc tcagggtccg | 2760 |
| | | ggttcaggag gtcagcaggg ccctggtgga caaggacctt atggacctag tgcggctgca | 2820 |
| | | gcagctgccg ccgca | 2835 |
| 18B polypeptide sequence | 21 | GGYGPGAGQQGPGSGGQQGPGGQGPYGSGQQGPGGAGQQGPGGQGPYGPAAAAAAAAGGYGPGAGQQG PGGAGQQGPGSQGPGGQGPYGPGAGQQGPGSQGPGSGGQQGPGGQGPYGPSAAAAAAAAGGYGPGAGQR SQGPGGQGPYGPGAGQQGPGSQGPGSGGQQGPGGQGPYGPSAAAAAAAAGGYGPGAGQQGPGSQGPGSGG QQGPGGQGPYGPGAAAAAAAVGGYGPGAGQQGPGSQGPGSGGQQGPGGQGPYGPSAAAAAAAAGGYGPGA GQQGPGSQGPGSGGQQGPGGQGPYGPSAAAAAAAAGGYGPGAGQQGPGSGGQQGPGGQGPYGSGQQGPGG AGQQGPGGQGPYGPGAAAAAAAAGGYGPGAGQQGPGSQGPGGQGPYGPGAGQQGPGSQGPG SGGQQGPGGQGPYGPSAAAAAAAAGGYGPGAGQRSQGPGGQGPYGPGAGQQGPGSQGPGSGGQQGPGGQ GPYGPSAAAAAAAAGGYGPGAGQQGPGSQGPGSGGQQGPGGQGPYGPGAAAAAAAVGGYGPGAGQQGPGS QGPGSGGQQGPGGQGPYGPSAAAAAAAAGGYGPGAGQQGPGSQGPGSGGQQGPGGQGPYGPSAAAAAAAA GGYGPGAGQQGPGSGGQQGPGGQGPYGSGQQGPGGAGQQGPGGQGPYGPAAAAAAAAGGYGPGAGQQG PGGAGQQGPGSQGPGGQGPYGPGAGQQGPGSQGPGSGGQQGPGGQGPYGPSAAAAAAAAGGYGPGAGQR SQGPGGQGPYGPGAGQQGPGSQGPGSGGQQGPGGQGPYGPSAAAAAAAAGGYGPGAGQQGPGSQGPGSGG QQGPGGQGPYGPGAAAAAAAVGGYGPGAGQQGPGSQGPGSGGQQGPGGQGPYGPSAAAAAAAAGGYGPGA GQQGPGSQGPGSGGQQGPGGQGPYGPSAAAAAAAA |
| Repeat sequence of a silk-like polypeptide | 22 | GGYGPGAGQQGPGSGGQQGPGGQGPYGSGQQGPGGAGQQGPGGQGPYGPAAAAAAAAGGYGPGAGQQG PGGAGQQGPGSQGPGGQGPYGPGAGQQGPGSQGPGSGGQQGPGGQGPYGPSAAAAAAAAGGYGPGAGQR SQGPGGQGPYGPGAGQQGPGSQGPGSGGQQGPGGQGPYGPSAAAAAAAAGGYGPGAGQQGPGSQGPGSGG QQGPGGQGPYGPGAAAAAAAVGGYGPGAGQQGPGSQGPGSGGQQGPGGQGPYGPSAAAAAAAAGGYGPGA GQQGPGSQGPGSGGQQGPGGQGPYGPSAAAAAAAA |

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1: Production of Recombinant Yeast Expressing 18B

Strains of *P. pastoris* were modified to recombinantly express 18B silk-like polypeptides as follows:

First, we transformed a strain of *P. pastoris* to abrogate KU70 function to facilitate further editing and engineering. A HIS+ derivative of *Pichia pastoris* (*Komagataella phaffii*) strain GS115 (NRRL Y15851) was electroporated with a DNA cassette consisting of homology arms flanking a zeocin resistance marker and targeting the KU70 locus. Sequences are provided in Table 12. Transformants were plated on YPD agar plates supplemented with zeocin. This resulted in abrogation of KU70 function.

Then, we modified this strain to express a recombinant gene encoding a silk-like polypeptide. A HIS+ derivative of *Pichia pastoris* (*Komagataella phaffii*) strain GS115 (NRRL Y15851) was transformed with a recombinant vector (SEQ ID NO: 20) to cause expression and secretion of a silk-like polypeptide ("18B") (SEQ ID NO: 21). Transformation was accomplished by electroporation as described in PMID 15679083, incorporated by reference herein.

Each vector includes an 18B expression cassette with the polynucleotide sequence encoding the silk-like protein in the recombinant vectors flanked by a promoter (pGCW14) and a terminator (tAOX1 pA signal). The recombinant vectors further comprised dominant resistance markers for selection of bacterial and yeast transformants, and a bacterial origin of replication. The first recombinant vector included targeting regions that directed integration of the 18B polynucleotide sequences immediately 3' of the AOX2 loci in the *Pichia pastoris* genome. The resistance marker in the first vector conferred resistance to G418 (aka geneticin). The second recombinant vector included targeting regions that directed integration of the 18B polynucleotide sequences immediately 3' of the TEF1 loci in the *Pichia pastoris* genome. The resistance marker in the second vector conferred resistance to Hygromycin B.

Example 2: Production of Recombinant Δsec72 Strain

Cells modified to express 18B were transformed with a vector comprising a DNA cassette with 5' and 3' homology arms targeting sec72 (SEQ ID NO: 1). The homology arms flank a yeast selection marker, as shown in the plasmid map in FIG. 2, which knocks out the sec72 gene when inserted into the sec72 gene. Transformants were plated on YPD agar plates supplemented with yeast selection medium, and incubated for 48 hours at 30° C.

Example 3: Production of Recombinant Δsec72 Strain Overexpressing an SSH1 Translocon Complex

*P. pastoris* (Δsec72) cells modified to express 18B (SEQ ID NO: 21) were transformed with a vector for overexpression of the SSH1 translocon complex. A plasmid map of the vector is shown in FIG. 3. The vector comprises open reading frames for SSH1 (SEQ ID NO: 3), SSS1 (SEQ ID NO: 5), and SBH2 (SEQ ID NO: 7). Each open reading frame is operatively linked to a promoter and a terminator. Transformants were plated on YPD agar plates supplemented with yeast selection medium, and incubated at 48 hours at 30° C.

Example 4: Production of Protease Double Knock-Out Strain

Figure 4A:
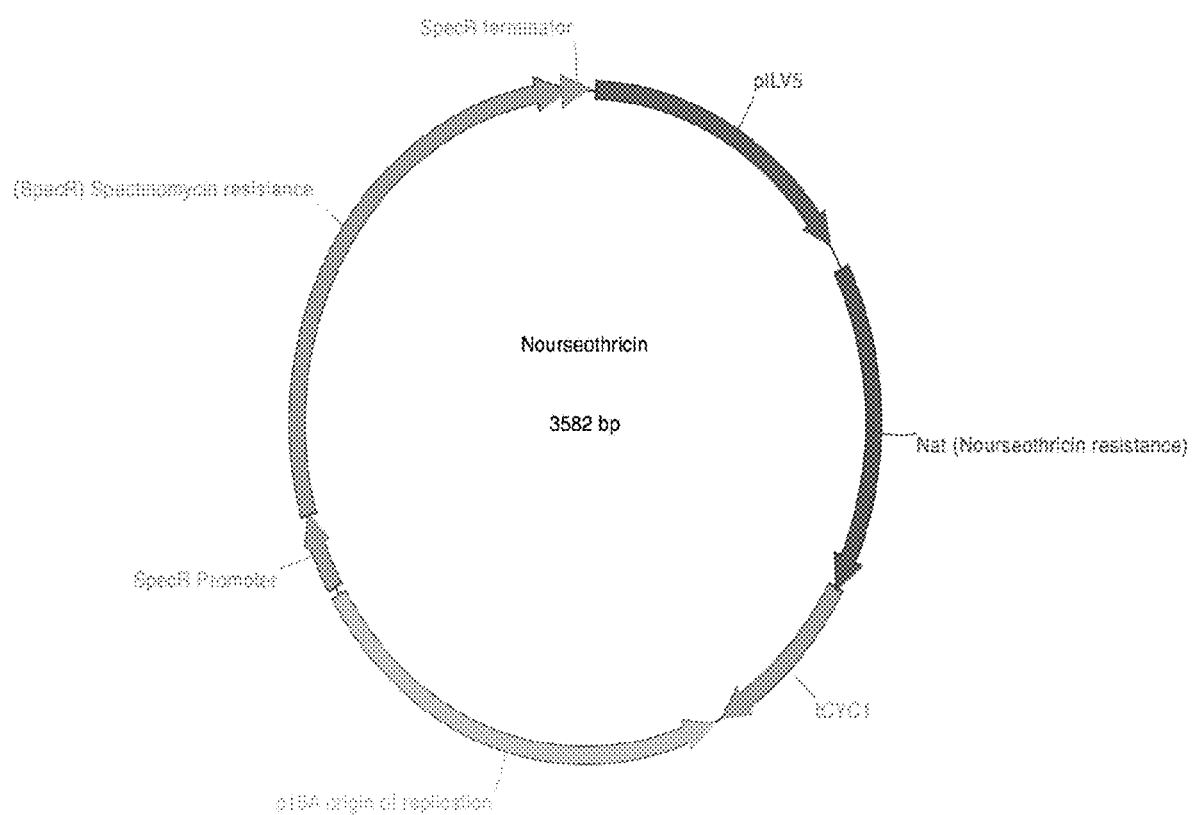
FIG. 4A is a plasmid map of a vector comprising a nourseothricin marker used with homology arms for targeted protease gene deletion.
Figure 4B:
FIG. 4B and FIG. 4C are cassettes for protease knockout with homology arms targeting the desired protease gene flanking a nourseothricin resistance marker.
Figure 4C:

To generate ΔΔprotease strains (i.e., double protease knock-out), a selected yeast strain was transformed with vector comprising a DNA cassette with ~1150 bp homology arms flanking a nourseothricin resistance marker. A plasmid map comprising the nourseothricin resistance marker is shown in FIG. 4A, and sequences provided in Table 13. Homology arms used for each target were amplified by the primers provided in Table 8, and inserted into the nourseothricin resistance plasmid. Homology arms were inserted into the nourseothricin plasmid to generate cassettes comprising a nourseothricin resistance marker flanded by 3' and 5' homology arms to the target protease as shown in FIG. 4B and FIG. 4C. In FIG. 4B, the resistance cassette (Nour Resistance Cassette) is shown flanked by homology arms (HA1 and HA2). In FIG. 4C, details of the nourseothricin marker are shown, including the promoter from ILV5 gene from *Saccharomyces cerevisiae* (pILV5), the Nourseothricin acetyltransferase gene from *Streptomyces noursei* (nat), and the polyA signal from CYC1 gene from *Saccharomyces cerevisiae*.

A vector with homology arms targeting YPS1-1 (SEQ ID NO: 77) was used to transform modified yeast strains. Transformants were plated on YPD agar plates supplemented with nourseothricin, and incubated for 48 hours at 30° C.

TABLE 6

Proteases targeted for deletion in *P. pastoris* strain.

| Protease Gene Symbol | Protease ORF Sequence (SEQ ID NO:) | Protease polypeptide sequence (SEQ ID NO:) |
|---|---|---|
| PAS_chr4_0584 (YPS1-1) | 9 | 10 |
| PAS_chr3_1157 (YPS1-2) | 11 | 12 |

To generate double knockouts, nourseothricin resistance was eliminated from the single protease knock-out strains produced above. A vector with homology arms targeting YPS1-2 (SEQ ID NO: 80) was used to transform the single protease knock-out strains. Transformants were plated on YPD agar plates supplemented with nourseothricin, and incubated for 48 hours at 30° C.

Example 5: Δsec72 Improves MFα-18B Secretion Across Integration Copy Numbers

*Pichia pastoris* strains modified to express two, four, or six copies of 18B (Ab MaSp2 79 kDa) comprising the MFα1(sc) pre-pro leader sequence were prepared using techniques described in Example 1.

Δsec72 strains of each of the above were prepared using techniques described in Example 2. Δsec72 and WT strains for each of the 2×, 4×, and 6×18B expressing strains were prepared. Secretion of MFα-18B from WT and Δsec72 strains (i.e, SEC72 KO strains) from each of the 2×, 4× and 6×18B expressing strains was measured by ELISA, with the results shown in FIG. 6.

Figure 6:
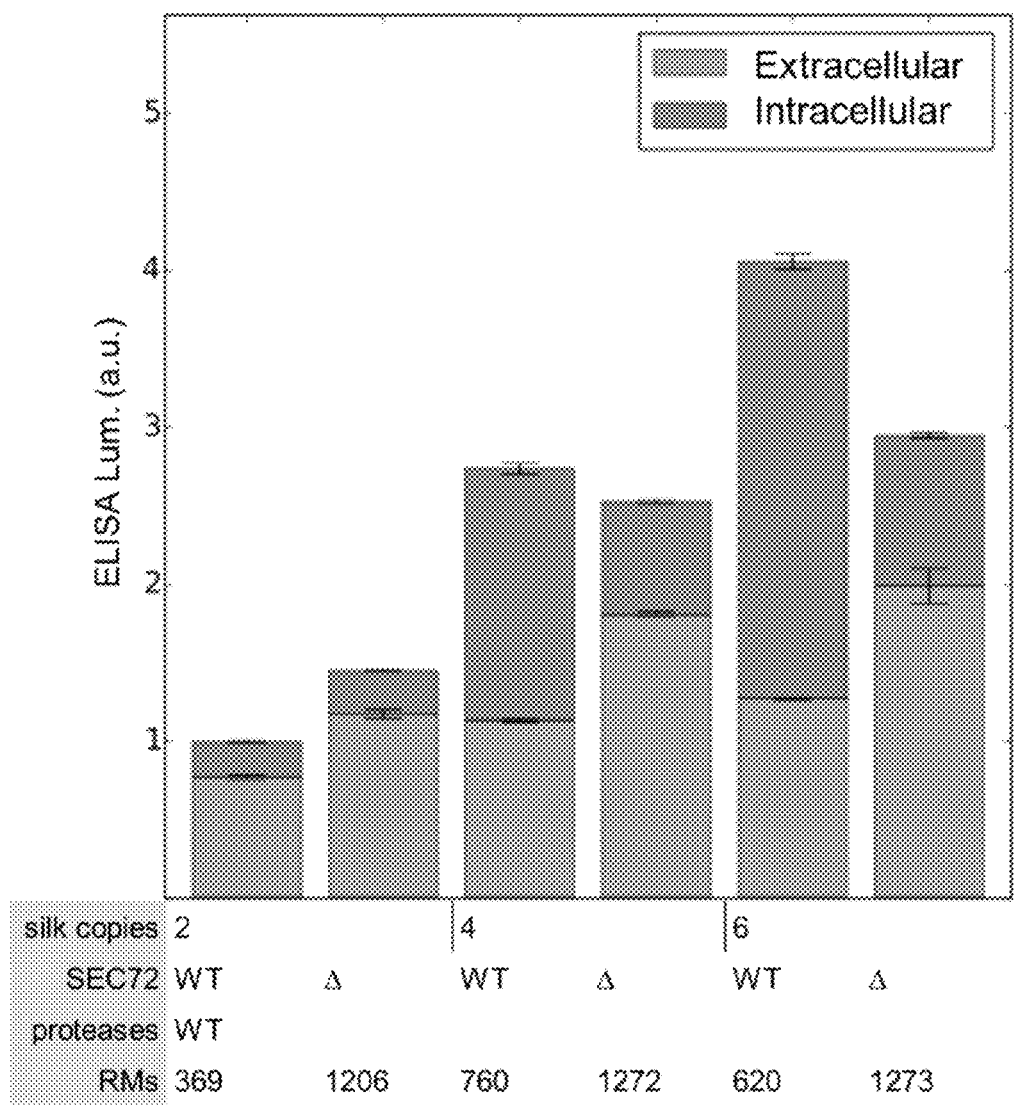
FIG. 6 shows secretion of recombinant 18B silk-like polypeptide expressed by wild-type (WT) and Δsec72 (Δ) strains expressing 2×, 4×, or 6× copies of 18B, as measured by an enzyme-linked immunosorbent assay (i.e., ELISA).

Referring to FIG. 6, "silk copies" are the number of expression cassettes for 18B (Ab MaSp2 79 kDa) using the MFα1(sc) pre-pro leader sequence in each strain. The 18B is C-terminally tagged with a 3×FLAG epitope for ELISA detection. Error bars show standard error of the mean among n≥4 biological replicates. The results show that deletion of the sec72 gene improves MFα-18B secretion across integration copy numbers (i.e., 2×, 4×, and 6× silk copies).

Example 6: Δsec72 Improves Secretion from Non-MFα Signals

Figure 7:
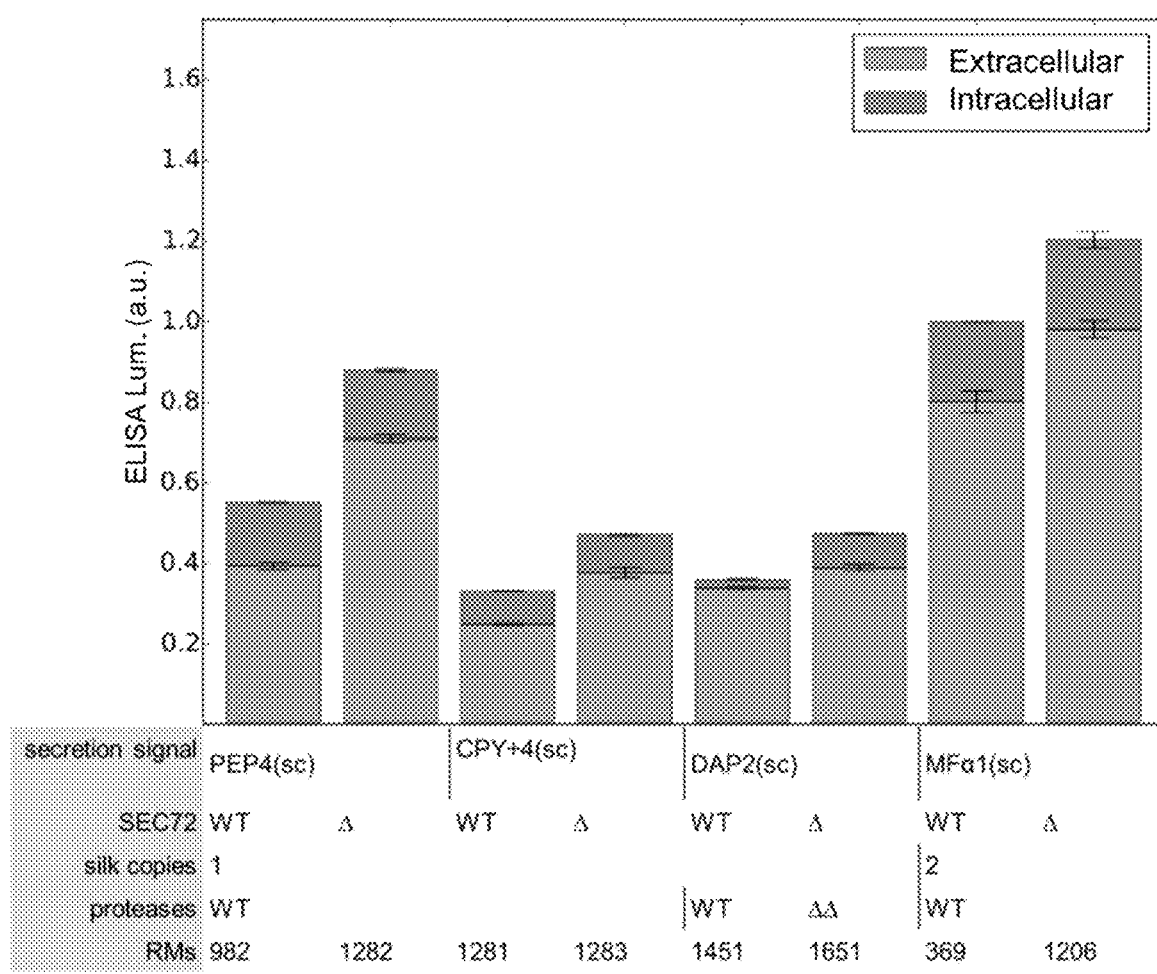
FIG. 7 shows shows secretion of recombinant protein comprising PEP4(sc), CPY+4(sc), DAP2(sc), or MFα1(sc) signal peptides as expressed by wild-type (WT) and Δsec72 (Δ) strains and measured by ELISA. (sc) indicates the signal peptide derives from *S. cerevisiae*.

*P. pastoris* strains were modified according to Example 1 to express 4 different silk polypeptides each comprising a different secretion signal: PEP4(sc), CPY+4(sc), DAP2(sc), and MFα1(sc). Each complete leader sequence is a hybrid composed of the indicated signal peptide with the MFα1(sc) propeptide (*S. cerevisiae* ortholog systematic name: YPL187W). (sc) indicates the signal peptide derives from *S. cerevisiae*. Strains recombinantly expressing polypeptides with PEP4(sc), CPY+4(sc), and DAP2(sc) each comprise a single expression cassette (i.e., 1 silk copy). Strains recombinantly expressing MFα1(sc) comprise 2 expression cassettes (i.e., 2 silk copies). Δsec72 strains of each of the above were prepared using techniques described in Example 2 to compare secretion from WT and Δsec72 strains. For the Δsec72 strain comprising DAP2(sc), the strain was additionally modified to knockout YPS1-1 and YPS1-2 proteases, as described in Example 4. Secretion of polypeptides with each secretion signal from WT and Δsec72 strains was measured by ELISA, with the results shown in FIG. 7.

The results indicate that the deletion of the sec72 gene improves secretion for polypeptides comprising non-MFα1(sc) signal peptides. Error bars show standard error of the mean among n≥4 biological replicates.

TABLE 7A

MFα1(sc) propeptide sequence

| | Sequence | SEQ ID NO: |
|---|---|---|
| MFα1(sc) propeptide Nucleotide Encoding Sequence (5' to 3') | gctccagtcaacactacaacagaagatga aacggcacaaattccggctgaagctgtca tcggttactcagatttagaaggggatttc gatgttgctgttttgccattttccaacag cacaaataacggggttattgtttataaata ctactattgccagcattgctgctaaagaa gaaggggtatctctcgagaaaagagaggc tgaa | 105 |
| MFα1(sc) propeptide Polypeptide Sequence | APVNTTTEDETAQIPAEAVIGYSDLEGDF DVAVLPFSNSTNNGLLFINTTIASIAAKE EGVSLEKREAE | 106 |

TABLE 7B

Silk Secretion Signals

| Secretion Signal | Sequence | SEQ ID NO: |
|---|---|---|
| PEP4 Nucleotide Encoding Sequence (5' to 3') | atgttcagcttgaaagcattattgccatt ggccttgttgttggtcagcgccaaccaag ttgctgca | 83 |
| PEP4 Polypeptide Sequence | MFSLKALLPLALLLVSANQVAA | 84 |
| PRC1, mutant (i.e., CPY + 4) Nucleotide Encoding Sequence (5' to 3') | atgaaagcattcctgttgttactacttttt actaggcctgtccactacactcgctaagg ca | 85 |
| PRC1, mutant (i.e., CPY + 4) Polypeptide Sequence | MKAFLLLLLLLGLSTTLAKA | 86 |

TABLE 7B-continued

Silk Secretion Signals

| Secretion Signal | Sequence | SEQ ID NO: |
|---|---|---|
| DAP2 Nucleotide Encoding Sequence (5' to 3') | atggaaggtggcgaagaagaagttgagcg cattcctgatgaactttcgatacaaaaa agaagcatttgttagataagctcataagg gtcggaataatccttgtactcctgatatg gggcactgttttgttgctaaaaagtatt | 87 |
| DAP2 Polypeptide Sequence | MEGGEEEVERIPDELFDTKKKHLLDKLIR VGIILVLLIWGTVLLLKSI | 88 |
| MF(alpha) 1, variant Nucleotide Encoding Sequence (5' to 3') | atgagatttccttcaattttttactgctgt tttattcgcagcatcctccgcattagct | 89 |
| MF(alpha) 1, variant Polypeptide Sequence | MRFPSIFTAVLFAASSALA | 90 |

Example 7: Δsec72 Improves Secretion of Longer Silks and Distinct Silk Sequences

*P. pastoris* strains were modified according to Example 1 to express long silk polypeptides *Argioppe bruennichi* (Ab) MaSp2 (106 kDa) (SEQ ID NO: 43), *Latrodectus hesperus* (Lh) MaSp1 (55 kDa) (SEQ ID NO: 44). Ab MaSp2 106 kDa (aka 24B) is a longer concatemer of Ab MaSp2 79 kDa (18B). Lh MaSp1 55 kDa is distinct sequence from another class of spidroins.

Figure 8:
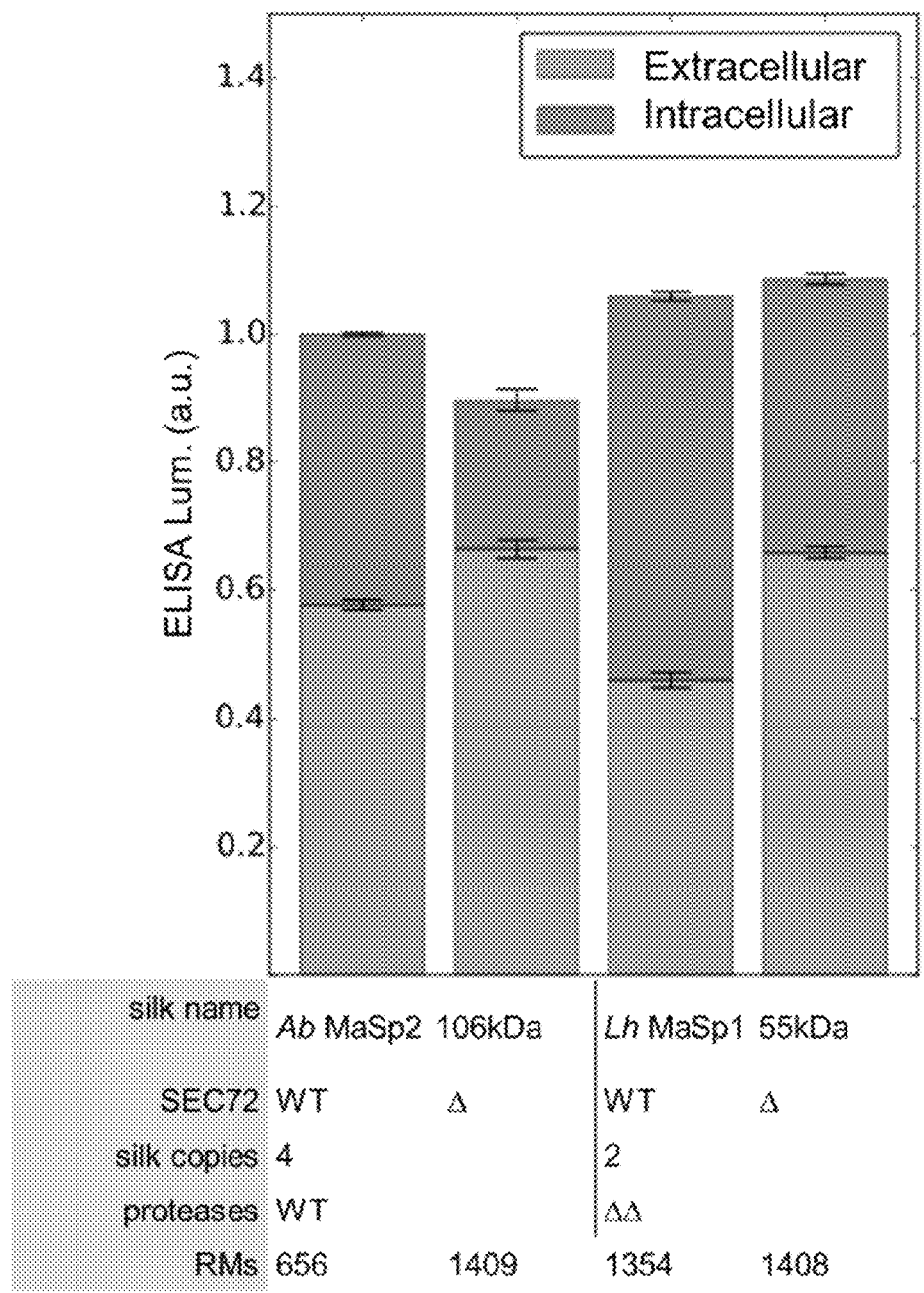
FIG. 8 shows secretion of long silk polypeptides *Argiope bruennichi* Major ampullate spidron 2 (i.e., Ab MaSp2) (106 kDa), and *Latrodectus hesperus* Major ampullate spidron 1 (i.e., Lh MaSp1 (55 kDa)) as expressed by wild-type (WT) and Δsec72 (Δ) strains and measured by ELISA.

Δsec72 strains of each were prepared using techniques described in Example 2 to compare secretion from WT and Δsec72 strains. The strains comprising Lh MaSp1 (55 kDa) were additionally modified to knockout YPS1-1 and YPS1-2 proteases, as described in Example 4. Secretion of the long silk polypeptides from WT and Δsec72 strains was measured by ELISA, with the results shown in FIG. 8. Error bars show standard error of the mean among n≥4 biological replicates.

```
Argioppe bruennichi MaSp2 protein amino acid
sequence (SEQ ID NO: 43):
MNWSIRLALLGFVVLSTQTVFAVGQAATPWENSQLAEDFINSFLRFIAQS

GAFSPNQLDDMSSIGDTLKTAIEKMAQSRKSSKSKLQALNMAFASSMAEI

AVAEQGGLSLEAKTNAIANALASAFLETTGFVNQQFVSEIKSLIYMIAQA

SSNEISGSAAAAGGGSGGGGGSGQGGYGQGASASASAAAAYGSAPQGAGG

PAPQGPSQQGPVSQGPYGPGAAAAAAAAGGYGPGAGQQGPGSQGPGSGGQ

QGPGSQGPGSGGQQGPGGQGPYGPSAAAAAAAAGGYGPGAGQQGPGSQG

PGSGGQQGPGGQGPYGPGAAAAAAVGGYGPGAGQQGPGSQGPGSGGQQG

PGGQGPYGPSAAAAAAAAGGYGPGAGQQGPGSQGPGSGGQQGPGGQPYG

PSAAAAAAAAGGYGPGAGQQGPGSGGQQGPGGQPYGSGQQGPGGAGQQG

PGGQGPYGPGAAAAAAAAGGYGPGAGQQGPGGAGQQGPGSQGPGGQPY

GPGAGQQGPGSQGPGSGGQQGPGGQPYGPSAAAAAAAAGGYGPGAGQQG

PGSQGPGSGGQQGPGSQGPGSGGQQGPGGQPYGPSAAAAAAAAGGYGPG

AGQQGPGSQGPGSGGQQGPGGQPYGPGAAAAAAVGGYGPGAGQQGPGS

QGPGSGGQQGPGGQPYGPSAAAAAAAAGGYGPGAGQQGPGSGGQQGPGGQPYGSGQ

QGPGGAGQQGPGGQPYGPGAAAAAAAAGGYGPGAGQQGPGGAGQQGPG

SQGPGGQPYGPSAAAAAAAAAGPGAGRQGPGSQGPGSGGQQGPGGQPYGP

SAAAAAAAAGPGAGRQGPGSQGPGSGGQQGPGGQPYGPSAAAAAAAAGP

GARRQGPGSQGPGSGGQQGPGGQPYGSGQQGPGGAGQQGPGGQPYGPG

AAAAAAAAGGYGPGAGQQGPGGAGQQGPGSQGPGGQPYGPGAGQQGPG

SQGPGSGGQQGPGSQGPGSGGQQGPGGQPYGPSAAAAAAAAGGYGPGAGQQGPGSQGPGSG

GQQGPGGQPYGPSAAAAAAAAGGYGPGAGQQGPGSGGQQGPGGQPYGS

QGPGGQPYGPGAGQQGPGSQGPGSGGQQGPGGQPYGPSAAAAAAAAGP

GAGRQGPGSQGPGSGGQQGPGGQPYGPSAAAAAAAAGPGARRQGPGSQG

PGSGGQQGPGGQPYGSGQQGPGGAGQQGPGGQPYGPGAAAAAAAAGGY

GPGAGQQGPGSQGPGSGGQQGPGGQPYGPGAGQQGPGSQGPGSGGQQGP

GGQGPYGPGAAAAAAVGGYGPGAGQQGPGSQGPGSGGQQGPGGQPYGP

SAAAAAAAAGGYGPGAGQQGPGSGGQQGPGGQPYGSGQQGPGGAGQQGPGGQPYGP

GAAAAAAAAGGYGPGAGQQGPGGAGQQGPGSQGPGGQPYGPGAGQQGP

GSQGPGSGGQQGPGGQPYGPSAAAAAAAAGGYGPGAGQQGPGSQGPGSG

GQQGPGSQGPGSGGQQGPGGQPYGPSAAAAAAAAGGYGPGAGQQGPGSG

GQQGPGGQPYGPSAAAAAAAAGGYGPGAGQQGPGSGGQQGPGGQPYGS
```

-continued

GQQGPGGAGQQGPGGQGPYGPGAAAAAAAAGGYGPGAGQQGPGSQGPGS
GGQQGPGSQGPGSGGQQGPGGQGPYGPSAAAAAAAAAGGYGPGAGQQGPG
SQGPGSGGQQGPGGQGPYGPGAAAAAAAVGGYGPGAGQQGPGSQGPGSGG
QQGPGGQGPYGPSAAAAAAAAGGYGPGAGQQGPGSQGPGSGGQQGPGGQG
PYGPSAAAAAAAAGGYGPGAGQQGPGSGGQQGPGGQGPYGSGQQGPGGAG
QQGPGGQGPYGPGAAAAAAAAGGYGPGAGQQGPGGAGQQGPGSQGPGGQ
GPYGPGAGQQGPGSQGPGSGGQQGPGGQGPYGPSAAAAAAAAGGYGPGAG
QQGPGSQGPGSGGQQGPGGQGPYGPGAAAAAAAVGGYGPGAGQQGPGSQG
PGSGGQQGPGGQGPYGPSAAAAAAAAGGYGPGAGQQGPGSQGPGSGGQQG
PGGQGPYGPSAAAAAAAAGGYGPGAGQQGPGSGGQQGPGGQGPYGSGQQG
PGGAGQQGPGGQGPYGPGAAAAAAAAGGYGPGAGQQGPGGAGQQGPGSQ
GPGGQGPYGPGAGQQGPGSQGPGSGGQQGPGGQGPYGPSAAAAAAAAGGY
GPGAGQQGPGSQGPGSGGQQGPGGQGPYGPSAAAAAAAAGGYGPGAGQQG
PSSQAPVASAAASRLSSPQASARVSSAVSTLVSSGPTSPAALSNAISSVV
SQVSASNPGLSGCDVLVQALLEIVSALVHILGSSSIGQINYAASSQYAQM
VGNSVAQALG

*Latrodectus hesperus* MaSp1 protein amino acid
sequence (SEQ ID NO: 44):
MTWSTRLALSFLFVLCTQSLYALAQANTPWSSKANADAFINSFISAASNT
GSFSQDQMEDMSLIGNTLMAAMDNMGGRITPSKLQALDMAFASSVAEIAA
SEGGDLGVTTNAIADALTSAFYQTTGVVNSRFISEIRSLIGMFAQASAND
VYASAGSSGGGYGASSASAASASAAAPSGVAYQAPAQAQISFTLRGQQP
VSYGQGGAGPGGAGAAAAAAAAGGAGQGGQGGYGQGGYGQGGAGQGGSG
AAAAAAAAGGTGQGGAGQGGAGAAAAAAAAGGAGQGGQGGYGQGGYGQ
GGTGQGGAGAAAAAAAAGGAGQGGQGGYGQGGYGQGGYGQGGSAAAAAA
AAGGAGQGGQGGYGQGGYGQGGAGQGGAGAAAAAAAAGGAGQGGYGRG
GAGQGGAAAAAAAGAGQGGYGGQGAGQGGSAAAAAAAAGGAGQGGQG
GYGQGGYGQGGSAAAAAAAAGGAGQGGQGGYGQGGYGQGGAGQGGAGAA
AAAAAGGAGQGGQGGYGQGGYGQGGAGQGGAGAAAAAAAAGGAGQGGQG
GYGQGGYGQGGAGQGGAGAAAAAAAAGGAGQGGQGGYGQGGYGQGGAGQGG
GAAAAAAAAGGAGQGGYGRGGAGQGGAAAAAGAGQGGYGGQGAGQGGAG
AAAAAAAAGGAGQGGQGGYGRGGYGQGGAGQGGAGAAAAAAAAGGAGQGG
QGGYGQGGYGQGGAGQGGAAAAAAAAGGAGQGGYGRGGAGQGGAAAAAA
AAGAGQGGYGGQGAGQGGAGAAAAAAAAGGAGQGGQGDYGRGGYGQGGAG
QGGAGAAAAAAAAGGAGQGGQGGYGQGGYGQGGAGQGGAAAAASAAAAGG
AGQGGYGRGGAGQGGAAAAAGAGQGGYGGQGAGQGGAGAAAAAAAAGGAG
QGGQGGYGRGGYGQGGAGQGGAAAAATAAGGAGQGGQGGYGQGGYGQG
GAGQGGAAAAAAAAGGAGQGGYGRGGAGQGGAAAAAAAAGAGQGGYGG
QGGAGQGGAAAAAGGAGQGGQGGYGRGGYGQGGAGQGGAGAAAAAAA
GGAGQGGQGGYGQGGYGQGGAGQGGAAAAAAAAGGAGQGGYGRGGAGQGG
GAAAAAGAGQGGYGGQGAGQGGAGAAAAASRGAGQGGQGGYGRGGYGQGG -continued AGQGGAGAAAAAAAAGGAGQGGQGGYGQGGYGQGGAGQGGAAAAAAAAGG
AGQGGYGRGGAGQGGAAAAAGAGQGGYGGQGAGQGGAGAAAAAAAAGGAG
QGGQGGYGRGGYGQGGAGQGGAGAAAAAAAAGGAGQGGQGGYGQGGYGQG
GAGQGGAAAAAAAAGGAGQGGYGRGGAGQGGAAAAAAAAGSGQGGYGG
QGAGQGGAGAAAAAAAAGGAGQGGQGGYGRGGYGQGGAGQGGAGAAAAAA
AAGGAGQGGQGGYGQGGYGQGGAGQGGAAAAAAAAGGAGQGGYGRGGA
GQGGAAAAAGAGQGGYGGQGAGQGGAGAAAAAAAAGGAGQGGQGGYGRGG
YGQGGAGQGGAGTAAAAAAGGAGQGGQGGYGQGGYGQGGAGQGGAAAAAA
AAAGGAGQGGYGRGGAGQGGAAAAAGAGQGGYGGQGAGQGGAGAAAAAAAA
AAGGAGQGGQGGYGRGGYGQGGAGQGGAGAAAAAAAAGGASQGGQGG
YGQGDYGQGGAGQGGAAAAAAAAGGAGQGGYGRGGAGQGGAAAAAGAGQ
GGYGGQGAGQGGAGAAAAAAAAGGAGRGGQGGYGRGGYGQGGAGQGGAGA
AAAAAAAGGAGQGGQGGYGQGGYGQGGTGQGGAAAAAAAAGGAGQGGYG
RGGAGQGGAAAAAGAGQGGYGGQGAGQGGAGAAAAAAAAGGAGQGG
QGGYGRGGYGQGGAGQGGAGAAAAAAAAGGAGQGGQGGYGQGGYGQGGYG
QGGAGQGGAAAAAAAAGGAGQGGYGRGGAGQGGAAAAAGAGQGGYGGQGA
GQGGAGAAAAAAAAGGAGQGGQGGYGRGGYGQGGAGQGGAGAAAAAAAAG
GAGQGGQGGYGQGGYGQGGNGQGGAGAAAAAAAAGGAGQGGYGRGGAAAAAA
AAGAGQGGYGGQGAGQGGAGAAAAAAAAGGAGQGGQGGYGRGGYGQGGAG
QGGAGAAAAAGGASQGGQGGYGQGDYGQGGAGQGGAAAAAAAAGGAG
QGGYGRGGAGQGGAAAAAGAGQGGYGGQGAGQGGAGAAAAAAAAGGAGRG
GQGGYGRGGYGQGGAGQGGAGAAAAAAAAGGAGQGGQGGYGQGGYGQGGA
GQGGAAAAAAAAGGAGQGGYGRGGAGQGGAAAAAGAGQGGYGGQGAGQG
GAGAAAAAAAAGGAGRGGQGGYGRGGYGQGGAGQGGAGAAAAAAAAGGAG
QGGQGGYGQGGYGQGGAGQGGAAAAAAAAVGGAGQGGYGRGGAGQGGAAA
AAAAAGSGQGGYGGQGAGQGGAGAAAAAAAAGGAGQGGQGGYGGGYG
QGGAGQGGAGAAAAAAAAGGAGQGGQGGYGQGGYGQGGAGQGGAAAAAA
AAGGAGQGGYGRGGAGQGGAAATGAGQGGYGGQGAGQGGAGAAAAAAAA
GGAGQGGQGGYGRGGYGQGGAGQGGAGAAAAAAAAGGAGQGGQGGYGQGG
YGQGGAGQGGAAAAAAAAGGAGQGGYGRGGAGQGGAAAAAAGAGQGG
YGGQGAGQGGAAAAAAAAGGAGQGGQGGYGQGGYGQGGAGQGGAAAA
AGGAGQGGQGGYGQGGYGQGGAGQGGAAAAAAAAGGAGQGGYGGYGQQ
GGAGAAAAASGPGQIYYGPQSVAAPAAAASALAAPATSARISSHASAL
LSNGPTNPASISNVISNAVSQISSSNPGASACDVLVQALLELVTALLTII
GSSNIGSVNYDSSGQYAQVVTQSVQNAFA

Example 8: Secretion Improves with SEC72 Deletion, but Neither Knockdown Nor Overexpression

*P. pastoris* strains were modified according to Example 1 to comprise 4 copies of DNA cassettes comprising recombinant genes expressing 18B silk-like polypeptide. Δsec72 strains were prepared using techniques described in Example 2. The strains were additionally modified to knockout YPS1-1 and YPS1-2 proteases, as described in Example 4.

From this strain, a strain overexpressing sec72 was prepared by transforming with a vector comprising a recombinant sec72 gene operably linked to a THI11 promoter (pTHI11). pTHI11 is de-repressed in minimal media that lacks the vitamin thiamine. From prior RNAseq and promoter fusion studies, pTHI11 is among the strongest promoters in block and tank minimal media, which lack thiamine.

Additionally, from the *P. pastoris* strain modified to express 4 copies of recombinant genes expressing 18B silk-like polypeptide, instead of knocking out sec72, expression of SEC72 was knocked down using DAmP (decreased abundance by mRNA perturbation), a transcriptional knockdown strategy that disrupts the 3' UTR of a gene with a marker cassette.

Figure 9A:
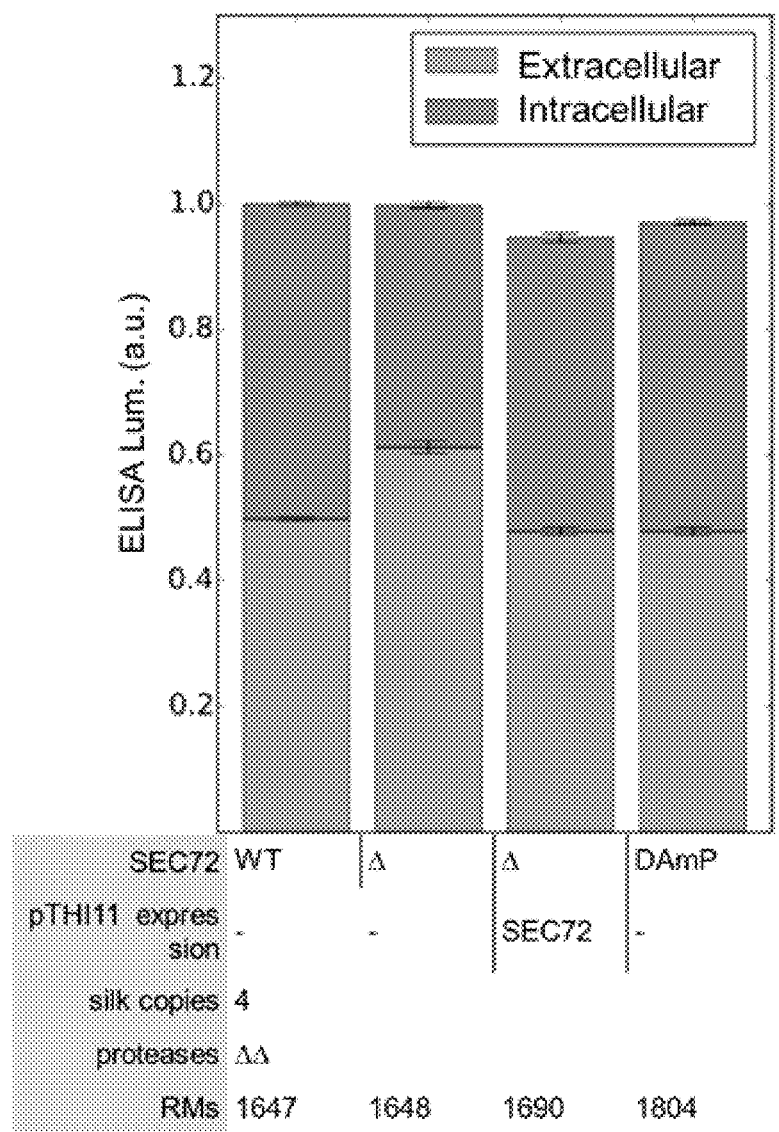
FIG. 9A shows secretion of of recombinant 18B silk-like polypeptide expressed by wild-type (WT), Δsec72 (Δ) strains, strains overexpressing sec72 under the control of pTHI11, and strains where SEC72 was knocked down by DAmP (Decreased Abundance by mRNA Perturbation), as measured by ELISA.

Secretion of the 18B silk-like polypeptides from WT, Δsec72, Δsec72 with recombinantly overexpressed sec72 (operably linked to pTHI11), and sec72 knockdown strains was measured by ELISA, with the results shown in FIG. 9A.

The Δsec72 phenotype reverts upon complementation with an inducible allele of sec72. Similarly, the knockdown of SEC72 did not measurably affect silk secretion as compared to WT. Thus, secretion improves with sec72 deletion, but not with knockdown nor overexpression of sec72.

Example 9: Other Disruptions to SEC63 Complex Stoichiometry do not Affect Silk Secretion

*P. pastoris* strains were modified according to Example 1 to comprise 4 copies of DNA cassettes comprising recombinant genes expressing 18B silk-like polypeptide. Δsec72 strains were prepared using techniques described in Example 2.

Figure 9B:
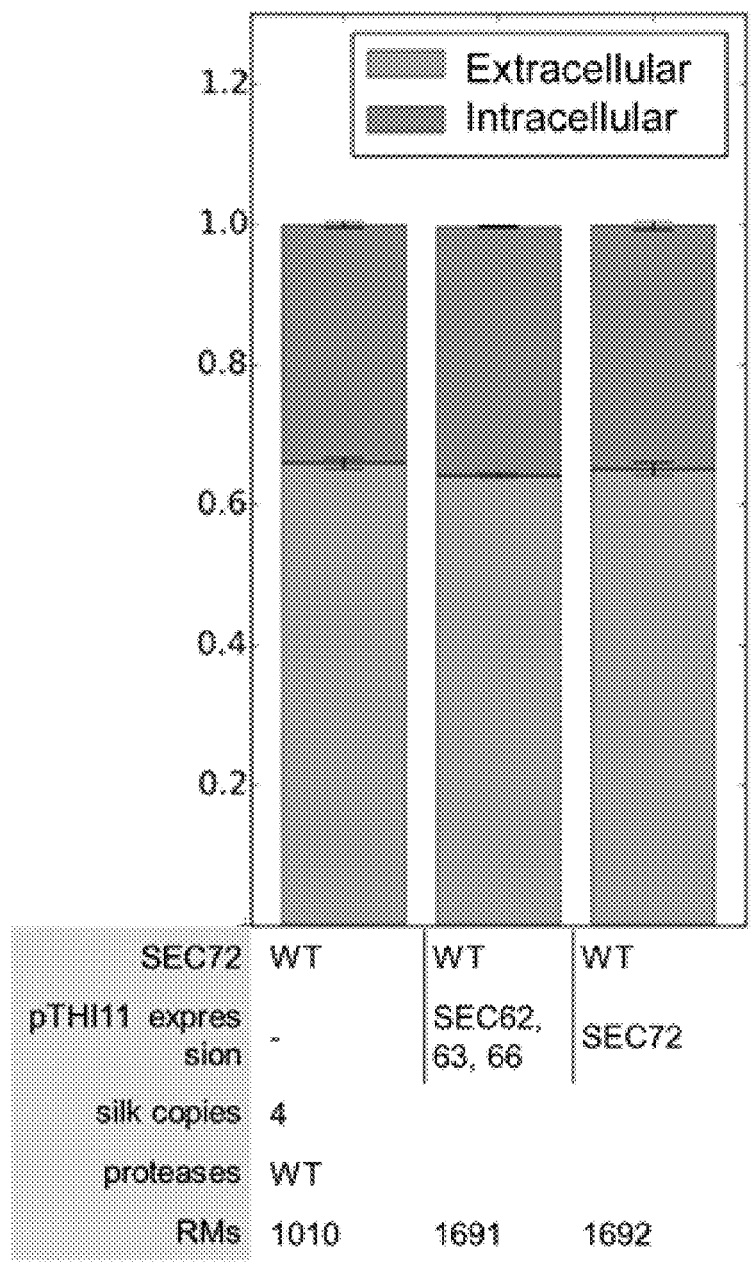
FIG. 9B shows secretion of of recombinant 18B silk-like polypeptide expressed by wild-type (WT), strains overexpressing non-SEC72 proteins from the SEC63 complex (i.e., sec62, sec63 and sec66) and strains overexpressing sec72, as measured by ELISA.

To test whether the Δsec72 phenotype is a direct effect of removal of SEC72 or an indirect effect of disrupting the SEC63 complex stoichiometry, pTHI11 was used to overexpress the 3 non-SEC72 complex members (SEC62, SEC63, and SEC66) simultaneously (by transforming the strain with a vector comprising 3 concatenated expression cassettes with sec62, sec63, and sec66). In addition, pTHI11 was used to overexpress SEC72. Secretion of 18B was measured from each strain and compared with Δsec72 strains using ELISA, with the results shown in FIG. 9B.

Neither stoichiometric change (overexpression of SEC62, SEC63, and SEC66, or overexpression of SEC72) measurably affected silk secretion. Error bars show standard error of the mean among n≥3 biological replicates.

Example 10: RTqPCR Shows Transcriptional Adaptation to Δsec72, Including Translocon Levels Δsec72 strains were prepared using techniques described in Example 2. mRNA was isolated after growth and RTqPCR was performed on selected markers to analyze transcriptional adaptation to Δsec72.

Figure 10A:
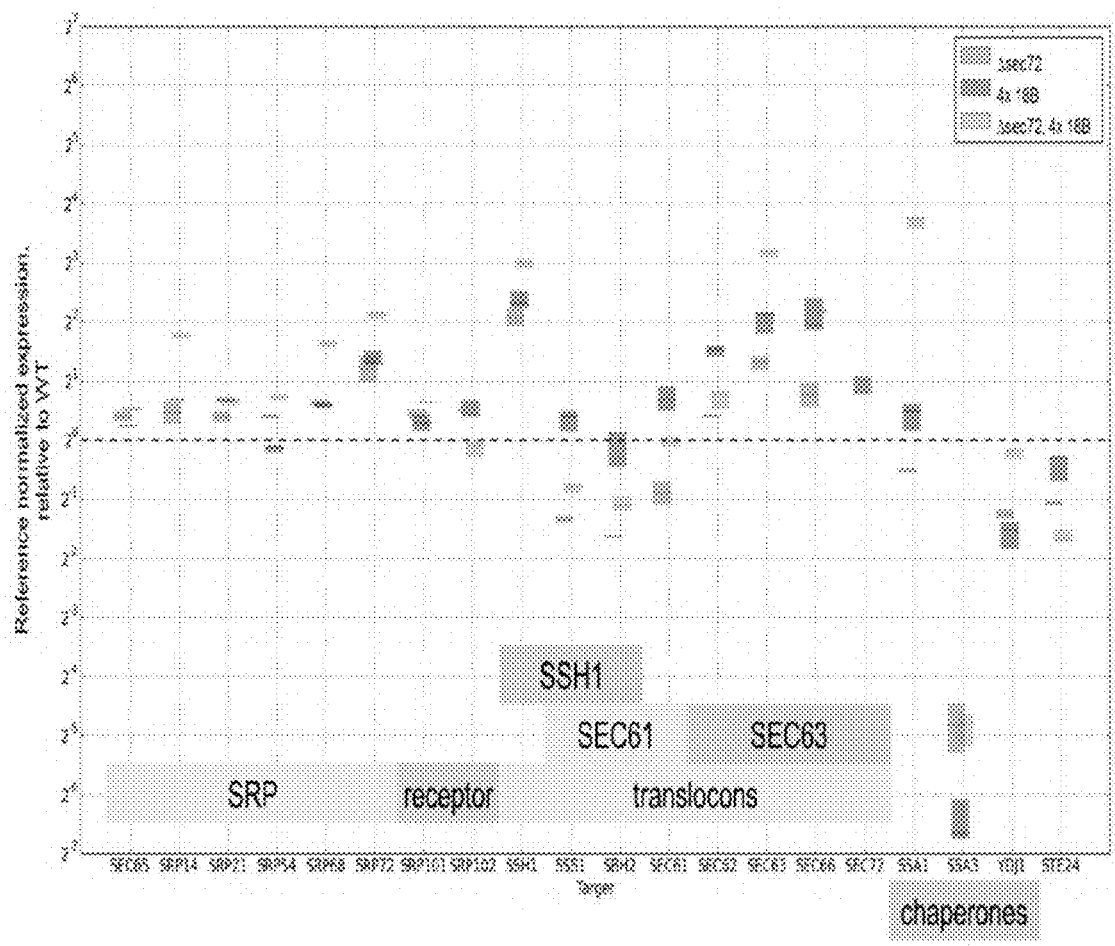
FIG. 10A shows reference-normalized expression in Δsec72 strains as a fold-change from the WT strain. Shading indicates range and center bar represents median among n=3 biological replicates (except n=2 for Δsec72).

Reference normalized expression (ALG9 or ACT1) as a fold change from the "WT" strain RMs71 in minimal media is shown in FIG. 10A. Shading indicates range and center bar represents median among n=3 biological replicates (except n=2 for Δsec72). SSH1 transcript levels increase 4-8 fold across all 3 perturbations. Δsec72 leads to a 2-4 fold reduction in SEC61 translocon component expression.

Figure 10B:
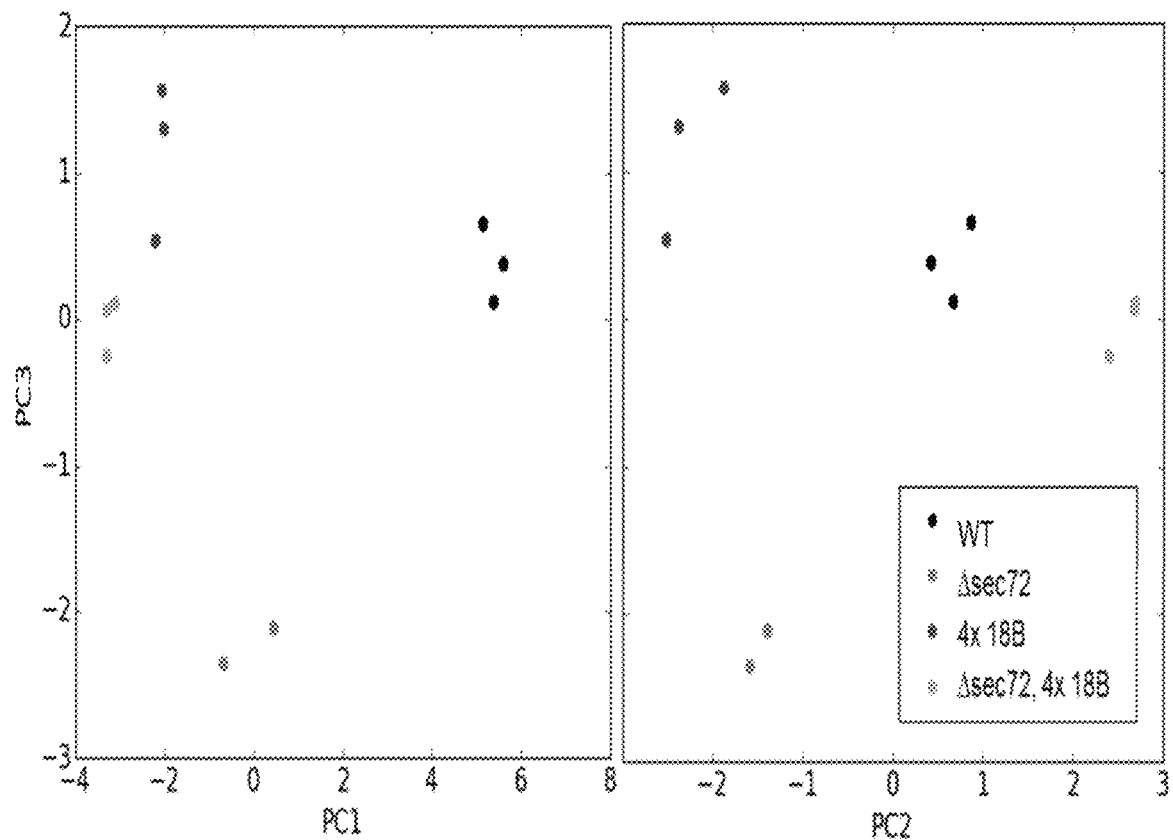
FIG. 10B shows a projection of centered, log-scaled, reference normalized expression data onto principal component space, left=PC1 vs. 3, right=PC2 vs. 3. Replicates are colored by strain genotype, showing low within-genotype variance compared variance across genotypes.

FIG. 10B shows a projection of centered, log-scaled, reference normalized expression data onto principal component space, left=PC1 vs. 3, right=PC2 vs. 3. Replicates are colored by strain genotype, showing low within-genotype variance compared variance across genotypes. Examining the loading coefficients revealed that most variation along PC1 is driven by strong SSA3 repression and along PC3 by SEC61 translocon complex repression. These 3 PCs reconstruct 99% of the variance from the original 20 dimensions.

Example 11: Overexpression of SSH1 Improves Growth Rate of the Δsec72 Silk Secretion Strain Though SSH1 also functions in ER translocation, it is distinct from SEC61 in its dispensability for *S. cerevisiae* growth and lack of interaction with the SEC63 complex. SSH1 may show translocation substrate preferences, but they broadly overlap with those of SEC61.

To test whether overexpression of SSH1 could aid growth of Δsec72 strains, *P. pastoris* Δsec72 strains were prepared using techniques described in Example 2. The regulatory and coding sequences for the SEC61 and SSH1 complexes (SSS1, SBH2, and one of SEC61 or SSH1) were assembled by PCR onto an integrating plasmid. The resulting integration duplicates the gene copy number of one of the SEC61 or SSH1 complexes. *P. pastoris* (Δsec72) cells were transformed with a vector for overexpression of the SSH1 translocon complex as described in Example 3. Similarly, *P. pastoris* (Δsec72) cells were transformed with a vector for overexpression of SEC61. Selected strains (as indicated by "ΔΔ" in FIG. 11) were additionally modified to knockout YPS1-1 and YPS1-2 proteases, as described in Example 4.

Figure 11:
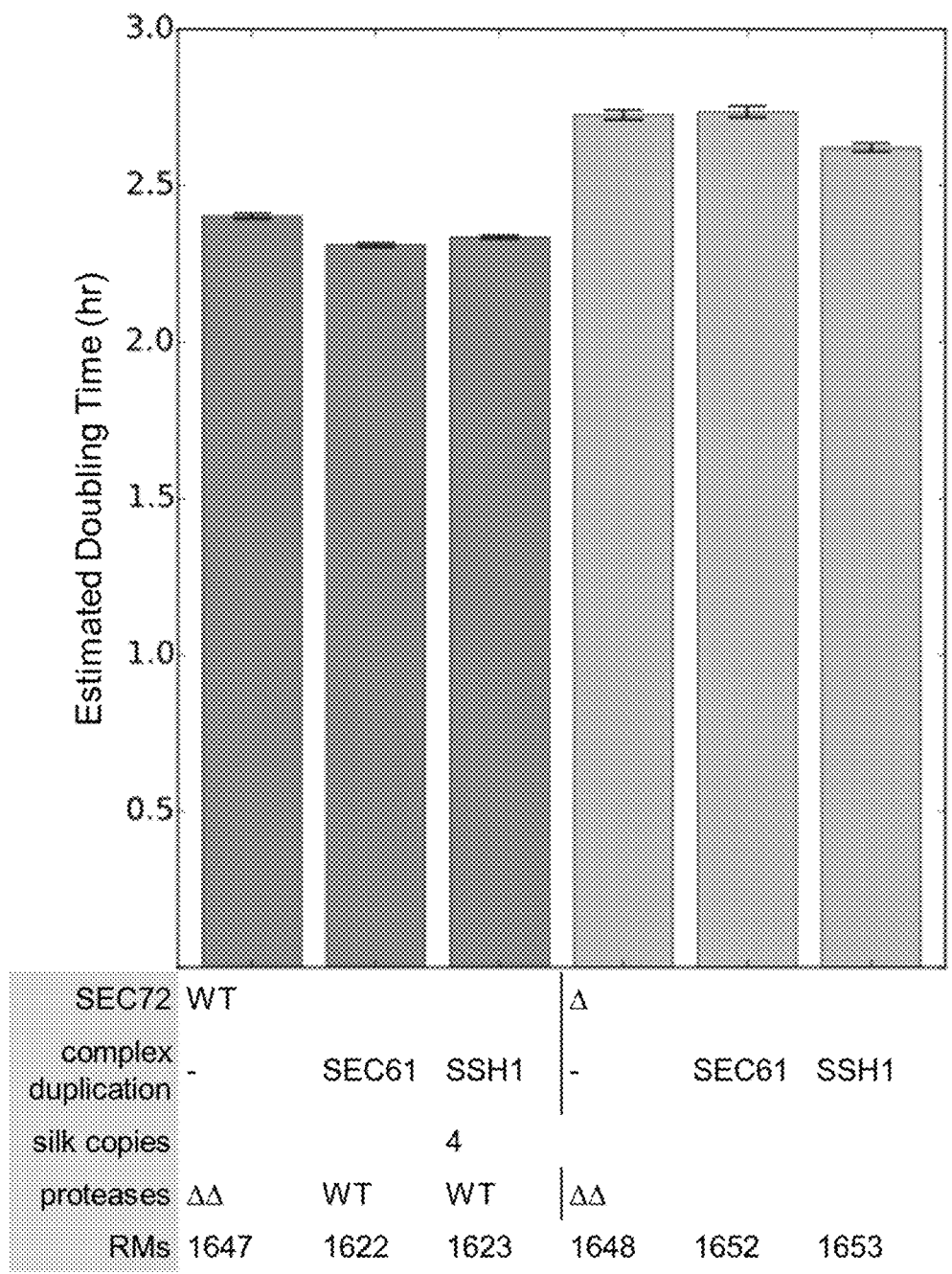
FIG. 11 shows growth rates observed for WT and Δsec72 strains, and comparison of each with growth rates for strains modified to overexpress the SSH1 translocon complex or SEC61.

Pre-cultures in YPD were diluted 1:1600 into minimal media (RMm17). OD600 was recorded over 6 timepoints spanning 8 hours of exponential growth beginning 19 hours after dilution. A linear model fit log(OD600) vs. time to estimate doubling rate and the standard error of the slope among n=6 biological replicates. The measured growth for each strain is shown in FIG. 11. Doubling times are shown as the reciprocal of doubling rate. Error bars are asymmetrical due to the reciprocal transformation of the estimates.

SEC61 and SSH1 duplication promote faster doubling of the SEC72 silk production strain (FIG. 11, left). This effect may be due to decreasing the load of intracellularly accumulated silk. However, Δsec72 leads to a significant growth defect, which is partially restored by duplication of SSH1 but not SEC61 (FIG. 11, right).

Example 12: SSH1 Duplication Improves Fermentation Performance of Δsec72 Strain

*P. pastoris* strains were modified according to Example 1 to comprise 4 copies or 6 copies of DNA cassettes comprising recombinant genes expressing 18B silk-like polypeptide. Δsec72 strains were prepared from recombinant cells expressing 4 copies of the DNA cassette using techniques described in Example 2. Some of the resulting *P. pastoris* (Δsec72) cells were also transformed with a vector for overexpression of the SSH1 translocon complex as described in Example 3. Secretion of 18B from each strain was measured using ELISA, with the results shown in FIG. 12A and FIG. 12B.

Figure 12A:
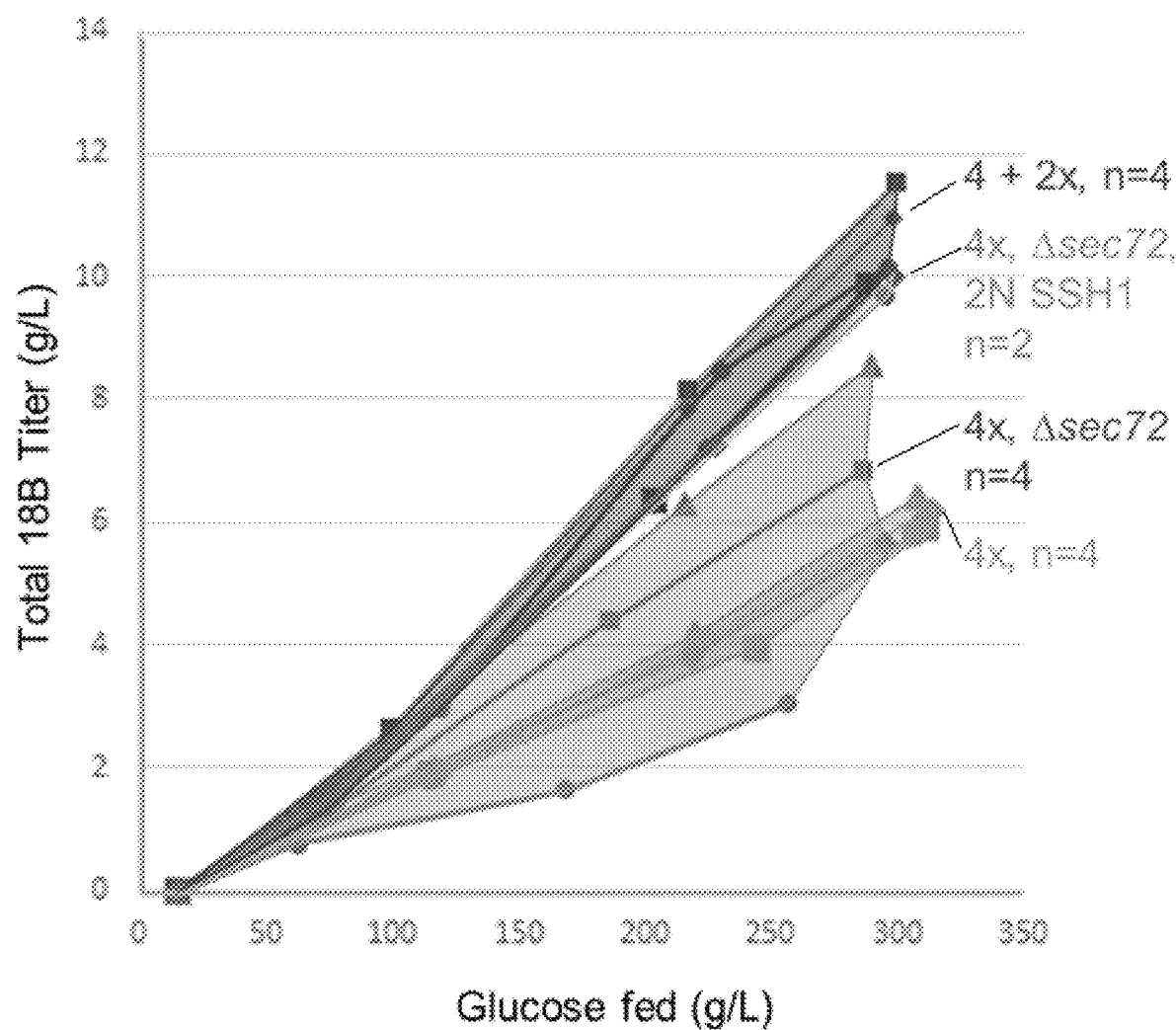
FIG. 12A shows the production of 18B as a function of glucose (yield) for wild-type (WT) strains expressing 4 (4×) or 6 (4+2×) copies of 18B, as compared to a Δsec72 strain (4×, Δsec72) and a Δsec72 strain overexpressing the SSH1 translocon complex (4×, Δsec72, 2N SSH1).

In FIG. 12A, each trajectory represents an independent batch-fed fermentation. Marked points are samples taken for analytes including the concentration of secreted silk protein in the broth ("18B titer", y-axis). The x-axis is cumulative glucose fed, since the feed program is time-varying. Shading depicts the range of all runs of the same strain. The Δsec72 deletion strain shows highly variable performance. When SSH1 is duplicated in this strain ("2N SSH1"), performance improves and variability decreases. The Δsec72 2N SSH1 strain with only 4 silk expression cassettes secretes approaches the range of a reference strain with 6 silk expression cassettes.

Figure 12B:
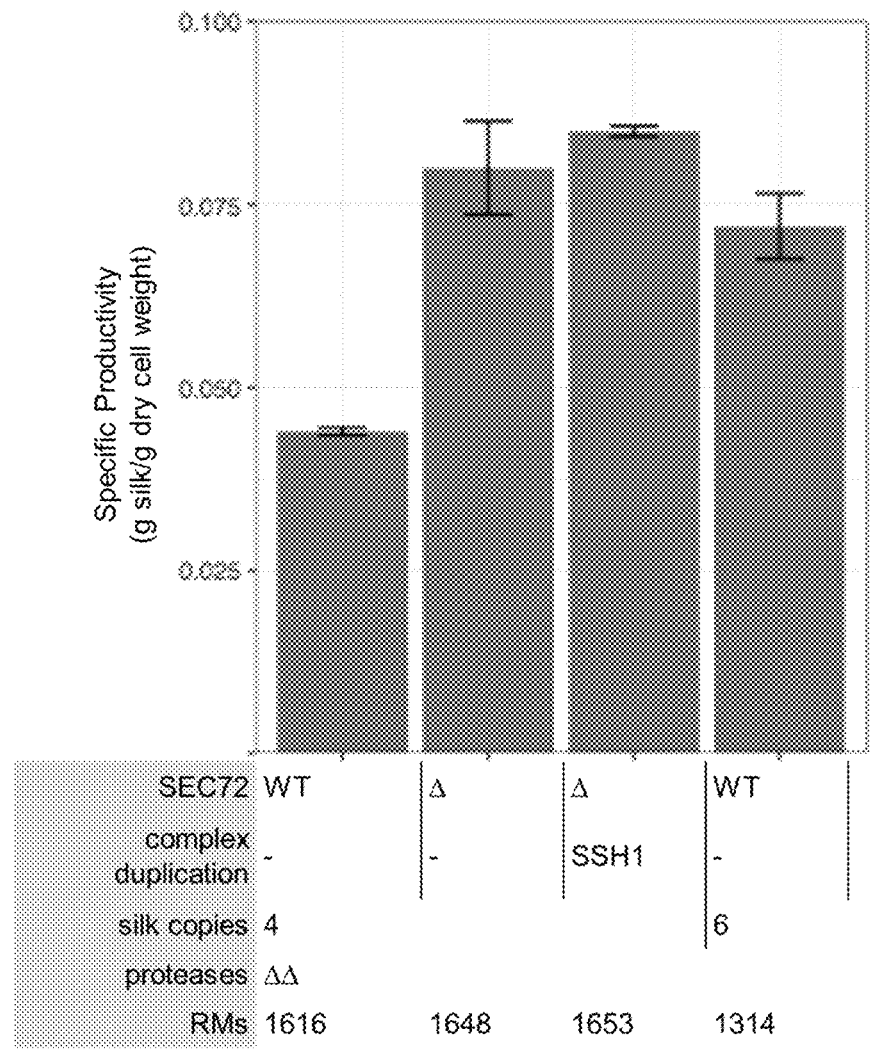
FIG. 12B shows the specific productivity (product-per biomass) of each strain.

Specific productivity (the ratio of product to biomass) was measured for each strain culture and shown in FIG. 12B. Δsec72 backgrounds grow more slowly and generate less biomass, elevating their metrics above that of the higher-expressing, highest-titer strain. Due to high variability in the Δsec72 strain, summarized data show only the top n=2 runs. Error bars are standard error of the mean.

OTHER EMBODIMENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

SEQUENCES

TABLE 8

Forward (F) and Reverse (R) Primers for 5' and 3' homology arms (HA) targeting protease ORF

| Description | SEQ ID NO: | 5' to 3' Sequence |
|---|---|---|
| KO_PAS_chr4_0584 5' HA F | 45 | TACTACAGGCTGGCTGTTCC |

TABLE 8-continued

Forward (F) and Reverse (R) Primers for 5' and 3' homology arms (HA) targeting protease ORF

| Description | SEQ ID NO: | 5' to 3' Sequence |
|---|---|---|
| KO_PAS_chr4_0584 5' HA R | 46 | CTCACTTAATCTTCTGTACTCTGAAGAAGTCCAACTGTTGAACGCC |
| KO_PAS_chr4_0584 3' HA F | 47 | AGAAGTTGATTGAGACTTTCAACGAGGGTCCCCTTCAGCTACCTTT |
| KO_PAS_chr4_0584 3' HA R | 48 | TCCCTGCTAAGCCCTAATCG |
| KO_PAS_chr3_1157 5' HA F | 49 | CTCTGATTGCACGAGAAGGC |
| KO_PAS_chr3_1157 5' HA R | 50 | CTCACTTAATCTTCTGTACTCTGAAGTGAAAGGCGATTGGAGTTGC |
| KO_PAS_chr3_1157 3' HA F | 51 | AGAAGTTGATTGAGACTTTCAACGAGCTGGCTCTGCTTCTGGTACT |
| KO_PAS_chr3_1157 3' HA R | 52 | GATGTTGAGGCGGGCATAAG |

TABLE 9

Forward and reverse primers for amplifying modified sequences

| Description | SEQ ID NO: | Sequence (5' to 3') |
|---|---|---|
| KO_PAS_chr4_0584 Verification F | 53 | ACTTGTCAGGACGATACGGA |
| KO_PAS_chr4_0584 Verification R | 54 | CCGGTCTCCCTGGAAATAGA |
| KO_PAS_chr3_1157 Verification F | 55 | AGTTGTCCGTCATTAGCCCT |
| KO_PAS_chr3_1157 Verification R | 56 | TGTTCCCTTTCGGCTAGACA |

TABLE 10 sec72 KO vector

| Description | SEQ ID NO: | Sequence (5' to 3') |
|---|---|---|
| SEC72 KO full plasmid | 91 | ggcgcgccgtttaaaccctccaccagccatataccactacaacaccacagaagagaaagagctcatatcatccgtcatgagagagtaccagcacagaaatacagtcaagtaaaactagtatgcaagcattacgtaataatagcaactttatgacaaatcattccatttttttccactggagcgtgcactgcgtaaatcattctctttggaaggcaagggaagaacaacaaaattttccttccgttatacaaacattgaatcatgtctactgaacccacttttaaattggtccttgtcggtgatggtggtaccggtaaagtaagtgcaaattatttgatgagtcggataatgttttccgcccttagttccctcatgattactaacaattcatagaccaccttcgttaagagacaccttactggagagttccgtaagaagtacattgctactttgggagtcgaagttcatcccttgtcattccacactaactgtggtcctatcacattcaacgtttgggacactgctggacaagagaagtttggtggactgagagatggttattacattaacggtgactgtggtatcatcatgttcgacgttacatcgagaatta |

TABLE 10-continued sec72 KO vector

| Description | SEQ ID NO: | Sequence (5' to 3') |
|---|---|---|
| | | cttacaagaacgttccaaactggcaccgtgacttggtcagagtgtgtgagaacattccaattgtgctttgtggtaacaaggttgatgt<br>caaggaaagaaaggtcaaggctaagaccatcactttccacagaaagaagaacttgcaatactttgacatttctgccaagtccaactac<br>aactttgagaagccattcttgtgggttagctagaaagttgtctggtgagccccaattagagttcgttgctgctcccgacttgcaagccc<br>cagaggttcaaattgatgccgatttaataaagaagtacgagcaagagaacgccgaggctgccgctatgccattgcctgatgaagatga<br>tgccgacttgtaagcttttacttacagtacattgagaaccatacatagggcacgtatcgtaagtttagttgtttgctgatgtaagcta<br>gtttgtttctgtagtgtttcgaggtcgcagagggatctctctagccttagacaaaaaaaaaaggttgacacgttgatacactctctg<br>tttcatccgatctttcacctacgagtcccactcctcttcagagtacagaagattaagtgagagaattctaccgttcgtatagcataca<br>ttatacgaagttatttcagtaatgtcttgtttcttttgttgcagtggtgagccattttgacttcgtgaaagtttctttagaatagttg<br>tttccagaggccaaacattccaccgtagtaaagtgcaagcgtaggaagtccaagactggcataaatcaggtataagtgtcgagcact<br>ggcaggtgatcttctgaaagtttctactagcagataagatccagtagtcatgcatatggcaacaatgtaccgtgtggatctaagaacg<br>cgtcctactaaccttcgcattcgttggtccagtttgttgttatcgatcaacgtgacaaggttgtcgattccgcgtaagcatgcataccc<br>caaggacgcctgttgcaattccaagtgagccagttccaacaatctttgtaatattagagcacttcattgtgttgcgcttgaaagtaaa<br>atgcgaacaaattaagagataatctcgaaaccgcgacttcaaacgccaatatgatgtgcggcacacaataagcgttcatatccgctgg<br>gtgactttctcgctctttaaaaaattatccgaaaaattttttgacggctagctcagtcctaggtacgctagcattaaagaggagaaatg<br>gctaaactgacctctgctgttccggttctgaccgctcgtgacgtgctggtgctgttgagttctggaccgaccgtctgggtttctctc<br>gtgacttcgttgaggacgacttcgctggtgttgttcgtgacgacgttaccctgttcatctctgctgttcaggaccaggttgttccgga<br>caacaccctggcttgggtttgggttcgtggtctggacgaactgtacgctgaatggtctgaagttgtttctaccaacttccgtgacgct<br>tctggtccggctatgaccgaaatcggtgaacagccgtggggtcgtgagttcgctctgcgtgacccggctggtaactgcgttcacttcg<br>ttgctgaagaacaggactaacacgtccgacggcgggcccacgggtcccaggcctcggagatccgtccccctttttccttttgtcgatatca<br>tgtaattagttatgtcacgcttacattcacgccctccccccacatccgctctaaccgaaaaggaaggagttagacaacctgaagtcta<br>ggtccctatttattttttttatagttatgttagtattaagaacgttatttatatttcaaattttttcttttttttctgtacagacgcgtg<br>tacgcatgtaacattatactgaaaaccttgcttgagaaggttttgggacgctcgaaggctttaatttgcaagctataacttcgtatag<br>catacattatgcttgttatgcggccgcagatctaacatccaaagacgaaaggttgaatgaaacctttttgccatccgacatccacag<br>gagagtttatagagctgctgatgcgtgtaaaaatagtttaaatcttcgtaaagtatgttagtccatgtaatttgctatgaatcgatacgc<br>taatctggatgctgaacggatgcttactggcatgcattattcattacccatctaagctgcgccacaacccagtaaattgcagtgaggg<br>aagcttccctgtaaccgtcctgtccctttagggaccatcgatccccaacgatcaaatcgcgatacatctatcaactgtccctttccat<br>ctatctatgcaaggtaatgacagactctgttaactctgatgattctgatctggaaatcatagaggtgactgagcctactccaaaagtg<br>gacctttggccccccaatccagcatttaattttactgccccccataagcaacagtaacggcacaactccaataaggagaaaacttgatg<br>accaatccaactccaattcttttgccagactggaatcgttacgggaatcatcagtgaaaccacaagctagtacgttcaatagtagtag<br>gttcatccccaagccgaccaatttccaataatcagaataatgaacttgataacaacaatggattcgccgactggatttctaagtcc<br>caacctgaatttcccttttccacttaatgatggaccaaaaagtccagcaatcaacctacaaactcaaattttgaagagatcatcgatt<br>taactgaagatatcgagataaatacatctgtccccgcatctacatcatcttctacccccagttcctccagcacacagaatcagagcca<br>tcatatagccaacaacaacacagcacaagatgcgcatatcttccaaggggaaacgacctctccaatcatattcagatgatgaagacgaa<br>gatttgcaaattgtaggatccaatattgttcagcagcctctaggaattatgccaggaactttcaacgcccctgcaaacatactccatt<br>ttgacggttcaaaccagaatgaacaagccagatggctggacttgcggataaaagatttgttagataatcttcacaatcttcgagttca<br>tgctcagtcgaatattatggagatcaataggttcatttccactttggggcatttaaacagagaagttaaaccctgcagggcgctcgg<br>tcgttcggctgcggcgagcggtatcagctcactcaaaggcggtaatacggttatccacagaatcaggggataacgcaggaaagaacat<br>gtgagcaaaaggccagcaaaaggccaggaaccgtaaaaaggccgcgttgctggcgtttttccataggctccgcccccctgacgagcat<br>cacaaaaatcgacgctcaagtcagaggtggcgaaacccgacaggactataaagataccaggcgtttccccctggaagctccctcgtgc<br>gctctcctgttccgaccctgccgcttaccggatacctgtccgcctttctcccttcgggaagcgtggcgctttctcatagctcacgctg<br>taggtatctcagttcggtgtaggtcgttcgctccaagctgggctgtgtgcacgaaccccccgttcagcccgaccgctgcgccttatcc<br>ggtaactatcgtcttgagtccaacccggtaagacacgacttatcgccactggcagcagccactggtaacaggattagcagagcgaggt<br>atgtaggcggtgctacagagttcttgaagtggtggcctaactacggctacactagaagaacagtatttggtatctgcgctctgctgaa<br>gccagttaccttcggaaaaagagttggtagctcttgatccggcaaacaaaccaccgctggtagcggtggttttttgtttgcaagcag<br>cagattacgcgcagaaaaaaaggatctcaagaagatcctttgatcttttctacggggtctgacgctcagtggaacgaaaactcacgtt<br>aagggattttggtcatgagattatcaaaaaggatcttcacctagatccttttaaattaaaaatgaagttttaaatcaatctaaagtat<br>atatgagtaaacttggtctgacagttaccaatgcttaatcagtgaggcacctatctcagcgatctgtctatttcgttcatccatagtt<br>gcctgactccccgtcgtgtagataactacgatacgggagggcttaccatctggccccagtgctgcaatgataccgcgagacccacgct<br>caccggctccagatttatcagcaataaaccagccagccggaagggccgagcgcagaagtggtcctgcaactttatccgcctccatcca<br>gtctattaattgttgccgggaagctagagtaagtagttcgccagttaatagtttgcgcaacgttgttgccattgctacaggcatcgtg<br>gtgtcacgctcgtcgtttggtatggcttcattcagctccggttcccaacgatcaaggcgagttacatgatccccatgttgtgcaaaa<br>aagcggttagctccttcggtcctccgatcgttgtcagaagtaagttggccgcagtgttatcactcatggttatggcagcactgcataa<br>ttctcttactgtcatgccatccgtaagatgcttttctgtgactggtgagtactcaaccaagtcattctgagaatagtgtatgcggcga<br>ccgagttgctcttgcccggcgtcaatacgggataataccgcgccacatagcagaactttaaaagtgctcatcattggaaaacgttctt<br>cggggcgaaaactctcaaggatcttaccgctgttgagatccagttcgatgtaacccactcgtgcacccaactgatcttcagcatcttt<br>tactttcaccagcgtttctgggtgagcaaaaacaggaaggcaaaatgccgcaaaaaagggaataagggcgacacggaaatgttgaata<br>ctcatactcttcctttttcaatattattgaagcatttatcagggttattgtctcatgagcggatacatatttgaatgtatttagaaaa<br>ataaacaaataggggttccgcgcacatttccccgaaaagtgccacct |
| SEC72 5' homology arm | 92 | aaaccctccaccagccatataccactacaacaccacagaagagaaagagctcatatcatccgtcatgagagagtaccagcacagaaat<br>acagtcaagtaaactagtactgcaagcattacgtaataatagcaactttatgacaaatcattccattttttttccactggacgtgcac<br>tgcgtaaatcattctcttttggaaggcaaggagaagaacaacaaaattttttccttccgtttatacaaacattgaatcatgtctactgaacc<br>cacttttaaattggtccttgtcggtgatggtggtaccggtaaagtaagtgcaaattatttgatgagtcggataatgttttccgcccct<br>tagttcccctcatgattactaacaattcatagaccaccttcgttaagagacaccttactggagagttccgtaagaagtacattgctac<br>tttgggagtcgaagttcatcccttgtcattccacactaactgtggtcctatcacattcaacgtttgggacactgctggacaaagagaag<br>tttggtggactgagagatggtttattacattaacggtgactgtgtgatcatcatgttcgacgttacatcgagaattacttacaagaacg<br>ttccaaactggcaccgtgacttggtcagagtgtgtgagaacattccaattgtgctttgtggtaacaaggttgatgtcaaggaaagaaa<br>ggtcaaggctaagaccatcactttccacagaaagaagaacttgcaatactttgacatttctgccaagtccaactacaactttgagaag<br>ccattcttgtgggttagctagaaagttgtctggtgagccccaattagagttcgttgctgctcccgacttgcaagccccagaggttcaa<br>ttgatgccgatttaataaagaagtacgagcaagagaacgccgaggctgccgctatgccattgcctgatgaagatgatgccgacttgta<br>agcttttacttacagtacattgagaaccatacatagggcacgtatcgtaagtttagttgtttgctgatgtaagctagtttgtttctgt<br>agtgtttcgaggtcgcagagggatctctctagccttagacaaaaaaaaaaggttgacacgttgatacactctctgtttcatccgatc<br>tttcacctacgag |

TABLE 10-continued sec72 KO vector

| Description | SEQ ID NO: | Sequence (5' to 3') |
|---|---|---|
| SEC72 5' homology arm | 93 | ggagagttatagagctgctatgcgtgtaaaaatagtttaaatcttcgtaaagtatgttagtccatgtaatttgctatgaatcgatacg<br>ctaatctggatgctgaacggatgcttactggcatgcattattcattacccatctaagctgcgccacaacccagtaaattgcagtgagg<br>gaagcttccctgtaaccgtcctgtcccttttagggaccatcgatccccaacgatcaaatcgcgatacatctatcaactgtcccttcca<br>tctatctatgcaaggtaatgacagactctgttaactctgatgattctgatctggaaatcatagaggtgactgagcctactccaaaagt<br>ggaccttttggccccaatccagcatttaattttactgccccataagcaacagtaacggcacaactccaataaggagaaaacttgat<br>gaccaatccaactccaattcttttgccagactggaatcgttacgggaatcatcagtgaaaccacaagctagtacgttcaatagtagta<br>ggttcatccccaagccgaccaattttccaataatcagaataatgaacttgataacaacaatggattcgccgactggatttctaagtc<br>caacctgaatttcccttccacttaatgatggaccaaaaaagtccagcaatcaacctacaaactcaaattttgaagagatcatcgat<br>ttaactgaagatatcgagataaatacatctgtccccgcatctacatcatcttctaccccagttccctccagcacacagaatcagagcc<br>atcatatagccaacaacaacacagcacaagatgcgcatatcttccaagggaaacgacctctccaatcatattcagatgatgaagacga<br>agatttgcaaattgtaggatccaatattgttcagcagcctctaggaattatgccaggaaacttcaacgcccctgcaaacatactccat<br>tttgacggttcaaaccagaatgaacaagccagatggctggacttgcggataaaagatttgttagataatcttcacaatcttcgagttc<br>atgctcagtcgaatattatggagatcaataggttcatttccacttggggcatttaaacagagaagttt |
| Yeast selection marker (Sh ble) for SEC72 KO (nucleotide sequence) | 94 | ttcagtaatgtcttgttctttgttgcagtggtgagccattttgacttcgtgaaagtttctttagaatagttgtttccagaggccaa<br>acattccaccgtagtaaagtgcaagcgtaggaagtccaagactggcataaatcaggtataagtgtcgagcactggcaggtgatcttc<br>tgaaagtttctactagcagataagatccagtagtcatgcatatggcaacaatgtaccgtgtggatctaagaacgcgtcctactaacct<br>tcgcattcgttggtccagtttgttgttatcgatcaacgtgacaaggttgtcgattccgcgtaagcatgcatacccaaggacgcctgtt<br>gcaattccaagtgagccagttccaacaatcttttgtaatattagagcacttcattgtgttgcgcttgaaagtaaaatgcgaacaaatta<br>agagataatctcgaaaccgcgacttcaaacgccaatatgatgtgcggcacacaataagcgttcatatccgctgggtgactttctcgct<br>ttaaaaaattatccgaaaaaattttttgacggctagctcagtcctaggtacgctagcattaaagaggagaaaatggctaaactgacctc<br>tgctgttccggttctgaccgctcgtgacgttgctggtgctgttgagttctggaccgaccgtctgggttttctctcgtgacttcgttgag<br>gacgacttcgctggtgttgttcgtgacgacgttaccctgttcatctctgctgttcaggacaggttgttccggacaacaccctggctt<br>gggtttgggttcgtggtctggacgaactgtacgctgaatggtctgaagttgtttctaccaacttccgtgacgcttctggtccggctat<br>gaccgaaatcggtgaacagccgtggggtcgtgagttcgctctgcgtgaccggctggtaactgcgttcacttcgttgctgaagaacag<br>gactaacacgtccgacggcggcccacgggtcccaggcctcggagatccgtcccccttttcctttgtcgatatcatgtaattagttatg<br>tcacgcttacattcacgcctccccccacatccgctctaaccgaaaaggaaggagttagacaacctgaagtctaggtccctatttatt<br>tttttatagttatgttagtattaagaacgttatttatatttcaaattttctttttttttctgtacagacgcgtgtacgcatgtaacat<br>tatactgaaaaccttgcttgagaaggttttgggacgctcgaaggctttaatttgcaagct |
| Yeast selection marker (Sh ble) for SEC72 KO (protein sequence) | 95 | MAKLTSAVPVLTARDVAGAVEFWTDRLGFSRDFVEDDFAGVVRDDVTLFISAVQDQVVPDNTLAWVWVRGLDELYAEWSEVVSTNFRD<br>ASGPAMTEIGEQPWGREFALRDPAGNCVHFVAEEQD |

TABLE 11

SSH1 Complex Overexpression vector

| Description | SEQ ID NO: | Sequence (5' to 3') |
|---|---|---|
| Full Plasmid | 96 | ccagccaggacagaaatgcctcgacttcgctgctgcccaaggttgccgggtgacgcacaccgtggaaacggatgaaggcacgaacc<br>cagtggacataagcctgttcggttcgtaagctgtaatgcaagtagcgtatgcgctcacgcaactggtccagaaccttgaccgaacg<br>cagcggtggtaacggcgcagtggcggttttcatggcttgttatgactgtttttttgggggtacagtctatgcctcgggcatccaag<br>agcaagcgcgttacgccgtgggtcgatgtttgatgttatggagcagcaacgatgttacgcagcagggcagtcgccctaaaacaaag<br>ttaaacatcatgagggaagcggtgatcgccgaagtatcgactcaactatcagaggtagttggcgtcatcgagcgccatctcgaacc<br>gacgttgctggccgtacatttgtacggctccgcagtggatggcggcctgaagcacacagtgatattgatttgctggttacggtga<br>ccgtaaggcttgatgaaacaacgcggcagagcgtttgatcaacgaccttttggaaacttcggcttccccttggagagagcgagattctc<br>cgcgctgtagaagtcaccattgttgtgcacgacgacatcattccgtggcgttatccagctaagcgcgaactgcaatttggagaatg<br>gcagcgcaatgacattcttgcaggtatcttcgagccagccacgatcgacattgatctggctatcttgctgacaaaagcaagagaac<br>atagcgttgccttggtaggtccagcggcggaggaactctttgatccggttcctgaacaggatctatttgaggcgctaaatgaaacc<br>ttaacgctatggaactcgccgcccgactgggctggtgatgagcgaaatgtagtgcttacgttgtcccgcatttggtacagcgcagt<br>aaccggcaaaatcgcgccgaaggatgtcgctgccgactgggcaatggagcgcctgccggcccagtatcagcccgtcatacttgaag<br>ctagacaggcttatcttggacaagaagaagatcgcttggcctcgcgcgcagatcagttggaagaatttgtccactacgtgaaaggc<br>gagatcaccaaggtagtcggcaaataacattactcgcatccattctcaggcgtctcgtctcgtctccaactttctgccgccaatc<br>tcctttccattcaaattctctacaacaaggcaggcttcgtccgttgatgtgaagtttgcaaaagccaaaccacgaaaaacaccatt<br>gtcaaaatggtagttgaaggcataaaggcaaaggccaaacttttgtcataacgtctaaaagttgctcttttttatggcaaaag<br>gatgttctttatcacaatagcagtgggaatgacatcttcatcatcattcgtatcatcaataccatcgagttctgaatccaaaggt<br>ttctgttgttgggataagcatcagattcttgagcaggtcgtccttggcgtcctcctctagatgaaatttgccatcgttaggagg<br>tgagtattgggaaacgttgacttgttgctcaatccaaggatcaacgttgaccatcggattgccgttctgaggagacagccaggcat<br>tatacggtggttgaccggcgtttacgcgcagaggattgttcgtggtgttgacagaagacgcataccagactgctgcggatgac<br>atcgacgaaattgaaggcgacgttgcatacccatttgttgctgatccaagaaacttggtgtttcagtcaattgtctcaggtccat<br>attgatcaatgtgttcaactgtttcaatctggttccggagggtggctattacgacaagcgtggctactatctaagtgggaagt<br>aacggaacacattgatgagacacaggaattacagggcgtgcatccaccaataacaattagtcgagatttcaaccaattacgtaagc<br>gctcaacccttttttcgaacacgtatcgagcaaagtccaggtgaaacctcatccattatatccaaagtcgaccgaagctttaaca |

TABLE 11-continued

SSH1 Complex Overexpression vector

| Description | SEQ ID NO: | Sequence (5' to 3') |
|---|---|---|
| | | acatccataatggtaagtgtccagtttgatgagtgcagaatggttccaagttttagaccagttactaatatttaaagtctacagca
attccaggaggacagagaacgttagctaaaagaagagcagcaaacttggataagaaacaggatgaaccaacctccgccagatctgc
cggtgctggaggttcttcgtctaccatgctaaagttgtacacagacgaggcccaaggtttgaaagttgatcctttaattgttcttg
ttcttgctgttggtttcattttcagtgtcattggttttgcacgttgttgctaagctgacaggaaagttgatcaactaagacctat
ttaaacaggtttcatcatatctgtactatatttacaagtccactgcgtttaggtatatactaaagacattcaagaagcacatccac
aacttgtgcaagtcctgtcaaatgtactagatgcttttcagaacatcctgcggtttgaggagattcctgaatttcccagtcccaag
tctttctcttgtagaggtctttgagttcttgtgaatgctgaattggggttcttacctcaatttctattagtgggaaatgcttccc
acaattatttgcaatgggatcccggcaactttacttgcttcaacttatgtcccatactgaacttccgtcacggttgtcaacttg
aacgtcgaatgagctcagtatttcggtgacagtgtctagattcttttacttgatgttttattcgaaagtagcgtgatttgatatg
gtgcgataattgtggccagggctgggagttcgtagacggaaacaaacgcagaatccaagcagacaagtggagagtggacaaattc
ttgatgttaattcgtaagatccttaacaaatcttagcaaagtgaaaagtgaagactacgataggattactgaaaatatat
tcaagttttgtcagaatacccactccatattaacgatattattgtccctagaactattacgtaccacttgtgtgatatttatactg
atgagtggaaaaggtatgttagtgggcttcctggatttgaagaagaagaagattacgaggaagaagatgaagtctcggctcct
atcgaaaaaaaaccagagatactgataattcagacgatgaggcctctgataccgatccagaaacgagtgacgaagaagacgaagg
tgagaatactgaaaacgagtcagaaggagaacgatcaaactctctgcggaagaagaaacggctctgtggaaaacaaagatggaga
ttatccatgaaactcctatcgacaaattactctcacctttgtctcattgaagaaagatacctcaaatacaccattaaaattgaaa
atccaagaagcagttcttgctgatccaagactcggcaaattggaaagttaaatcgtaccgaaagcctaaaccaaaaccaaaacctct
tcaggtgctacagaaacagttatacgaacagatcaaatataaaaagggtaaagcagtcacaggtgaagacgacgatgaactcaaag
acgaagacgaagatgacgatgacgaggtcatctcggagagtgaagctgataactctgatgaagaagaagatgaagaatggaatggc
tttggaactatctagaatacatatgtaaaaccataataggcaataacaattctcgctattttgcatcccaacacctcgaccgacg
tgttcagttcgacccttacctacagtgtctttaactcccatttggatctcctaaataacctacacaaatgtcccaaaaagtcacc
gacgtccctctggaatttgttaaggaaggttccaaattcatctctaaatgtactaaaccctctcagaaggagtacttaaagatagt
aagagctgttggagttgggttttaatgatgggcgtggttggttacgttgtcaagctcattcatattccaatcagatatttgattg
tttaaagtttaggtttgaatacaatgtgtatgcttaattatattcacttcgtttcattgattttttgctatccctgttgtgcgtta
atcatctctatcgtgatcctctcaagttgcacctcaaatagaagacaacttatggaggtgtacacccaatatcagtcttgacgtt
tctagtttcgttgtatgctgcataccaatttcagttcttccgtagtgttttgagcataggcttgtttacccgtcttctttacactc
tgatatgagcaccttatcaaacctcttatacacgctgaaaggagaaggcggtggtggttcttctggtcagaatcggcccagaactg
tggatcctgctgttgcaagattgaaagcagaaaggagagatggaaaggagaagcaagctcttaaagaggctcagcaagccaggaa
gctcgggaaaggcgaagaattagtcatgctaccagataggtttgagaccaaccagtaaagctcccagcactgaaggtcctcaatc
gcactggaaacatcaaggtcgatgaccgcactaacagaaggagctaaactattcgaaaggagattccttacattacgaattaga
gggtgatgtcgaaggaatgaaattcattatcaagggcgagggtactggtgacgctactaccggtacgattaaagcaaagtacatct
gtacaacaggtgacttcctgttccgtgggctactctggtgagcttgtcttatggagttcaatgttttgctaaataccctcg
cacattaaagacttttcaaaagtgcaatgcctgagggctatactcaggagagaacaatatctttcgaaggagatggtgtgtataa
gactagggctatggtcacgtatgaaagaggatccatctacaatagagtaactttaactggtgaaaacttcaaaaaggacggtcaca
tccttagaaagaatgttgcctttcaatgcccaccatccatcttgtacattttgccagacacagttaacaatggtatcagagttgag
tttaaccaagcttatgacataggggtgtcaccgaaaagttgttacaaaatgttcacagatgaatcgtcccctggcaggatcagc
tgccgtccatatcccacgttaccatcatatccacttatcataccaagctgtccaaagatcgtgatgagagaagggatcacatgtgtt
tggttgaagtggtaaaggccgtggatttggatacttaccaatgactgacctcctgccagcaatagtaagacaacacgcaaagtctc
tgaacgggtctttgagctgtctgtgtcatcaaacatatcttcatctgtagttgtattgttttctttatcactaggagtccatcct
tctggatgctgtcttagccactccaaaaatgccgggtctgggagatgaccgcagccaccattgacaccatatcgga
gagtatcgagactcctctggttttccagtcttgcatgggaattcataaatgtctcctatcttaccttgttccatcagtgtttgtag
ttccaccctcatctggtcgacaaatggttttaactggttccaataaatcaacctatcacaaactttatgcagaaatctcttgtca
cgcggccaataccggcaccaaagtctataccatatttgattttgtcaggatcgttagagaaacgactcttaactttcttaaaaag
gtcatcgatccaacaacatctgcttttggaaccgaaagttgtctcaccgtacccaccaaactccgtcgacagtgctgggacgt
gttccagtatttcagggcatcgtcatagttgatcaaactgtccacctgttttagggtcatccccattatgttctgtcattgtgtaa
aaatgggatacagtgtatatattgaaggggaatggttataagagcctacctgagaaataaaattattatgcgccatccgacatccag
aaaaattgatgaaagattggctattgttgacggttcttgatcccaaaaaaaaaaaaaacaagaaatgctgccgtcctagttttgc
ttcaaagaatggttcgtgctatgccattcccaacccaagaaacgtgtccatcccatccaatcttggttgtgctgactgattatgttgcaca
atccagtgtcgtgattacctccaacatcgcacgcgaattcgccatggctgggaaacccaaattcttcggtcgtccatcaaactct
gaagtcattcaacaccaaactcaacagctatcatagaaaatatggcggggttgcgttttttagacattgcaagaccattgtca
gctggatcccggaagttaacttccttatgaaaactgggggttcgatgaaaagctgattactcattttcactgctgccatctat
ttgattctgtccctgcctatacgtgtcaaatcctctgaagtcgtggacccagttcccattgcgttctgcttagggagtga
gaagggaacattgctggagcttgggttactgcctgtgattacttcggcatttatcttgcagttgttggcgtctggttggaagttttca
aagtaaacttgatctggttagtgacagaatattgttccaaactttgcaaaagatcacttcagtcgttatcagcatcgtatatgct
gttcttctcacatttgtgactacttactccaggtgtgtccactgataacgtcttgtggtcccaatttctgatcatcttacagat
agtggtggtcaacttcttggttactctactcgttgaagtcattgacaaggattacggattttcttcaggagctctattgttgcttg
cggtttattccgccaccaactcgtttttggcacgattggtcttagcaccgtcaaccacctccagatgaacgaatctattggtgct
ctgattcaattattccgcaattttgagctcaaaccaattggttgccatatatgactccttcttcagataaaccttcctaactt
gactcaattttatctggggattgccattatttgtgtttgtctgttcttgaataatgcaagatacgaagtaccaattaagccaaaca
aggttcgtgccatggcctcagcttacccaatcaagctacttttcaatggttctttgccacttctgtacacgtggactgtgctgtac
aacttgaacctattggttctttgtctttcaagcttaccaacttttctcttttagggaacttcaaagtggacccattcggcaacaa
ctactacgaaattacatctggactgctgtatttattgactcctacttcaacgctgaagctggactttaccaatgttgctaagc
catttgttttcattgccttctatgttggtgttagcacttctttgctagatcgtggtccaacattaacgggtcgtcaggcaagac
attgccaagttttcaaggctcaaggaatctcattgttaggaaaaagagatgcctctgtgtctaaagagtttaacaccctagttcc
tgttgcttcgcctctggagcttttcctatgtcttttccagttgccgtccgtgagttattgggtggctctggtgttccaacctcta
tcggaatcggtcttttgagtggtttggctattttggaaactgttttgcaagaatggcaacagtctggaggtgcctcacagttctcc
caatacttccagacttcttaggtttagaaatccttgaagactatccagacattcacccgcacctcaatttaccttctacatacatc
acatattctatagaggagagttccattgctcgtactgaaccccacaccactcttcttttatccctacaaactcttcgtccaactca
atgccgtcattcgtgctgatgataaatgggatcccagtgccattcaaagttgtcttttcaagatgtctttttcgatatccatgattaatttggg
cattatttgaagttcgaactgttttcctggcactttagcttgtgatgatcgttgatatatttcatccttggagttatacagtagtg
gctttcctcccaggtggtatcgtaaaacctgggaaggattgtgctcaagagcaactccctttacaacctcactcaagtccgttag
agggcgcgccgcacatgaagctgtacatggaaggcacggtgaataacaccacttcaaatgcaccagcgaggtgagggtaaaccg
tatgaaggcacccaaacgatgcgtatcaaagttgttgagggtggcccgttgccgtttgcgttcgacattttagcgacgagctttat
gtatggctctcgtacgtttatcaagtacccgaagggtattccggactttttcaaaacaatcttttccagagggtttcacctgggagc |

TABLE 11-continued

SSH1 Complex Overexpression vector

| Description | SEQ ID NO: | Sequence (5' to 3') |
|---|---|---|
| | | gcgtgactcgctacgaagatggcggcgtcgtgaccgcaacgcaggatacctccctggaagatggctgcctggtctaccacgttcag<br>gtccgtggtgtcaatttcccgagcaatggtccggttatgcagaagaaaaccctgggttgggaaccgaacaccgagatgttgtatcc<br>tgcagatggtggcctggaaggtcgcagcgacatggcattgaaactggtcggtggcggccatctgagctgtagcttcgtgaccacgt<br>atcgttcgaagaaaacggtcggtaacatcaaaatgccgggtattcacgcggttgaccaccgtctggtgcgcattaaagaagccgac<br>aaagagacttacgtggagcaacatgaagtagccgttgcgaaatttgctggttttgggcggtggtatggacgaactgtacagttcctt<br>atcatctggcgaatcggacccacaagagcactgggttccgttttacattccaggaagagtttcagtaatgtcttgtttcttttgtt<br>gcagtggtgagccatttttgacttcgtgaaagttttcttagaatagttgtttccagaggccaaacattccacccgtagtaaagtgca<br>agcgtaggaagaccaagactggcataaatcaggtataagtgtcgagcactggcaggtgatcttctgaaagtttctactagcagata<br>agatccagtagtcatgcatatggcaacaatgtaccgtgtggatctaagaacgcgtcctactaaccttcgcattcgttggtccagtt<br>tgttgttatcgatcaacgtgacaaggttgtcgattccgcgtaagcatgcatacccaaggacgcctgttgcaattccaagtgagcca<br>gttccaacaatctttgtaatattagagcacttcattgtgttgcgcttgaaagtaaaatgcgaacaaattaagagataatctcgaaa<br>ccgcgacttcaaacgccaatatgatgtgcggcacacaataagcgttcatatccgctgggtgacttttctcgctttaaaaaattatcc<br>gaaaaaattttttgacggctagctcagtcctaggtacgctagcattaaagaggagaaaatgactactcttgatgacacagcctacag<br>atataggacatcagttccgggtgacgcagaggctatcgaagccttggacggttcattcactactgatacggtgtttagagtcaccg<br>ctacaggtgatggcttcacctttgagagaggttcctgtagaccccaccctttaacgaaagtttccctgatgacgaatcggatgacgag<br>tctgatgctggtgaggacggtgaccctgattccagaacatttgtcgcatacggagatgatggtgacctggctggctttgttgtggt<br>gtcctacagcggatggaatcgtagactcacagttgaggacatcgaagttgcacctgaacatcgtggtcacggtgttggtcgtgcac<br>tgatgggactggcaacagagtttgctagagaaagaggagccggacatttgtggttagaagtgaccaatgtcaacgctcctgctatt<br>cacgcatataggcgaatgggtttcacttttgtcggtcttgatactgctttgtatgacggaactgcttctgatggtgaacaagctct<br>ttacatgagtatgccatgtccatagcacgtccgacggcggcccacgggtcccaggcctcggagatccgtcccccttttcctttgtc<br>gatatcatgtaattagttatgtcacgcttacattcacgcctcccccacatccgctctaaccgaaaaggaaggagttagacaacc<br>tgaagtctaggtccctattttatttttttatagttatgttagtattaagaacgttatttatattttcaaatttttcttttttttctgt<br>acagacggtagtacattatactgaaaaccttgcttgagaaggttttgggacgctcgaaggctttaatttgcaagctc<br>cgaataacttcgtatagcatacattatacctgttattacagcggccgcaaatattttatctgattaataagatgatcttcttgag<br>atcgttttggtctgcgcgtaatctcttgctctgaaaacgaaaaaaccgccttgcagggcggttttcgaaggttctctgagctacc<br>aactctttgaaccgaggtaactggcttggaggagcgcagtcaccaaaacttgtcctttcagtttagccttaaccggcgcatgactt<br>caagactaactcctctaaatcaattaccagtggctgctgccagtggtgcttttgcatgtcttccgggttggactcaagacgatag<br>ttaccggataaggcgcagcggtcggactgaacggggggttcgtgcatacagtccagcttggagcgaactgcctacccggaactgag<br>tgtcaggcgtggaatgagacaaacgcggccataacagcggaatgacaccggtaaaccgaaaggcaggaacaggagagcgcacgagg<br>gagccgccaggggggaaacgcctggtatctttatagtcctgtcgggtttcgccaccactgatttgagcgtcagatttcgtgatgctt<br>gtcaggggggcggagcctatggaaaaacggctttgccgcggccctctcacttccctgttaagtatcttcctggcatcttccaggaa<br>atctccgccccgttcgtaagccattcgctcgccgcagtcgaacgaccgagcgtagcagtcagtgagcgaggaagcggaatata<br>tcctgtatcacatattctgctgacgcaccggtgcagcttttttctcctgccacatgaagcacttcactgacaccctcatcagtgc<br>caacatagtaagccagtatacactccgctagcgctgatgtccggccggtgcgacgtc |
| SBH2<br>Promoter | 97 | caactttctgccgccaatctcctttccattcaaattctctacaacaaggcaggcttcgtccgttgatgtgaagtttgcaaaagcca<br>aaccacgaaaaacaccattgtcaaaatggtagttgaaggcataaggcaaaggcaagctaaactttgtcataacgtctaaaagttgc<br>tcttttttttatggcaaaagggatgttcttttatcacaatagcagtgggaatgacatcttcatcatcattcgtatcatcaataccatc<br>gagttctgaatccaaaggtttctgttgttgggataaggcatcagattctttgagcaggtcgtccttggcgtcctcctctagatgaa<br>atttgccatcgttaggaggtgagtattgggaaacgttgacttgttgctcaatccaaggatcaacgttgaccatcggattgccgttc<br>tgaggagacagccaggcattatccgtggttgaccgggatttacgcgcagaggatttgttgctggtgttgttgacagaagacgcata<br>cccagacgctgcggatgacatcgacgaaattgaagggcgacgttgcataccctttgttgctgatccaagaaacttggtgtttcag<br>tcaattgtctcaggtccatattgatcaatgtgttcaactgtttcaatctggttccggagggtggctattacgacaagctgtggcta<br>ctatctaagtgggagaagtaacgaacacattgatgagacacaggaattacagggcgtgcatccaccaataacaattagtcgagat<br>ttcaaccaattacgtaagcgctcaaccccttttttcgaacacgtatcgagcaaagtccaggtgaaaccttcatccattatatccaaa<br>gtcgaccgaagctttaacaacatccata |
| SSS1<br>Promoter | 98 | agacaagtggagagtggacaaattcttgatgttaattcgtaagatccttaacaaatcttagcaaaactgaaaagtgaagactacg<br>atagggatttacttgaaaaatatattcaagttttgtcagaataccccactccatattaacgatattattgtccctagaactattacg<br>taccacttgtgtgatatttatactgatgagttggaaaaggttatgtttagtgggcttcctggatttgaagaagaagaagattacga<br>ggaagaagtgaagtctcggctcctatcgaaaaaaaaaccagagatactgataattcagacgatgaggcctctgataccgatccag<br>aaacgagtgacgaagaagacgaaggtgagaatactgaaaacgagtcagaagaggaaccgatcaaactctctgcggaagaagaaacg<br>gctctgtgaaaacaaagatggagattatccatgaaactcctatcgacaaattactctcaccttttgtctcattgaagaaagatac<br>ctcaaataaaccattaaaattgaaaatccaagaagcagttcttgctgatccaagactcggcaaatgaaagttaaatcgtaccgaa<br>agcctaaaccaaaaccaaaacctcttcaggtgctacagaaacagttatacgaacagatcaaatataaaaagggtaaagcagtcaca<br>ggtgaagacgacgatgaactcaaagacgaagacgaagatgacgatgacgaggtcatctcggagagtgaagctgataactctgatga<br>agaagaagtgaagaatggaatggctttggaactatctagaatacatatgtaaaaccatatcaggcaataacaatttctcgctatt<br>ttgcatccaacacctcgaccgacgtgttcagttcgacccttacctacagtgtcttaactcccatttggatctcctaaataacc<br>tacacaa |
| SSH1<br>Promoter | 99 | tctgaacgggtctttgagctgtctgtgtcatcaaacatatcttcatctgtagttgtattgtttcttttatcactaggagtccatc<br>cttctggatggctgtcttgcacttatttagccactccaaaaatgccgggtctgggagatgaccgcagcaccattgacaccatatca<br>gagagtatcgagactcctctggtttccagtcttgcatgggaatttcataaatgtctcctatcttaccttgttccatcagtgtttgt<br>agttccaccctcatctggtcgacaaatggtttaactggttccaataaatcaaccttatcacaaactttatgcagaaaatctcttgt<br>cacgcggccaatccggcaccaaagtctataccatatttgattttgtcaggatcgttagagaaacgactctttaactttcttaaaa<br>aggtcatcgatccaacaacatctgcttttggaaccgaagttgtctcaccgtacccacccaaaactccgtcgacagatgctgggacg<br>ctgttccagtatttcagggcatcgtcatagttgatcaaactgtccacctgttcaactgtttatgtctcattatgttgat<br>aaaaatgggatacagtgatatattgaagggaatggttataagacgtacctgagaaataaaattattatgcgccatccgacatcc<br>agaaaaattgatgaaagattggctattgttgacggttcttgatcccaaaaaaaaaaaaacaagaaatgctgccgtcctagtttt<br>gcttcaaagaatggtttcgtgctatgccattcccaacccaaagagctgtcccatcccattaagttgtgctgactgattatgttgca<br>caatccagtgtcgtgattacctccaacatcgcacgcgaatttcgccatggctgggaaacccaaattcttcggtcgtccatcaaact<br>ctgaagtcatttcaacaccaaactcaacagctatcatagaaaaat |

TABLE 11-continued

SSH1 Complex Overexpression vector

| Description | SEQ ID NO: | Sequence (5' to 3') |
|---|---|---|
| SBH2 Terminator | 100 | gacctatatttaaacaggtttcatcatatctgtactatatttacaagtccactgcgtttaggtatatactaaagacattcaagaag cacatccacaacttgtgcaagtcctgtcaaatgtactagatgcttttcagaacatcctgcggtttgaggagattcctgaatttccc agtcccaagtcttttctcttgtagaggtcttttgagttcttgtgaatgctgaattggggttcttacctcaatttctattagtgggaaa tgctttcccacaattatttgcaatgggatcccggcaactttactttgcttcaacttatgtcccatactgaactttccgtcacggtt gtcaacttgaacgtcgaatgagctcagtatttcggtgacagtgtctagattcttttttacttgatgttttattcgaaagtagcgtga tttgatatggtgcgataatttgtggccagg |
| SSS1 Terminator | 101 | aagtttaggtttgaatacaatgtgtatgcttaattatattcacttcgtttcattgattttgctatccctgttgtgcgttaatcat ctctatcgtgatcctctcaagttgcacctcaaatagaagacaacttatggaggtgtactacccaatatcagtcttgacgtttctag tttcgttgtatgctgcatacaattcagttcttccgtagtgttttgagcataggcttgtttacccgtcttctttacactctgata tgagcaccttatcaaacctcttatcacagctgaaaggaaggcggtggtggttcttctggtcagaatcggcccagaactgtggat cctgctgttgcaagattgaaagcagaaaggaagatggaaagagagaagcaagctcttaaagaggctcagcaagcccaggaagctcg ggaaaggcgaagaattagtcatgctacccagataggtttgagaccaaccagtaaagctccca |
| SSH1 Terminator | 102 | gtttagaaatccttgaagactatccagacattcacccgcacctcaatttaccttctacatacatcacatattctatagaggagagt tccattgctcgtactgaaccccacaccactcttcttttataccctacaaactcttcgtccaactcaatgcgtcattcgtgtcggta tagacaataatggtaccccagtccatttcaaagttgtcttttctcgatatccatgattaatttgggcattatttgaagttcgaactg ttttcctggcactttagctttgatgatcgtttgatatatttcatccttggagttatacagtagtggctttcctcccaggtggtatc gtaaaacctgggaaggattgtgctcaa |
| Yeast Selection Marker (Nat) for SSH1 overexpression genes (Nucleotide) | 103 | ttcagtaatgtcttgtttcttttgttgcagtggtgagccattttgacttcgtgaaagtttctttagaatagttgtttccagaggcc aaacattccaccgtagtaaagtgcaagcgtaggaagaccaagactggcataaatcaggtataagtgtcgagcactggcaggtgat cttctgaaagttctactagcagataagatccagtagtcatgcatatgggcaacaatgtaccgtgtggatctaagaacgcgtcctac taaccttcgcattcgttggtccagtttgttgttatcgatcaacgtgacaaggttgtcgattccgcgtaagcatgcatacccaagga cgcctgttgcaattccaagtgagccagttccaacaatctttgtaatattagagcactcattcgttgttgcgcttgaaagtaaaatgc gaacaaattaagagataatctcgaaaccgcgacttcaaacgccaatatgatgtgcggcacacaataagcgttcatatccgctgggt gactttctcgcttaaaaattatccgaaaaaattttgcggctagctcagtcctaggtacgtagctagcattaaagaggagaaatg actactcttgatgacacagcctacagatataggacatcagttccgggtgacgcagaggctatcgaagccttggacggttcattcac tactgatacggtgtttagagtcaccgctacaggtgatgcttcaccttgagagaggttcctgtagacccacccttaacgaaagttt tccctgatgacgaatcggatgacgagtctgatgctggtgaggacggtgaccctgattccagaacatttgtcgcatacggagatgat ggtgacctggctggctttgttggtgtcctacagcggatggaatcgtagactcacagttgaggacatcgaagttgcacctgaaca tcgtggtcacggtgttggtcgtgcactgatgggactggcaacagagtttgctagagaaagaggagccggacatttgtggttagaag tgaccaatgtcaacgctcctgctattcacgcatataggcgaatgggtttcactttgtgcggtcttgatactgctttgtatgacgga actgcttctgatggtgaacaagctctttacatgagtatgccatgtccatagcacgtccgacggcggcccacgggtcccaggcctcg gagatccgtcccccttttccttttgtcgatatcatgtaattagttatgtcacgcttacattcacgccctccccccacatccgctcta accgaaaggaaggagttagacaacctgaagtctaggtccctatttatttttttatagttatgttagtattaagaacgttattat atttcaaattttctttttttttctgtacagacgcgtgtacgcatgtaacattactgaaaaccttgcttgagaaggttttgggac gctcgaaggctttaatttgcaagct |
| Y Yeast Selection Marker (Nat) for SSH1 overexpression genes (Amino Acid) | 104 | MTTLDDTAYRYRTSVPGDAEAIEALDGSFTTDTVFRVTATGDGFTLREVPVDPPLTKVFPDDESDDESDAGEDGDPDSRTFVAYGD DGDLAGFVVVSYSGWNRRLTVEDIEVAPEHRGHGVGRALMGLATEFARERGAGHLWLEVTNVNAPAIHAYRRMGFTLCGLDTALYD GTASDGEQALYMSMPCP |

TABLE 12

Zeocin Cassette with HA arms for KU70 deletion in P. pastoris

| Description | SEQ ID NO: | 5' to 3' Sequence |
|---|---|---|
| Plasmid sequence | 57 | ggagttgaatcacatcttactggatagcgagcttttgacgaagtgaaaatttctaattttaaacaagaggaagggtca aaaacgagatatcttatacttggaaaaagagatgacaatcagtgatttcatcaattttgtatctagttggccttctgtg ttttcgtggaagcagcaacgaggaaaggagggtatcctagatgatttttacaacgaactgaacgactgctttgagggggg taacatgaaagtaatatggaactccgtcctagtatttgccaggaggaacaaaggggttgataggctttagtacttatag aggaaacggggttacgtgcaagcgcgcatgcctgagctttgagggggggggactttcacatctcttcttctcacacttagc cctaacacagagaataataaaaagcattgcaagatgagtgttgtcagcaagcaatacgacatccacgaaggcattatctt tgtaattgaattgaccccggagcttcacgcgccggcttcagaagggaaatctcagctccagatcatcttagagaatgtca gtgaggttattctgagctaatcattaccttgcccggtacaggaataggggtgttacctttattaattacgacggtggtcaa aacgacgaaatttaccccattttgagttacaagacctgaatttggaaatgatgaaacaattgtaccaagtcttggagga ccatgtaagtgggcttaatcctctcgagaagcaattcccaattgaacacagtaaaccgttatcagccactctgttctttc acttaaggtctcttttttacatggcgaagactcataagcgtactggaagacattacaacttgaaaaagattttcttgttc actaataacgataaaccttacaatggaaactctcagctgagagttcccttgaagaaaaccctggctgattacaatgacgt |

TABLE 12-continued

Zeocin Cassette with HA arms for KU70 deletion in *P. pastoris*

| Description | SEQ ID NO: | 5' to 3' Sequence |
|---|---|---|
| | | agacattactttgattccgtttcttctgaacaagccttcaggtgtcaagtttgacaagacggaatactcagaaattttgt<br>tctatgataaagatgcttgttcgatgtcaattgaggagatccgccaacgaatttctagacataaggagatcaagcgggtt<br>tacttcacctgtcctttgaaaatcgcaaataacttgtgcatttctgtgaaaggttattctatgttttatcatgaaactcc<br>aaggaagatcaaatttgtcgtcaatgagggttcaactttcaaagatgtggagacaaaatctcagtttgtcgatccaacat<br>ccggaaaagagttttccagtgaacagctgatcaaagcatatcctctaggtgccgatgcttacattcctttaaactcagag<br>caagtcaaaacaataaatcgatttaatgatatcatcaatatcccctctttggaaattctaggtttcagggatatatctaa<br>ttggttgccacagtatcagtttggcaaagcatcgtttttatcccctaataactatggtgattttacacattcgcagagaa<br>catttagttgtcttcagtaatgtcttgtttcttttgttgcagtggtgagccattttgacttcgtgaaagtttctttagaa<br>tagttgtttccagaggccaaacattccaccgtagtaaagtgcaagcgtaggaagaccaagactggcataaatcaggtat<br>aagtgtcgagcactggcaggtgatcttctgaaagtttctactagcagataagatccagtagtcatgcatatggcaacaat<br>gtaccgtgtggatctaagaacgcgtcctactaaccttcgcattcgttggtccagtttgttgttatcgatcaacgtgacaa<br>ggttgtcgattccgcgtaagcatgcataccccaaggacgcctgttgcaattccaagtgagccagttccaacaatctttgta<br>atattagagcacttcattgtgttgcgcttgaaagtaaaatgcgaacaaattaagagataatctcgaaaccgcgacttcaa<br>acgccaatatgatgtgcggcacacaataagcgttcatatccgctgggtgactttctcgctttaaaaaattatccgaaaaa<br>attttttgacggctagctcagtcctaggtacgctagcattaaagaggagaaaatggctaaactgacctctgctgttccggt<br>tctgaccgctcgtgacgttgctggtgctgttgagttctggaccgaccgtctgggtttctctcgtgacttcgttgaagacg<br>acttcgctggtgttgttcgtgacgacgttaccctgttcatctctgctgttcaggaccaggttgttccggacaacaccctg<br>gcttgggttggttcgtggtctgacgaactgtacgctgaatggtctgaagttgtttctaccaacttccgtgacgcttc<br>tggtccggctatgaccgaaatcggtgaacagcgtggggtcgtgagttcgctctgcgtgacccggctggtaactgcgttc<br>acttcgttgctgaagaacaggactaaacacgtccgacggcggccacagggtcccaggcctcggagatccgtccccttttc<br>ctttgtcgatatcatgtaattagttatgtcacgcttacattcacgccctcccccacatccgctctaaccgaaaaggaag<br>gagttagacaacctgaagtctaggtcccctatttattttttatagttatgttagtattaagaacgttatttatatttcaa<br>attttctttttttctgtacagacgcgtgtacgcatgtaacattatactgaaaaccttgcttgagaagtttttgggacg<br>ctcgaaggctttaatttgcaagctgtattagttcacttttcagcaacctggtcggaaagatccacatcaagaatggata<br>ccaaccccaagagtatgaaaatccttccctacaatggcacttcaaaatgttacgtgacgattaccttcaattggaacacg<br>atatcgacatcagtgaccccctttgagaaacaaagtacataaacagcctcgatgagacaaaaaccaagatcatgaaacta<br>cgggactatgtcaaggaaactgccgatgatgacgacccttcacggcttgccaacactctcaaagagctcaaccaagagct<br>gaacaaaatttccaactttgatatcatcgccaataagaagccaaagacccccacgacagtagacccttgttcctactgatg<br>atgacattcatcaacgcctggaaggcaggaactctgaacggtttcaaggtggatcaattacgaaaatacgtaaggtcacga<br>aacaactttctggagacggcctccaaaaaggcagatctcatcgccaacattgacaagtactttcagcagaagttcaaaga<br>gactaaggcctgattcgtgttccttacttttttcctcgcaacgtgttttttttcccaccacattgcctatgttgtaatgcaa<br>tgcagatgctggcccagttttttgacgattctcgaaaattggctttccgtcgatgcgcattggccaaactgaaaattcaag<br>acaaaatagattggatttttatctgcaacgtcttccacctacacaaccactctacaaacttcagacaaacatgtttataaa<br>agcagctactagatccaaaatgacaagttcgttattctctactacgtttgttgtggcatttggattggtggctagcaaca<br>acctcttgccatgtcctgttgaccactctatgaataacgagactccgcaagaattgaaaccattgcaggctgaatcttct<br>actagaaagttgaactcttccgcttaagtcaaataaaaactaccagatgatgcacagaaacaacggatcacgctct<br>tgactgattagtcccgtcatttttggttctcatttttcttcacagtcacctatcaatgtatgatcacctgtgaaggatttccc<br>tacgatacttcaaatctttttacttgataatattactcattatggctcaggaatgcagactgcctgattcaagacgctgct<br>cttcttatttaacacttgtacactaaccccatggaagccagggaagggaataaccatctctctggtaataaatcggtctt<br>tatttatgcatagaaaaggaatctattatattttcgttcatttggcactctgctaacgtagttagattaacgggtctcgtaaat<br>tcaaaatcttcttccgatcaaaccggggtgaaatattacttctcgtgcatagctaattttcaaataaccgtcctaaaatg<br>aacggtcatttacctggactctcttgccaaatgggcaacaaaacataaagctgatcagaacgtaactagtctctcggaat<br>ccat |
| HA F | 58 | ggagttgaatcacatcttactg |
| KU70 HA 1 | 59 | gacaactaaatgttctctgcgaatgtgtaaaatcaccatagttattaggggataaaaacgatgctttgccaaactgatac<br>tgtggcaaccaattagatatatccctgaaacctagaattccaaagagggatattgatgatatcattaaatcgatttat<br>tgttttgacttgctctgagtttaaaggaatgtaagcatcggcacctagatgatgctttgatcagctgttcactggaaa<br>actcttttccggatgttggatcgacaaactgagattttgtctccacatcttttgaaagttgaaccctcattgacgacaaat<br>ttgatcttccttggagtttcatgataaaacatagaataaccttttcacagaaatgcacaagttatttgcgattttcaaagg<br>acaggtgaagtaaacccgcttgatctccttatgtctagaaattcgttggcggatctcctcaattgacatcgaacaagcat<br>ctttatcatagaacaaaattctgagtattccgtccttgtcacacctgaaggcttgttcagaaggaacggaatc<br>aaagtaatgtctacgtcattgtaatcagccagggttttcttcaagggaactctcagctgagagtttccattgtaaggttt<br>atcgttattagtgaacaagaaaatcttttttcaagttgtaatgtcttccagtacgcttatgagtcttcgccatgtaaaaaa<br>gagacccttaagtgaaagaacagagtggctgataacggtttactgtgttcaattgggaattgcttctcgagaggattaagc<br>ccacttacatggtcctccaagacttggtacaattgtttcatcattttccaaattcaggtcttgtaactcaaaaatggggta<br>aatttcgtcgttttgaccaccgtcgtaattaataaggtaacaccctattcctgtaccggggcaaggtaatgattagctcag<br>aaataaccttcactgacattctctaagatgatctggagctgagatttcccttctgaagccggcgcgtgaagctccggggtc<br>aattcaattacaaagataatgccttcgtggatgtcgtattgcttgctgacaacactcat |
| KU70 HA 2 | 60 | tcaggcctagtctctctttgaacttctgctgaaagtacttgtcaatgtggcgatgagatctgccttttttggaggccgtct<br>ccagaaagttgtttcgtgaccttacgtatttcgtaattgatccaccttgaaaccgttcagagttcctgccttccaggcg<br>ttgatgatgtcatcatcagtaggaacagggtctactgtcgtgggggtctttggcttcttattggcgatgatatcaaagtt<br>ggaaatttgttcagctcttgttgagctctttgagagtgttggcaagccgtgaagggtcgtcatcatcggcagtttcct<br>tgacatagtcccgtagtttcatgatcttggttttttgtctcatcgaggctgtttatgtacttttgtttctcaaggggtca<br>ctgatgtcgatatcgtgttccaattgaaggtaatcgtcacgtaacatttttgaagtgccattgtagggaaggattttcata<br>ctcttgggggttggtatccattcttgatgtggatctttccgaccaggttgctgaaaagtgaaactaatac |
| pILV5 | 61 | ttcagtaatgtcttgtttcttttgttgcagtggtgagccattttgacttcgtgaaagtttctttagaatagttgtttcca<br>gaggccaaacattccaccgtagtaaagtgcaagcgtaggaagaccaagactggcataaatcaggtataagtgtcgagca<br>ctggcaggtgatcttctgaaagtttctactagcagataagatccagtagtcatgcatatggcaacaatgtaccgtgtgga<br>tctaagaacgcgtcctactaaccttcgcattcgttggtccagtttgttgttatcgatcaacgtgacaaggttgtcgattc<br>cgcgtaagcatgcataccccaaggacgcctgttgcaattccaagtgagccagttccaacaatctttgtaatattagagcac |

TABLE 12-continued

Zeocin Cassette with HA arms for KU70 deletion in *P. pastoris*

| Description | SEQ ID NO: | 5' to 3' Sequence |
|---|---|---|
| | | ttcattgtgttgcgcttgaaagtaaaatgcgaacaaattaagagataatctcgaaaccgcgacttcaaacgccaatatga<br>tgtgcggcacacaataagcgttcatatccgctgggtgactttctcgctttaaaaaattatccgaaaaattt |
| RM2734; testR | 62 | cagaggccaaacattccacc |
| pproRBS | 63 | ttaaagaggagaaa |
| Sh ble (codon optimized) | 64 | atggctaaactgacctctgctgttccggttctgaccgctcgtgacgttgctggtgctgttgagttctggaccgaccgtct<br>gggtttctctcgtgacttcgttgaagacgacttcgctggtgttgttcgtgacgacgttaccctgttcatctctgctgttc<br>aggaccaggttgttccggacaacaccctggctgggtttgggttcgtggtctggacgaactgtacgctgaatggtctgaa<br>gttgtttctaccaacttccgtgacgcttctggtccggctatgaccgaaatcggtgaacagccgtggggtcgtgagttcgc<br>tctgcgtgacccggctggtaactgcgttcacttcgttgctgaagaacaggactaa |
| CYC1 terminator | 65 | cacgtccgacggcggcccacgggtcccaggcctcggagatccgtcccccttttccttttgtcgatatcatgtaattagtta<br>tgtcacgcttacattcacgccctccccccacatccgctctaaccgaaaaggaaggagttagacaacctgaagtctaggtc<br>cctatttatttttttatagttatgttagtattaagaacgttatttatatttcaaatttttcttttttttctgtacagacg<br>cgtgtacgcatgtaacattatactgaaaaccttgcttgagaaggttttgggacgctcgaaggctttaatttgcaagct |
| Rm3386; F test oligo | 66 | aggagttagacaacctgaag |
| HA R | 67 | gtaactagtctctcggaatccat |

TABLE 13

Template Nourseothricin Cassette for protease deletion in *P. pastoris*

| Description | SEQ ID NO: | 5' to 3' Sequence |
|---|---|---|
| Plasmid sequence | 68 | cttcagagtacagaagattaagtgagagaattctaccgttcgtatagcatacattatacgaagttatttcagtaatgtct<br>tgtttctttgttgcagtggtgagccatttgacttcgtgaaagtttctttagaatagttgtttccagaggccaaacatt<br>ccaccgtagtaaagtgcaagcgtaggaagaccaagactggcataaatcaggtataagtgtcgagcactggcaggtgatc<br>ttctgaaagtttctactagcagataagatccagtagtcatgcatatgcgaacaatgtaccgtgtggatctaagaacgcgt<br>cctactaaccttcgcattcgttggtccagtttgttgttatcgatcaacgtgacaaggttgtcgattccgcgtaagcatgc<br>atacccaaggacgcctgttgcaattccaagtgagccagttccaacaatctttgtaatattagagcacttcattgtgttgc<br>gcttgaaagtaaaatgcgaacaaattaagagataatctcgaaaccgcgacttcaaacgccaatatgatgtgcggcacaca<br>ataagcgttcatatccgctgggtgactttctcgctttaaaaaattatccgaaaaattttgacggctagctcagtccta<br>ggtacgctagcattaaagaggagaaaatgactacttcttgatgacacagcctacagatagacatcagttccgggtgac<br>gcagaggctatcgaagccttggacggttcattcactactgatacggtgtttagagtcaccgctacaggtgatggcttcac<br>cttgagagaggttcctgtagacccaccctaacgaaagttttccctgatgacgaatcggatgacgagtctgatgctggtg<br>aggacggtgaccctgattccagaacattgtcgcatacggagatgatggtgacctggctggctttgttgtggtgtcctac<br>agcggatggaatcgtagactcacagttgaggacatcgaagttgcacctgaacatcgtggtcacggtgttggtcgtgcact<br>gatgggactggcaacagagtttgctagagaaagaggagccggacatttgtggttagaagtgaccaatgtcaacgctcctg<br>ctattcacgcatataggcgaatgggttttcacttttgtcgggtcttgatactgctttgtatgacggaactgcttctgatggt<br>gaacaagctcttacatgagtatgccatgtccatagcacgtccgacggcggcccacgggtcccaggcctcggagatccgt<br>cccccttttccttttgtcgatatcatgtaattagttatgtcacgcttacattcacgccctccccccacatccgctctaacc<br>gaaaaggaaggagttagacaacctgaagtctaggtccctatttatttttttatagttatgttagtattaagaacgttatt<br>tatatttcaaatttttcttttttttctgtacagacgcgtgtacgcatgtaacattatactgaaaaccttgcttgagaagg<br>ttttgggacgctcgaaggctttaatttgcaagctataacttcgtatagcatacattataccttgttatgcggccgcaaga<br>agttgattgagactttcaacgag |
| AOX1 pA terminator | 69 | cttcagagtacagaagattaagtgaga |
| Lox71 F | 70 | taccgttcgtatagcatacattatacgaagttat |
| pILV5 | 71 | ttcagtaatgtcttgtttctttgttgcagtggtgagccatttgacttcgtgaaagtttctttagaatagttgtttcca<br>gaggccaaacattccaccgtagtaaagtgcaagcgtaggaagaccaagactggcataaatcaggtataagtgtcgagca<br>ctggcaggtgatcttctgaaagtttctactagcagataagatccagtagtcatgcatatggcaacaatgtaccgtgtgga<br>tctaagaacgcgtcctactaaccttcgcattcgttggtccagtttgttgttatcgatcaacgtgacaaggttgtcgattc<br>cgcgtaagcatgcatacccaaggacgcctgttgcaattccaagtgagccagttccaacaatctttgtaatattagagcac<br>ttcattgtgttgcgcttgaaagtaaaatgcgaacaaattaagagataatctcgaaaccgcgacttcaaacgccaatatga<br>tgtgcggcacacaataagcgttcatatccgctgggtgactttctcgctttaaaaaattatccgaaaaattt |

TABLE 13-continued

Template Nourseothricin Cassette for protease deletion in P. pastoris

| Description | SEQ ID NO: | 5' to 3' Sequence |
|---|---|---|
| pproRBS | 72 | ttaaagaggagaaa |
| nat (Nourseothricin resistance) | 73 | atgactactcttgatgacacagcctacagatataggacatcagttccgggtgacgcagaggctatcgaagccttggacgg ttcattcactactgatacggtgtttagagtcaccgctacaggtgatggcttccaccttgagagaggttcctgtagacccac ccttaacgaaagttttccctgatgacgaatcggatgacgagtctgatgctggtgaggacggtgaccctgattccagaaca tttgtcgcatacggagatgatggtgacctggctggctttgttgtggtgtcctacagcggatggaatcgtagactcacagt tgaggacatcgaagttgcacctgaacatcgtggtcacggtgttggtcgtgcactgatgggactggcaacagagtttgcta gagaaagaggagccggacatttgtggttagaagtgaccaatgtcaacgctcctgctattcacgcatataggcgaatgggt ttcactttgtgcggtcttgatactgctttgtatgacggaactgcttctgatggtgaacaagctctttacatgagtatgcc atgtccatag |
| CYC1 terminator | 74 | cacgtccgacggcgggcccacgggtcccaggcctcggagatccgtcccccttttcctttgtcgatatcatgtaattagtta tgtcacgcttacattcacgcccctccccccacatccgctctaaccgaaaaggaaggagttagacaacctgaagtctaggtc cctatttatttttttatagttatgttagtattaagaacgttatttatatttcaaattttttcttttttttctgtacagacg cgtgtacgcatgtaacattatactgaaaaccttgcttgagaaggttttgggacgctcgaaggctttaatttgcaagct |
| LoxKR3 F | 75 | ataacttcgtatagcatacattataccttgttat |
| HSP82 | 76 | gcggccgcaagaagttgattgagactttcaacgag |

TABLE 14

Exemplary nourseothricin cassettes with HA arms for YPS1-1 and YPS1-2 protease deletion in P. pastoris

| Description | SEQ ID NO: | 5' to 3' Sequence |
|---|---|---|
| Nourseothricin cassette with homology arms targeting PAS_chr4_0584 (YPS1-1) | 77 | tactacaggctggctgttcctcgcatggtgtttaatgtcctgactgggttttcgtttatcggtattaccggagccaccttg actgtaagggaacgatactggactaagagagtaatgcgaaaggcaacagcgtttctggcgaacctaatcaatgacggttac gagtttactactcctaaagccagtcttattttgctagtagagcgagtcaacgcttacttaaagggccagggacctaattatgac atcgatttttgacgagcaggaggcgttcattaaagaaatggaggagttgaggacctctggtggatatgagaacagatactca tattcaggaaccgatgaaacacccagagatccgggttgcctgtttcttcccattgctttaaataaatggcactttgatgtg ctagactgcctgaggatatacggtactcaggaagatctggaatctaaattattaagtgttcagcaattggtgttacaatgt tgcatgaagcacagtggcatgactccagacatggtctttgcaacggaagtagctcagaagccgaccttcgaagacgacata gtttgtgatgatattgacgcttatgcccaggggggtgattgtctagattattgttacacgccaagcaattactccagaact ttagaaattcatggcaagattgctaccttacaacgagagctggggctatgctataatattctcggaattttggaccgtttt tccgattaaggttttttagctccattgcgccaaccccgctctccagactccttcgttatccagcattcagcatggacaggt tcaaaaaataaaattttcttgatatgggtccacttcaaacatgcgcctacctgtaggaaaaaaaaagagaacataaatatgc cgcgaacagaaaacgtaatgtactgttctatatataaactgttcagatcaatcataaattctcagtttcaaactttccgct cagccagatttttattcgtaaagaacgcatcattggctctatgttgaaggatcagttcttgttatgggttgctttgatagcg agcgtaccggttcccggcgtgatggcagctcctagcgagtccgggcataacacggttgaaaaacgagatgccaaaaacgtt gttggcgttcaacagttggacttcttcagagtacagaagattaagtgagagaattctaccgttcgtatagcatacattata cgaagttatttcagtaatgtcttgtttctttttgttgcagtggtgagccattttgacttcgtgaaatctttgaatattaga tgtttccagaggccaaacattccaccccgtagtaaagtgcaagcgtaggaagaccaagactggcataaatcaggtataagtg tcgagcactggcaggtgatcttctgaaagtttctactagcagataagatccagtagtcatgcatatggcaacaatgtaccg tgtggatctaagaacgcgtcctactaaccttcgcattcgttggtccagtttgttgttatcgatcaacgtgacaaggttgtc gattccgcgtaagcatgcatacccaaggacgcctgttgcaattccaagtgagccagttccaacaatctttgtaatattaga gcacttcattgtgttgcgcttgaaagtaaaatgcgaacaaattaagagataatctcgaaaccgcgacttcaaacgccaata tgatgtgcggcacacaataagcgttcatatccgctgggtgactttctcgctttaaaaaattatccgaaaaaattttttgacg gctagctcagtcctaggtacgctagcattaaagaggagaaaatgactactcttgatgacacagcctacagatataggacat cagttccgggtgacgcagaggctatcgaagccttggacgttcattcactactgatacggtgtttagagtcaccgctacag gtgatggcttccaccttgagagaggttcctgtagacccaccttaacgaaagttttccctgatgacgaatcggatgacgagt ctgatgctggtgaggacggtgaccctgattccagaacatttgtcgcatacggagatgatggtgacctggctggctttgttg tggtgtcctacagcggatggaatcgtagactcacagttgaggacatcgaagttgcacctgaacatcgtggtcacggtgttg gtcgtgcactgatgggactggcaacagagtttgctagagaaagaggagccggacatttgtggttagaagtgaccaatgtca acgctcctgctattcacgcatataggcgaatgggtttcactttgtgcggtcttgatactgctttgtatgacggaactgctt ctgatggtgaacaagctctttacatgagtatgccatgtccatagcacgtccgacggcgggcccacgggtcccaggcctcgga gatccgtcccccttttcctttgtcgatatcatgtaattagttatgtcacgcttacattcacgcccctccccccacatccgct ctaaccgaaaaggaaggagttagacaacctgaagtctaggtccctatttatttttttatagttatgttagtattaagaacg ttatttatatttcaaattttttcttttttttctgtacagacgcgtgtacgcatgtaacattatactgaaaaccttgcttgag aaggttttgggacgctcgaaggctttaatttgcaagctataacttcgtatagcatacattataccttgttatgcggccgca agaagttgattgagactttcaacgagggtccccttcagctaccttttctctctgtttggtagttattctcggcgtgtgtata gtatagtataaaagggcctacattggataggcttcaacattcctcaataaacaaacatccaacatcgcgcattccgcattt cgcatttcacatttcgcgcctccttcctttaggtctttgaatcatcatcaatcgtcgccgtctacatcagagcaggact tatctttgccttccccaaaaattgccactccgtcaaatagattcttttgaatccttgactattttttgcctaaataggtttt tgtagttttttcttcaaagcccaaaagaaactctatttagattcatccagaaacaatctttttctcacccccatttcgaagt gccgtggagcacagacataaaaagatgactaccgttcaacctacagggccagacaggctcaccctgccgcatattctactg gaattcaacgatggctcctcgcagcatgcagtgatcgagctaagcatgaacgagggggattaatatatccacccatgagtgg |

TABLE 14-continued

Exemplary nourseothricin cassettes with HA arms for YPS1-1 and YPS1-2 protease deletion in *P. pastoris*

| Description | SEQ ID NO: | 5' to 3' Sequence |
|---|---|---|
| | | aatccatccactaatgagcaatcgccacgggaagagagagcaccaccccaacaatccaatccatcgcatcatccagaatca tcgaacatagctactcaaagtcccgctcaggaaaccgagactcagcccggcattccaggactagataggcctgcctttgat acctcggcaacggggtcgtcagaacaggttgacccagtacagggaaggatcctggatgatattataggccaatcattaagg acttccgaagaagacgataccgaatcccgccagagaccacgagaccagaagaacattatgatcaccgtgaattacttgtac gcagacgacacaaattccagaagtgctaatacaaacaaccagacgcccaataacacttctagaacttccgacagtgaacgt gtgggctccttatcgttgcacgttccggatctaccagataatgccgacgattactatatcgatgtactcattaaactaacc acaagcattgccctcagcgtcatcacgtccatgatcaagaaacgattagggcttagcaggga |
| PAS_chr4_0584 Homology Arm 1 | 78 | tactacaggctggctgttcctcgcatggtgtttaatgtcctgactgggttttcgtttatcggtattaccggagccaccttg actgtaaggaacgatactggactaagagagtaatgcgaaaggcaacagcgtttctggcgaacctaatcaatgacggttac gagtttactactcctaaagccagtcttattttgctagagcgagtcaacgcttacttaaagggcaggggacctaattatgac atcgattttgacgagcaggaggcgttcattaaagaaatggaggagttgaggacctctggtggatatgagaacagatactca tattcaggaaccgatgaaacacccagagatccgggttgcctgtttcttcccattgctttaaataaatggcactttgatgtg ctagactgcctgaggatatacggtactcaggaagatctggaatctaaattattaagtgttcagcaattggtgttacaatgt tgcatgaagcacagtggcatgactccagacatggtctttgcaacggaagtagctcagaagccgaccttcgaagacgacata gtttgtgatgatattgacgcttatgcccagggggtgattgtctagattattgttacacgccaagcaattactccagaact ttagaaattcatggcaagattgctaccttacaacgagagctggggctatgctataatattctcggaattttggaccgtttt tccgattaaggttttttagctccattgcgccaaccccgctctccagactccttcgttatccagcattcagcatggacaggt tcaaaaaaataaaatttcttgatatgggtccacttcaaacatgcgcctacctgtaggaaaaaaaaagagaacataaatgc cgcgaacagaaaacgtaatgtactgttctatatataaactgttcagatcaatcataaattctcagtttcaaactttccgct cagccagatttattcgtaaagaacgcatcattggctctatgttgaaggatcagttcttgttatgggttgctttgatagcg agcgtaccggtttccggcgtgatggcagctcctagcgagtccgggcataacacggttgaaaaacgagatgccaaaaacgtt gttggcgttcaacagttggactt |
| PAS_chr4_0584 Homology Arm 2 | 79 | ggtccccttcagctacctttctctctgtttggtagttattctcggcgtgtgtatagtatagtataaaagggcctacattgg ataggcttcaacattcctcaataaacaaacatccaacatcgcgcattccgcatttcgcatttcactttcgcgcctgcctt cctttaggttctttgaatcatcatcaatcgtcgccgtctacatcagagcaggacttatctttgccttccccaaaaattgc actccgtcaaatagattcttttgaatcctttgactattttgcctaaataggtttttgttagttttttcttcaaagcccaaa gaaactctatttagattcatccagaaacaatctttttctcaccccatttcgaagtgccgtggagcacagacataaaaagat gactaccgttcaacctacagggccagacaggctcaccctgccgcatattctactggaattcaacgatggctcctcgcagca tgcagtgatcgagctaagcatgaacgaggggaattaatatatccacccatgagtgaatcatccactaatgagcaatcgcc acgggaagagagagcaccaccccaacaatccaatccatcgcatcatccagaatcatcgaacatagctactcaaagtcccgc tcaggaaaccgagactcagcccggcattccaggactagataggcctgcctttgatacctcggcaacggggtcgtcagaaca ggttgacccagtacagggaaggatcctggatgatattataggccaatcattaaggacttccgaagaagacgataccgaatc ccgccagagaccacgagaccagaagaacattatgatcaccgtgaattacttgtacgcagacgacacaaattccagaagtgc taatacaaacaaccagacgcccaataacacttctagaacttccgacagtgaacgtgtgggctccttatcgttgcacgttcc ggatctaccagataatgccgacgattactatatcgatgtactcattaaactaaccacaagcattgccctcagcgtcatcac gtccatgatcaagaaacgattagggcttagcaggga |
| Nourseothricin cassette with homology arms targeting PAS_chr3_1157 (YPS1-2) | 80 | gccttctcgtgcaatcagagctgttgaaagagagaagagggcacacgaagctgctgttcaattgtgtgaattgaccggat tacaacctgctggagtgataggagagctggttcgtgacgaggacggctctatgatgcgattagacgactgtgttcagtttg gtctccgccacaacgtaaaaattatcaaccttgaccagatcattgaatacatggattccaagaacagctagatacgatgga taggaatacagagatatgattgaggaacgtaagagctttttcgaaagtgcagttgagtttgtggtgagggccaggcagttg gaggtggtggggagcctccttggtcgaatgtagatatagtaagcaagacacaagagcgcgcgaagtcttcaacgaggcggc gttgggtcttgtacgcaacgtaatgactacacagttgagcttgtcgcgaaccggtcgacattttgatcatgcatactatgt tgagacaccatctcgtactattgcggcaaccagctgtaaatttgactaattaaagctgatgaaggatgcagggcgtcgtca atttttgattgattgcatttaattgttttgagccattcaaggctgaatgcccggcaccctagacccttcttgtgagtacta taaacccgcaggcagggtaccctttggcctcgagagactaccagtcataacgtatatccacaatgtactagtaatagcc cggaaaactctaatcccacagaacgtctaacgcctcctatgtcatcgatacccattcgcactactgccatggccccccta cgtgatcatttcacttactcccgcctaagcttcgcccacatgcctgcgtttgccaagatttactgacgagtttggtttac tcatcctctatttataactactagactttcaccattcttcaccaccctcgtgccaatgatcatcaaccacttggtattgac agccctcagcattgcactagcaagtgcgcaactccaatcgcctttcacttcagagtacgaagattaagtgagagaattct accgttcgtatagcatacattatacgaagttattccagtaatgtccttgtttctttgttgcagtggtgagccattttgact tcgtgaaagtttctttagaatagttgtttccagaggccaaacattccaccgtagtaaagtgcaagcgtaggaagaccaag actggcataaatcaggtataagtgtcgagcactggcaggtgatcttctgaaagtttctactagcagataagatccagtagt catgcatatggcaacaatgtaccgtgtggatctaagaacgcgtcctactaaccttcgcattcgttggtccagtttcgttgtt atcgatcaacgtgacaaggttgtcgattccgcgtaagcatgcatacccaaggacgcctgttgcaattccaagtgagccagt tccaacaatctttgtaatattagagcacttcattgtgttgcgcttgaaagtaaaatgcgaacaaattaagagataatctcg aaaccgcgacttcaaacgccaatatgatgtgcggcacacaataagcgttcatatccgctgggtgactttctcgctttaaaa aattatccgaaaaaattttttgacggctagctcagtcctaggtacgctagcattaaagagggaaaatgactactcttgatg acacagcctacagatataggacatcagttccgggtgacgcagagctatcgaagcgttggacggttcattcactactgata cggtgtttagagtcaccgctacaggtgatggcttcaccttgagagaggttcctgtagacccacccttaacgaaagttttcc ctgatgacgaatcggatgacgagtctgatgctggtgaggacggtgaccctgattccagaacatttgtcgcatacggagatg atggtgacctggctggctttgttggtgtcctacagcggtgaactagactcacagttgaggacatcgaagttgcac ctgaacatcgtggtcacggtgttggtcgtgcactgatgggactgcaacagattttgctagagaagaggagccggacatt tgtggttagaagtgaccaatgtcaacgctcctgctattcacgcatataggcgaatgggtttcacttgtgcggtcttgata ctgctttgtatgacggaactgcttctgatggtgaacaagtcttttacatgagtatgccatgtccatagcacgtccgacggc ggcccacgggtccacaggcctcggagatccgtccccccttccttttgtcgatatcatgtaattagttatgtcacgcttacat tcacgccctcccccccacatccgctctaacgcgaaaaggaaggagttagacaacctgaagtctaggtccctatttattttt atagttatgttagtattaagaacgttatttatttcaaattttttcttttttttctgtacagacgcgtgtacgcatgtaac attatactgaaaaccttgcttgagaaggttttgggacgctcgaaggctttaatttgcaagctataacttcgtatagcatac attataccttgttatgcggccgcaagaagttgattgagactttcaacgagctggctctgcttctggtacttcttcaggtgc atccttctgctactcaaaatgacgaaacatccactgatcttggagctccagctgcatcttttaagtgcaacgccatgtcttttt |

TABLE 14-continued

Exemplary nourseothricin cassettes with HA arms for YPS1-1 and YPS1-2 protease deletion in *P. pastoris*

| Description | SEQ ID NO: | 5' to 3' Sequence |
|---|---|---|
| | | tgccatcttgctgctcatgttgtagtagactttttttttcactgagtttttatgtactactgattacattgtgtaggtgta<br>atgatgtgcactataatactaatatagtcaaaatgctacagaggaaagtgcaggttgccttggtggttttttcttattagc<br>accctctgaacactctttacctctaacatcctcagccatgctaatcgcgcataaaataaatcttcgaacttttttccattt<br>tatgctcataaagcttccttactgtcaccttatcaaaagagcttttgccactaaagtagtcacacccagaattgctcccga<br>atatcgtccaacaatgctaggatctgtgaaagtttgacaaataatttgaacaccttgagcttgaagcttcctgaagttaa<br>tatccaaggctccttttccagaaagtaacccagtggacctttgagaaactacatcactcaagaacttagtaaaatttctgg<br>agttgacaaagaattgattttcccagccttggaatggggtaccacactggaaaaaggtgatcttttgatcccagttcctcg<br>tctgagaataaagggtgctaatcctaaagatttagccgaacaatgggctgctgcattcccaaagggtggatatcttaaaga<br>cgttattgcgcaaggacctttcttgcagttcttttttaacacatcggttctgtacaagttggtgatatctgatgctctgga<br>gagaggcgatgactttggtgcacttcctctaggaaagggacaaaaagttatagtggagtttcttctccaaatattgccaa<br>acctttccacgctggccatcttagaagtacaatcatcggtggttttatttccaatctgtatgaaaagctgggtcatgaagt<br>tatgaggatgaattatttgggagactggggaaaacaatttggtgttcttgcagtaggatttgagcgttacggtgatgaggc<br>aaaattaaagactgatccaatcaaccatttgtttgaggtctatgttaaaatcaaccaagatattaaggctcaatcagagtc<br>tactgaggagattgcagaagggcaatcattagatgaccaggcaagagcttttttcaagaaaatggaaatggcgacgaatc<br>ggctgtaagcttgtggaaaagattccgtgagttatccattgagaagtacattgatacttatgcccgcctcaacatc |
| PAS_chr3_1157 Homology Arm 1 | 81 | gccttctcgtgcaatcagagctgttgaaagagagaagagggcacacggaagctgctgttcaattgtgtgaattgaccggat<br>tacaacctgctggagtgataggagagctggttcgtgacgaggacggctctatgatgcgattagacgactgtgttcagtttg<br>gtctccgccacaacgtaaaaattatcaaccttgaccagatcattgaatacatggattccaagaacagctagatacgatgga<br>taggaatacagagatatcatgattgaggaacgtaagagcttttttcgaaagtgtgagtttgtggtgagggccaggcggtggg<br>gaggtggtggggagcctccttggtcgaatgtagatatagtaagcaagacacaagagcgcgcgaagtcttcaacgaggcggc<br>gttgggtcttgtacgcaacgtaatgactacacagttgagcttgtcgcgaaccggtcgacattttgatcatgcatactatgt<br>tgagacaccatctcgtactattgcggcaaccagctgtaaatttgactaattaaagctgatgaaggatgcaggggcgtcgtca<br>atttttttgattgattgcatttaattgtttgagccattcaaggctgaatgcccggcacctctagacccttcttgtgagtacta<br>taaacccgcaggcagggtacccttggccttctgcgagactaccagtcataacgtatatccacaatgtactagtaatagccc<br>cggaaaactctaatcccacagaacgtctaacgcctcctatgtcatcgatacccattcgcactactgccatggccccccctta<br>cgtgatcatttcacttactcccgcctaagcttcgcccacatgcctgcgttttgccaagatttactgacgagtttggtttac<br>tcatcctctattataactactagactttcaccattcttcaccaccctcgtgccaatgatcatcaaccacttggtattgac<br>agccctcagcattgcactagcaagtgcgcaactccaatcgcctttca |
| PAS_chr3_1157 Homology Arm 2 | 82 | ctggctctgcttctggtacttcttcaggtgcatcttctgctactcaaaatgacgaaacatccactgatcttggagctccag<br>ctgcatctttaagtgcaacgccatgtcttttgccatcttgctgctcatgttgtagtagactttttttttcactgagttttt<br>tatgtactactgattacattgtgtaggtgtaatgatgtgcactataatactaatatagtcaaaatgctacagaggaaagtg<br>caggttgcctgtggtggttttcttattagcaccctctgaacactctttacctctaacatcctcagccatgctaatcgcgc<br>ataaaataaatcttcgaacttttttccattttatgctcataaagcttccttactgtcaccttatcaaaagagcttttgcca<br>ctaaagtagtcacacccagaattgctcccgaatatcgtccaacaatgctaggatctgtgaaagtttgacaaataatttgaa<br>acaccttgagcttgaagcttcctgaagttaatatccaaggctccttccagaaagtaacccagtggaccttttgagaaact<br>acatcactcaagaacttagtaaaatttctggagttgacaaagaattgattttcccagccttggaatggggtaccacactgg<br>aaaaaggtgatcttttgatcccagttcctcgtctgagaataaagggtgctaatcctaaagatttagccgaacaatgggctg<br>ctgcattcccaaagggtggatatcttaaagacgttattgcgcaaggacctttcttgcagttcttttttaacacatcggttc<br>tgtacaagttggtgatatctgatgctctggagagaggcgatgactttggtgcacttcctctaggaaagggacaaaaagtta<br>tagtggagttttcttctccaaatattgccaaacctttccacgctggccatcttagaagtacaatcatcggtggttttatttt<br>ccaatctgtatgaaaagctgggtcatgaagttatgaggatgaattatttgggagactggggaaaacaatttggtgttcttg<br>cagtaggatttgagcgttacggtgatgaggcaaaattaaagactgatccaatcaaccatttgtttgaggtctatgttaaaa<br>tcaaccaagatattaaggctcaatcagagtctactgaggagattgcagaagggcaatcattagatgaccaggcaagagctt<br>ttttcaagaaaatggaaatggcgacgaatcggctgtaagcttgtggaaaagattccgtgagttatccattgagaagtaca<br>ttgatacttatgcccgcctcaacatc |

TABLE 15

Information on genes and sequences disclosed herein

| *S. cerevisiae* ortholog standard name | *S. cerevisiae* ortholog systematic name | *P. pastoris* (*K. phaffii*) gene ID | *P. pastoris* (*K. phaffii*) ORF coordinates (strand) | Open Reading Frame (ORF) SEQ ID NO: | Peptide SEQ ID NO: |
|---|---|---|---|---|---|
| SEC72 | YLR292C | PAS_chr2-1_0448 | chr2: 827202-827789(−) | 1 | 2 |
| SBH2 | YER019C-A | PAS_chr2-2_0210 | chr2: 1994927-1995252(+) | 7 | 8 |
| SSS1 | YDR086C | PAS_chr1-1_0023 | chr1: 580942-581136(+) | 5 | 6 |
| SSH1 | YBR283C | PAS_chr1-4_0629 | chr1: 2584924-2586363(−) | 3 | 4 |
| PEP4 | YPL154C | n/a | n/a | 83 | 84 |
| PRC1, mutant | YMR297W | n/a | n/a | 85 | 86 |
| DAP2 | YHR028C | n/a | n/a | 87 | 88 |
| MF(alpha)1, variant | YPL187W | n/a | n/a | 89 | 90 |

TABLE 16

Information on promoters and terminators for the SSH1 complex genes

| S. cerevisiae ortholog standard name | S. cerevisiae ortholog systematic name | Promoter/ Terminator | P. pastoris (K. phaffii) ORF coordinates (strand) | Nucleotide Sequence SEQ ID NO: |
|---|---|---|---|---|
| SBH2 | YER019C-A | Promoter | chr2: 1994039-1994926(+) | 97 |
| SBH2 | YER019C-A | Terminator | chr2: 1995253-1995712(+) | 100 |
| SSS1 | YDR086C | Promoter | chr1: 579989-580941(+) | 98 |
| SSS1 | YDR086C | Terminator | chr1: 581137-581628(+) | 101 |
| SSH1 | YBR283C | Promoter | chr1: 2586364-2587353(−) | 99 |
| SSH1 | YBR283C | Terminator | chr1: 2584553-2584923(−) | 102 |

SEQUENCE LISTING

```
Sequence total quantity: 107
SEQ ID NO: 1            moltype = DNA  length = 588
FEATURE                 Location/Qualifiers
source                  1..588
                        mol_type = other DNA
                        organism = Pichia pastoris
SEQUENCE: 1
atgctaccat tttcgtacga cgtgagctca aagaaactga aagtcacagg tgactacgca   60
gacttagaat atgacataca gcagctgaac accttgagcg ggagatcct ggccaataaa   120
gcagatgttc cttctccacc aagtaaggag tcgtttgaca agaaattgtc ccacatggct   180
cagaaattac acgagtcggc tgtatccaac ataaagacga gcaagtatcc tgaggctatc   240
aaattgttga cgacgggtct tgaaatggtt aacagaaggc ccaagtacga gagttttcag   300
atgacgttga gtgaaatgac gatctttatt gtcactgaga ctgacgctta catgatgaat   360
ggagactttg aagggcatt caatgatgca gatttactgg taacgctcct gccatccatt   420
ccagataatt acattagaag aggggtagcc cttttcaaga tgggggagata cgttgatgca   480
aaaaacaatt ttgagagagg actttcattt gacccagata atgcaaaatt gaagaaggag   540
ttagattttg tgctgaagaa gatcgacgag gagaatggag agttatag             588

SEQ ID NO: 2            moltype = AA   length = 195
FEATURE                 Location/Qualifiers
source                  1..195
                        mol_type = protein
                        organism = Pichia pastoris
SEQUENCE: 2
MLPFSYDVSS KKLKVTGDYA DLEYDIQQLN TLSGEILANK ADVPSPPSKE SFDKKLSHMA   60
QKLHESAVSN IKTGKYPEAI KLLTTGLEMV NRRPKYESFQ MTLSEMTIFI VTRADAYMMN  120
GDFEGAFNDA DLLVTLLPSI PDNYIRRGVA LFKMGRYVDA KNNFERGLSF DPDNAKLKKE  180
LDFVLKKIDE ENGEL                                                  195

SEQ ID NO: 3            moltype = DNA  length = 1440
FEATURE                 Location/Qualifiers
source                  1..1440
                        mol_type = other DNA
                        organism = Pichia pastoris
SEQUENCE: 3
atggcggggt tgcgtttttt agacattgca agaccatttg tcagctggat cccggaagtt   60
gaacttcctt atgaaaactg ggggttcgat gaaaagctga tttactcatt tttcactgct  120
gccatctatt tgattctgtc cctgcctata tacggtgtca aatcctcga agtcgtggac  180
ccagttcccc atttgcgttc tgccttaggg agtgagaagg gaacattgct ggagcttggg  240
ttactgcctg tgattacttc ggcatttatc ttgcagttgt tggctggttg gaaagttttc  300
aaagtaaact ttgatctggt tagtgacaga atattgttcc aaacttttgca aaagatcact  360
tcagtcgtta tcagcatcgt atatgctgtt cttctcacat tttgtgactca cttactcca  420
ggtgtgtcca ctgataacgt cttgtgtcc caatttctga tcatcttaca gatagtggtg  480
gtcaacttct tggttactct actcgttgaa gtcattgaca aggattacgg attttcttca  540
ggagctctat tgttgcttgc ggtttattcc gccaccaact tcgtttttgg cacgattggt  600
cttagcaccg tcaacaccct cagatcgaac gaatcctatg gtgctctgat tcaattattc  660
cgcaatttga gctctaaacc aattggtgtt gccatatatg actccttctc cagagtaaac  720
cttcctaact tgactcaatt ttatctgggg attgccatta tttgttgtttg tctgttcttg  780
aataatgcaa gatacgaagt accaattaag ccaaacaagg ttcgtgccat ggcctcagct  840
tacccaatca agctacttt caatggttct ttgccacttc tgtacacgtg gactgtgctg  900
tacaacttga accttattgg tttcttttgtc ttcaagctta ccaactttc tcttttaggg  960
aacttcaaag tggaccatt cggcaacaac tactacgaaa ttacatctga actgctgtat 1020
ttattgactc ctactttcaa cgctgaagct ggacttttac ccaatgttgc taagccattt 1080
gttttcattg ccttctatgt tggtgttagc actttctttg ctagatcgtg gtccaacatt 1140
aacgggtcgt caggcaagga cattgccaag ttttcaagg ctcaaggaat ctcattgtta 1200
ggaaaaagag atgcctctgt gtctaaagag tttaacaccc tagttcctgt tgcttctgcc 1260
tctggagctt tccttattgtc ttttccagtt gccgtcgctg agttattggg tggtctctggt 1320
```

```
gttccaacct ctatcggaat cggtcttttg agtggtttgg ctattttgga aactgttttg    1380
caagaatggc aacagtctgg aggtgcctca cagttctccc aatacttcca gacttcttag    1440

SEQ ID NO: 4              moltype = AA  length = 479
FEATURE                   Location/Qualifiers
source                    1..479
                          mol_type = protein
                          organism = Pichia pastoris
SEQUENCE: 4
MAGLRFLDIA RPFVSWIPEV ELPYENWGFD EKLIYSFFTA AIYLILSLPI YGVKSSEVVD     60
PVPHLRSALG SEKGTLLELG LLPVITSAFI LQLLAGWKVF KVNFDLVSDR ILFQTLQKIT    120
SVVISIVYAV LLTFCDYFTP GVSTDNVLWS QFLIILQIVV VNFLVTLLVE VIDKDYGFSS    180
GALLLLAVYS ATNFVFGTIG LSTVNTSRSN ESIGALIQLF RNLSSKPIGV AIYDSFFRVN    240
LPNLTQFYLG IAIICVCLFL NNARYEVPIK PNKVRAMASA YPIKLLFNGS LPLLYTWTVL    300
YNLNLIGFFV FKLTNFSLLG NFKVDPFGNN YYEITSGLLY LLTPTFNAEA GLLPNVAKPF    360
VFIAFYVGVS TFFARSWSNI NGSSGKDIAK FFKAQGISLL GKRDASVSKE FNTLVPVASA    420
SGAFLLSFPV AVAEELLGGSG VPTSIGIGLL SGLAILETVL QEWQQSGGAS QFSQYFQTS    479

SEQ ID NO: 5              moltype = DNA  length = 195
FEATURE                   Location/Qualifiers
source                    1..195
                          mol_type = other DNA
                          organism = Pichia pastoris
SEQUENCE: 5
atgtcccaaa aagtcaccga cgtccctctg gaatttgtta aggaaggttc caaattcatc     60
tctaaatgta ctaaaccctc tcagaaggag tactaaaaga tagtaagagc tgttggagtt    120
gggttttttaa tgatgggcgt ggttggttac gttgtcaagc tcattcatat tccaatcaga    180
tatttgattg tttaa                                                     195

SEQ ID NO: 6              moltype = AA  length = 64
FEATURE                   Location/Qualifiers
source                    1..64
                          mol_type = protein
                          organism = Pichia pastoris
SEQUENCE: 6
MSQKVTDVPL EFVKEGSKFI SKCTKPSQKE YLKIVRAVGV GFLMMGVVGY VVKLIHIPIR     60
YLIV                                                                  64

SEQ ID NO: 7              moltype = DNA  length = 326
FEATURE                   Location/Qualifiers
source                    1..326
                          mol_type = other DNA
                          organism = Pichia pastoris
SEQUENCE: 7
atggtaagtg tccagtttga tgagtgcaga atgttccaa gttttagacc agttactaat      60
atttaaagtc tacagcaatt ccaggaggac agagaacgtt agctaaaaga gagcagcaa     120
acttggataa gaaacaggat gaaccaacct ccgccagatc tgccggtgct ggaggttctt    180
cgtctaccat gctaaagttg tacacagacg aggcccaagg tttgaaagtt gatccttaa     240
ttgttcttgt tcttgctgtt ggtttcattt tcagtgtcat tggtttgcac gttgttgcta    300
agctgacagg aaagttgatc aactaa                                         326

SEQ ID NO: 8              moltype = AA  length = 86
FEATURE                   Location/Qualifiers
source                    1..86
                          mol_type = protein
                          organism = Pichia pastoris
SEQUENCE: 8
MSTAIPGGQR TLAKRRAANL DKKQDEPTSA RSAGAGGSSS TMLKLYTDEA QGLKVDPLIV     60
LVLAVGFIFS VIGLHVVAKL TGKLIN                                          86

SEQ ID NO: 9              moltype = DNA  length = 1800
FEATURE                   Location/Qualifiers
source                    1..1800
                          mol_type = other DNA
                          organism = Pichia pastoris
SEQUENCE: 9
atgttgaagg atcagttctt gttatgggtt gctttgatag cgagcgtacc ggtttccggc     60
gtgatggcag ctcctagcga gtccgggcat aacacggttg aaaaacgaga tgccaaaaac    120
gttgttggcg ttcaacagtt ggacttcagc gttctgaggg gtgattcctt cgaaagtgcc    180
tcttcagaga acgtgcctcg gcttgtgagg agagatgaca cgctagaagc tgagctaatc    240
aaccagcaat cattctactt gtcacgactg aaagttggat cacatcaagc ggatattgga    300
atcctagtgg acacaggatc ctctgattta tgggtaatgg actcggtaaa cccatactgc    360
agtagccgtt cccgcgtgaa gagagatata cgcgatgaga gatcgccga atgggatccc    420
atcaatctca agaaaaatga aacttctcag aataaaaatt tttgggattg gctcgttgga    480
actagcacta gttctccttc caccgccacg gcaactggta gtggtagtgg tagtggtagt    540
ggtagtggta gtggtagtgc tgccacagcc gtatcggtaa gttctgcaca ggcaacattg    600
gattgctcta cgtatggaac gtttgatcac gctgattcct cgacgttcca tgacaataat    660
acagactttt tcatctcata cgctgatacc acttttgctt caggaatctg ggttatgac    720
gacgtcatta tcgacggcat agaggtgaaa gaactttcct tcgccgttgc agacatgacc    780
```

```
aattcctcta ttggtgtgtt aggtattgga ctgaaaggcc tagaatccac atatgctagt    840
gcatcttcgg tcagtgaaat gtatcagtat gacaatttgc cagccaagat ggtcaccgat    900
gggttgatca acaaaaatgc atactccttg tacttgaact ccaaggacgc tcaagtggt     960
tccatcctct ttggaggtgt ggatcatgaa aaatattcgg acaattgtt gacagttcca    1020
gtcatcaaca cactcgcttc cagtggttac agagaggcaa ttcgtttaca aattacttta   1080
aatggaatag atgtgaaaaa gggttctgac cagggaactc ttttacaagg gagatttgct   1140
gcattattgg actctggagc tacgctaacg tatgctcctt cttctgtttt aaattcaatt   1200
ggccggaacc tgggcggctc ctatgattcg tcaagacaag cttataccat tcgttgtgtt   1260
tctgcatcag ataccacttc tctggtattc aattttgggg gtgctacagt ggaagtttcc   1320
ctgtacgatc tacagattgc aacatattac accgggggaa gtgccacgca atgtcttatt   1380
ggaatattca gctctggaag tgatgagttt gtgctcggtg ataccttctt gaggtcagcc   1440
tacgtggttt acgatcttga tgggcttgaa gtgtcgcttg cccaagccaa cttcaacgaa   1500
accgattctg atgttgaggc tattacctcc agtgtacctt ccgctactcg tgcatccgga   1560
tacagttcta catggtctgg ttctgccagc ggtacagttg acacttcggt tcagatggaa   1620
tccggtgctg cttccagctc caactcttct ggatcgaata tgggttcctc ttcctcatcg   1680
tcctcttcat cgtcctcgac ttccagtgga gacgaagaag gagggagctc cgccaacagg   1740
gtccccttca gctacctttc tctctgtttg gtagttattc tcggcgtgtg tatagtatag   1800

SEQ ID NO: 10            moltype = AA   length = 599
FEATURE                  Location/Qualifiers
source                   1..599
                         mol_type = protein
                         organism = Pichia pastoris
SEQUENCE: 10
MLKDQFLLWV ALIASVPVSG VMAAPSESGH NTVEKRDAKN VVGVQQLDFS VLRGDSFESA     60
SSENVPRLVR RDDTLEAELI NQQSFYLSRL KVGSHQADIG ILVDTGSSDL WVMDSVNPYC    120
SSRSRVKRDI HDEKIAEWDP INLKKNETSQ NKNFWDWLVG TSTSSPSTAT ATGSGSGSGS    180
GSGSGSAATA VSVSSAQATL DCSTYGTFDH ADSSTFHDNN TDFFISYADT TFASGIWGYD    240
DVIIDGIEVK ELSFAVADMT NSSIGVLGIG LKGLESTYAS ASSVSEMYQY DNLPAKMVTD    300
GLINKNAYSL YLNSKDASSG SILFGGVDHE KYSGQLLTVP VINTLASSGY REAIRLQITL    360
NGIDVKKGSD QGTLLQGRFA ALLDSGATLT YAPSSVLNSI GRNLGGSYDS SRQAYTIRCV    420
SASDTTSLVF NFGGATVEVS LYDLQIATYY TGGSATQCLI GIFSSGSDEF VLGDTFLRSA    480
YVVYDLDGLE VSLAQANFNE TDSDVEAITS SVPSATRASG YSSTWSGSAS GTVYTSVQME    540
SGAASSSNSS GSNMGSSSSS SSSSSSTSSG DEEGGSSANR VPFSYLSLCL VVILGVCIV     599

SEQ ID NO: 11            moltype = DNA   length = 1781
FEATURE                  Location/Qualifiers
source                   1..1781
                         mol_type = other DNA
                         organism = Pichia pastoris
SEQUENCE: 11
atgatcatca accacttggt attgacagcc ctcagcattg cactagcaag tgcgcaactc     60
caatcgcctt tcaaggctaa caagttgcca ttcaaaaagt ttatcattcc aacgacccaa    120
aggaccgttt aattaagaga gatgactacg agtccctcga cttgagacac atcggagtct    180
tgtacactgc agagatccaa attggatctg acgaaactga aattgaggtc attgtcgaca    240
ctggttctgc cgacttgtgg gtcatcgatt ccgacgctgc cgtctgtgag ttatcctacg    300
atgagattga ggccaatagc tttcctcgg ctttctgccaa attcatgacc agatagctc     360
ctccatcaca agagctcctg gatgggctga gtgagtttgg atttgctctc gatggtgaaa    420
tttctcaata acctagccgat aaatctggac gtgtttcgaa aagagaggaa atcaacaag    480
atttcaacat taaccgtgac gagcctgtgt gtgaacagtt tggttccttc gattctagtt    540
cttccgacac ttttccaaagc aacaattcag cttttggtat tgcttaccttt gatgaaacca   600
ctgctaacgg aacttgggtc agggacacag tccgcatcgg cgactttgcc atcagccaac    660
agagttttgc cttagtcaac atcacagata actacatggg aatctgtggt ctcggtcctg    720
ctacccaaca aaccaccaat agtaacccaa ttgcagcaaa cagatttact tatgatggtg    780
ttgtggattc attgcggtcc caaggatta tcaattcagc atcgtttttct gtttacttgt    840
ctccagatga agataacgag cacgacgaat tcagcgacgg agaaattta tttggtgcta    900
ttgatagggc caagatagac gggccattta gacttttccc atatgtcaat ccttacaaac    960
cagtttaccc gatcaatat acttcctacg ttacagtgtc cacaattgcg gtgtcttcgt   1020
cagatgaaac tctcattatt gaaagacgtc ctcgtttggc attaatcgat acaggtgcca   1080
ccttctccta tttgccaacc tacccattga ttcgtttagc gttttccatc catgcaggct   1140
ttgaatatgt ttctcaattg ggactatttg tcattcgtac aagttctctg tctgttgcta   1200
gaaataaggt gattgagttc aagtttgtg aagacgttgt gatccaatcc ccagtttctg   1260
atcatctatt ggacgtctca ggcctttta ctgatggcca acaatactcc gcattaactg   1320
tacgtgaaag tcttgacgga ctttccattc taggtatac attcatcaaa tcggcctact   1380
tattctttga caatgaaaac agccagctgg gtattggtca gatcaacgtc actgatgacg   1440
aggatattga ggtggtcggt gatttcacta ttgaacgaga cccagcctac tcctctactt   1500
ggtctagcga tttacctcat gaaacaccca ctagggcttt gagtactgct tcaggggag    1560
gccttggtac cggaataaac acggccacaa gtcgtgcaag ttctcgttcc acatctggct   1620
ctacttcacg aacttcttct acatctggct tgttcttca ggtgcatctt                1680
ctgctactca aaatgacgaa acatccactg atcttggagc tccagctgca tctttaagtg   1740
caacgccatg tcttttttgcc atcttgctgc tcatgttgta g                       1781

SEQ ID NO: 12            moltype = AA   length = 562
FEATURE                  Location/Qualifiers
source                   1..562
                         mol_type = protein
                         organism = Pichia pastoris
SEQUENCE: 12
MIINHLVLTA LSIALANDYE SLDLRHIGVL YTAEIQIGSD ETEIEVIVDT GSADLWVIDS     60
```

```
DAAVCELSYD EIEANSFSSA SAKFMDKIAP PSQELLDGLS EFGFALDGEI SQYLADKSGR    120
VSKREENQQD FNINRDEPVC EQFGSFDSSS SDTFQSNNSA FGIAYLDGTT ANGTWVRDTV    180
RIGDFAISQQ SFALVNITDN YMGILGLGPA TQQTTNSNPI AANRFTYDGV VDSLRSQGFI    240
NSASFSVYLS PDEDNEHDEF SDGEILFGAI DRAKIDGPFR LFPYVNPYKP VYPDQYTSYV    300
TVSTIAVSSS DETLIIERRP RLALIDTGAT FSYLPTYPLI RLAFSIHGGF EYVSQLGLFV    360
IRTSSLSVAR NKVIEFKFGE DVVIQSPVSD HLLDVSGLFT DGQQYSALTV RESLDGLSIL    420
GDTFIKSAYL FFDNENSQLG IGQINVTDDE DIEVVGDFTI ERDPAYSSTW SSDLPHETPT    480
RALSTASGGG LGTGINTATS RASSRSTSGS TSRTSSTSGS ASGTSSGASS ATQNDETSTD    540
LGAPAASLSA TPCLFAILLL ML                                            562

SEQ ID NO: 13           moltype = AA  length = 1800
FEATURE                 Location/Qualifiers
VARIANT                 1..1800
                        note = Description of Artificial Sequence: Synthetic
                        polypeptide
VARIANT                 7..11
                        note = MISC_FEATURE - This region may encompass "SGGQQ,"
                        "GAGQQ," "GQGPY," "AGQQ" or "SQ," wherein some positions
                        may be absent
VARIANT                 15..19
                        note = MISC_FEATURE - This region may encompass "SGGQQ,"
                        "GAGQQ," "GQGPY," "AGQQ" or "SQ," wherein some positions
                        may be absent
VARIANT                 23..27
                        note = MISC_FEATURE - This region may encompass "SGGQQ,"
                        "GAGQQ," "GQGPY," "AGQQ" or "SQ," wherein some positions
                        may be absent
VARIANT                 31..35
                        note = MISC_FEATURE - This region may encompass "SGGQQ,"
                        "GAGQQ," "GQGPY," "AGQQ" or "SQ," wherein some positions
                        may be absent
VARIANT                 39..43
                        note = MISC_FEATURE - This region may encompass "SGGQQ,"
                        "GAGQQ," "GQGPY," "AGQQ" or "SQ," wherein some positions
                        may be absent
VARIANT                 47..51
                        note = MISC_FEATURE - This region may encompass "SGGQQ,"
                        "GAGQQ," "GQGPY," "AGQQ" or "SQ," wherein some positions
                        may be absent
VARIANT                 55..59
                        note = MISC_FEATURE - This region may encompass "SGGQQ,"
                        "GAGQQ," "GQGPY," "AGQQ" or "SQ," wherein some positions
                        may be absent
VARIANT                 63..67
                        note = MISC_FEATURE - This region may encompass "SGGQQ,"
                        "GAGQQ," "GQGPY," "AGQQ" or "SQ," wherein some positions
                        may be absent
VARIANT                 4..67
                        note = MISC_FEATURE - This region may encompass 4-8
                        repeating "GPG-X1" repeating units, wherein X1 is "SGGQQ,"
                        "GAGQQ," "GQGPY," "AGQQ" or "SQ," and some positions may
                        be absent
VARIANT                 71..90
                        note = MISC_FEATURE - This region may encompass 6-20
                        residues
VARIANT                 97..101
                        note = MISC_FEATURE - This region may encompass "SGGQQ,"
                        "GAGQQ," "GQGPY," "AGQQ" or "SQ," wherein some positions
                        may be absent
VARIANT                 105..109
                        note = MISC_FEATURE - This region may encompass "SGGQQ,"
                        "GAGQQ," "GQGPY," "AGQQ" or "SQ," wherein some positions
                        may be absent
VARIANT                 113..117
                        note = MISC_FEATURE - This region may encompass "SGGQQ,"
                        "GAGQQ," "GQGPY," "AGQQ" or "SQ," wherein some positions
                        may be absent
VARIANT                 121..125
                        note = MISC_FEATURE - This region may encompass "SGGQQ,"
                        "GAGQQ," "GQGPY," "AGQQ" or "SQ," wherein some positions
                        may be absent
VARIANT                 129..133
                        note = MISC_FEATURE - This region may encompass "SGGQQ,"
                        "GAGQQ," "GQGPY," "AGQQ" or "SQ," wherein some positions
                        may be absent
VARIANT                 137..141
                        note = MISC_FEATURE - This region may encompass "SGGQQ,"
                        "GAGQQ," "GQGPY," "AGQQ" or "SQ," wherein some positions
                        may be absent
```

-continued

| | |
|---|---|
| VARIANT | 145..149<br>note = MISC_FEATURE - This region may encompass "SGGQQ," "GAGQQ," "GQGPY," "AGQQ" or "SQ," wherein some positions may be absent |
| VARIANT | 153..157<br>note = MISC_FEATURE - This region may encompass "SGGQQ," "GAGQQ," "GQGPY," "AGQQ" or "SQ," wherein some positions may be absent |
| VARIANT | 94..157<br>note = MISC_FEATURE - This region may encompass 4-8 repeating "GPG-X1" repeating units, wherein X1 is "SGGQQ," "GAGQQ," "GQGPY," "AGQQ" or "SQ," and some positions may be absent |
| VARIANT | 161..180<br>note = MISC_FEATURE - This region may encompass 6-20 residues |
| VARIANT | 187..191<br>note = MISC_FEATURE - This region may encompass "SGGQQ," "GAGQQ," "GQGPY," "AGQQ" or "SQ," wherein some positions may be absent |
| VARIANT | 195..199<br>note = MISC_FEATURE - This region may encompass "SGGQQ," "GAGQQ," "GQGPY," "AGQQ" or "SQ," wherein some positions may be absent |
| VARIANT | 203..207<br>note = MISC_FEATURE - This region may encompass "SGGQQ," "GAGQQ," "GQGPY," "AGQQ" or "SQ," wherein some positions may be absent |
| VARIANT | 211..215<br>note = MISC_FEATURE - This region may encompass "SGGQQ," "GAGQQ," "GQGPY," "AGQQ" or "SQ," wherein some positions may be absent |
| VARIANT | 219..223<br>note = MISC_FEATURE - This region may encompass "SGGQQ," "GAGQQ," "GQGPY," "AGQQ" or "SQ," wherein some positions may be absent |
| VARIANT | 227..231<br>note = MISC_FEATURE - This region may encompass "SGGQQ," "GAGQQ," "GQGPY," "AGQQ" or "SQ," wherein some positions may be absent |
| VARIANT | 235..239<br>note = MISC_FEATURE - This region may encompass "SGGQQ," "GAGQQ," "GQGPY," "AGQQ" or "SQ," wherein some positions may be absent |
| VARIANT | 243..247<br>note = MISC_FEATURE - This region may encompass "SGGQQ," "GAGQQ," "GQGPY," "AGQQ" or "SQ," wherein some positions may be absent |
| VARIANT | 184..247<br>note = MISC_FEATURE - This region may encompass 4-8 repeating "GPG-X1" repeating units, wherein X1 is "SGGQQ," "GAGQQ," "GQGPY," "AGQQ" or "SQ," and some positions may be absent |
| VARIANT | 251..270<br>note = MISC_FEATURE - This region may encompass 6-20 residues |
| VARIANT | 277..281<br>note = MISC_FEATURE - This region may encompass "SGGQQ," "GAGQQ," "GQGPY," "AGQQ" or "SQ," wherein some positions may be absent |
| VARIANT | 285..289<br>note = MISC_FEATURE - This region may encompass "SGGQQ," "GAGQQ," "GQGPY," "AGQQ" or "SQ," wherein some positions may be absent |
| VARIANT | 293..297<br>note = MISC_FEATURE - This region may encompass "SGGQQ," "GAGQQ," "GQGPY," "AGQQ" or "SQ," wherein some positions may be absent |
| VARIANT | 301..305<br>note = MISC_FEATURE - This region may encompass "SGGQQ," "GAGQQ," "GQGPY," "AGQQ" or "SQ," wherein some positions may be absent |
| VARIANT | 309..313<br>note = MISC_FEATURE - This region may encompass "SGGQQ," "GAGQQ," "GQGPY," "AGQQ" or "SQ," wherein some positions may be absent |
| VARIANT | 317..321<br>note = MISC_FEATURE - This region may encompass "SGGQQ," "GAGQQ," "GQGPY," "AGQQ" or "SQ," wherein some positions |

|          |                                                                                                                                                                                                 |
|----------|-------------------------------------------------------------------------------------------------------------------------------------------------------------------------------------------------|
|          | may be absent                                                                                                                                                                                   |
| VARIANT  | 325..329<br>note = MISC_FEATURE - This region may encompass "SGGQQ,"<br>"GAGQQ," "GQGPY," "AGQQ" or "SQ," wherein some positions<br>may be absent                                               |
| VARIANT  | 333..337<br>note = MISC_FEATURE - This region may encompass "SGGQQ,"<br>"GAGQQ," "GQGPY," "AGQQ" or "SQ," wherein some positions<br>may be absent                                               |
| VARIANT  | 274..337<br>note = MISC_FEATURE - This region may encompass 4-8<br>repeating "GPG-X1" repeating units, wherein X1 is "SGGQQ,"<br>"GAGQQ," "GQGPY," "AGQQ" or "SQ," and some positions may<br>be absent |
| VARIANT  | 341..360<br>note = MISC_FEATURE - This region may encompass 6-20<br>residues                                                                                                                    |
| VARIANT  | 367..371<br>note = MISC_FEATURE - This region may encompass "SGGQQ,"<br>"GAGQQ," "GQGPY," "AGQQ" or "SQ," wherein some positions<br>may be absent                                               |
| VARIANT  | 375..379<br>note = MISC_FEATURE - This region may encompass "SGGQQ,"<br>"GAGQQ," "GQGPY," "AGQQ" or "SQ," wherein some positions<br>may be absent                                               |
| VARIANT  | 383..387<br>note = MISC_FEATURE - This region may encompass "SGGQQ,"<br>"GAGQQ," "GQGPY," "AGQQ" or "SQ," wherein some positions<br>may be absent                                               |
| VARIANT  | 391..395<br>note = MISC_FEATURE - This region may encompass "SGGQQ,"<br>"GAGQQ," "GQGPY," "AGQQ" or "SQ," wherein some positions<br>may be absent                                               |
| VARIANT  | 399..403<br>note = MISC_FEATURE - This region may encompass "SGGQQ,"<br>"GAGQQ," "GQGPY," "AGQQ" or "SQ," wherein some positions<br>may be absent                                               |
| VARIANT  | 407..411<br>note = MISC_FEATURE - This region may encompass "SGGQQ,"<br>"GAGQQ," "GQGPY," "AGQQ" or "SQ," wherein some positions<br>may be absent                                               |
| VARIANT  | 415..419<br>note = MISC_FEATURE - This region may encompass "SGGQQ,"<br>"GAGQQ," "GQGPY," "AGQQ" or "SQ," wherein some positions<br>may be absent                                               |
| VARIANT  | 423..427<br>note = MISC_FEATURE - This region may encompass "SGGQQ,"<br>"GAGQQ," "GQGPY," "AGQQ" or "SQ," wherein some positions<br>may be absent                                               |
| VARIANT  | 364..427<br>note = MISC_FEATURE - This region may encompass 4-8<br>repeating "GPG-X1" repeating units, wherein X1 is "SGGQQ,"<br>"GAGQQ," "GQGPY," "AGQQ" or "SQ," and some positions may<br>be absent |
| VARIANT  | 431..450<br>note = MISC_FEATURE - This region may encompass 6-20<br>residues                                                                                                                    |
| VARIANT  | 457..461<br>note = MISC_FEATURE - This region may encompass "SGGQQ,"<br>"GAGQQ," "GQGPY," "AGQQ" or "SQ," wherein some positions<br>may be absent                                               |
| VARIANT  | 465..469<br>note = MISC_FEATURE - This region may encompass "SGGQQ,"<br>"GAGQQ," "GQGPY," "AGQQ" or "SQ," wherein some positions<br>may be absent                                               |
| VARIANT  | 473..477<br>note = MISC_FEATURE - This region may encompass "SGGQQ,"<br>"GAGQQ," "GQGPY," "AGQQ" or "SQ," wherein some positions<br>may be absent                                               |
| VARIANT  | 481..485<br>note = MISC_FEATURE - This region may encompass "SGGQQ,"<br>"GAGQQ," "GQGPY," "AGQQ" or "SQ," wherein some positions<br>may be absent                                               |
| VARIANT  | 489..493<br>note = MISC_FEATURE - This region may encompass "SGGQQ,"<br>"GAGQQ," "GQGPY," "AGQQ" or "SQ," wherein some positions<br>may be absent                                               |
| VARIANT  | 497..501<br>note = MISC_FEATURE - This region may encompass "SGGQQ,"                                                                                                                            |

```
                              "GAGQQ," "GQGPY," "AGQQ" or "SQ," wherein some positions
                              may be absent
VARIANT           505..509
                              note = MISC_FEATURE - This region may encompass "SGGQQ,"
                              "GAGQQ," "GQGPY," "AGQQ" or "SQ," wherein some positions
                              may be absent
VARIANT           513..517
                              note = MISC_FEATURE - This region may encompass "SGGQQ,"
                              "GAGQQ," "GQGPY," "AGQQ" or "SQ," wherein some positions
                              may be absent
VARIANT           454..517
                              note = MISC_FEATURE - This region may encompass 4-8
                              repeating "GPG-X1" repeating units, wherein X1 is "SGGQQ,"
                              "GAGQQ," "GQGPY," "AGQQ" or "SQ," and some positions may
                              be absent
VARIANT           521..540
                              note = MISC_FEATURE - This region may encompass 6-20
                              residues
VARIANT           547..551
                              note = MISC_FEATURE - This region may encompass "SGGQQ,"
                              "GAGQQ," "GQGPY," "AGQQ" or "SQ," wherein some positions
                              may be absent
VARIANT           555..559
                              note = MISC_FEATURE - This region may encompass "SGGQQ,"
                              "GAGQQ," "GQGPY," "AGQQ" or "SQ," wherein some positions
                              may be absent
VARIANT           563..567
                              note = MISC_FEATURE - This region may encompass "SGGQQ,"
                              "GAGQQ," "GQGPY," "AGQQ" or "SQ," wherein some positions
                              may be absent
VARIANT           571..575
                              note = MISC_FEATURE - This region may encompass "SGGQQ,"
                              "GAGQQ," "GQGPY," "AGQQ" or "SQ," wherein some positions
                              may be absent
VARIANT           579..583
                              note = MISC_FEATURE - This region may encompass "SGGQQ,"
                              "GAGQQ," "GQGPY," "AGQQ" or "SQ," wherein some positions
                              may be absent
VARIANT           587..591
                              note = MISC_FEATURE - This region may encompass "SGGQQ,"
                              "GAGQQ," "GQGPY," "AGQQ" or "SQ," wherein some positions
                              may be absent
VARIANT           595..599
                              note = MISC_FEATURE - This region may encompass "SGGQQ,"
                              "GAGQQ," "GQGPY," "AGQQ" or "SQ," wherein some positions
                              may be absent
VARIANT           603..607
                              note = MISC_FEATURE - This region may encompass "SGGQQ,"
                              "GAGQQ," "GQGPY," "AGQQ" or "SQ," wherein some positions
                              may be absent
VARIANT           544..607
                              note = MISC_FEATURE - This region may encompass 4-8
                              repeating "GPG-X1" repeating units, wherein X1 is "SGGQQ,"
                              "GAGQQ," "GQGPY," "AGQQ" or "SQ," and some positions may
                              be absent
VARIANT           611..630
                              note = MISC_FEATURE - This region may encompass 6-20
                              residues
VARIANT           637..641
                              note = MISC_FEATURE - This region may encompass "SGGQQ,"
                              "GAGQQ," "GQGPY," "AGQQ" or "SQ," wherein some positions
                              may be absent
VARIANT           645..649
                              note = MISC_FEATURE - This region may encompass "SGGQQ,"
                              "GAGQQ," "GQGPY," "AGQQ" or "SQ," wherein some positions
                              may be absent
VARIANT           653..657
                              note = MISC_FEATURE - This region may encompass "SGGQQ,"
                              "GAGQQ," "GQGPY," "AGQQ" or "SQ," wherein some positions
                              may be absent
VARIANT           661..665
                              note = MISC_FEATURE - This region may encompass "SGGQQ,"
                              "GAGQQ," "GQGPY," "AGQQ" or "SQ," wherein some positions
                              may be absent
VARIANT           669..673
                              note = MISC_FEATURE - This region may encompass "SGGQQ,"
                              "GAGQQ," "GQGPY," "AGQQ" or "SQ," wherein some positions
                              may be absent
VARIANT           677..681
```

```
VARIANT         685..689
                note = MISC_FEATURE - This region may encompass "SGGQQ,"
                "GAGQQ," "GQGPY," "AGQQ" or "SQ," wherein some positions
                may be absent
VARIANT         693..697
                note = MISC_FEATURE - This region may encompass "SGGQQ,"
                "GAGQQ," "GQGPY," "AGQQ" or "SQ," wherein some positions
                may be absent
VARIANT         634..697
                note = MISC_FEATURE - This region may encompass 4-8
                repeating "GPG-X1" repeating units, wherein X1 is "SGGQQ,"
                "GAGQQ," "GQGPY," "AGQQ" or "SQ," and some positions may
                be absent
VARIANT         701..720
                note = MISC_FEATURE - This region may encompass 6-20
                residues
VARIANT         727..731
                note = MISC_FEATURE - This region may encompass "SGGQQ,"
                "GAGQQ," "GQGPY," "AGQQ" or "SQ," wherein some positions
                may be absent
VARIANT         735..739
                note = MISC_FEATURE - This region may encompass "SGGQQ,"
                "GAGQQ," "GQGPY," "AGQQ" or "SQ," wherein some positions
                may be absent
VARIANT         743..747
                note = MISC_FEATURE - This region may encompass "SGGQQ,"
                "GAGQQ," "GQGPY," "AGQQ" or "SQ," wherein some positions
                may be absent
VARIANT         751..755
                note = MISC_FEATURE - This region may encompass "SGGQQ,"
                "GAGQQ," "GQGPY," "AGQQ" or "SQ," wherein some positions
                may be absent
VARIANT         759..763
                note = MISC_FEATURE - This region may encompass "SGGQQ,"
                "GAGQQ," "GQGPY," "AGQQ" or "SQ," wherein some positions
                may be absent
VARIANT         767..771
                note = MISC_FEATURE - This region may encompass "SGGQQ,"
                "GAGQQ," "GQGPY," "AGQQ" or "SQ," wherein some positions
                may be absent
VARIANT         775..779
                note = MISC_FEATURE - This region may encompass "SGGQQ,"
                "GAGQQ," "GQGPY," "AGQQ" or "SQ," wherein some positions
                may be absent
VARIANT         783..787
                note = MISC_FEATURE - This region may encompass "SGGQQ,"
                "GAGQQ," "GQGPY," "AGQQ" or "SQ," wherein some positions
                may be absent
VARIANT         724..787
                note = MISC_FEATURE - This region may encompass 4-8
                repeating "GPG-X1" repeating units, wherein X1 is "SGGQQ,"
                "GAGQQ," "GQGPY," "AGQQ" or "SQ," and some positions may
                be absent
VARIANT         791..810
                note = MISC_FEATURE - This region may encompass 6-20
                residues
VARIANT         817..821
                note = MISC_FEATURE - This region may encompass "SGGQQ,"
                "GAGQQ," "GQGPY," "AGQQ" or "SQ," wherein some positions
                may be absent
VARIANT         825..829
                note = MISC_FEATURE - This region may encompass "SGGQQ,"
                "GAGQQ," "GQGPY," "AGQQ" or "SQ," wherein some positions
                may be absent
VARIANT         833..837
                note = MISC_FEATURE - This region may encompass "SGGQQ,"
                "GAGQQ," "GQGPY," "AGQQ" or "SQ," wherein some positions
                may be absent
VARIANT         841..845
                note = MISC_FEATURE - This region may encompass "SGGQQ,"
                "GAGQQ," "GQGPY," "AGQQ" or "SQ," wherein some positions
                may be absent
VARIANT         849..853
                note = MISC_FEATURE - This region may encompass "SGGQQ,"
                "GAGQQ," "GQGPY," "AGQQ" or "SQ," wherein some positions
                may be absent
```

-continued

| | | |
|---|---|---|
| VARIANT | 857..861 | |
| | note = MISC_FEATURE - This region may encompass "SGGQQ," "GAGQQ," "GQGPY," "AGQQ" or "SQ," wherein some positions may be absent | |
| VARIANT | 865..869 | |
| | note = MISC_FEATURE - This region may encompass "SGGQQ," "GAGQQ," "GQGPY," "AGQQ" or "SQ," wherein some positions may be absent | |
| VARIANT | 873..877 | |
| | note = MISC_FEATURE - This region may encompass "SGGQQ," "GAGQQ," "GQGPY," "AGQQ" or "SQ," wherein some positions may be absent | |
| VARIANT | 814..877 | |
| | note = MISC_FEATURE - This region may encompass 4-8 repeating "GPG-X1" repeating units, wherein X1 is "SGGQQ," "GAGQQ," "GQGPY," "AGQQ" or "SQ," and some positions may be absent | |
| VARIANT | 881..900 | |
| | note = MISC_FEATURE - This region may encompass 6-20 residues | |
| VARIANT | 907..911 | |
| | note = MISC_FEATURE - This region may encompass "SGGQQ," "GAGQQ," "GQGPY," "AGQQ" or "SQ," wherein some positions may be absent | |
| VARIANT | 915..919 | |
| | note = MISC_FEATURE - This region may encompass "SGGQQ," "GAGQQ," "GQGPY," "AGQQ" or "SQ," wherein some positions may be absent | |
| VARIANT | 923..927 | |
| | note = MISC_FEATURE - This region may encompass "SGGQQ," "GAGQQ," "GQGPY," "AGQQ" or "SQ," wherein some positions may be absent | |
| VARIANT | 931..935 | |
| | note = MISC_FEATURE - This region may encompass "SGGQQ," "GAGQQ," "GQGPY," "AGQQ" or "SQ," wherein some positions may be absent | |
| VARIANT | 939..943 | |
| | note = MISC_FEATURE - This region may encompass "SGGQQ," "GAGQQ," "GQGPY," "AGQQ" or "SQ," wherein some positions may be absent | |
| VARIANT | 947..951 | |
| | note = MISC_FEATURE - This region may encompass "SGGQQ," "GAGQQ," "GQGPY," "AGQQ" or "SQ," wherein some positions may be absent | |
| VARIANT | 955..959 | |
| | note = MISC_FEATURE - This region may encompass "SGGQQ," "GAGQQ," "GQGPY," "AGQQ" or "SQ," wherein some positions may be absent | |
| VARIANT | 963..967 | |
| | note = MISC_FEATURE - This region may encompass "SGGQQ," "GAGQQ," "GQGPY," "AGQQ" or "SQ," wherein some positions may be absent | |
| VARIANT | 904..967 | |
| | note = MISC_FEATURE - This region may encompass 4-8 repeating "GPG-X1" repeating units, wherein X1 is "SGGQQ," "GAGQQ," "GQGPY," "AGQQ" or "SQ," and some positions may be absent | |
| VARIANT | 971..990 | |
| | note = MISC_FEATURE - This region may encompass 6-20 residues | |
| VARIANT | 997..1001 | |
| | note = MISC_FEATURE - This region may encompass "SGGQQ," "GAGQQ," "GQGPY," "AGQQ" or "SQ," wherein some positions may be absent | |
| VARIANT | 1005..1009 | |
| | note = MISC_FEATURE - This region may encompass "SGGQQ," "GAGQQ," "GQGPY," "AGQQ" or "SQ," wherein some positions may be absent | |
| VARIANT | 1013..1017 | |
| | note = MISC_FEATURE - This region may encompass "SGGQQ," "GAGQQ," "GQGPY," "AGQQ" or "SQ," wherein some positions may be absent | |
| VARIANT | 1021..1025 | |
| | note = MISC_FEATURE - This region may encompass "SGGQQ," "GAGQQ," "GQGPY," "AGQQ" or "SQ," wherein some positions may be absent | |
| VARIANT | 1029..1033 | |
| | note = MISC_FEATURE - This region may encompass "SGGQQ," "GAGQQ," "GQGPY," "AGQQ" or "SQ," wherein some positions | |

-continued

```
                         may be absent
VARIANT                  1037..1041
                         note = MISC_FEATURE - This region may encompass "SGGQQ,"
                         "GAGQQ," "GQGPY," "AGQQ" or "SQ," wherein some positions
                         may be absent
VARIANT                  1045..1049
                         note = MISC_FEATURE - This region may encompass "SGGQQ,"
                         "GAGQQ," "GQGPY," "AGQQ" or "SQ," wherein some positions
                         may be absent
VARIANT                  1053..1057
                         note = MISC_FEATURE - This region may encompass "SGGQQ,"
                         "GAGQQ," "GQGPY," "AGQQ" or "SQ," wherein some positions
                         may be absent
VARIANT                  994..1057
                         note = MISC_FEATURE - This region may encompass 4-8
                         repeating "GPG-X1" repeating units, wherein X1 is "SGGQQ,"
                         "GAGQQ," "GQGPY," "AGQQ" or "SQ," and some positions may
                         be absent
VARIANT                  1061..1080
                         note = MISC_FEATURE - This region may encompass 6-20
                         residues
VARIANT                  1087..1091
                         note = MISC_FEATURE - This region may encompass "SGGQQ,"
                         "GAGQQ," "GQGPY," "AGQQ" or "SQ," wherein some positions
                         may be absent
VARIANT                  1095..1099
                         note = MISC_FEATURE - This region may encompass "SGGQQ,"
                         "GAGQQ," "GQGPY," "AGQQ" or "SQ," wherein some positions
                         may be absent
VARIANT                  1103..1107
                         note = MISC_FEATURE - This region may encompass "SGGQQ,"
                         "GAGQQ," "GQGPY," "AGQQ" or "SQ," wherein some positions
                         may be absent
VARIANT                  1111..1115
                         note = MISC_FEATURE - This region may encompass "SGGQQ,"
                         "GAGQQ," "GQGPY," "AGQQ" or "SQ," wherein some positions
                         may be absent
VARIANT                  1119..1123
                         note = MISC_FEATURE - This region may encompass "SGGQQ,"
                         "GAGQQ," "GQGPY," "AGQQ" or "SQ," wherein some positions
                         may be absent
VARIANT                  1127..1131
                         note = MISC_FEATURE - This region may encompass "SGGQQ,"
                         "GAGQQ," "GQGPY," "AGQQ" or "SQ," wherein some positions
                         may be absent
VARIANT                  1135..1139
                         note = MISC_FEATURE - This region may encompass "SGGQQ,"
                         "GAGQQ," "GQGPY," "AGQQ" or "SQ," wherein some positions
                         may be absent
VARIANT                  1143..1147
                         note = MISC_FEATURE - This region may encompass "SGGQQ,"
                         "GAGQQ," "GQGPY," "AGQQ" or "SQ," wherein some positions
                         may be absent
VARIANT                  1084..1147
                         note = MISC_FEATURE - This region may encompass 4-8
                         repeating "GPG-X1" repeating units, wherein X1 is "SGGQQ,"
                         "GAGQQ," "GQGPY," "AGQQ" or "SQ," and some positions may
                         be absent
VARIANT                  1151..1170
                         note = MISC_FEATURE - This region may encompass 6-20
                         residues
VARIANT                  1177..1181
                         note = MISC_FEATURE - This region may encompass "SGGQQ,"
                         "GAGQQ," "GQGPY," "AGQQ" or "SQ," wherein some positions
                         may be absent
VARIANT                  1185..1189
                         note = MISC_FEATURE - This region may encompass "SGGQQ,"
                         "GAGQQ," "GQGPY," "AGQQ" or "SQ," wherein some positions
                         may be absent
VARIANT                  1193..1197
                         note = MISC_FEATURE - This region may encompass "SGGQQ,"
                         "GAGQQ," "GQGPY," "AGQQ" or "SQ," wherein some positions
                         may be absent
VARIANT                  1201..1205
                         note = MISC_FEATURE - This region may encompass "SGGQQ,"
                         "GAGQQ," "GQGPY," "AGQQ" or "SQ," wherein some positions
                         may be absent
VARIANT                  1209..1213
                         note = MISC_FEATURE - This region may encompass "SGGQQ,"
```

-continued

```
                         "GAGQQ," "GQGPY," "AGQQ" or "SQ," wherein some positions
                         may be absent
VARIANT                  1217..1221
                         note = MISC_FEATURE - This region may encompass "SGGQQ,"
                         "GAGQQ," "GQGPY," "AGQQ" or "SQ," wherein some positions
                         may be absent
VARIANT                  1225..1229
                         note = MISC_FEATURE - This region may encompass "SGGQQ,"
                         "GAGQQ," "GQGPY," "AGQQ" or "SQ," wherein some positions
                         may be absent
VARIANT                  1233..1237
                         note = MISC_FEATURE - This region may encompass "SGGQQ,"
                         "GAGQQ," "GQGPY," "AGQQ" or "SQ," wherein some positions
                         may be absent
VARIANT                  1174..1237
                         note = MISC_FEATURE - This region may encompass 4-8
                         repeating "GPG-X1" repeating units, wherein X1 is "SGGQQ,"
                         "GAGQQ," "GQGPY," "AGQQ" or "SQ," and some positions may
                         be absent
VARIANT                  1241..1260
                         note = MISC_FEATURE - This region may encompass 6-20
                         residues
VARIANT                  1267..1271
                         note = MISC_FEATURE - This region may encompass "SGGQQ,"
                         "GAGQQ," "GQGPY," "AGQQ" or "SQ," wherein some positions
                         may be absent
VARIANT                  1275..1279
                         note = MISC_FEATURE - This region may encompass "SGGQQ,"
                         "GAGQQ," "GQGPY," "AGQQ" or "SQ," wherein some positions
                         may be absent
VARIANT                  1283..1287
                         note = MISC_FEATURE - This region may encompass "SGGQQ,"
                         "GAGQQ," "GQGPY," "AGQQ" or "SQ," wherein some positions
                         may be absent
VARIANT                  1291..1295
                         note = MISC_FEATURE - This region may encompass "SGGQQ,"
                         "GAGQQ," "GQGPY," "AGQQ" or "SQ," wherein some positions
                         may be absent
VARIANT                  1299..1303
                         note = MISC_FEATURE - This region may encompass "SGGQQ,"
                         "GAGQQ," "GQGPY," "AGQQ" or "SQ," wherein some positions
                         may be absent
VARIANT                  1307..1311
                         note = MISC_FEATURE - This region may encompass "SGGQQ,"
                         "GAGQQ," "GQGPY," "AGQQ" or "SQ," wherein some positions
                         may be absent
VARIANT                  1315..1319
                         note = MISC_FEATURE - This region may encompass "SGGQQ,"
                         "GAGQQ," "GQGPY," "AGQQ" or "SQ," wherein some positions
                         may be absent
VARIANT                  1323..1327
                         note = MISC_FEATURE - This region may encompass "SGGQQ,"
                         "GAGQQ," "GQGPY," "AGQQ" or "SQ," wherein some positions
                         may be absent
VARIANT                  1264..1327
                         note = MISC_FEATURE - This region may encompass 4-8
                         repeating "GPG-X1" repeating units, wherein X1 is "SGGQQ,"
                         "GAGQQ," "GQGPY," "AGQQ" or "SQ," and some positions may
                         be absent
VARIANT                  1331..1350
                         note = MISC_FEATURE - This region may encompass 6-20
                         residues
VARIANT                  1357..1361
                         note = MISC_FEATURE - This region may encompass "SGGQQ,"
                         "GAGQQ," "GQGPY," "AGQQ" or "SQ," wherein some positions
                         may be absent
VARIANT                  1365..1369
                         note = MISC_FEATURE - This region may encompass "SGGQQ,"
                         "GAGQQ," "GQGPY," "AGQQ" or "SQ," wherein some positions
                         may be absent
VARIANT                  1373..1377
                         note = MISC_FEATURE - This region may encompass "SGGQQ,"
                         "GAGQQ," "GQGPY," "AGQQ" or "SQ," wherein some positions
                         may be absent
VARIANT                  1381..1385
                         note = MISC_FEATURE - This region may encompass "SGGQQ,"
                         "GAGQQ," "GQGPY," "AGQQ" or "SQ," wherein some positions
                         may be absent
VARIANT                  1389..1393
```

-continued

```
                            note = MISC_FEATURE - This region may encompass "SGGQQ,"
                            "GAGQQ," "GQGPY," "AGQQ" or "SQ," wherein some positions
                            may be absent
VARIANT                     1397..1401
                            note = MISC_FEATURE - This region may encompass "SGGQQ,"
                            "GAGQQ," "GQGPY," "AGQQ" or "SQ," wherein some positions
                            may be absent
VARIANT                     1405..1409
                            note = MISC_FEATURE - This region may encompass "SGGQQ,"
                            "GAGQQ," "GQGPY," "AGQQ" or "SQ," wherein some positions
                            may be absent
VARIANT                     1413..1417
                            note = MISC_FEATURE - This region may encompass "SGGQQ,"
                            "GAGQQ," "GQGPY," "AGQQ" or "SQ," wherein some positions
                            may be absent
VARIANT                     1354..1417
                            note = MISC_FEATURE - This region may encompass 4-8
                            repeating "GPG-X1" repeating units, wherein X1 is "SGGQQ,"
                            "GAGQQ," "GQGPY," "AGQQ" or "SQ," and some positions may
                            be absent
VARIANT                     1421..1440
                            note = MISC_FEATURE - This region may encompass 6-20
                            residues
VARIANT                     1447..1451
                            note = MISC_FEATURE - This region may encompass "SGGQQ,"
                            "GAGQQ," "GQGPY," "AGQQ" or "SQ," wherein some positions
                            may be absent
VARIANT                     1455..1459
                            note = MISC_FEATURE - This region may encompass "SGGQQ,"
                            "GAGQQ," "GQGPY," "AGQQ" or "SQ," wherein some positions
                            may be absent
VARIANT                     1463..1467
                            note = MISC_FEATURE - This region may encompass "SGGQQ,"
                            "GAGQQ," "GQGPY," "AGQQ" or "SQ," wherein some positions
                            may be absent
VARIANT                     1471..1475
                            note = MISC_FEATURE - This region may encompass "SGGQQ,"
                            "GAGQQ," "GQGPY," "AGQQ" or "SQ," wherein some positions
                            may be absent
VARIANT                     1479..1483
                            note = MISC_FEATURE - This region may encompass "SGGQQ,"
                            "GAGQQ," "GQGPY," "AGQQ" or "SQ," wherein some positions
                            may be absent
VARIANT                     1487..1491
                            note = MISC_FEATURE - This region may encompass "SGGQQ,"
                            "GAGQQ," "GQGPY," "AGQQ" or "SQ," wherein some positions
                            may be absent
VARIANT                     1495..1499
                            note = MISC_FEATURE - This region may encompass "SGGQQ,"
                            "GAGQQ," "GQGPY," "AGQQ" or "SQ," wherein some positions
                            may be absent
VARIANT                     1503..1507
                            note = MISC_FEATURE - This region may encompass "SGGQQ,"
                            "GAGQQ," "GQGPY," "AGQQ" or "SQ," wherein some positions
                            may be absent
VARIANT                     1444..1507
                            note = MISC_FEATURE - This region may encompass 4-8
                            repeating "GPG-X1" repeating units, wherein X1 is "SGGQQ,"
                            "GAGQQ," "GQGPY," "AGQQ" or "SQ," and some positions may
                            be absent
VARIANT                     1511..1530
                            note = MISC_FEATURE - This region may encompass 6-20
                            residues
VARIANT                     1537..1541
                            note = MISC_FEATURE - This region may encompass "SGGQQ,"
                            "GAGQQ," "GQGPY," "AGQQ" or "SQ," wherein some positions
                            may be absent
VARIANT                     1545..1549
                            note = MISC_FEATURE - This region may encompass "SGGQQ,"
                            "GAGQQ," "GQGPY," "AGQQ" or "SQ," wherein some positions
                            may be absent
VARIANT                     1553..1557
                            note = MISC_FEATURE - This region may encompass "SGGQQ,"
                            "GAGQQ," "GQGPY," "AGQQ" or "SQ," wherein some positions
                            may be absent
VARIANT                     1561..1565
                            note = MISC_FEATURE - This region may encompass "SGGQQ,"
                            "GAGQQ," "GQGPY," "AGQQ" or "SQ," wherein some positions
                            may be absent
```

-continued

| | |
|---|---|
| VARIANT | 1569..1573<br>note = MISC_FEATURE - This region may encompass "SGGQQ,"<br>"GAGQQ," "GQGPY," "AGQQ" or "SQ," wherein some positions<br>may be absent |
| VARIANT | 1577..1581<br>note = MISC_FEATURE - This region may encompass "SGGQQ,"<br>"GAGQQ," "GQGPY," "AGQQ" or "SQ," wherein some positions<br>may be absent |
| VARIANT | 1585..1589<br>note = MISC_FEATURE - This region may encompass "SGGQQ,"<br>"GAGQQ," "GQGPY," "AGQQ" or "SQ," wherein some positions<br>may be absent |
| VARIANT | 1593..1597<br>note = MISC_FEATURE - This region may encompass "SGGQQ,"<br>"GAGQQ," "GQGPY," "AGQQ" or "SQ," wherein some positions<br>may be absent |
| VARIANT | 1534..1597<br>note = MISC_FEATURE - This region may encompass 4-8<br>repeating "GPG-X1" repeating units, wherein X1 is "SGGQQ,"<br>"GAGQQ," "GQGPY," "AGQQ" or "SQ," and some positions may<br>be absent |
| VARIANT | 1601..1620<br>note = MISC_FEATURE - This region may encompass 6-20<br>residues |
| VARIANT | 1627..1631<br>note = MISC_FEATURE - This region may encompass "SGGQQ,"<br>"GAGQQ," "GQGPY," "AGQQ" or "SQ," wherein some positions<br>may be absent |
| VARIANT | 1635..1639<br>note = MISC_FEATURE - This region may encompass "SGGQQ,"<br>"GAGQQ," "GQGPY," "AGQQ" or "SQ," wherein some positions<br>may be absent |
| VARIANT | 1643..1647<br>note = MISC_FEATURE - This region may encompass "SGGQQ,"<br>"GAGQQ," "GQGPY," "AGQQ" or "SQ," wherein some positions<br>may be absent |
| VARIANT | 1651..1655<br>note = MISC_FEATURE - This region may encompass "SGGQQ,"<br>"GAGQQ," "GQGPY," "AGQQ" or "SQ," wherein some positions<br>may be absent |
| VARIANT | 1659..1663<br>note = MISC_FEATURE - This region may encompass "SGGQQ,"<br>"GAGQQ," "GQGPY," "AGQQ" or "SQ," wherein some positions<br>may be absent |
| VARIANT | 1667..1671<br>note = MISC_FEATURE - This region may encompass "SGGQQ,"<br>"GAGQQ," "GQGPY," "AGQQ" or "SQ," wherein some positions<br>may be absent |
| VARIANT | 1675..1679<br>note = MISC_FEATURE - This region may encompass "SGGQQ,"<br>"GAGQQ," "GQGPY," "AGQQ" or "SQ," wherein some positions<br>may be absent |
| VARIANT | 1683..1687<br>note = MISC_FEATURE - This region may encompass "SGGQQ,"<br>"GAGQQ," "GQGPY," "AGQQ" or "SQ," wherein some positions<br>may be absent |
| VARIANT | 1624..1687<br>note = MISC_FEATURE - This region may encompass 4-8<br>repeating "GPG-X1" repeating units, wherein X1 is "SGGQQ,"<br>"GAGQQ," "GQGPY," "AGQQ" or "SQ," and some positions may<br>be absent |
| VARIANT | 1691..1710<br>note = MISC_FEATURE - This region may encompass 6-20<br>residues |
| VARIANT | 1717..1721<br>note = MISC_FEATURE - This region may encompass "SGGQQ,"<br>"GAGQQ," "GQGPY," "AGQQ" or "SQ," wherein some positions<br>may be absent |
| VARIANT | 1725..1729<br>note = MISC_FEATURE - This region may encompass "SGGQQ,"<br>"GAGQQ," "GQGPY," "AGQQ" or "SQ," wherein some positions<br>may be absent |
| VARIANT | 1733..1737<br>note = MISC_FEATURE - This region may encompass "SGGQQ,"<br>"GAGQQ," "GQGPY," "AGQQ" or "SQ," wherein some positions<br>may be absent |
| VARIANT | 1741..1745<br>note = MISC_FEATURE - This region may encompass "SGGQQ,"<br>"GAGQQ," "GQGPY," "AGQQ" or "SQ," wherein some positions |

|  |  |
|---|---|
|  | may be absent |
| VARIANT | 1749..1753 |
|  | note = MISC_FEATURE - This region may encompass "SGGQQ," "GAGQQ," "GQGPY," "AGQQ" or "SQ," wherein some positions may be absent |
| VARIANT | 1757..1761 |
|  | note = MISC_FEATURE - This region may encompass "SGGQQ," "GAGQQ," "GQGPY," "AGQQ" or "SQ," wherein some positions may be absent |
| VARIANT | 1765..1769 |
|  | note = MISC_FEATURE - This region may encompass "SGGQQ," "GAGQQ," "GQGPY," "AGQQ" or "SQ," wherein some positions may be absent |
| VARIANT | 1773..1777 |
|  | note = MISC_FEATURE - This region may encompass "SGGQQ," "GAGQQ," "GQGPY," "AGQQ" or "SQ," wherein some positions may be absent |
| VARIANT | 1714..1777 |
|  | note = MISC_FEATURE - This region may encompass 4-8 repeating "GPG-X1" repeating units, wherein X1 is "SGGQQ," "GAGQQ," "GQGPY," "AGQQ" or "SQ," and some positions may be absent |
| VARIANT | 1781..1800 |
|  | note = MISC_FEATURE - This region may encompass 6-20 residues |
| VARIANT | 1..1800 |
|  | note = MISC_FEATURE - This sequence may encompass 2-20 "GGY-[GPG-X1]n1-GPS-(A)n2" repeating units, wherein X1 is "SGGQQ," "GAGQQ," "GQGPY," "AGQQ" or "SQ," n1 is 4-8 and n2 is 6-20 and some positions may be absent |
| source | 1..1800 |
|  | mol_type = protein |
|  | organism = synthetic construct |

SEQUENCE: 13

```
GGYGPGXXXX XGPGXXXXXG PGXXXXXXGPG XXXXXGPGXX XXXGPGXXXX XGPGXXXXXG    60
PGXXXXXGPS AAAAAAAAAA AAAAAAAAAA GGYGPGXXXX XGPGXXXXXG PGXXXXXXGPG   120
XXXXXGPGXX XXXGPGXXXX XGPGXXXXXG PGXXXXXGPS AAAAAAAAAA AAAAAAAAAA   180
GGYGPGXXXX XGPGXXXXXG PGXXXXXXGPG XXXXXGPGXX XXXGPGXXXX XGPGXXXXXG   240
PGXXXXXGPS AAAAAAAAAA AAAAAAAAAA GGYGPGXXXX XGPGXXXXXG PGXXXXXXGPG   300
XXXXXGPGXX XXXGPGXXXX XGPGXXXXXG PGXXXXXGPS AAAAAAAAAA AAAAAAAAAA   360
GGYGPGXXXX XGPGXXXXXG PGXXXXXXGPG XXXXXGPGXX XXXGPGXXXX XGPGXXXXXG   420
PGXXXXXGPS AAAAAAAAAA AAAAAAAAAA GGYGPGXXXX XGPGXXXXXG PGXXXXXXGPG   480
XXXXXGPGXX XXXGPGXXXX XGPGXXXXXG PGXXXXXGPS AAAAAAAAAA AAAAAAAAAA   540
GGYGPGXXXX XGPGXXXXXG PGXXXXXXGPG XXXXXGPGXX XXXGPGXXXX XGPGXXXXXG   600
PGXXXXXGPS AAAAAAAAAA AAAAAAAAAA GGYGPGXXXX XGPGXXXXXG PGXXXXXXGPG   660
XXXXXGPGXX XXXGPGXXXX XGPGXXXXXG PGXXXXXGPS AAAAAAAAAA AAAAAAAAAA   720
GGYGPGXXXX XGPGXXXXXG PGXXXXXXGPG XXXXXGPGXX XXXGPGXXXX XGPGXXXXXG   780
PGXXXXXGPS AAAAAAAAAA AAAAAAAAAA GGYGPGXXXX XGPGXXXXXG PGXXXXXXGPG   840
XXXXXGPGXX XXXGPGXXXX XGPGXXXXXG PGXXXXXGPS AAAAAAAAAA AAAAAAAAAA   900
GGYGPGXXXX XGPGXXXXXG PGXXXXXXGPG XXXXXGPGXX XXXGPGXXXX XGPGXXXXXG   960
PGXXXXXGPS AAAAAAAAAA AAAAAAAAAA GGYGPGXXXX XGPGXXXXXG PGXXXXXXGPG  1020
XXXXXGPGXX XXXGPGXXXX XGPGXXXXXG PGXXXXXGPS AAAAAAAAAA AAAAAAAAAA  1080
GGYGPGXXXX XGPGXXXXXG PGXXXXXXGPG XXXXXGPGXX XXXGPGXXXX XGPGXXXXXG  1140
PGXXXXXGPS AAAAAAAAAA AAAAAAAAAA GGYGPGXXXX XGPGXXXXXG PGXXXXXXGPG  1200
XXXXXGPGXX XXXGPGXXXX XGPGXXXXXG PGXXXXXGPS AAAAAAAAAA AAAAAAAAAA  1260
GGYGPGXXXX XGPGXXXXXG PGXXXXXXGPG XXXXXGPGXX XXXGPGXXXX XGPGXXXXXG  1320
PGXXXXXGPS AAAAAAAAAA AAAAAAAAAA GGYGPGXXXX XGPGXXXXXG PGXXXXXXGPG  1380
XXXXXGPGXX XXXGPGXXXX XGPGXXXXXG PGXXXXXGPS AAAAAAAAAA AAAAAAAAAA  1440
GGYGPGXXXX XGPGXXXXXG PGXXXXXXGPG XXXXXGPGXX XXXGPGXXXX XGPGXXXXXG  1500
PGXXXXXGPS AAAAAAAAAA AAAAAAAAAA GGYGPGXXXX XGPGXXXXXG PGXXXXXXGPG  1560
XXXXXGPGXX XXXGPGXXXX XGPGXXXXXG PGXXXXXGPS AAAAAAAAAA AAAAAAAAAA  1620
GGYGPGXXXX XGPGXXXXXG PGXXXXXXGPG XXXXXGPGXX XXXGPGXXXX XGPGXXXXXG  1680
PGXXXXXGPS AAAAAAAAAA AAAAAAAAAA GGYGPGXXXX XGPGXXXXXG PGXXXXXXGPG  1740
XXXXXGPGXX XXXGPGXXXX XGPGXXXXXG PGXXXXXGPS AAAAAAAAAA AAAAAAAAAA  1800
```

|  |  |
|---|---|
| SEQ ID NO: 14 | moltype = AA length = 5 |
| FEATURE | Location/Qualifiers |
| VARIANT | 1..5 |
|  | note = Description of Artificial Sequence: Synthetic peptide |
| source | 1..5 |
|  | mol_type = protein |
|  | organism = synthetic construct |

SEQUENCE: 14
SGGQQ                                                                  5

|  |  |
|---|---|
| SEQ ID NO: 15 | moltype = AA length = 5 |
| FEATURE | Location/Qualifiers |
| VARIANT | 1..5 |
|  | note = Description of Artificial Sequence: Synthetic peptide |

```
source                      1..5
                            mol_type = protein
                            organism = synthetic construct
SEQUENCE: 15
GAGQQ                                                                    5

SEQ ID NO: 16               moltype = AA  length = 5
FEATURE                     Location/Qualifiers
VARIANT                     1..5
                            note = Description of Artificial Sequence: Synthetic peptide
source                      1..5
                            mol_type = protein
                            organism = synthetic construct
SEQUENCE: 16
GQGPY                                                                    5

SEQ ID NO: 17               moltype = AA  length = 4
FEATURE                     Location/Qualifiers
VARIANT                     1..4
                            note = Description of Artificial Sequence: Synthetic peptide
source                      1..4
                            mol_type = protein
                            organism = synthetic construct
SEQUENCE: 17
AGQQ                                                                     4

SEQ ID NO: 18               moltype = AA  length = 70
FEATURE                     Location/Qualifiers
VARIANT                     1..70
                            note = Description of Artificial Sequence: Synthetic
                             polypeptide
VARIANT                     7..11
                            note = MISC_FEATURE - This region may encompass "SGGQQ,"
                             "GAGQQ," "GQGPY," "AGQQ" or "SQ," wherein some positions
                             may be absent
VARIANT                     15..19
                            note = MISC_FEATURE - This region may encompass "SGGQQ,"
                             "GAGQQ," "GQGPY," "AGQQ" or "SQ," wherein some positions
                             may be absent
VARIANT                     23..27
                            note = MISC_FEATURE - This region may encompass "SGGQQ,"
                             "GAGQQ," "GQGPY," "AGQQ" or "SQ," wherein some positions
                             may be absent
VARIANT                     31..35
                            note = MISC_FEATURE - This region may encompass "SGGQQ,"
                             "GAGQQ," "GQGPY," "AGQQ" or "SQ," wherein some positions
                             may be absent
VARIANT                     39..43
                            note = MISC_FEATURE - This region may encompass "SGGQQ,"
                             "GAGQQ," "GQGPY," "AGQQ" or "SQ," wherein some positions
                             may be absent
VARIANT                     47..51
                            note = MISC_FEATURE - This region may encompass "SGGQQ,"
                             "GAGQQ," "GQGPY," "AGQQ" or "SQ," wherein some positions
                             may be absent
VARIANT                     55..59
                            note = MISC_FEATURE - This region may encompass "SGGQQ,"
                             "GAGQQ," "GQGPY," "AGQQ" or "SQ," wherein some positions
                             may be absent
VARIANT                     63..67
                            note = MISC_FEATURE - This region may encompass "SGGQQ,"
                             "GAGQQ," "GQGPY," "AGQQ" or "SQ," wherein some positions
                             may be absent
VARIANT                     4..67
                            note = MISC_FEATURE - This region may encompass 4-8
                             "GPG-X1" repeating units, wherein X1 is "SGGQQ," "GAGQQ,"
                             "GQGPY," "AGQQ" or "SQ," and some positions may be absent
source                      1..70
                            mol_type = protein
                            organism = synthetic construct
SEQUENCE: 18
GGYGPGXXXX XGPGXXXXXG PGXXXXXGPG XXXXXGPGXX XXXGPGXXXX XGPGXXXXXG         60
PGXXXXXGPS                                                               70

SEQ ID NO: 19               moltype = AA  length = 20
FEATURE                     Location/Qualifiers
VARIANT                     1..20
                            note = Description of Artificial Sequence: Synthetic peptide
VARIANT                     1..20
```

```
                        note = MISC_FEATURE - This sequence may encompass 6-20
                         residues
source                  1..20
                        mol_type = protein
                        organism = synthetic construct
SEQUENCE: 19
AAAAAAAAAA AAAAAAAAAA                                                      20

SEQ ID NO: 20           moltype = DNA  length = 2835
FEATURE                 Location/Qualifiers
misc_feature            1..2835
                        note = Description of Artificial Sequence: Synthetic
                         polynucleotide
source                  1..2835
                        mol_type = other DNA
                        organism = synthetic construct
SEQUENCE: 20
ggtggttacg gtccaggcgc tggtcaacaa ggtccaggaa gtggtggtca acaaggacct    60
ggcggtcaag gaccctacgg tagtggccaa caaggtccag gtggagcagg acagcagggt   120
ccgggaggcc aaggacctta cggaccaggt gctgctgctg ccgccgctgc cgctgccgga   180
ggttacggtc caggagccgg acaacagggt ccaggtggag ctggacaaca aggtccagga   240
tcacaaggtc ctggtggaca aggtcctac gtcctggtg ctggtcaaca gggaccaggt    300
agtcaaggac ctggttcagg tggtcagcag ggtccaggag acagggtcc ttacggccct   360
tctgccgctg cagcagcagc cgctgccgca ggaggatacg gacctggtgc tggacaacga   420
tctcaaggac caggaggaca aggtccttat ggacctggcg ctgccaaca aggacctggt    480
tctcaaggtc caggttcagg aggccaacaa ggcccaggag gtcaaggacc atacggacca   540
tccgctgcgg cagctgcagc tgctgcaggt ggatatggcc caggagccgg acaacagggt   600
cctggttcac aaggtccagg atctggtggt caacagggac caggcggcca gggaccttat   660
ggtccaggag ccgctgcagc agcagcagct gttggaggtt acggcctgg tgccggtcaa    720
caaggcccag gatctcaggg tcctggatct ggaggacaac aaggtcctgg aggtcagggt   780
ccatacggac cttcagcagc agctgctgct gcagccgctg tggttatgg acctggtgct    840
ggtcaacaag gaccgggttc tcagggtccg ggttcaggag gtcagcaggg ccctggtgga   900
caaggacctt atggacctag tgcggctgca gcagctgccg ccgcaggtgg ttacggtcca   960
ggcgctggtc aacaaggtcc aggaagtggt ggtcaacaag gacctggcgg tcaaggaccc   1020
tacggtagtg gccaacaagg tccaggtgga gcaggacagc agggtccgg gaggccaagga   1080
ccttacggac caggtgctgc tgctgccgcc gctgccgctg ccggaggtta cggtccagga   1140
gccgacaac agggtccagg tggagctgga caacaaggtc aggatcaca aggtcctggt    1200
ggacaaggtc catacggtcc tggtgctggt caacaggga caggtagtca aggacctggt   1260
tcaggtggtc agcaggtcc aggagacag ggtccttacg gcccttctgc cgctgcagca    1320
gcagccgctg ccgcaggagg atacggacct ggtgctggac aacgatctca aggaccagga   1380
ggacaaggtc cttatggacc tggcgctgg caacaaggac ctggttctca gggtccaggt    1440
tcaggaggcc aacaaggccc aggaggtcaa ggaccatacg gaccatccgc tgcggcagct   1500
gcagctgctg caggtggata tgcccagga gccggacaac agggtccagg ttcacaaggt    1560
ccaggatctg gtggtcaaca gggaccaggc ggcagggac cttatggtcc aggagccgct   1620
gcagcagcag cagctgttgg aggttacggc cctggtgccg gtcaacaagg cccaggatct   1680
cagggtcctg gatctggagg acaacaaggt cctgaggtc agggtccata cggaccttca    1740
gcagcagctg ctgctgcagc cgctggtgg tatggacctg gtgctggtca acaaggaccg     1800
ggttctcagg gtccgggttc aggaggtcag cagggccctg gtggacaagg acttatgga    1860
cctagtgcgg ctgcagcagc tgccgccgca ggtggttacg gtccaggcgc tggtcaacaa   1920
ggtccaggaa gtggtggtca acaaggacct ggcggtcaag gaccctacgg tagtggccaa   1980
caaggtccag gtggagcagg acagcagggt ccgggaggcc aaggaccta cggaccaggt    2040
gctgctgctg ccgccgctgc cgctgccgga ggttacggtc caggagccgg acaacagggt   2100
ccaggtggag ctggacaaca aggtccagga tcacaaggtc ctggtggaca aggtccatac   2160
ggtcctggtg ctggtcaaca gggaccaggt agtcaaggac ctggttcagg tggtcagcag   2220
ggtccaggag acagggtcc ttacggccct tctgccgctg cagcagcagc cgctgccgca    2280
ggaggatacg gacctggtgc tggacaacga tctcaaggac caggaggaca aggtccttat   2340
ggacctggcg ctgccaaca aggacctggt tctcagggtc caggttcagg aggccaacaa    2400
ggcccaggag gtcaaggacc atacggacca tccgctgcgg cagctgcagc tgctgcaggt   2460
ggatatggcc caggagccgg acaacagggt cctggttcac aaggtccagg atctggtggt   2520
caacagggac caggcggcca gggaccttat ggtccaggag ccgctgcagc agcagcagct   2580
gttggaggtt acggcctgg tgccggtcaa caaggcccag gatctcaggg tcctggatct    2640
ggaggacaac aaggtcctgg aggtcagggt ccatacggac cttcagcagc agctgctgct   2700
gcagccgctg tggttatgg acctggtgct ggtcaacaag gaccgggttc tcagggtccg    2760
ggttcaggag gtcagcaggg ccctggtgga caaggacctt atggacctag tgcggctgca   2820
gcagctgccg ccgca                                                   2835

SEQ ID NO: 21           moltype = AA  length = 945
FEATURE                 Location/Qualifiers
VARIANT                 1..945
                        note = Description of Artificial Sequence: Synthetic
                         polypeptide
source                  1..945
                        mol_type = protein
                        organism = synthetic construct
SEQUENCE: 21
GGYGPGAGQQ GPGSGGQQGP GGQGPYGSGQ QGPGGAGQQG PGGQGPYGPG AAAAAAAAG     60
GYGPGAGQQG PGGAGQQGPG SQGPGGQGPY GPGAGQQGPG SQGPGSGGQQ GPGGQGPYGP    120
SAAAAAAAAA GGYGPGAGQR SQGPGGQGPY GPGAGQQGPG SQGPGSGGQQ GPGGQGPYGP    180
SAAAAAAAAG GYGPGAGQQG PGSQGPGSGG QQGPGGQGPY GPGAAAAAAA VGGYGPGAGQ    240
```

```
QGPGSQGPGS GGQQGPGGQG PYGPSAAAAA AAAGGYGPGA GQQGPGSQGP GSGGQQGPGG  300
QGPYGPSAAA AAAAAGGYGP GAGQQGPGSG GQQGPGGQGP YGSGQQGPGG AGQQGPGGQG  360
PYGPGAAAAA AAAAGGYGPG AGQQGPGGAG QQGPGSQGPG GQPYGPGAG QQGPGSQGPG   420
SGGQQGPGGG GPYGPSAAAA AAAAGGYGP GAGQRSQGPG GQPYGPGAG QQGPGSQGPG    480
SGGQQGPGGG GPYGPSAAAA AAAAGGYGPG AGQQGPGSQG PGSGGQQGPG GQPYGPGAA   540
AAAAAVGGYG PGAGQQGPGS QGPGSGGQQG PGGQGPYGPS AAAAAAAAGG YGPGAGQQGP  600
GSQGPGSGGQ QGPGGQGPYG PSAAAAAAAA GGYGPGAGQQ GPGSGGQQGP GGQGPYGSGQ  660
QGPGGAGQQG PGGQGPYGPG AAAAAAAAAG GYGPGAGQQG PGGAGQQGPG SQGPGGQGPY  720
GPGAGQQGPG SQGPGSGGQQ GPGGQGPYGP SAAAAAAAAG GGYGPGAGQR SQGPGGQGPY  780
GPGAGQQGPG SQGPGSGGQQ GPGGQGPYGP SAAAAAAAAG GYGPGAGQQG PGSQGPGSGG  840
QQGPGGQGPY GPGAAAAAAA VGGYGPGAGQ QGPGSQGPGS GGQQGPGGQG PYGPSAAAAA  900
AAAGGYGPGA GQQGPGSQGP GSGGQQGPGG QGPYGPSAAA AAAAA                 945

SEQ ID NO: 22          moltype = AA  length = 315
FEATURE                Location/Qualifiers
VARIANT                1..315
                       note = Description of Artificial Sequence: Synthetic
                        polypeptide
source                 1..315
                       mol_type = protein
                       organism = synthetic construct
SEQUENCE: 22
GGYGPGAGQQ GPGSGGQQGP GGQGPYGSGQ QGPGGAGQQG PGGQGPYGPG AAAAAAAAAG   60
GYGPGAGQQG PGGAGQQGPG SQGPGGQGPY GPGAGQQGPG SQGPGSGGQQ GPGGQGPYGP  120
SAAAAAAAAG GGYGPGAGQR SQGPGGQGPY GPGAGQQGPG SQGPGSGGQQ GPGGQGPYGP  180
SAAAAAAAAG GYGPGAGQQG PGSQGPGSGG QQGPGGQGPY GPGAAAAAAA VGGYGPGAGQ  240
QGPGSQGPGS GGQQGPGGQG PYGPSAAAAA AAAGGYGPGA GQQGPGSQGP GSGGQQGPGG  300
QGPYGPSAAA AAAAA                                                   315

SEQ ID NO: 23          moltype = AA  length = 5
FEATURE                Location/Qualifiers
VARIANT                1..5
                       note = Description of Artificial Sequence: Synthetic peptide
source                 1..5
                       mol_type = protein
                       organism = synthetic construct
SEQUENCE: 23
SGAGG                                                                5

SEQ ID NO: 24          moltype = AA  length = 5
FEATURE                Location/Qualifiers
VARIANT                1..5
                       note = Description of Artificial Sequence: Synthetic peptide
source                 1..5
                       mol_type = protein
                       organism = synthetic construct
SEQUENCE: 24
GSGAG                                                                5

SEQ ID NO: 25          moltype = AA  length = 5
FEATURE                Location/Qualifiers
VARIANT                1..5
                       note = Description of Artificial Sequence: Synthetic peptide
source                 1..5
                       mol_type = protein
                       organism = synthetic construct
SEQUENCE: 25
GGSGA                                                                5

SEQ ID NO: 26          moltype = AA  length = 181
FEATURE                Location/Qualifiers
source                 1..181
                       mol_type = protein
                       organism = Aliatypus gulosus
SEQUENCE: 26
GAASSSSTII TTKSASASAA ADASAAATAS AASRSSANAA ASAFAQSFSS ILLESGYFCS    60
IFGSSISSSY AAAIASAASR AAAESNGYTT HAYACAKAVA SAVERVTSGA DAYAYAQAIS  120
DALSHALLYT GRLNTANANS LASAFAYAFA NAAAQASASS ASAGAASASG AASASGAGSA  180
S                                                                  181

SEQ ID NO: 27          moltype = AA  length = 126
FEATURE                Location/Qualifiers
source                 1..126
                       mol_type = protein
                       organism = Plectreurys tristis
SEQUENCE: 27
GAGAGAGAGA GAGAGAGSGA STSVSTSSSS GSGAGAGAGS GAGSGAGAGS GAGAGAGAGG   60
AGAGFGSGLG LGYGVGLSSA QAQAQAQAAA QAQAQAQAQA YAAAQAQAQA QAQAAAAAA   120
AAAAAA                                                             126
```

```
SEQ ID NO: 28             moltype = AA  length = 239
FEATURE                   Location/Qualifiers
source                    1..239
                          mol_type = protein
                          organism = Plectreurys tristis
SEQUENCE: 28
GAAQKQPSGE SSVATASAAA TSVTSGGAPV GKPGVPAPIF YPQGPLQQGP APGPSNVQPG    60
TSQQGPIGGV GGSNAFSSSF ASALSLNRGF TEVISSASAT AVASAFQKGL APYGTAFALS   120
AASAAADAYN SIGSGANAFA YAQAFARVLY PLVQQYGLSS SAKASAFASA IASSFSSGTS   180
GQGPSIGQQQ PPVTISAASA SAGASAAAVG GGQVGQGPYG GQQQSTAASA SAAAATATS    239

SEQ ID NO: 29             moltype = AA  length = 182
FEATURE                   Location/Qualifiers
source                    1..182
                          mol_type = protein
                          organism = Araneus gemmoides
SEQUENCE: 29
GNVGYQLGLK VANSLGLGNA QALASSLSQA VSAVGVGASS NAYANAVSNA VGQVLAGQGI    60
LNAANAGSLA SSFASALSSS AASVASQSAS QSQAASQSQA AASAFRQAAS QSASQSDSRA   120
GSQSSTKTTS TSTSGSQADS RSASSSASQA SASAFAQQSS ASLSSSSSFS SAFSSATSIS   180
AV                                                                  182

SEQ ID NO: 30             moltype = AA  length = 180
FEATURE                   Location/Qualifiers
source                    1..180
                          mol_type = protein
                          organism = Argiope aurantia
SEQUENCE: 30
GSLASSFASA LSASAASVAS SAAAQAASQS QAAASAFSRA ASQSASQSAA RSGAQSISTT    60
TTTSTAGSQA ASQSASSAAS QASASSFARA SSASLAASSS FSSAFSSANS LSALGNVGYQ   120
LGFNVANNLG IGNAAGLGNA LSQAVSSVGV GASSSTYANA VSNAVGQFLA GQGILNAANA   180

SEQ ID NO: 31             moltype = AA  length = 199
FEATURE                   Location/Qualifiers
source                    1..199
                          mol_type = protein
                          organism = Deinopis spinosa
SEQUENCE: 31
GASASAYASA ISNAVGPYLY GLGLFNQANA ASFASSFASA VSSAVASASA SAASSAYAQS    60
AAAQAQAASS AFSQAAAQSA AAASAGASAG AGASAGAGAV AGAGAVAGAG AVAGASAAAA   120
SQAAASSSAS AVASAFAQSA SYALASSSAF ANAFASATSA GYLGSLAYQL GLTTAYNLGL   180
SNAQAFASTL SQAVTGVGL                                                199

SEQ ID NO: 32             moltype = AA  length = 171
FEATURE                   Location/Qualifiers
source                    1..171
                          mol_type = protein
                          organism = Nephila clavipes
SEQUENCE: 32
GATAASYGNA LSTAAAQFFA TAGLLNAGNA SALASSFARA FSASAESQSF AQSQAFQQAS    60
AFQQAASRSA SQSAAEAGST SSSTTTTTSA ARSQAASQSA SSSYSSAFAQ AASSSLATSS   120
ALSRAFSSVS SASAASSLAY SIGLSAARSL GIADAAGLAG VLARAAGALG Q            171

SEQ ID NO: 33             moltype = AA  length = 268
FEATURE                   Location/Qualifiers
source                    1..268
                          mol_type = protein
                          organism = Argiope trifasciata
SEQUENCE: 33
GGAPGGGPGG AGPGGAGFGP GGGAGFGPGG GAGFGPGGAA GGPGGPGGPG GPGGAGGYGP    60
GGAGGYGPGG VGPGGAGGYG PGGAGGYGPG GSGPGGAGPG GAGGEGPVTV DVDVTVGPEG   120
VGGGPGGAGP GGAGFGPGGG AGFGPGGAPG APGPGGPGG PGGPGGPGGV GPGGAGGYGP    180
GGAGGVGPAG TGGFGPGGAG GFGPGGAGGF GPGGAGGFGP AGAGGYGPGG VGPGGAGGFG   240
PGGVGPGGSG PGGAGGEGPV TVDVDVSV                                      268

SEQ ID NO: 34             moltype = AA  length = 420
FEATURE                   Location/Qualifiers
source                    1..420
                          mol_type = protein
                          organism = Nephila clavipes
SEQUENCE: 34
GVSYGPGGAG GPYGPGGPYG PGGEGPGGAG GPYGPGGVGP GGSGPGGYGP GGAGPGGYGP    60
GGSGPGGYGP GGSGPGGYGP GGSGPGGYGP GGYGPGGSGP GGSGPGGSGP                120
GGYGPGGTGP GGSGPGGYGP GGSGPGGSGP GGYGPGGSGP GGFGPGGSGP GGYGPGGSGP   180
GGAGPGGVGP GGFGPGGAGP GGAAPGGAGP GGAGPGGAGP GGAGPGGAGP GGAGPGGAGG   240
AGGAGGSGGA GGSGGTTIIE DLDITIDGAD GPITISEELP ISGAGGSGPG GAGPGGVGPG   300
GSGPGGVGPG GSGPGGVGPG GSGPGGVGPG GAGGPYGPGG SGPGGAGGAG GPGGAYGPGG   360
SYGPGGSGGP GGAGGPYGPG GEGPGGAGGP YGPGGAGGPY GPGGAGGPYG PGGEGGPYGP   420
```

```
SEQ ID NO: 35            moltype = AA  length = 376
FEATURE                  Location/Qualifiers
source                   1..376
                         mol_type = protein
                         organism = Latrodectus hesperus
SEQUENCE: 35
GINVDSDIGS VTSLILSGST LQMTIPAGGD DLSGGYPGGF PAGAQPSGGA PVDFGGPSAG   60
GDVAAKLARS LASTLASSGV FRAAFNSRVS TPVAVQLTDA LVQKIASNLG LDYATASKLR  120
KASQAVSKVR MGSDTNAYAL AISSALAEVL SSSGKVADAN INQIAPQLAS GIVLGVSTTA  180
PQFGVDLSSI NVNLDISNVA RNMQASIQGG PAPITAEGPD FGAGYPGGAP TDLSGLDMGA  240
PSDGSRGGDA TAKLLQALVP ALLKSDVFRA IYKRGTRKQV VQYVTNSALQ QAASSLGLDA  300
STISQLQTKA TQALSSVSAD SDSTAYAKAF GLAIAQVLGT SGQVNDANVN QIGAKLATGI  360
LRGSSAVAPR LGIDLS                                                 376

SEQ ID NO: 36            moltype = AA  length = 200
FEATURE                  Location/Qualifiers
source                   1..200
                         mol_type = protein
                         organism = Argiope trifasciata
SEQUENCE: 36
GAGYTGPSGP STGPSGYPGP LGGGAPFGQS GFGGSAGPQG GFGATGGASA GLISRVANAL   60
ANTSTLRTVL RTGVSQQIAS SVVQRAAQSL ASTLGVDGNN LARFAVQAVS RLPAGSDTSA  120
YAQAFSSALF NAGVLNASNI DTLGSRVLSA LLNGVSSAAQ GLGINVDSGS VQSDISSSSS  180
FLSTSSSSAS YSQASASSTS                                             200

SEQ ID NO: 37            moltype = AA  length = 357
FEATURE                  Location/Qualifiers
source                   1..357
                         mol_type = protein
                         organism = Uloborus diversus
SEQUENCE: 37
GASAADIATA IAASVATSLQ SNGVLTASNV SQLNQLASY VSSGLSSTAS SLGIQLGASL    60
GAGFGASAGL SASTDISSSV EATSASTLSS SASSTSVVSS INAQLVPALA QTAVLNAAFS  120
NINTQNAIRI AELLTQQVGR QYGLSGSDVA TASSQIRSAL YSVQQGSASS AYVSAIVGPL  180
ITALSSRGVV NASNSSQIAS SLATAILQFT ANVAPQFGIS IPTSAVQSDL STISQSLTAI  240
SSQTSSSVDS STSAFGGISG PSGPSPYGPQ PSGPTFGPGP SLSGLTGFTA TFASSFKSTL  300
ASSTQFQLIA QSNLDVQTRS SLISKVLINA LSSLGISASV ASSIAASSSQ SLLSVSA     357

SEQ ID NO: 38            moltype = AA  length = 32
FEATURE                  Location/Qualifiers
source                   1..32
                         mol_type = protein
                         organism = Euprosthenops australis
SEQUENCE: 38
GGQGGQGQGR YGQGAGSSAA AAAAAAAAAA AA                                32

SEQ ID NO: 39            moltype = AA  length = 42
FEATURE                  Location/Qualifiers
source                   1..42
                         mol_type = protein
                         organism = Tetragnatha kauaiensis
SEQUENCE: 39
GGLGGGQGAG QGGQQGAGQG GYGSGLGGAG QGASAAAAAA AA                     42

SEQ ID NO: 40            moltype = AA  length = 42
FEATURE                  Location/Qualifiers
source                   1..42
                         mol_type = protein
                         organism = Argiope aurantia
SEQUENCE: 40
GGYGPGAGQQ GPGSQGPGSG GQQGPGGLGP YGPSAAAAAA AA                     42

SEQ ID NO: 41            moltype = AA  length = 46
FEATURE                  Location/Qualifiers
source                   1..46
                         mol_type = protein
                         organism = Deinopis spinosa
SEQUENCE: 41
GPGGYGGPGQ QGPGQGQYGP GTGQQGQGPS GQQGPAGAAA AAAAAA                 46

SEQ ID NO: 42            moltype = AA  length = 42
FEATURE                  Location/Qualifiers
source                   1..42
                         mol_type = protein
                         organism = Nephila clavata
SEQUENCE: 42
GPGGYGLGQQ GPGQQGPGQQ GPAGYGPSGL SGPGGAAAAA AA                     42
```

```
SEQ ID NO: 43           moltype = AA   length = 3360
FEATURE                 Location/Qualifiers
source                  1..3360
                        mol_type = protein
                        organism = Argiope bruennichi
SEQUENCE: 43
MNWSIRLALL GFVVLSTQTV FAVGQAATPW ENSQLAEDFI NSFLRFIAQS GAFSPNQLDD    60
MSSIGDTLKT AIEKMAQSRK SSKSKLQALN MAFASSMAEI AVAEQGGLSL EAKTNAIANA   120
LASAFLETTG FVNQQFVSEI KSLIYMIAQA SSNEISGSAA AAGGGSGGGG GSGQGGYGQG   180
ASASASAAAA YGSAPQGAGG PAPQGPSQQG PVSQGPYGPG AAAAAAAAGG YGPGAGQQGP   240
GSQGPGSGGQ QGPGSQGPGS GGQQGPGGQG PYGPSAAAAA AAAAGGYGPG AGQQGPGSQG   300
PGSGGQQGPG GQGPYGPGAA AAAAVGGYG PGAGQQGPGS QGPGSGGQQG PGGQGPYGPS   360
AAAAAAAAGG YGPGAGQQGP GSQGPGSGGQ QGPGGQGPYG PSAAAAAAAA GGYGPGAGQQ   420
GPGSGGQQGP GGQGPYGSGQ QGPGAGQQGP PGGQGPYGPG AAAAAAAAAG GYGPGAGQQG   480
PGGAGQQGPG SQGPGGQGPY GPGAGQQGPG SQGPGSGGQQ GPGGQGPYGP SAAAAAAAAG   540
GYGPGAGQQG PGSQGPGSGG QQGPGSQGPG SGGQQGPGGQ GPYGPSAAAA AAAAGGYGPG   600
AGQQGPGSQG PGSGGQQGPG GQGPYGPGAA AAAAVGGYG PGAGQQGPGS QGPGSGGQQG   660
PGGQGPYGPS AAAAAAAAGG YGPGAGQQGP GSQGPGSGGQ QGPGGQGPYG PSAAAAAAAA   720
GGYGPGAGQQ GPGSGGQQGP GGQGPYGSGQ QGPGGAGQQG PGGQGPYGPG AAAAAAAAAG   780
GYGPGAGQQG PGGAGQQGPG SQGPGGQGPY GPGAGQQGPG SQGPGSGGQQ GPGGQGPYGP   840
SAAAAAAAAA GGYGPGAGQR SQGPGGQGPY GPGAGQQGPG SQGPGSGGQQ GPGGQGPYGP   900
SAAAAAAAAG PGAGRQGPGS QGPGSGGQQG PGGQGPYGPS AAAAAAAAAG GARRQGPGSQ   960
GPGSGGQQGP GGQGPYGSGQ QGPGAGQQGP PGGQGPYGPG AAAAAAAAAG GYGPGAGQQG  1020
PGGAGQQGPG SQGPGGQGPY GPGAGQQGPG SQGPGSGGQQ GPGGQGPYGP SAAAAAAAAG  1080
GYGPGAGQQG PGSQGPGSGG QQGPGGQGPY GPGAAAAAAA VGGYGPGAGQ QGPGSQGPGS  1140
GGQQGPGGQG PYGPSAAAAA AAAGGYGPGA GQQGPGSGGQ QGPGGQGPYG QGPYGPSAAA  1200
AAAAAGGYGP GAGQQGPGSG GQQGPGGQGP YGSGQQGPGG AGQQGPGGQG PYGPGAAAAA  1260
AAAAGGYGPG AGQQGPGGAG QQGPEGPGSQ GPGSGGQQGP GGQGPYGPGA AAAAAAVGGY  1320
GPGAGQQGPG SQGPGSGGQQ GPGGQGPYGP SAAAAAAAAG GYGPGAGQQG PGSQGPGSGG  1380
QQGPGGQGPY GPSAAAAAAA AGGYGPGAGQ QGPGSGGQQG PGGQGPYGSA AAAAAAAAG  1440
GPGGQGPYGP GAAAAAAAAA GGYGPGAGQQ GPGAGQQGPG SQGPGGQGPY GPGAGQQGP   1500
GSQGPGSGGQ QGPGGQGPYG PSAAAAAAAA GGYGPGAGQQ GPGSQGPGSG GQQGPGSQGP  1560
GSGGQQGPGG QGPYGPSAAA AAAAAGGYG PGAGQQGPGS QGPGSGGQQG PGGQGPYGPG  1620
AAAAAAVGG YGPGAGQQGP GSQGPGSGGQ QGPGGQGPYG PSAAAAAAAA GGYGPGAGQQ   1680
GPGSQGPGSG GQQGPGGQGP YGPSAAAAAA AAGGYGPGAG QQGPGSGGQQ GPGGQGPYGS  1740
GQQGPGGAGQ QGPGGQGPYG PGAAAAAAAA AGGYGPGAGQ QGPGGAGQQG PGSQGPGGQG  1800
PYGPGAGQQG PGSQGPGSGG QQGPGGQGPY GPSAAAAAAA AGGYGPGAGQ QGPGSQGPGS  1860
GGQQGPGGQG PYGPSAAAAA AAAGGYGPGA GQQGPGSGGQ QGPGGQGPYG SGQQGPGGAG  1920
QQGPGGQGPY GGGYGPGAGQ QGPGSQGPGS GGQQGPGGQG PYGPSAAAAA AAAGPGARRQ  1980
GPGSQGPGSG GQQGPGGQGP YGSGQQGPGG AGQQGPGGQG PYGPGAAAAA AAAAGGYGPG  2040
AGQQGPGGAG QQGPGSQGPG GQGPYGPGAG QQGPGSQGPG SGGQQGPGGQ GPYGPSAAAA  2100
AAAAGGYGPG AGQQGPGSQG PGSGGQQGPG GQGPYGPGAA AAAAAVGGY GPGAGQQGPG   2160
SQGPGSGGQQ GPGGQGPYGP SAAAAAAAAG GYGPGAGQQG PGSQGPGSGG QQGPGGQGPY  2220
GPSAAAAAAA AGGYGPGAGQ QGPGSGGQQG PGGQGPYGSG QQGPGGAGQQ GPGGQGPYGP  2280
GAAAAAAAAA GGYGPGAGQQ GPGGAGQQGP GSQGPGGQGP YGPGAGQQGP GSQGPGSGGQ  2340
QGPGGQGPYG PSAAAAAAAA GPGAGRQGPG SQGPGSGGQQ GPGGQGPYGP SAAAAAAAAG  2400
PGARRQGPGS QGPGSGGQQG PGGQGPYGSG QQGPGGAGQQ GPGGQGPYGP GAAAAAAAAA  2460
GGYGPGAGQQ GPGGAGQQGP GSQGPGGQGP YGPGAGQQGP GSQGPGSGGQ QGPGSQGPYG  2520
PSAAAAAAAA GGYGPGAGQQ GPGSQGPGSG GQQGPGGQGP YGPSAAAAAA AAGGYGPGAG  2580
QQGPGSGGQQ GPGGQGPYGS GQQGPGGAGQ QGPGGQGPYG PGAAAAAAAA AGGYGPGAGQ  2640
QGPGSQGPGS GGQQGPGGQG PGSGGQQGPG GQGPYGPSAA AAAAAAGGY GPGAGQQGPG   2700
SQGPGSGGQQ GPGGQGPYGP GAAAAAAAVG GYGPGAGQQG PGSQGPGSGG QQGPGGQGPY  2760
GPSAAAAAAA AGGYGPGAGQ QGPGSQGPGS GGQQGPGGQG PYGPSAAAAA AAAGGYGPGA  2820
GQQGPGSGGQ QGPGGQGPYG SGQQGPGGAG QQGPGGQGPY GPGAAAAAAA AGGYGPGAG   2880
QQGPGGAGQQ GPGSQGPGGQ GPYGPGAGQQ GPGSQGPGSG GQQGPGGQGP YGPSAAAAAA  2940
AAGGYGPGAG QQGPGSQGPG SGGQQGPGGQ GPYGPGAAAA AAAVGGYGPG AGQQGPGSQG  3000
PGSGGQQGPG GQGPYGPSAA AAAAGGYG PGAGQQGPGS QGPGSGGQQG PGGQGPYGPS   3060
AAAAAAAAGG YGPGAGQQGP GSGGQQGPGG QGPYGSGQQG PGGAGQQGPG GQGPYGPGAA  3120
AAAAAAGGY GPGAGQQGPG GAGQQGPGSQ GPGGQGPYGP GAGQQGPGSQ GPGSGGQQGP   3180
GGQGPYGPSA AAAAAAGGY GPGAGQQGPG SQGPGSGGQQ GPGGQGPYGP SAAAAAAAAG  3240
GYGPGAGQQG PSSQAPVASA AASRLSSPQA SARVSSAVST LVSSGPTSPA ALSNAISSVV  3300
SQVSASNPGL SGCDVLVQAL LEIVSALVHI LGSSSIGQIN YAASSQYAQM VGNSVAQALG  3360

SEQ ID NO: 44           moltype = AA   length = 3129
FEATURE                 Location/Qualifiers
source                  1..3129
                        mol_type = protein
                        organism = Latrodectus hesperus
SEQUENCE: 44
MTWSTRLALS FLFVLCTQSL YALAQANTPW SSKANADAFI NSFISAASNT GSFSQDQMED    60
MSLIGNTLMA AMDNMGGRIT PSKLQALDMA FASSVAEIAA SEGGDLGVTT NAIADALTSA   120
FYQTTGVVNS RFISEIRSLI GMFAQASAND VYASAGSSGG GGYGASSASA ASASAAAPSG   180
VAYQAPAQAQ ISFTLRGQQP VSYGQGGAGP GGAGAAAAAA AAGGAGQGGG QGGYGQGGYG   240
QGGAGQGGSG AAAAAAAAAG GTGQGGAGA GAGAAAAAAA AAGGAGQGGQ GGYGQGGGYGQ   300
GGTGQGGAGA AAAAAAAGGA GQGGQGGYGQ GGYGQGGYGQ GGSGAAAAAA AAGGAGQGGQ   360
QGGYGQGGYG QGGAGQGGAG AAAAAAAAGG GAGQGGYGRG GAGQGGAAAA AAAAGAGQG   420
GYGQGAGQG GSGAAAAAAA AGGAGQGGQG GYGQGGYGQG GSGAAAAAAA AGGAGQGGQG  480
GYGQGGYGQG GAGQGGAGAA AAAAAGGAG QGGQGGYGQG GYGQGGAGQG GAGAAAAAAA   540
AGGAGQGGQG GYGQGGYGQG GAGQGGAGAA AAAAAGGAG QGGQGGYGQG GYGQGGAGQG   600
```

```
GAAAAAAAAA GGAGQGGYGR GGAGQGGAAA AAGAGQGGYG GQGAGQGGAG AAAAAAAAGG    660
AGQGGQGGYG RGGYGQGGAG QGGAGAAAAA AAAGGAGQGG QGGYGQGGYG QGGAGQGGAA    720
AAAAAAGGAG QGGYGRGGAG QGGAGAAAAA AAGAGQGGYG GQGAGQGGYG AAAAAAAAGG    780
AGQGGQGDYG RGGYGQGGAG QGGAGAAAAA AAAGGAGQGG QGGYGQGGYG QGGAGQGGAA    840
AAASAAAAGG AGQGGYGRGG AGQGGAAAAA GAGQGGYGGA GAGQGGAGAA AAAAAGGAGA    900
QGGQGGYGRG GYGQGGAGQG GAGAAAAATA AGGAGQGGGG GYGQGGYGQG GAGQGGAAAA    960
AAAAAGGAGQ GGYGRGGAGQ GGAAAAAAAA AGAGQGGYGG QGAGQGGAGA AAAAGGAGQ    1020
GGQGGYGRGG YGQGGAGQGG AGAAAAAAAA GGAGQGGQGG YGQGGYGQGG AGQGGAAAAA   1080
AAAAGGAGQG GYGRGGAGQG GAAAAAGAGQ GGYGQGAGQG GAGAAAAAS RGAGQGGGGQ    1140
YGRGGYGQGG AGQGGAGAAA AAAAGGAGQ GGQGGYGQGG YGQGGAGQGG AAAAAAAAGG    1200
AGQGGYGRGG AGQGGAAAAA GAGQGGYGGQ GAGQGGAGAA AAAAAGGAG QGGQGGYGRG    1260
GYGQGGAGQG GAGAAAAAAA AGGAGQGGQG GYGQGGYGQG GAGQGGAAAA AAAAGGAGQ    1320
GGYGRGGAGQ GGAAAAAAA AGSGQGGYGG QGAGQGGAGA AAAAAAGGAG GQGGQGGYGR    1380
GGYGQGGAGQ GGAGAAAAAA AAGGAGQGGG GGYGQGGYGQ GGAGQGGAAA AAAAAAGGA    1440
GQGGYGRGGA GQGGAAAAAG AGQGGYGGQG AGQGGAGAAA AAAAGGAGQ GGQGGYGRGG    1500
YGQGGAGQGG AGTAAAAAAA GGAGQGGQGG YGQGGYGQGG AGQGGAAAAA AAAAGGAGQG   1560
GYGRGGAGQG GAAAAAAAAA GAGQGGYGGQ GAGQGGAGAA AAAAAGGAG QGGQGGYGRG    1620
GYGQGGAGQG GAGAAAAAAA AGGASQGGQG GYGQGDYGQG GAGQGGAAA AAAAAAGGAG    1680
GYGRGGAGQG GAAAAGAGQ GGYGGQGAGQ GGAGAAAAAA AAGGAGRGGQ GGYGRGGYGQ    1740
GGAGQGGAGA AAAAAAGGA GQGGQGGYGQ GGYGQGGVTGQ GGAAAAAAAA AGGAGQGGYG   1800
RGGAGQGGAA AAAAAAGAG QGGYGGQGAG QGGAGAAAAA AAAGGAGQGG QGGYGRGGYG    1860
QGGAGQGGAA AAAAAAAGG AGQGGQGGYG QGGYGQGGYG QGGAGQGGAA AAAAAAGGAG    1920
QGGYGRGGAG QGGAAAAAGA GQGGYGQGGA GQGGAGAAAA AAAGGAGQG GQGGYGRGGY    1980
GQGGAGQGGA GAAAAAAAAG GAGQGGQGGY GQGGYGQGGA GQGGAAAAAA AAAGGAGQGG   2040
YGRGGAGQGG AAAAAAAAAG SGQGGYGGQG AGQGGAGAAA AAAAGGAGQ GGQGGYGRGG    2100
YGQGGAGQGG AGAAAAAAAA GAGQGGYGGQ YGQGGYGQGG YGQGGAGQGG AAAAAAAAAA   2160
GGAGQGGYGR GGAGQGGAAA AAGAGQGGYG GQGAGQGGAG AAAAAAAAGG AGQGGQGGYG   2220
RGGYGQGGAG QGGAGAAAAA AAAGGAGQGG QGGYGQGGNG QGGAGQGGAA AAAAAAGGAG    2280
QGGYGRGGAG QGGAAAAAAA AAGAGQGGYG GQGAGQGGAG AAAAAAAAGG AGQGGQGGYG   2340
RGGYGQGGAG QGGAAAAAGA AAAGGASQGG QGGYGQGDYG QGGAGQGGAA AAAAAAGGAG    2400
QGGYGRGGAG QGGAAAAAGA GQGGYGQGGA GQGGAGAAAA AAAAGGAGRG GQGGYGRGGY    2460
GQGGAGQGGA GAAAAAAAAG GAGQGGQGGY GQGGYGQGGA GQGGAAAAAA AAAGGAGQGG   2520
YGRGGAGQGG AAAAGAGQG GYGGQGAGQG GAGAAAAAAA AGGAGRGGQG GYGRGGYGQG    2580
GAGQGGAGAA AAAAGGAGG QGGGGYGQG GYGQGGAGQG GAGAAAAAAV GGAGQGGYGR    2640
GGAGQGGAAA AAAAAAGSG QGGYGGQGAG QGGAGAAAAA AAAGGAGQG GQGGYGGGYG    2700
QGGAGQGGAG AAAAAAAAGG AGQGGQGGYG QGGYGQGGAG QGGAAAAAA AAGGAGQGGY    2760
GRGGAGQGGA AAATGAGQGG YGGQGAGQGG AGAAAAAAAA GGAGQGGQGG YGRGGYGQGG   2820
AGQGGAGAAA AAAAAGGAGQ GGQGGYGQGG YGQGGYGQGG AAAAAAAAGG AGQGGYGRGG   2880
AGQGGAAAAA AAAAGAGQGG YGGQGAGQGG AGAAAAAAAA GGAGQGGQGG YGRGGYGQGG   2940
AGQGGAGAAA AGGAGQGGQG GYGQGGYGQG GAGQGGAAAA AAAAGGAGQ GGYGGYGQQ    3000
GGAGAAAAAA SGPGQIYYGP QSVAAPAAAA ASALAAPATS ARISSHASAL LSNGPTNPAS   3060
ISNVISNAVS QISSSNPGAS ACDVLVQALL ELVTALLTII GSSNIGSVNY DSSGQYAQVV   3120
TQSVQNAFA                                                          3129

SEQ ID NO: 45           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 45
tactacaggc tggctgttcc                                                     20

SEQ ID NO: 46           moltype = DNA  length = 46
FEATURE                 Location/Qualifiers
misc_feature            1..46
                        note = Description of Artificial Sequence: Synthetic primer
source                  1..46
                        mol_type = other DNA
                        organism = synthetic construct
SEQUENCE: 46
ctcacttaat cttctgtact ctgaagaagt ccaactgttg aacgcc                         46

SEQ ID NO: 47           moltype = DNA  length = 46
FEATURE                 Location/Qualifiers
misc_feature            1..46
                        note = Description of Artificial Sequence: Synthetic primer
source                  1..46
                        mol_type = other DNA
                        organism = synthetic construct
SEQUENCE: 47
agaagttgat tgagactttc aacgagggtc cccttcagct acctttt                        46

SEQ ID NO: 48           moltype = DNA  length = 20
FEATURE                 Location/Qualifiers
misc_feature            1..20
                        note = Description of Artificial Sequence: Synthetic primer
source                  1..20
```

```
                              mol_type = other DNA
                              organism = synthetic construct
SEQUENCE: 48
tccctgctaa gccctaatcg                                                      20

SEQ ID NO: 49                 moltype = DNA  length = 20
FEATURE                       Location/Qualifiers
misc_feature                  1..20
                              note = Description of Artificial Sequence: Synthetic primer
source                        1..20
                              mol_type = other DNA
                              organism = synthetic construct
SEQUENCE: 49
ctctgattgc acgagaaggc                                                      20

SEQ ID NO: 50                 moltype = DNA  length = 46
FEATURE                       Location/Qualifiers
misc_feature                  1..46
                              note = Description of Artificial Sequence: Synthetic primer
source                        1..46
                              mol_type = other DNA
                              organism = synthetic construct
SEQUENCE: 50
ctcacttaat cttctgtact ctgaagtgaa aggcgattgg agttgc                          46

SEQ ID NO: 51                 moltype = DNA  length = 46
FEATURE                       Location/Qualifiers
misc_feature                  1..46
                              note = Description of Artificial Sequence: Synthetic primer
source                        1..46
                              mol_type = other DNA
                              organism = synthetic construct
SEQUENCE: 51
agaagttgat tgagactttc aacgagctgg ctctgcttct ggtact                          46

SEQ ID NO: 52                 moltype = DNA  length = 20
FEATURE                       Location/Qualifiers
misc_feature                  1..20
                              note = Description of Artificial Sequence: Synthetic primer
source                        1..20
                              mol_type = other DNA
                              organism = synthetic construct
SEQUENCE: 52
gatgttgagg cgggcataag                                                      20

SEQ ID NO: 53                 moltype = DNA  length = 20
FEATURE                       Location/Qualifiers
misc_feature                  1..20
                              note = Description of Artificial Sequence: Synthetic primer
source                        1..20
                              mol_type = other DNA
                              organism = synthetic construct
SEQUENCE: 53
acttgtcagg acgatacgga                                                      20

SEQ ID NO: 54                 moltype = DNA  length = 20
FEATURE                       Location/Qualifiers
misc_feature                  1..20
                              note = Description of Artificial Sequence: Synthetic primer
source                        1..20
                              mol_type = other DNA
                              organism = synthetic construct
SEQUENCE: 54
ccggtctccc tggaaataga                                                      20

SEQ ID NO: 55                 moltype = DNA  length = 20
FEATURE                       Location/Qualifiers
misc_feature                  1..20
                              note = Description of Artificial Sequence: Synthetic primer
source                        1..20
                              mol_type = other DNA
                              organism = synthetic construct
SEQUENCE: 55
agttgtccgt cattagccct                                                      20

SEQ ID NO: 56                 moltype = DNA  length = 20
FEATURE                       Location/Qualifiers
misc_feature                  1..20
                              note = Description of Artificial Sequence: Synthetic primer
```

| source | 1..20 |
| --- | --- |
| | mol_type = other DNA |
| | organism = synthetic construct |

SEQUENCE: 56

```
tgttcccttt cggctagaca                                                   20
```

| SEQ ID NO: 57 | moltype = DNA   length = 4324 |
| --- | --- |
| FEATURE | Location/Qualifiers |
| misc_feature | 1..4324 |
| | note = Description of Artificial Sequence: Synthetic polynucleotide |
| source | 1..4324 |
| | mol_type = other DNA |
| | organism = synthetic construct |

SEQUENCE: 57

```
ggagttgaat cacatcttac tggatagcga gcttttgac gaagtgaaaa tttctaattt        60
taaacaagag aaggggtca aaacggaga tatcttatac ttggaaaaag agatgacaat       120
cagtgatttc atcaatttg tatctagttg gccttctgtg ttttcgtgga agcagcaacg       180
aggaaaggag ggtatcctag atgattttta caacgaactg aacgactgct ttgaggggg      240
taacatgaaa gtaatatgga actccgtcct agtatttgcc aggaggaagc aaagggttgt     300
ataggcttta gtacttatag aggaaacggg gttacgtgca agcgcgcatg cctgagcttt     360
gagggggggg actttcacat ctcttcttct cacacttagc cctaacacag agaataataa     420
aaagcattgc aagatgagtg ttgtcagcaa gcaatacgac atccacgaag gcattatctt     480
tgtaattgaa ttgaccccgg agcttcacgc gccggcttca gaagggaaat ctcagctcca     540
gatcatctta gagaatgtca gtgaggttat ttctgagcta atcattacct tgcccggtac     600
aggaataggg tgttaccta ttaattacga cggtggtcaa aacgacgaaa tttaccccat     660
ttttgagtta caagacctga atttggaaat gatgaaacaa ttgtaccaag tcttggagga     720
ccatgtaagt gggcttaatc ctctcgagaa gcaattccca attgaacaca gtaaaccgtt     780
atcagccact ctgttctttc acttaaggtc tctttttac atggcgaaga ctcataagcg     840
tactggaaga cattacaact tgaaaaagat tttcttgttc actaataacg ataaacctta     900
caatggaaac tctcagctga gagttccctt gaagaaaacc ctggctgatt acaatgacgt     960
agacattact ttgattccgt ttcttctgaa caagccttca ggtgtcaagt ttgacaagac    1020
ggaatactca gaaattttgt tctatgataa agatgcttgt tcgatgtcaa ttgaggagat    1080
ccgccaacga atttctagac ataaggagat caagcgggtt tacttcacct gtcctttgaa    1140
aatcgcaaat aacttgtgca tttctgtgaa aggttattct atgtttatc atgaaactcc    1200
aaggaagatc aaatttgtcg tcaatgaggg ttcaactttc aaagatgtgg agacaaaatc    1260
tcagtttgtc gatccaacat ccggaaaaga gttttccagt gaacagctga tcaaagcata    1320
tcctctaggt gccgatgctt acattccttt aaactcagag caagtcaaaa caataaatcg    1380
atttaatgat atcatcaata tcccctcttt ggaaattcca ggtttcaggg atatatctaa    1440
ttggttgcca cagtatcagt ttggcaaagc atcgttttta tcccctaata actatggtga    1500
ttttacacat tcgcagagaa catttagttg tcttcagtaa tgtcttgttt cttttgttgc    1560
agtggtgagc cattttgact tcgtgaaagt ttctttagaa tagttgtttc cagaggccaa    1620
acattccacc cgtagtaaaa tgcaagcgta ggaagaccaa gactggcata aatcaggtat    1680
aagtgtcgag cactggcagg tgatcttctg aaagtttcta ctagcagata agatccagta    1740
gtcatgcata tggcaacaat gtaccgtgtg atctaagaa cgcgtcctac taaccttcgc     1800
attcgttggt ccagtttgtt gttatcgatc aacgtgacaa ggttgtcgat tccgcgtaag    1860
catgcatacc caaggacgcc tgttgcaatt ccaagtgacc ttccaac aatctttgta      1920
atattagagc acttcattgt gttgcgcttg aaagtaaaat gcgaacaaat taagagataa    1980
tctcgaaacc gcgacttcaa acgcaatat gatgtgcggc acacaataag cgttcatatc     2040
cgctgggtga ctttctcgct ttaaaaaatt atccgaaaaa attttgacg gctagctcag    2100
tcctaggtac gctagcatta aagaggagaa aatggctaaa ctgacctctg ctgttccggt    2160
tctgaccgct cgtgacgttg ctggtgctgt tgagttctgg accgaccgtc tgggtttctc    2220
tcgtgacttc gttgaaacg acttcgctgg tgttgttcgt gacgacgtta ccctgttcat    2280
ctctgctgtt caggaccagg ttgttccgga caacaccctg gctgggttt gggttcgtgg    2340
tctgcacgaa ctgtacgctg aatggtctga agttgtttct accaacttcc gtgacgcttc    2400
tggtccggct atgaccgaaa tcggtgaaca gccgtggggt cgtgagtcg ctctgcgtga    2460
cccggctggt aactgcgttc acttcgttgc tgaagaacag gactaacacg tccgacggcg    2520
gcccacgggt cccaggcctc ggagatccgt cccccttttc ctttgtcgat atcatgtaat    2580
tagttatgtc acgcttacat tcacgccctc ccccccacatc cgctctaacc gaaaaggaag    2640
gagttagaca acctgaagtc taggtcccta tttatttttt tatagttatg ttagtattaa    2700
gaacgttatt tatatttcaa attttcttt tttttctgta cagacgcgtg tacgcatgta    2760
acattatact gaaaaccttg cttgagaagg ttttgggacg ctcgaaggct ttaatttgca    2820
agctgtatta gtttcacttt tcagcaacct ggtcggaaag atccacatca agaatggata    2880
ccaaccccaa gagtatgaaa atccttccct acaatgtgac ttcacgtgac aa            2940
ttaccttcaa ttggaacacg atatcgacat cagtgacccc cttgagaaac aaaagtacat    3000
aaacagcctc gatgagacaa aaaccaagat catgaaacta cggactatg tcaaggaaac    3060
tgccgatgat gacgacccctt cacggcttgc caacactctc aaagagctca accaagagct    3120
gaacaaaatt tccaactttg tatatcatcgc caataagaca ccaaagaccc ccacgacagt    3180
agaccctgtt cctactgatg atgacatcat caacgcctgg aaggcaggaa ctctgaacgg    3240
tttcaaggtg gatcaattac gaaaatacgt aaggtcacga aacaactttc tggagacggc    3300
ctccaaaaag gcagatctca tcgccaacat tgacaagtac tttcagcaga agttcaaaga    3360
gactaaggcc tgattcgtgt tccttactt ttcctcgcaa cgtgtttttt tcccaccaca    3420
ttgcctatgt tgtaatgcaa tgcagatgct ggccagttt ttgacgattc tcgaaatttg    3480
tcgttcgatgc catt ggccaaactg aaaatcaag acaaaataga ttgatttta    3540
tctgcaacgt cttccaccta cacaaccact ctacaaactt cagacaaaca tgtttataaa    3600
agcagctact agatccaaaa tgacaagttc gttattctct actacgtttg ttgtggcatt    3660
tggattggtg gctagcaaca acctcttgcc atgtcctgtt gaccactcta tgaataacga    3720
gactccgcaa gaattgaaac cattgcaggc tgaatcttct actagaaagt tgaactcttc    3780
cgcttaagtc aaataaaact actgacacag atgatgcaca gaaacaacgg atcacgctct    3840
```

```
tgactgatta gtcccgtcat tttggttctc attttcttca cagtcaccta tcaatgtatg    3900
atcacctgga aggatttccc tacgatactt caaatctttt acttgataat attactcatt    3960
atggctcagg aatgcagact gcctgattca agacgctgct cttcttattt aacacttgta    4020
cactaacccc atgaagcca gggaagggaa taaccatctc tctggtaata aatcggtctt     4080
tatttatgca tagaaaagga atctattata tttcgttcat ttggcactct gctaactgta    4140
gattaacggg tctcgtaaat tcaaaatctt cttccgatca aaccggggtg aaatattact    4200
tctcgtgcat agctaatttt caaataaccg tcctaaaatg aacggtcatt tacctggact    4260
ctcttgccaa atgggcaaca aaacataaag ctgatcagaa cgtaactagt ctctcggaat    4320
ccat                                                                 4324

SEQ ID NO: 58          moltype = DNA   length = 22
FEATURE                Location/Qualifiers
misc_feature           1..22
                       note = Description of Artificial Sequence: Synthetic
                         oligonucleotide
source                 1..22
                       mol_type = other DNA
                       organism = synthetic construct
SEQUENCE: 58
ggagttgaat cacatcttac tg                                             22

SEQ ID NO: 59          moltype = DNA   length = 1099
FEATURE                Location/Qualifiers
misc_feature           1..1099
                       note = Description of Artificial Sequence: Synthetic
                         polynucleotide
source                 1..1099
                       mol_type = other DNA
                       organism = synthetic construct
SEQUENCE: 59
gacaactaaa tgttctctgc gaatgtgtaa aatcaccata gttattaggg gataaaaacg    60
atgctttgcc aaactgatac tgtggcaacc aattagatat atccctgaaa cctagaattt    120
ccaaagaggg gatattgatg atatcattaa atcgatttat tgttttgact tgctctgagt    180
ttaaaggaat gtaagcatcg gcacctagag gatatgcttt gatcagctgt tcactggaaa    240
actcttttcc ggatgttgga tcgacaaact gagattttgt ctccacatct ttgaaagttg    300
aaccctcatt gacgacaaat ttgatcttcc ttggagtttc atgataaaac atagaataac    360
cttttcacaga aatgcacaag ttatttgcga ttttcaaagg acaggtgaag taaacccgct    420
tgatctcctt atgtctagaa attcgttggc ggatctcctc aattgacatc gaacaagcat    480
ctttatcata gaacaaaatt tctgagtatt ccgtcttgtc aaacttgaca cctgaaggct    540
tgttcagaag aaacggaatc aaagtaatgt ctacgtcatt gtaatcagcc agggttttct    600
tcaagggaac tctcagctga gagtttccat tgtaaggttt atcgttatta gtgaacaaga    660
aaatcttttt caagttgtaa tgtcttccag tacgcttatg agtcttcgcc atgtaaaaaa    720
gagaccttaa gtgaaagaac agagtggctg ataacggttt actgtgttca attgggaatt    780
gcttctcgag aggattaagc ccacttacat ggtcctccaa gacttggtac aattgtttca    840
tcatttccaa attcaggtct tgtaactcaa aaatggggta aatttcgtcg ttttgaccac    900
cgtcgtaatt aataaggtaa caccctattc ctgtaccggg caaggtaatg attagctcag    960
aaataacctc actgacattc tctaagatga tctggagctg agatttccct tctgaagccg    1020
gcgcgtgaag ctccggggtc aattcaatta caaagataat gccttcgtgg atgtcgtatt    1080
gcttgctgac aacactcat                                                 1099

SEQ ID NO: 60          moltype = DNA   length = 549
FEATURE                Location/Qualifiers
misc_feature           1..549
                       note = Description of Artificial Sequence: Synthetic
                         polynucleotide
source                 1..549
                       mol_type = other DNA
                       organism = synthetic construct
SEQUENCE: 60
tcaggcctta gtctctttga acttctgctg aaagtacttg tcaatgttgg cgatgagatc    60
tgcctttttg gaggccgtct ccagaaagtt gtttcgtgac cttacgtatt ttcgtaattg    120
atccaccttg aaaccgttca gagttcctgc cttccaggcg ttgatgatgt catcatcagt    180
aggaacaggg tctactgtcg tgggggtctt tggcttctta ttggcgatga tatcaaagtt    240
ggaaattttg ttcagctctt ggttgagctc tttgagagtg ttggcaagcc gtgaagggtc    300
gtcatcatcg gcagttttcct tgacatagtc ccgtagtttc atgatcttgg ttttttgtctc    360
atcgaggctg tttatgtact tttgtttctc aaggggtca ctgatgtcga tatcgtgttc     420
caattgaagg taatcgtcac gtaacatttt gaagtgccat tgtagggaag gattttcata    480
ctcttggggt tggtatccat tcttgatgtg gatctttccg accaggttgc tgaaaagtga    540
aactaatac                                                            549

SEQ ID NO: 61          moltype = DNA   length = 552
FEATURE                Location/Qualifiers
misc_feature           1..552
                       note = Description of Artificial Sequence: Synthetic
                         polynucleotide
source                 1..552
                       mol_type = other DNA
                       organism = synthetic construct
SEQUENCE: 61
```

```
ttcagtaatg tcttgtttct tttgttgcag tggtgagcca ttttgacttc gtgaaagttt    60
ctttagaata gttgtttcca gaggccaaac attccaccg tagtaaagtg caagcgtagg    120
aagaccaaga ctggcataaa tcaggtataa gtgtcgagca ctggcaggtg atcttctgaa   180
agtttctact agcagataag atccagtagt catgcatatg caacaatgt accgtgtgga    240
tctaagaacg cgtcctacta accttcgcat tcgttggtcc agtttgttgt tatcgatcaa   300
cgtgacaagg ttgtcgattc cgcgtaagca tgcataccca aggacgcctg ttgcaattcc   360
aagtgagcca gttccaacaa tctttgtaat attagagcac ttcattgtgt tgcgcttgaa   420
agtaaaatgc gaacaaatta agagataatc tcgaaaccgc gacttcaaac gccaatatga   480
tgtgcggcac acaataagcg ttcatatccg ctgggtgact ttctcgcttt aaaaaattat   540
ccgaaaaaat tt                                                       552

SEQ ID NO: 62           moltype = DNA   length = 20
FEATURE                 Location/Qualifiers
misc_feature            1..20
                        note = Description of Artificial Sequence: Synthetic
                          oligonucleotide
source                  1..20
                        mol_type = other DNA
                        organism = synthetic construct
SEQUENCE: 62
cagaggccaa acattccacc                                                20

SEQ ID NO: 63           moltype = DNA   length = 14
FEATURE                 Location/Qualifiers
misc_feature            1..14
                        note = Description of Artificial Sequence: Synthetic
                          oligonucleotide
source                  1..14
                        mol_type = other DNA
                        organism = synthetic construct
SEQUENCE: 63
ttaaagagga gaaa                                                      14

SEQ ID NO: 64           moltype = DNA   length = 375
FEATURE                 Location/Qualifiers
misc_feature            1..375
                        note = Description of Artificial Sequence: Synthetic
                          polynucleotide
source                  1..375
                        mol_type = other DNA
                        organism = synthetic construct
SEQUENCE: 64
atggctaaac tgacctctgc tgttccggtt ctgaccgctc gtgacgttgc tggtgctgtt    60
gagttctgga ccgaccgtct gggttttctct cgtgacttcg ttgaagacga cttcgctggt   120
gttgttcgtg acgacgttac cctgttcatc tctgctgttc aggaccaggt tgttccggac   180
aacaccctg cttgggtttg ggttcgtggt ctggacgaac tgtacgctga atggtctgaa    240
gttgtttcta ccaacttccg tgacgcttct ggtccggcta tgaccgaaat cggtgaacag   300
ccgtggggtc gtgagttcgc tctgcgtgac ccggctggta actgcgttca cttcgttgct   360
gaagaacagg actaa                                                    375

SEQ ID NO: 65           moltype = DNA   length = 318
FEATURE                 Location/Qualifiers
misc_feature            1..318
                        note = Description of Artificial Sequence: Synthetic
                          polynucleotide
source                  1..318
                        mol_type = other DNA
                        organism = synthetic construct
SEQUENCE: 65
cacgtccgac ggcggcccac gggtcccagg cctcggagat ccgtccccct tttcctttgt    60
cgatatcatg taattagtta tgtcacgctt acattcacgc cctcccccca catccgctct   120
aaccgaaaag gaaggagtta gacaacctga agtctaggtc cctatttatt tttttatagt   180
tatgttagta ttaagaacgt tatttatatt tcaaattttt cttttttttc tgtacagacg   240
cgtgtacgca tgtaacatta tactgaaaac cttgcttgag aaggttttgg gacgctcgaa   300
ggctttaatt tgcaagct                                                 318

SEQ ID NO: 66           moltype = DNA   length = 20
FEATURE                 Location/Qualifiers
misc_feature            1..20
                        note = Description of Artificial Sequence: Synthetic
                          oligonucleotide
source                  1..20
                        mol_type = other DNA
                        organism = synthetic construct
SEQUENCE: 66
aggagttaga caacctgaag                                                20

SEQ ID NO: 67           moltype = DNA   length = 23
FEATURE                 Location/Qualifiers
```

| | | |
|---|---|---|
| misc_feature | 1..23 | |
| | note = Description of Artificial Sequence: Synthetic oligonucleotide | |
| source | 1..23 | |
| | mol_type = other DNA | |
| | organism = synthetic construct | |

SEQUENCE: 67

```
gtaactagtc tctcggaatc cat                                              23
```

| | | |
|---|---|---|
| SEQ ID NO: 68 | moltype = DNA  length = 1623 | |
| FEATURE | Location/Qualifiers | |
| misc_feature | 1..1623 | |
| | note = Description of Artificial Sequence: Synthetic polynucleotide | |
| source | 1..1623 | |
| | mol_type = other DNA | |
| | organism = synthetic construct | |

SEQUENCE: 68

```
cttcagagta cagaagatta agtgagagaa ttctaccgtt cgtatagcat acattatacg    60
aagttatttc agtaatgtct tgtttctttt gttgcagtgg tgagccattt tgacttcgtg   120
aaagtttctt tagaatagtt gtttccagag gccaaacatt ccacccgtag taaagtgcaa   180
gcgtaggaag accaagactg gcataaatca ggtataagtg tcgcacactg gcaggtgatc   240
ttctgaaagt ttctactagc agataagatc cagtagtcat gcatatggca acaatgtacc   300
gtgtggatct aagaacgcgt cctactaacc ttcgcattcg ttggtccagt ttgttgttat   360
cgatcaacgt gacaaggttg tcgattccgc gtaagcatgc atacccaagg acgcctgttg   420
caattccaag tgagccagtt ccaacaatct ttgtaatatt agagcacttc attgtgttgc   480
gcttgaaagt aaaatgcgaa caaattaaga gataatctcg aaaccgcgac ttcaaacgcc   540
aatatgatgt gcggcacaca ataagcgttc atatccgctg ggtgactttc tcgctttaaa   600
aaattatccg aaaaaatttt tgacggctag ctcagtccta ggtacgctag cattaaagag   660
gagaaaatga ctactcttga tgacacagcc tacagatata agacatcagt tccgggtacg   720
gcagaggcta tcgaagcctt ggacggttca ttcactactg atacggtgtt tagagtcacc   780
gctacaggtg atggcttcac cttgagagag gttcctgtag acccacccctt aacgaaagtt   840
ttccctgatg acgaatcgga tgacgagtct gatgctggtg aggacggtga ccctgattcc   900
agaacatttg tcgcatacgg agatgatggt gacctggctg gcttgttgt ggtgtcctac   960
agcggatgga atcgtagact cacagttgag gacatcgaag ttgcacctga acatcgtggt  1020
cacggtgttg gtcgtgcact gatgggactg gcaacagagt ttgctagaga aagaggagcg  1080
ggacatttgt ggttagaagt gaccaatgtc aacgctcctg ctattcacgc atataggcga  1140
atgggtttca ctttgtgcgg tcttgatact gctttgtatg acggaactgc ttctgatggt  1200
gaacaagctc tttacatgag tatgccatgt ccatagcacg tccgacggcg gccacgggt  1260
cccaggcctc ggagatccgt cccccttttc ctttgtcgat atcatgtaat tagttatgtc  1320
acgcttacat tcacgccctc cccccacatc cgctctaacc gaaaggaag gagttagaca  1380
acctgaagtc taggtcccta tttatttttt tatagttatg ttagtattaa gaacgttatt  1440
tatatttcaa atttttcttt tttttctgta cagacgcgtg tacgcatgta acattatacc  1500
gaaaaccttg cttgaaagg ttttgggacg ctcgaaggct ttaatttgca agctataact  1560
tcgtatagca tacattatac cttgttatgc ggccgcaaga agttgattga gactttcaac  1620
gag                                                                1623
```

| | | |
|---|---|---|
| SEQ ID NO: 69 | moltype = DNA  length = 27 | |
| FEATURE | Location/Qualifiers | |
| misc_feature | 1..27 | |
| | note = Description of Artificial Sequence: Synthetic oligonucleotide | |
| source | 1..27 | |
| | mol_type = other DNA | |
| | organism = synthetic construct | |

SEQUENCE: 69

```
cttcagagta cagaagatta agtgaga                                         27
```

| | | |
|---|---|---|
| SEQ ID NO: 70 | moltype = DNA  length = 34 | |
| FEATURE | Location/Qualifiers | |
| misc_feature | 1..34 | |
| | note = Description of Artificial Sequence: Synthetic oligonucleotide | |
| source | 1..34 | |
| | mol_type = other DNA | |
| | organism = synthetic construct | |

SEQUENCE: 70

```
taccgttcgt atagcataca ttatacgaag ttat                                 34
```

| | | |
|---|---|---|
| SEQ ID NO: 71 | moltype = DNA  length = 552 | |
| FEATURE | Location/Qualifiers | |
| misc_feature | 1..552 | |
| | note = Description of Artificial Sequence: Synthetic polynucleotide | |
| source | 1..552 | |
| | mol_type = other DNA | |
| | organism = synthetic construct | |

SEQUENCE: 71

```
ttcagtaatg tcttgtttct tttgttgcag tggtgagcca ttttgacttc gtgaaagttt    60
```

-continued

```
ctttagaata gttgtttcca gaggccaaac attccacccg tagtaaagtg caagcgtagg   120
aagaccaaga ctggcataaa tcaggtataa gtgtcgagca ctggcaggtg atcttctgaa   180
agtttctact agcagataag atccagtagt catgcatatg caacaatgt accgtgtgga    240
tctaagaacg cgtcctacta accttcgcat tcgttggtcc agtttgttgt tatcgatcaa   300
cgtgacaagg ttgtcgattc cgcgtaagca tgcataccaa aggacgcctg ttgcaattcc   360
aagtgagcca gttccaacaa tctttgtaat attagagcac ttcattgtgt tgcgcttgaa   420
agtaaaatgc gaacaaatta agagataatc tcgaaaccgc gacttcaaac gccaatatga   480
tgtgcggcac acaataagcg ttcatatccg ctgggtgact ttctcgcttt aaaaaattat   540
ccgaaaaaat tt                                                        552
```

SEQ ID NO: 72          moltype = DNA   length = 14
FEATURE                Location/Qualifiers
misc_feature           1..14
                       note = Description of Artificial Sequence: Synthetic
                       oligonucleotide
source                 1..14
                       mol_type = other DNA
                       organism = synthetic construct
SEQUENCE: 72
ttaaagagga gaaa                                                       14

SEQ ID NO: 73          moltype = DNA   length = 570
FEATURE                Location/Qualifiers
misc_feature           1..570
                       note = Description of Artificial Sequence: Synthetic
                       polynucleotide
source                 1..570
                       mol_type = other DNA
                       organism = synthetic construct
SEQUENCE: 73
```
```
atgactactc ttgatgacac agcctacaga tataggacat cagttccggg tgacgcagag   60
gctatcgaag ccttggacgg ttcattcact actgatacgg tgtttagagt caccgctaca   120
ggtgatggct tcaccttgag agaggttcct gtagacccac ccttaacgaa agttttccct   180
gatgacgaat cggatgacga gtctgatgct ggtgaggacg gtgaccctga ttccagaaca   240
tttgtcgcat acggagatga tggtgacctg gctggctttg ttgtggtgtc ctacagcgga   300
tggaatcgta gactcacagt tgaggacatc gaagttgcac ctgaacatcg tggtcacggt   360
gttggtcgtg cactgatggg actggcaaca gagtttgcta gagaaagagg agccggacat   420
ttgtggttag aagtgaccaa tgtcaacgct cctgctattc acgcatatag gcgaatgggt   480
ttcactttgt gcggtcttga tactgctttg tatgacggaa ctgcttctga tggtgaacaa   540
gctctttaca tgagtatgcc atgtccatag                                    570
```

SEQ ID NO: 74          moltype = DNA   length = 318
FEATURE                Location/Qualifiers
misc_feature           1..318
                       note = Description of Artificial Sequence: Synthetic
                       polynucleotide
source                 1..318
                       mol_type = other DNA
                       organism = synthetic construct
SEQUENCE: 74
```
```
cacgtccgac ggcggcccac gggtcccagg cctcggagat ccgtccccct tttcctttgt   60
cgatatcatg taattagtta tgtcacgctt acattcacgc cctccccca catccgctct    120
aaccgaaaag gaaggagtta gacaacctga agtctaggtc cctatttatt tttttatagt   180
tatgttagta ttaagaacgt tatttatatt tcaaattttt cttttttttc tgtacagacg   240
cgtgtacgca tgtaacatta tactgaaaac cttgcttgag aaggttttgg gacgctcgaa   300
ggctttaatt tgcaagct                                                  318
```

SEQ ID NO: 75          moltype = DNA   length = 34
FEATURE                Location/Qualifiers
misc_feature           1..34
                       note = Description of Artificial Sequence: Synthetic
                       oligonucleotide
source                 1..34
                       mol_type = other DNA
                       organism = synthetic construct
SEQUENCE: 75
ataacttcgt atagcataca ttataccttg ttat                                 34

SEQ ID NO: 76          moltype = DNA   length = 35
FEATURE                Location/Qualifiers
misc_feature           1..35
                       note = Description of Artificial Sequence: Synthetic
                       oligonucleotide
source                 1..35
                       mol_type = other DNA
                       organism = synthetic construct
SEQUENCE: 76
gcggccgcaa gaagttgatt gagactttca acgag                                35

| SEQ ID NO: 77 | moltype = DNA length = 3869 |
|---|---|
| FEATURE | Location/Qualifiers |
| misc_feature | 1..3869 |
| | note = Description of Artificial Sequence: Synthetic polynucleotide |
| source | 1..3869 |
| | mol_type = other DNA |
| | organism = synthetic construct |

SEQUENCE: 77

```
tactacaggc tggctgttcc tcgcatggtg tttaatgtcc tgactgggtt ttcgtttatc    60
ggtattaccg gagccacctt gactgtaagg gaacgatact ggactaagag agtaatgcga   120
aaggcaacag cgtttctggc gaacctaatc aatgacggtt acgagtttac tactcctaaa   180
gccagtctta ttttgctaga gcgagtcaac gcttacttaa agggccaggg acctaattat   240
gacatcgatt ttgacgagca ggaggcgttc attaaagaaa tggaggagtt gaggacctct   300
ggtggatatg agaacagata ctcatattca ggaaccgatg aaacacccag agatccgggt   360
tgcctgtttc ttcccattgc tttaaataaa tggcactttg atgtgctaga ctgcctgagg   420
atatacggta ctcaggaaga tctggaatct aaattattag tgttcagca attggtgtta    480
caatgttgca tgaagcacag tggcatgact ccagacatgg tctttgcaac ggaagtagct   540
cagaagccga ccttcgaaga cgacatagtt tgtgatgata ttgacgctta tgcccagggg   600
ggtgattgtc tagattattg ttacacgcca agcaattact ccagaacttt agaaattcat   660
ggcaagattg ctaccttaca acgagagctg gggctatgct ataatattct cggaattttg   720
gaccgttttt ccgattaagg ttttttagctc cattgcgctc acccccgctc tccagactcc   780
ttcgttatcc agcattcagc atggacaggt tcaaaaaata aaatttcttg atatgggtcc   840
acttcaaaca tgcgcctacc tgtaggaaaa aaaagagaa cataaatatg ccgcgaacag    900
aaaacgtaat gtactgttct atatataaac tgttcagatc aatcataaat tctcagtttc   960
aaactttccg ctcagccaga ttttattcgt aaagaacgca tcattggctc tatgttgaag  1020
gatcagttct tgttatgggt tgctttgata gcgagcgtac cggttccgg cgtgatggca   1080
gctcctagcg agtccgggca taacacggtt gaaaacgag atgccaaaaaa cgttgttggc  1140
gttcaacagt tggacttctt cagagtacag aagattaagt gagagaattc taccgttcgt  1200
atagcataca ttatacgaag ttatttcagt aatgtcttgt ttctttttgtt gcagtggtga  1260
gccatttga cttcgtgaaa gtttctttag aatagttgtt tccagaggcc aaacattcca   1320
cccgtagtaa agtgcaagcg taggaagacc aagactggca taaatcaggt ataagtgtcg  1380
agcactggca ggtgatcttc tgaaagtttc tactagcaga taagatccag tagtcatgca  1440
tatgcaaca atgtaccgtg tggactcaag aacgcgtcct actaaccttc gcattcgttg   1500
gtccagtttg ttgttatcga tcaacgtgac aaggttgtcg attccgcgta agcatgcata  1560
cccaaggacg cctgttgcaa ttccaagtga gccagttcca acaatctttg taatattaga  1620
gcacttcatt gtgttgcgct tgaaagtaaa atgcgaacaa attaagagat aatctcgaaa  1680
ccgcgacttc aaacgccaat atgatgtgcg gcacacaata agcgttcata tccgctgggt  1740
gactttctcg cttttaaaaaa ttatccgaaa aaatttttga cggctagctc agtcctagta  1800
acgctagcat taaagaggag aaaatgacta ctcttgatga cacagcctac agatatagga  1860
catcagttcc gggtgacgca gaggctatcg aagccttgga cggttcattc actactgata  1920
cggtgtttag agtcaccgct acaggtgatg gcttcacctt gagagaggtt cctgtagacc  1980
cacccttaac gaaagttttc cctgatgacg aatcggatga ggatctgat gctggtgagg   2040
acggtgaccc tgattccaga acatttgtcg catacggaga tgatggtgac ctggctggct  2100
ttgttgtggt gtcctacagc ggatggaatc gtagactcac agttgaggac atcgaagttg  2160
cacctgaaca tcgtggtcac ggtgttggtc gtgcactgat gggactggca acagagtttg  2220
ctagagaaag aggagccgga catttgtggt tagaagtgac caatgtcaac gctcctgcta  2280
ttcacgcata taggcgaatg ggtttcactt tgtgcggtct tgatactgct ttgtatgacg  2340
gaactgcttc tgatggtgaa caagctcttt acatgagtat gccatgtcca tagcacgtcc  2400
gacggcggcc cacgggtccc aggcctcgga gatccgtccc cctttttcctt tgtcgatatc  2460
atgtaattag ttatgtcacg cttacattca cgccctccc ccacatccgc tctaaccgaa    2520
aaggaaggag ttagacaacc tgaagtctag gtccctattt atttttttat agttatgtta  2580
gtattaagaa cgttatttat atttcaaatt tttctttttt ttctgtacag acgcgtgtac  2640
gcatgtaaca ttatactgaa aaccttgctt gagaaggttt tgggacgctc gaaggcttta  2700
atttgcaagc tataacttcg tatagcatac attatacgaa gttatgcggc cgcaagaagt  2760
tgattgagac tttcaacgag ggtccccttc agctaccttt ctctgtgttt ggtagttatt  2820
ctcggcgtgt gtatagtata gtataaaagg gcctacattg gataggcttc aacattcctc  2880
aataaacaaa catccaacat cgcgcattcc gcatttcgca tttcacattt cgcgcctgcc  2940
ttcctttagg ttctttgaat catcatcaat cgtcgccgtc tacatcagag caggacttat  3000
ctttgcccttc cccaaaaatt gccactccgt caaatagatt cttttgaatc cttgactatt  3060
tttgcctaaa taggttttg ttagttttc ttcaaagccc aaaagaaact ctatttagat    3120
tcatccagaa acaatctttt tctcacccca tttcgaagtg ccgtggagca cagacataaa  3180
aagatgacta ccgttcaacc tacagggcca gacaggctca ccctgccgca tattctactg  3240
gaattcaacg atggctcctc gcagcatgca gtgatcgagc taagcatgaa cgagggatt   3300
aatatatcca cccatgagtg gaatccatcc actaatgagc aatcgccacg ggaagagaga  3360
gcaccacccc aacaatccaa tccatcgcat catccagaat catcgaacat agctactcaa  3420
agtcccgctc aggaaaccga gactcagccc ggcattccag gactagatag gcctgccttt  3480
gatacctcgg caacggggtc gtcagaacag gttgacccga tacagggaag gatcctggat  3540
gatattatag gccaatcatt aaggacttcc gaagaagacg ataccgaatc ccgccagaga  3600
ccacgagacc agaagaacat tatgatcacc gtgaattact tgtacgcaga cgacacaaat  3660
tccagaagtg ctaatacaaa caaccagacg cccaataaca cttctagaac ttccgacagt  3720
gaacgtgtgg gctccttatc gttgcacgtt ccggatctac cagataatgc cgacgattac  3780
tatatcgatg tactcattaa actaaccaca agcattgccc tcagcgtcat cacgtccatg  3840
atcaagaaac gattagggct tagcaggga                                    3869
```

| SEQ ID NO: 78 | moltype = DNA length = 1157 |
|---|---|
| FEATURE | Location/Qualifiers |
| misc_feature | 1..1157 |
| | note = Description of Artificial Sequence: Synthetic |

-continued

```
                        polynucleotide
source                  1..1157
                        mol_type = other DNA
                        organism = synthetic construct
SEQUENCE: 78
tactacaggc tggctgttcc tcgcatggtg tttaatgtcc tgactgggtt ttcgtttatc   60
ggtattaccg gagccacctt gactgtaagg gaacgatact ggactaagag agtaatgcga  120
aaggcaacag cgtttctggc gaacctaatc aatgacggtt acgagtttac tactcctaaa  180
gccagtctta ttttgctaga gcgagtcaac gcttacttaa agggccaggg acctaattat  240
gacatcgatt ttgacgagca ggaggcgttc attaaagaaa tggagggagtt gaggacctct  300
ggtggatatg agaacagata ctcatattca ggaaccgatg aaacacccag agatccgggt  360
tgcctgtttc ttcccattgc tttaaataaa tggcactttg atgtgctaga ctgcctgagg  420
atatacggta ctcaggaaga tctggaatct aaattattaa gtgttcagca attggtgtta  480
caatgttgca tgaagcacag tggcatgact ccagacatgg tctttgcaac ggaagtagct  540
cagaagccga ccttcgaaga cgacatagtt tgtgatgata ttgacgctta tgcccagggg  600
ggtgattgtc tagattattg ttacacgcca agcaattact ccagaacttt agaaattcat  660
ggcaagattg ctaccttaca acgagagctg gggctatgct ataatattct cggaattttg  720
gaccgttttt ccgattaagg ttttagctc cattgcgcga accccgctc tccagactcc   780
ttcgttatcc agcattcagc atggacaggt tcaaaaata aaatttcttg atatgggtcc  840
acttcaaaca tgcgcctacc tgtaggaaaa aaaagagaa cataaatatg ccgcgaacag  900
aaaacgtaat gtactgttct atatataaac tgttcagatc aatcataaat tctcagtttc  960
aaactttccg ctcagccaga tttattcgt aaagaacga tcattggctc tatgttgaag  1020
gatcagttct tgttatgggt tgctttgata gcgagcgtac cggttccgg cgtgatggca  1080
gctcctagcg agtccgggca taacacggtt gaaaaacgag atgccaaaaa cgttgttggc  1140
gttcaacagt tggactt                                                 1157

SEQ ID NO: 79           moltype = DNA   length = 1089
FEATURE                 Location/Qualifiers
misc_feature            1..1089
                        note = Description of Artificial Sequence: Synthetic
                         polynucleotide
source                  1..1089
                        mol_type = other DNA
                        organism = synthetic construct
SEQUENCE: 79
ggtccccttc agctaccttt ctctctgttt ggtagttatt ctcggcgtgt gtatagtata   60
gtataaaagg gcctacattg gataggcttc aacattcctc aataaacaaa catccaacat  120
cgcgcattcc gcatttcgca tttcacattt cgcgcctgcc ttcctttagg ttctttgaat  180
catcatcaat cgtcgccgtc tacatcagag caggacttat ctttgccttc cccaaaatt   240
gccactccgt caaatagatt cttttgaatc cttgactatt tttgcctaaa taggtttttg  300
ttagtttttc ttcaaagccc aaaagaaact ctatttagat tcatccagaa acaatctttt  360
tctcacccca tttcgaagtg ccgtggagca cagacataaa aagatgacta ccgttcaacc  420
tacagggcca gacaggctca ccctgccgca tattctactg gaattcaacg atggctcatc  480
gcagcatgca gtgatcgagc taagcatgaa cgaggggatt aatatatcca cccatgagtg  540
gaatccatcc actaatgagc aatcgccacg ggaagagaga gcaccacccc aacaatccaa  600
tccatcgcat catccagaat catcgaacat agctactcaa agtcccgctc aggaaaccga  660
gactcagccc ggcattccag gactagatag gcctgccttt gatacctcgg caacgggtc   720
gtcagaacag gttgacccag tacagggaag gatcctggat gatattatag gccaatcatt  780
aaggacttcc gaagaagacg ataccgaatc ccgccagaga ccacgagacc agaagaacat  840
tatgatcacc gtgaattact tgtacgcaga cgacacaaat tccagaagtg ctaatacaaa  900
caaccagacg cccaataaca cttctagaac ttccgacagt gaacgtgtgg gctccttatc  960
gttgcacgtt ccggatctac cagataatgc cgacgattac tatatcgatg tactcattaa 1020
actaaccaca agcattgccc tcagcgtcat cacgtccatg atcaagaaac gattagggct 1080
tagcaggga                                                          1089

SEQ ID NO: 80           moltype = DNA   length = 3964
FEATURE                 Location/Qualifiers
misc_feature            1..3964
                        note = Description of Artificial Sequence: Synthetic
                         polynucleotide
source                  1..3964
                        mol_type = other DNA
                        organism = synthetic construct
SEQUENCE: 80
gccttctcgt gcaatcagag ctgttgaaag agagaagagg gcacacggaa gctgctgttc   60
aattgtgtga attgaccgga ttacaacctg ctggagtgat aggagagctg gttcgtgacg  120
aggacggtc tatgatgcga ttagacgact gtgttcagtt tggtctccgc cacaacgtaa  180
aaattatcaa ccttgaccag atcattgaat acatggttac caagaacagc tagatacgat  240
ggataggaat acagagatat catgattgag gaacgtaaga gctttttcga aagtgtgat   300
ttgtggtgag ggccaggcgg tgggggaggtg gtggggagcc tccttggtcg aatgtagata  360
tagtaagcaa gacacaagag cgcgcgaagt cttcaacgag gcggcgttgg gtcttgtacg  420
caacgtaatg actacacagt tgagcttgtc gcgaaccggt cgacatttg atcatgcata  480
ctatgttgag acaccatctc gtactattgc ggcaaccagc tgtaaatttg actaattaaa  540
gctgatgaag gatgcagggc gtcgtcaatt ttttgattga ttgcatttaa ttgtttgagg  600
cattcaaggc tgaatgcccg gcaccctaga cccttcttgt gagtactata aacccgcagg  660
cagggtaccc ttggccttct gcgagactac cagtcataac gtatatccac aatgtactag  720
taatagcccc ggaaaactct aatcccacag aacgtctaac gcctcctatg tcatcgatac  780
ccattcgcac tactgccatg gccccccttca cgtgatcatt tcacttactc ccgcctaagc  840
ttcgcccaca tgcctgcgtt tgccaagat ttactgacga gtttggttta ctcatcctct   900
```

```
atttataact actagacttt caccattctt caccaccctc gtgccaatga tcatcaacca    960
cttggtattg acagccctca gcattgcact agcaagtgcg caactccaat cgcctttcac   1020
ttcagagtac agaagattaa gtgagagaat tctaccgttc gtatagcata cattatacga   1080
agttatttca gtaatgtctt gtttcttttg ttgcagtggt gagccatttt gacttcgtga   1140
aagtttcttt agaatagttg tttccagagg ccaaacattc cacccgtagt aaagtgcaag   1200
cgtaggaaga ccaagactgg cataaatcag gtataagtgc cgagcactgg caggtgatct   1260
tctgaaagtt tctactagca gataagatcc agtagtcatg catatggcaa caatgtaccg   1320
tgtggatcta agaacgcgtc ctactaacct tcgcattcgt tggtccagtt tgttgttatc   1380
gatcaacgtg acaaggttgt cgattccgcg taagcatgca tacccaagga cgcctgttgc   1440
aattccaagt gagccagttc caacaatctt tgtaatatta gagcacttca ttgtgttgcg   1500
cttgaaagta aaatgcgaac aaattaagag ataatctcga aaccgcgact tcaaacgcca   1560
atatgatgtg cggcacacaa taagcgttca tatccgctgg gtgactttct cgctttaaaa   1620
aattatccga aaaaatttt gacggctagc tcagtcctag gtacgctagc attaaagagg    1680
agaaaatgac tactcttgat gacacagcct acagatatag gacatcagtt ccgggtgaca   1740
cagaggctat cgaagccttg gacggttcat tcactactga tacggtgttt agagtcaccg   1800
ctacaggtga tggcttcacc ttgagagagg ttcctgtaga cccaccctta acgaaagttt   1860
tccctgatga cgaatcggat gacgagtctg atgctggtga ggacggtgac cctgattcca   1920
gaacatttgt cgcatacgga gatgatggtg acctggctgg tgtgtcctaca             1980
gcggatggaa tcgtagactc acagttgagg acatcgaagt tgcacctgaa catcgtggtc   2040
acggtgttgg tcgtgcactg atgggactgg caacagagtt tgctagaaga gaggagccg    2100
gacatttgtg gttagaagtg accaatgtca acgctcctgc tattcacgca tataggcgaa   2160
tggtttcac tttgtgcggt cttgatactg ctttgtatga cggaactgct tctgatggtg    2220
aacaagctct ttacatgagt atgccatgtc catagcacgt ccgacggcgg cccacgggtc   2280
ccaggcctcg gagatccgtc cccctttttcc tttgtcgata tcatgtaatt agttatgtca   2340
cgcttacatt cacgccctcc ccccacatcc gctctaaccg aaaaggaagg agttagacaa   2400
cctgaagtct aggtccctat ttatttttt atagttatgt tagtattaag aacgttattt    2460
atatttcaaa ttttcttt ttttctgtac agacgcgtgt acgcatgtaa cattatactg      2520
aaaaccttgc ttgagaaggt tttgggacgc tcgaaggctt taatttgcaa gctataactt   2580
cgtatagcat acattatacc ttgttatgcg gccgcaagaa gttgattgag actttcaacg   2640
agctggctct gcttctggta cttcttcagg tgcatcttct gctactcaaa atgacgaaac   2700
atccactgat cttggagctc cagctgcatc tttaagtgca acgccatgtc ttttgccat    2760
cttgctgctc atgttgtagt agactttttt tttcactgag ttttatgta ctactgatta    2820
cattgtgtag gtgtaatgat gtgcactata atactaatat agtcaaaatg ctacagagga   2880
aagtgcaggt tgcctgtggt ggtttttctt attagcaccc tctgaacact ctttacctct   2940
aacatcctca gccatgctaa tcgcgcataa aataaatctt cgaacttttt tccattttat   3000
gctcataaag cttccttact gtcaccttat caaaagagct tttgccacta aagtagtcac   3060
acccagaatt gctcccgaat atcgtccaac aatgctagga tctgtggaaa gtttgacaaa   3120
taatttgaac accttgagct tgaagcttcc tgaagttaat atccaaggct cctttccaga   3180
aagtaaccca gtgacctttt tgagaaacta catcactcaa gaacttagta aaattctga    3240
agttgacaaa gaattgattt tcccagcctt ggaatggggt accacactgg aaaaaggtga   3300
tctttttgatc ccagttcctc gtctgagaat aaagggtgct aatcctaaag atttagccga   3360
acaatgggct gctgcattcc caaagggtgg atatcttaaa gacgttattg cgcaaggacc   3420
tttcttgcag ttcttttta acacatcggt tctgtacaag ttggtgatat ctgatgctct    3480
ggagagaggc gatgactttg gtgcacttcc tctaggaaag ggacaaaag ttatagtgga    3540
gttttcttct ccaaatattg ccaaaccttt ccacgctggc catcttagaa gtacaatcat   3600
cggtggtttt atttccaatc tgtatgaaaa gctgggtcat gaagttatga ggatgaatta   3660
tttgggagac tggggaaaac aatttggtgt tcttgcagta gattacggtga                3720
tgaggcaaaa ttaaagactg atccaatcaa ccatttgttt gaggtctatg ttaaaatcaa   3780
ccaagatatt aaggctcaat cagagtctac tgaggagatt gcagaagggc aatcattaga   3840
tgaccaggca agagctttt tcaagaaaat ggaaaatggc gacgaatcgg ctgtaagctt     3900
gtggaaaaga ttccgtgagt tatccattga gaagtacatt gatacttatg cccgcctcaa   3960
catc                                                                3964
```

SEQ ID NO: 81       moltype = DNA  length = 1019
FEATURE                Location/Qualifiers
misc_feature       1..1019
                        note = Description of Artificial Sequence: Synthetic
                        polynucleotide
source                   1..1019
                        mol_type = other DNA
                        organism = synthetic construct
SEQUENCE: 81

```
gccttctcgt gcaatcagag ctgttgaaag agagaagagg gcacacggaa gctgctgttc     60
aattgtgtga attgaccgga ttacaacctg ctggagtgat aggagagctg gttcgtgacg    120
aggacggctc tatgatgcga ttagacgact gtgttcagtt tggtctccgc cacaacgtaa    180
aaattatcaa ccttgaccag atcattgaat acatggattc caagaacagc tagatacgat    240
ggataggaat acagagatat catgattgag gaacgtaaga gcttttcga aagtgtgagt     300
ttgtggtgag ggccaggcgg tggggaggtg gtggggagcc tccttggtcg aatgtagata    360
tagtaagcaa gacacaagag cgcgcgaagt cttcaacgag gcgggcgttgg gtcttgtacg   420
caacgtaatg actacacagt tgagcttgtc gcgaaccggt cgacattttg atcatgcata   480
ctatgttgag acaccatctc gtactattgc ggcaaccagc tgtaaatttg actaattaaa   540
gctgatgaag gatgcagggc gtcgtcaatt ttttgattga ttgcatttaa ttgtttgagc   600
cattcaaggc tgaatgcccg gcaccctaga cccttcttgt gagtactata aacccgcagg   660
cagggtaccc ttggccttct gcgagactac cagtcatacc gtatatccac aatgtactag   720
taatagcccc ggaaaactct aatcccacag aacgtctaac gcctcctatg tcatcgatac    780
ccattcgcac tactgccatg gcccccctta cgtgatcatt tcacttactc ccgcctaagc   840
ttcgcccaca tgcctgcgtt tgccaagatt ttactgacga gtttggttta ctcatcctct   900
atttataact actagacttt caccattctt caccaccctc gtgccaatga tcatcaacca   960
cttggtattg acagccctca gcattgcact agcaagtgcg caactccaat cgcctttca    1019
```

```
SEQ ID NO: 82            moltype = DNA  length = 1322
FEATURE                  Location/Qualifiers
misc_feature             1..1322
                         note = Description of Artificial Sequence: Synthetic
                          polynucleotide
source                   1..1322
                         mol_type = other DNA
                         organism = synthetic construct
SEQUENCE: 82
ctggctctgc ttctggtact tcttcaggtg catcttctgc tactcaaaat gacgaaacat   60
ccactgatct tggagctcca gctgcatctt aagtgcaac gccatgtctt tttgccatct   120
tgctgctcat gttgtagtag acttttttt tcactgagtt tttatgtact actgattaca   180
ttgtgtaggt gtaatgatgt gcactataat actaatatag tcaaaatgct acagaggaaa   240
gtgcaggttg cctgtggtgg tttttcttat tagcaccctc tgaacactct ttacctctaa   300
catcctcagc catgctaatc gcgcataaaa taaatcttcg aacttttttc cattttatgc   360
tcataaagct tccttactgt caccttatca aaagagcttt tgccactaaa gtagtcacac   420
ccagaattgc tcccgaatat cgtccaacaa tgctaggatc tgtggaaagt ttgacaaata   480
atttgaacac cttgagcttg aagcttcctg aagttaatat ccaaggctcc tttccagaaa   540
gtaacccagt ggacctttg agaaactaca tcactcaaga acttagtaaa atttctggag   600
ttgacaaaga attgattttc ccagccttgg aatgggtac cacactggaa aaggtgatc   660
ttttgatccc cagttcctcgt ctgagaataa agggtgctaa tcctaaagat ttagccgaac   720
aatgggctgc tgcattccca aagggtggat atcttaaaga cgttattgcg caaggacctt   780
tcttgcagtt ctttttaac acatcggttc tgtacaagtt ggtgatatct gatgctctgg   840
agagaggcga tgactttggt gcacttcctc taggaaaggg acaaaaagtt atagtggagt   900
tttcttctcc aaatattgcc aaacctttcc acgctggcca tcttagaagt acaatcatcg   960
gtggttttat ttccaatctg tatgaaaagc tgggtcatga agttatgagg atgaattatt   1020
tgggagactg gggaaaacaa tttggtgttc ttgcagtagg atttgagcgt tacggtgatg   1080
aggcaaaatt aaagactgat ccaatcaacc atttgtttga ggtctatgtt aaaatcaacc   1140
aagatattaa ggctcaatca gagtctactg aggagatgca agaagggcaa tcattagatg   1200
accaggcaag agctttttc aagaaaatgg aaaatggcga cgaatcggct gtaagcttgt   1260
ggaaaagatt ccgtgagtta tccattgaga agtacattga tacttatgcc cgcctcaaca   1320
tc                                                                 1322

SEQ ID NO: 83            moltype = DNA  length = 66
FEATURE                  Location/Qualifiers
misc_feature             1..66
                         note = Description of Artificial Sequence: Synthetic
                          oligonucleotide
source                   1..66
                         mol_type = other DNA
                         organism = synthetic construct
SEQUENCE: 83
atgttcagct tgaaagcatt attgccattg gccttgttgt tggtcagcgc caaccaagtt   60
gctgca                                                             66

SEQ ID NO: 84            moltype = AA  length = 22
FEATURE                  Location/Qualifiers
VARIANT                  1..22
                         note = Description of Artificial Sequence: Synthetic peptide
source                   1..22
                         mol_type = protein
                         organism = synthetic construct
SEQUENCE: 84
MFSLKALLPL ALLLVSANQV AA                                           22

SEQ ID NO: 85            moltype = DNA  length = 60
FEATURE                  Location/Qualifiers
misc_feature             1..60
                         note = Description of Artificial Sequence: Synthetic
                          oligonucleotide
source                   1..60
                         mol_type = other DNA
                         organism = synthetic construct
SEQUENCE: 85
atgaaagcat tcctgttgtt actacttta ctaggcctgt ccactacact cgctaaggca   60

SEQ ID NO: 86            moltype = AA  length = 20
FEATURE                  Location/Qualifiers
VARIANT                  1..20
                         note = Description of Artificial Sequence: Synthetic peptide
source                   1..20
                         mol_type = protein
                         organism = synthetic construct
SEQUENCE: 86
MKAFLLLLLL LGLSTTLAKA                                              20

SEQ ID NO: 87            moltype = DNA  length = 144
FEATURE                  Location/Qualifiers
```

```
misc_feature            1..144
                        note = Description of Artificial Sequence: Synthetic
                          polynucleotide
source                  1..144
                        mol_type = other DNA
                        organism = synthetic construct
SEQUENCE: 87
atggaaggtg gcgaagaaga agttgagcgc attcctgatg aacttttcga tacaaaaaag   60
aagcatttgt tagataagct cataagggtc ggaataatcc ttgtactcct gatatggggc  120
actgttttgt tgctaaaaag tatt                                         144

SEQ ID NO: 88           moltype = AA  length = 48
FEATURE                 Location/Qualifiers
VARIANT                 1..48
                        note = Description of Artificial Sequence: Synthetic
                          polypeptide
source                  1..48
                        mol_type = protein
                        organism = synthetic construct
SEQUENCE: 88
MEGGEEEVER IPDELFDTKK KHLLDKLIRV GIILVLLIWG TVLLLKSI                 48

SEQ ID NO: 89           moltype = DNA  length = 57
FEATURE                 Location/Qualifiers
misc_feature            1..57
                        note = Description of Artificial Sequence: Synthetic
                          oligonucleotide
source                  1..57
                        mol_type = other DNA
                        organism = synthetic construct
SEQUENCE: 89
atgagatttc cttcaatttt tactgctgtt ttattcgcag catcctccgc attagct       57

SEQ ID NO: 90           moltype = AA  length = 19
FEATURE                 Location/Qualifiers
VARIANT                 1..19
                        note = Description of Artificial Sequence: Synthetic peptide
source                  1..19
                        mol_type = protein
                        organism = synthetic construct
SEQUENCE: 90
MRFPSIFTAV LFAASSALA                                                 19

SEQ ID NO: 91           moltype = DNA  length = 5679
FEATURE                 Location/Qualifiers
misc_feature            1..5679
                        note = Description of Artificial Sequence: Synthetic
                          polynucleotide
source                  1..5679
                        mol_type = other DNA
                        organism = synthetic construct
SEQUENCE: 91
ggcgcgccgt ttaaaccctc caccagccat ataccactac aacaccacag aagagaaaga    60
gctcatatca tccgtcatga gagagtacca gcacagaaat acagtcaagt aaaactagta   120
tgcaagcatt acgtaataat agcaacttta tgacaaatca ttccatttt ttccactgga   180
gcgtgcactg cgtaaatcat tctctttgga aggcaaggga agaacaacaa aatttttcct   240
tccgttatac aaacattgaa tcatgtctac tgaaccccact tttaaattgg tccttgtcgg   300
tgatggtggt accggtaaag taagtgcaaa ttatttgatg agtcggataa tgttttccgc   360
cccttagttc ccctcatgat tactaacaat tcatagacca ccttcgttaa gagacacctt   420
actgagagt tccgtaagaa gtacattgct actttgggag tcgaagttca tccccttgtca   480
ttccacacta actgtggtcc tatcacattc aacgttggg acactgctgg acaagagaag   540
tttggtggac tgagagatgg ttattacatt aacggtgact gtggtatcat catgttcgac   600
gttacatcga gaattactta caagaacgtt ccaaactggc accgtgactt ggtcagagtg   660
tgtgagaaca ttccaattgt gctttgtggt aacaaggttg atgtcaagga aagaagtca   720
aaggctaaga ccatcacttt ccacagaaag aagaacttgc aatactttga catttctgcc   780
aagtccaact acaactttga gaagccattc ttgtggttag ctagaaagtt gtctggtgag   840
ccccaattag agttcgttgc tgctcccgac ttgcaagccc cagaggttca aattgatgcc   900
gatttaataa agaagtacga gcaagagaac gccgaggctg ccgctatgcc attgcctgat   960
gaagatgatg ccgacttgta agctttact tacagtacat tgagaaccat acatagggca  1020
cgtatcgtaa gtttagttgt ttgctgatgt aagctagttt gtttctgtag tgtttcgagg  1080
tcgcagaggg atctctctag ccttagacaa aaaaaaaaag gttgacacgt tgatacactc  1140
tctgtttcat ccgatctttc acctacgagt cccactcctc ttcagagtac agaagattaa  1200
gtgagagaat tctaccgttc gtatagcata cattatacga agtatttca gtaatgtctt  1260
gttttctttg ttgcagtggt gagccatttt gacttcgtga aagttttctt agaatagttg  1320
tttccagagg ccaaacattc cacccgtagt aaagtgcaag cgtaggaagt ccaagactgg  1380
cataaatcag gtataagtgt cgagcactgg caggtgatct tctgaaagtt tctactagca  1440
gataagatcc agtagtcatg catatggcaa caatgtaccg tgtggatcta agaacgcgtc  1500
ctactaacct tcgcattcgt tggtccagtt tgttgttatc gatcaacgtg acaaggttgt  1560
cgattccgcg taagcatgca tacccaagga cgcctgttgc aattccaagt gagccagttc  1620
```

```
caacaatctt tgtaatatta gagcacttca ttgtgttgcg cttgaaagta aaatgcgaac  1680
aaattaagag ataatctcga aaccgcgact tcaaacgcca atatgatgtg cggcacacaa  1740
taagcgttca tatccgctgg gtgactttct cgctttaaaa aattatccga aaaaattttt  1800
gacggctagc tcagtcctag gtacgctagc attaaagagg agaaaatggc taaactgacc  1860
tctgctgttc cggttctgac cgctcgtgac gttgctgtg ctgttgagtt ctggaccgac  1920
cgtctgggtt tctctcgtga cttcgttgag gacgacttcg ctggtgttgt tcgtgacgac  1980
gttaccctgt tcatctctgc tgttcaggac caggttgttc cggacaacac cctggcttgg  2040
gtttgggttc gtggtctgga cgaactgtac gctgaatggt ctgaagttgt ttctaccaac  2100
ttccgtgacg cttctggtcc ggctatgacc gaaatcggtg aacagccgtg gggtcgtgga  2160
ttcgctctgc gtgaccggc tggtaactgc gttcacttcg ttgctgaaga acaggactaa  2220
cacgtccgac ggcggcccac gggtcccagg cctcggagat ccgtccccct tttcctttgt  2280
cgatatcatg taattagtta tgtcacgctt acattcacgc cctcccccca catccgctct  2340
aaccgaaaag gaaggagtta gacaacctga agtctaggtc cctatttatt tttttatagt  2400
tatgttagta ttaagaacgt tatttatatt tcaaattttt cttttttttc tgtacagacg  2460
cgtgtacgca tgtaacatta tactgaaaac cttgcttgag aaggttttgg gacgctcgaa  2520
ggctttaatt tgcaagctat aacttcgtat agcatacatt ataccttgtt atgcggccgc  2580
agatctaaca tccaaagacg aaaggttgaa tgaaacctttt ttgccatccg acatccacag  2640
gagagttata gagctgctat gcgtgtaaaa atagtttaaa tcttcgtaaa gtatgttagt  2700
ccatgtaatt tgctatgaat cgatacgcta atctggatgc tgaacggatg cttactggca  2760
tgcattattc attacccatc taagctgcgc cacaacccag taaattgcag tgagggaagc  2820
ttccctgtaa ccgtcctgtc cctttaggga ccatcgatcc ccaacgatca aatcgcgata  2880
catctatcaa ctgtcccttt ccatctatct atgcaaggta atgacagact ctgttaactc  2940
tgatgattct gatctggaaa tcatagaggt gactgagcct actccaaaag tggacctttt  3000
ggcccccaat ccagcattta atttactgc cccataagc aacagtaacg gcacaactcc  3060
aataaggaga aaacttgatg accaatccaa ctccaattcc tttgccagac tggaatcgtt  3120
acgggaatca tcagtgaaac cacaagctag tacgttcaat agtaggt tcatcccca  3180
agccgaccaa ttttccaata atcagaataa tgaacttgat aacaacaatg gattcgccga  3240
ctggatttct aagtcccaac ctgaatttcc ctttccactt aatgatggac caaaaaagtc  3300
cagcaatcaa cctacaaact caaatttga agagatcatc gatttaactg aagatatcga  3360
gataaataca tctgtccccg catctacatc atcttctacc ccagttcct ccagcacaca  3420
gaatcagagc catcatatag ccaacaacaa cacagcacaa gatgcgcata tcttccaagg  3480
gaaacgacct ctccaatcat attcagatga tgaagacgaa gatttgcaaa ttgtaggatc  3540
caatattgtt cagcagcctc taggaattat gccaggaact ttcaacgccc ctgcaaacat  3600
actccatttt gacggttcaa accagaatga acaagccaga tggctggact tgcgataaa  3660
agatttgtta gataatcttc acaatcttcg agttcatgct cagtcgaata ttatggagat  3720
caataggttc atttccactt tggggcattt aaacagagaa gtttaaaccc tgcagggcgc  3780
tcggtcgttc ggctgcggcg agcggtatca gctcactcaa aggcggtaat acggttatcc  3840
acagaatcag gggataacgc aggaaagaac atgtgagcaa aaggccagca aaaggccagg  3900
aaccgtaaaa aggccgcgtt gctggcgttt tccatagge tccgccccc tgacgagcat  3960
cacaaaaatc gacgctcaag tcagaggtgg cgaaacccga caggactata agataccag  4020
gcgtttcccc ctggaagctc cctcgtgcgc tctcctgttc cgaccctgcc gcttaccgga  4080
tacctgtccg ccttttctcc ttcgggaagc gtggcgcttt ctcatagctc acgctgtagg  4140
tatctcagtt cggtgtaggt cgttcgctcc aagctgggct gtgtgcacga accccccgtt  4200
cagcccgacc gctgcgcctt atccggtaac tatcgtcttg agtccaaccc ggtaagacac  4260
gacttatcgc cactggcagc agccactggt aacaggatta gcagagcgag gtatgtaggc  4320
ggtgctacag agttcttgaa gtggtggcct aactacggct acactagaag aacagtattt  4380
ggtatctgcg ctctgctgaa gccagttacc ttcggaaaaa gagttggtag ctcttgatcc  4440
ggcaaacaaa ccaccgctgg tagcggtggt tttttgttt gcaagcagca gattacgcgc  4500
agaaaaaaag gatctcaaga agatcctttg atcttttcta cggggtctga cgctcagtgg  4560
aacgaaaact cacgttaagg gatttttggtc atgagattat caaaaaggat cttcacctag  4620
atccttttaa attaaaaatg aagttttaaa tcaatctaaa gtatatatga gtaaacttgg  4680
tctgacagtt accaatgctt aatcagtgag gcacctatct cagcgatctg tctatttcgt  4740
tcatccatag ttgcctgact ccccgtcgtg tagataacta cgatacggga gggcttacca  4800
tctggcccca gtgctgcaat gataccgcgc gacccacgct caccggctcc agatttatca  4860
gcaataaacc agccagccgg aagggccgag cgcagaagtg gtcctgcaac tttatccgcc  4920
tccatccagt ctattaattg ttgccgggaa gctagagtaa gtagttcgcc agttaatagt  4980
ttgcgcaacg ttgttgccat tgctacaggc atcgtggtgt cacgctcgtc gtttggtatg  5040
gcttcattca gctccggttc ccaacgatca aggcgagtta catgatcccc catgttgtgc  5100
aaaaaagcgg ttagctcctt cggtcctccg atcgttgtca gaagtaagtt ggccgcagtg  5160
ttatcactca tggttatggc agcactgcat aattctctta ctgtcatgcc atccgtaaga  5220
tgcttttctg tgactggtga gtactcaacc aagtcattct gagaatagtg tatgcggcga  5280
ccgagttgct cttgcccggc gtcaatacgg gataataccg cgccacatag cagaacttta  5340
aaagtgctca tcattggaaa acgttcttcg gggcgaaaac tctcaaggat cttaccgctg  5400
ttgagatcca gttcgatgta acccactcgt gcacccaact gatcttcagc atcttttact  5460
ttcaccagcg tttctgggtg agcaaaaaca ggaaggcaaa atgccgcaaa aaagggaata  5520
agggcgacac ggaaatgttg aatactcata ctcttccttt tcaatatta ttgaagcatt  5580
tatcagggtt attgtctcat gagcggatac atatttgaat gtatttagaa aaataaacaa  5640
ataggggttc cgcgcacatt tccccgaaaa gtgccacct                         5679
```

SEQ ID NO: 92        moltype = DNA   length = 1157
FEATURE              Location/Qualifiers
misc_feature       1..1157
                      note = Description of Artificial Sequence: Synthetic
                      polynucleotide
source                1..1157
                      mol_type = other DNA
                      organism = synthetic construct
SEQUENCE: 92
aaaccctcca ccagccatat accactacaa caccacagaa gagaaagagc tcatatcatc  60

```
cgtcatgaga gagtaccagc acagaaatac agtcaagtaa aactagtatg caagcattac    120
gtaataatag caacttttatg acaaatcatt ccattttttt ccactggagc gtgcactgcg    180
taaatcattc tctttggaag gcaagggaag acaacaaaa ttttcttc cgttatacaa        240
acattgaatc atgtctactg aacccacttt taaattggtc cttgtcgtg atggtggtac      300
cggtaaagta agtgcaaatt attttgatgag tcggataatg ttttccgccc cttagttcca    360
ctcatgatta ctaacaattc atagaccacc ttcgttaaga gacaccttac tggagagttc    420
cgtaagaagt acattgctac tttgggagtc gaagttcatc ccttgtcatt ccacactaac    480
tgtggtccta tcacattcaa cgtttgggac actgctggac aagagaagtt tggtggactg    540
agagatggtt attacattaa cggtgactgt ggtatcatca tgttcgacgt tacatcgaga    600
attacttaca agaacgttcc aaactggcac cgtgacttgg tcagagtgtg tgagaacatt    660
ccaattgtgc tttgtggtaa caaggttgat gtcaaggaaa gaaaggtcaa ggctaagacc    720
atcactttcc acagaaagaa gaacttgcaa tactttgaca tttctgccaa gtccaactac    780
aactttgaga agccattctt gtggttagct agaaagttgt ctggtgagcc ccaattagag    840
ttcgttgctg ctcccgactt gcaagcccca gaggttcaaa tttaataaag                900
aagtacgagc aagagaacgc cgaggctgcc gctatgccat tgcctgatga agatgatgcc    960
gacttgtaag cttttactta cagtacattg agaaccatac ataggcacg tatcgtaagt    1020
ttagttgttt gctgatgtaa gctagtttgt ttctgtagtg tttcgaggtc gcagagggat    1080
ctctctagcc ttagacaaaa aaaaaaggt tgacacgttg atacactctc tgtttcatcc    1140
gatctttcac ctacgag                                                   1157

SEQ ID NO: 93          moltype = DNA  length = 1125
FEATURE                Location/Qualifiers
misc_feature           1..1125
                       note = Description of Artificial Sequence: Synthetic
                       polynucleotide
source                 1..1125
                       mol_type = other DNA
                       organism = synthetic construct
SEQUENCE: 93
ggagagttat agagctgcta tgcgtgtaaa aatagtttaa atcttcgtaa agtatgttag     60
tccatgtaat ttgctatgaa tcgatacgct aatctggatg ctgaacggat gcttactggc    120
atgcattatt cattacccat ctaagctgcg ccacaaccca gtaaattgca gtgagggaag    180
cttccctgta accgtcctgt ccctttaggg accatcgatc cccaacgatc aaatcgcgat    240
acatctatca actgtccctt tccatctatc tatgcaaggt aatgacagac tctgttaact    300
ctgatgattc tgatctggaa atcatagagg tgactgagcc tactccaaaa gtggaccttt    360
tggccccaa tccagcattt aattttactg ccccataag caacagtaac ggcacaactc      420
caataaggag aaaacttgat gaccaatcca actccaattc ttttgccaga ctggaatcgt    480
tacgggaatc atcagtgaaa ccacaagcta gtacgttcaa tagtagtagg ttcatccccc    540
aagccgacca attttcaat aatcagaata atgaacttga taacaacaat ggattcgccg     600
actggatttc taagtcccaa cctgaatttc ccttccact taatgatgga ccaaaaaagt     660
ccagcaatca acctacaaac tcaaatttg aagagatcat cgatttaact gaagatatcg      720
agataaaatac atctgtcccc gcatctacat catcttctac cccagttccc tccagcacac    780
agaatcagag ccatcatata gccaacaaca acacagcaca agatgcgcat atcttccaag    840
ggaaacgacc tctccaatca tattcagatg atgaagacga agatttgcaa attgtaggat    900
ccaatattgt tcagcagcct ctaggaatta tgccaggaac tttcaacgcc cctgcaaaca    960
tactccattt tgacggttca aaccagaatg aacaagccag atggctggac ttgcggataa    1020
aagatttgtt agataatctt cacaatcttc gagttcatgc tcagtcgaat attatggaga    1080
tcaataggtt catttccact ttggggcatt taaacagaga agttt                    1125

SEQ ID NO: 94          moltype = DNA  length = 1292
FEATURE                Location/Qualifiers
misc_feature           1..1292
                       note = Description of Artificial Sequence: Synthetic
                       polynucleotide
source                 1..1292
                       mol_type = other DNA
                       organism = synthetic construct
SEQUENCE: 94
ttcagtaatg tcttgtttct tttgttgcag tggtgagcca ttttgacttc gtgaaagttt     60
ctttagaata gttgtttcca gaggccaaac attccacccg tagtaaagtg caagcgtagg    120
aagtccaaga ctggcataaa tcaggtataa gtgtcgagca ctggcaggtg atcttctgaa    180
agtttctact agcagataag atccagtagt catgcatatg caacaatgt accgtgtgga    240
tctaagaacg cgtcctacta accttcgcat tcgttggtcc agtttgttgt tatcgatcaa    300
cgtgacaagg ttgtcgattc cgcgtaagca tgcatccca agacgcctg ttgcaattcc      360
aagtgagcca gttccaacaa tctttgtaat attgagcac ttcattgtgt tgcgcttgaa     420
agtaaaatgc gaacaaatta agagataatc tcgaaccgc gacttcaaac gccaatatga    480
tgtgcggcac acaataagcg ttcatatccg ctgggtgact ttctcgcttt aaaaaattat    540
ccgaaaaaat ttttgacggc tagctcagtc ctaggtacga tagcattaaa gaggagaaaa    600
tggctaaact gacctctgct gttccggttc tgaccgctcg tgacgttgct gtgctgttg     660
agttctggac cgaccgtctg ggtttctctc gtgacttcgt tgaggacgac ttcgctggtg    720
ttgttcgtga cgacgttacc ctgttcatct ctgctgttca ggaccaggtt gttccggaca    780
acaccctggc ttgggtttgg gttcgtggtc tggacgaact gtacgctgaa tggtctgaag    840
ttgtttctac caacttccgt gacgcttctg gtccggctat gaccgaaatc ggtgaacagc    900
gtgttggctcg tgagttcgct ctgcgtgacc cggtcggtaa ctgcgttcac ttcgttgctg    960
cgtggggtcg tgagttcgct ctgcgtgacc cggtcggtaa ctgcgttcac ttcgttgctg    960
aagaacagga ctaacacgtc cgacggcggc ccacgggtcc caggcctcgg agatccgtcc    1020
ccctttccct ttgtcgatat catgtaatta gttatgtcac gcttacattc acgccctccc    1080
cccacatccg ctctaaccga aaaggaagga gttagacaac ctgaagtcta ggtccctatt    1140
tattttttta tagttatgtt agtattaaga acgttattta tatttcaaat ttttcttttt    1200
tttctgtaca gacgcgtgta cgcatgtaac attatactga aaccttgct tgagaaggtt    1260
```

```
ttgggacgct cgaaggcttt aatttgcaag ct                               1292

SEQ ID NO: 95           moltype = AA  length = 124
FEATURE                 Location/Qualifiers
VARIANT                 1..124
                        note = Description of Artificial Sequence: Synthetic
                         polypeptide
source                  1..124
                        mol_type = protein
                        organism = synthetic construct
SEQUENCE: 95
MAKLTSAVPV LTARDVAGAV EFWTDRLGFS RDFVEDDFAG VVRDDVTLFI SAVQDQVVPD   60
NTLAWVWVRG LDELYAEWSE VVSTNFRDAS GPAMTEIGEQ PWGREFALRD PAGNCVHFVA  120
EEQD                                                               124

SEQ ID NO: 96           moltype = DNA  length = 11322
FEATURE                 Location/Qualifiers
misc_feature            1..11322
                        note = Description of Artificial Sequence: Synthetic
                         polynucleotide
source                  1..11322
                        mol_type = other DNA
                        organism = synthetic construct
SEQUENCE: 96
ccagccagga cagaaatgcc tcgacttcgc tgctgcccaa ggttgccggg tgacgcacac   60
cgtggaaacg gatgaaggca cgaacccagt ggacataagc ctgttcggtt cgtaagctgt  120
aatgcaagta gcgtatgcgc tcacgcaact ggtccagaac cttgaccgaa cgcagcggtg  180
gtaacgcgc  agtggcggtt ttcatggctt gttatgactg ttttttttgg gtacagtcta  240
tgcctcgggc atccaagcag caagcgcgtt acgccgtggg tcgatgtttg atgttatgga  300
gcagcaacga tgttacgcag cagggcagtc gccctaaaac aaagttaaac atcatgaggg  360
aagcggtgat cgccgaagta tcgactcaac tatcagaggt agttggcgtc atcgagcgcc  420
atctcgaacc gacgttgctg gccgtacatt tgtacggctc cgcagtggat ggcggcctga  480
agccacacag tgatattgat ttgctggtta cggtgaccgt aaggcttgat gaaacaacgc  540
ggcgagcttt gatcaacgac cttttggaaa cttcggcttc ccctggagag agcgagattc  600
tccgcgctgt agaagtcacc attgttgtgc acgacgacat cattccgtgg cgttatccga  660
ctaagcgcga actgcaattt ggagaatggc agcgcaatga cattcttgca ggtatcttcg  720
agccagccac gatcgacatt gatctggcta tcttgctgac aaaagcaaga gaacatagcg  780
ttgccttggt aggtccagcg gcggaggaac tctttgatcc ggttcctgaa caggatctat  840
ttgaggcgct aaatgaaacc ttaacgctat ggaactcgcc gcccgactgg gctggtgatg  900
agcgaaatgt agtgcttacg ttgtcccgca tttggtacag cgcagtaacc ggcaaaatcg  960
cgccgaagga tgtcgctgcc gactgggcaa tggagcgcct gccggcccag tatcagcccg 1020
tcatacttga agctagacag gcttatcttg acaagaagaa gatcgcttg gcctcgcgcg 1080
cagatcagtt ggaagaattt gtccactacg tgaaggcgga gatcaccaag gtagtcggca 1140
aataacatta ctcgcatcca ttctcaggct gtctcgtctc gtctccaact ttctgccgcc 1200
aatctccttt ccattcaaat tctctacaac aaggcaggct tcgtccgttg atgtgaagtt 1260
tgcaaaagcc aaaccacgaa aaacaccatt gtcaaatgg tagttgaagg cataaggcaa 1320
aggcaagtca aactttgtca taacgtctaa aagttgctct tttttttatgg caaaagggat 1380
gttctttatc acaatagcag tgggaatgac atcttcatca tcattcgtat catcaatacc 1440
atcgagttct gaatccaaag gtttctgttg ttgggataag gcatcagatt ctttgagcag 1500
gtcgtccttg gcgtcctcct ctagatgaaa tttgccatcg ttaggaggtg agtattggga 1560
aacgttgact tgttgctcaa tccaaggatc aacgttgacc atcggattgc cgttctgagg 1620
agacagccag gcattatacc gtggttgacc ggcgttacg cgcagaggat tgttgctggt 1680
gttgttgaca gaagacgcat acccagacgc tgccggatgac atcgacgaaa ttgaagggcg 1740
acgttgcata cccatttgtt gctgatccaa gaaacttggt gtttcagtca attgtctcag 1800
gtccatattg atcaatgtgt tcaactgttt caatctggtt ccggagggtg gctattacga 1860
caagctgtgg ctactatcta agtgggagaa gtaacgacaa cattgatga gacacaggaa 1920
ttacagggcg tgcatccacc aataacaatt agtcgagatt caaccaatt acgtaagcgc 1980
tcaacccttt tttcgaacac gtatcgagca agtccaggt gaaaccttca tccattatat 2040
ccaaagtcga ccgaagcttt aacaacatcc ataatgttaa gtgtccagtt tgatgagtgc 2100
agaatggttc caagttttag accagttact aatatttaaa gtctacagca attccaggag 2160
gacagagaac gttagctaaa agaagagcag caaacttgga taagaaacag gatgaaccaa 2220
cctccgccag atctgccggt gctggaggtt cttcgtctac catgctaaag ttgtacacag 2280
acgaggccca aggtttgaaa gttgatcctt taattgttct tgttcttgct gttggtttca 2340
ttttcagtgt cattggtttg cacgttgttg ctaagctgag aggaaagttg atcaactaag 2400
acctatattt aaacaggttt catcatatct gtactatatt tacaagtcca ctgcgtttag 2460
gtatatacta aagacattca agaagcacat ccacaacttg tgcaagtcct gtcaaatgta 2520
ctagatgctt tcagaacat cctgcggttt gaggagattc ctgaatttcc cagtcccaag 2580
tcttttctct tgtagaggtct ttgagttctt gtgaatgctg aattggggtt cttacctcaa 2640
tttctattag tgggaaatgc tttcccacaa ttattttgcaa tgggatcccg gcaactttac 2700
tttgcttcaa cttatgtccc atactgaact ttccgtcacg gttgtcaact gaacgtcga 2760
atgagctcag tatttcggtg acagtgtcta gattcttttt acttgatgtt ttattcgaaa 2820
gtagcgtgat ttgatatggt gcgataattt gtggccaggg ctgggagttc gtagacgaa 2880
acaaacgcag aatccaagca gacaagtgga gagtggacaa attcttgatg ttaattcgta 2940
agatcctaa caaatctta gcaaaactga aagtgaaga ctacgatagg gatttacttg 3000
aaaaatatat tcaagttttg tcagaatacc cactccatat taacgatatt attgtcccta 3060
gaactattac gtaccacttg tgtgatattt atactgatga gttggaaaag gttatgttta 3120
gtgggcttcc tggatttgaa gaagaagaag attacgagga agaagatgaa gtctcggctc 3180
ctatcgaaaa aaaaaccaga gatactgata attcagacga tgaggcctct gataccgatc 3240
cagaaacgag tgacgaagaa gacgaaggtg agaatactga aaacgagtca gaagaggaac 3300
```

```
cgatcaaact ctctgcggaa gaagaaacgg ctctgtggaa aacaaagatg gagattatcc   3360
atgaaactcc tatcgacaaa ttactctcac cttttgtctc attgaagaaa gatacctcaa   3420
ataaaccatt aaaattgaaa atccaagaag cagttcttgc tgatccaaga ctcggcaaat   3480
ggaaagttaa atcgtaccga aagcctaaac caaaaccaaa acctcttcag gtgctacaga   3540
aacagttata cgaacagatc aaatataaaa agggtaaagc agtcacaggt gaagacgacg   3600
atgaactcaa agacgaagac aagatgacg atgacgaggt catctcggag agtgaagctg   3660
ataactctga tgaagaagaa gatgaagaat ggaatggctt tggaactatc tagaatacat   3720
atgtaaaacc atatcaggca ataacaattt ctcgctattt tgcatcccaa cacctcgacc   3780
gacgtgttca gttcgaccct ttacctacag tgtctttaac tcccatttgg atctcctaaa   3840
taacctacac aaatgtccca aaaagtcacc gacgtccctc tggaatttgt taaggaaggt   3900
tccaaattca tctctaaatg tactaaaccc tctcagaagg agtacttaaa gatagtaaga   3960
gctgttggag ttgggttttt aatgatgggc gtggttggtt acgttgtcaa gctcattcat   4020
attccaatca gatatttgat tgtttaaaag tttaggtttg aatacaatgt gtatgcttaa   4080
ttatattcac ttcgtttcat tgattttgc tatccctgtt gtgcgttaat catctctatc   4140
gtgatcctct caagttgcac ctcaaataga agacaactta tggaggtgta ctacccaata   4200
tcagtcttga cgtttctagt ttcgttgtat gctgcatacc aatttcagtt cttccgtagt   4260
gttttgagca taggcttgtt tacccgtctt ctttacactc tgtatgagc accttatcaa   4320
acctcttatc acagctgaaa ggagaaggcg gtggtggttc ttctggtcag aatcggccca   4380
gaactgtgga tcctgctgtt gcaagattga aagcagaaaa gaagatggaa agagagaagc   4440
aagctcttaa agaggctcag caagcccagg aagctcggga aaggcgaaga attagtcatg   4500
ctacccagat aggtttgaga ccaaccagta aagctcccag cactgaaggt cctcaatcgc   4560
actggaaaca tcaaggtcga tgaccgcact aacagaagga gctaaactat tcgaaaagga   4620
gattccttac attacagaat tagagggtga tgtcgaagga atgaaattca ttatcaaggg   4680
cgagggtact ggtgacgcta ctaccggtac gattaaagca aagtcatctct gtacaacagg   4740
tgaccttcct gttccgtggg ctactctggt gagcactttg tcttatggag ttcaatgttt   4800
tgctaaatac ccttcgcaca ttaaagactt tttcaaaagt gcaatgcctg agggctatac   4860
tcaggagaga acaatatctt tcgaaggaga tggtgtgtat aagactaggg ctatggtcac   4920
gtatgaaaga ggatccatct acaatagagt aactttaact ggtgaaaact tcaaaaagga   4980
cggtcacatc cttagaaaga atgttgcctt tcaatgccca ccatccatct tgtacatttt   5040
gccagacaca gttaacaatg gtatcagagt tgagtttaac caagcttatg acatagaggg   5100
tgtcaccgaa aagttggtta caaatgttc acagatgaat cgtcccctgg caggatcagc   5160
tgccgtccat atcccacgtt accatacatat cacttatcat accaagctgt ccaaagatcg   5220
tgatgagaga agggatcaca tgtgtttggt tgaagtggta aaggccgtgg atttggatac   5280
ttaccaatga ctgacctcct gccagcaata gtaagacaac acgcaaagtc tctgaacgg   5340
tctttgagct gtctgtgtca tcaaacatat cttcatctgt agttgtattg ttttcttta   5400
tcactaggag tccatccttc tggatggctg tcttcacctt atttagccac tccaaaaatg   5460
ccgggtctgg gagatgaccg cagcaccatt gacaccatat cagagagtat cgagactcct   5520
ctggtttcca gtcttgcatg ggaatttcat aaatgtctcc tatcttacct tgttccatca   5580
gtgtttgtag ttccaccctc atctggtcga caaatgtttt aactggttcc aataaatcaa   5640
ccttatcaca aactttatgc agaaaatctc ttgtcacgcg gccaataccg gcaccaaagt   5700
ctataccata tttgatttg tcaggatcgt tagagaaacg actctttaac tttcttaaaa   5760
aggtcatcga tccaacaaca tctgcttttg gaaccaagt tgtctcaccg tacccaccca   5820
aaactccgtc gacagatgct gggacgctgt tccagtattt cagggcatcg tcatagttga   5880
tcaaactgtc cacctgttta gggtcatccc cattatgttc tgtcattgtg gtaaaaatgg   5940
gatacagtga tatattgaag gggaatggtt ataagagcct acctgagaaa taaaattatt   6000
atgcgccatc cgacatccag aaaaattgat gaaagattgg ctattgttga cggttcttga   6060
tcccaaaaaa aaaaaaaaac aagaaatgct gccgtcctag ttttgcttca aagaatggtt   6120
tcgtgctatg ccattcccaa cccaaagagc tgtcccatcc cattaagttg tgctgactga   6180
ttatgttgca caatccagtg tcgtgattac ctccaacatc gcacgcgaat tcgccatgg   6240
ctgggaaacc caaattcttc ggtcgtccat caaactctga agtcatttca acaccaaact   6300
caacagctat catagaaaaa tatggcgggg ttgcgttttt tagacattgc aagaccattt   6360
gtcagctgga tcccggaagt tgaacttcct tatgaaaact gggggttcga tgaaaagctg   6420
atttactcat ttttcactgc tgccatctat ttgattctgt ccctgcctat atacggtgtc   6480
aaatcctctg aagtcgtgga cccagttccc catttgcgtt ctgccttagg gagtgagaag   6540
ggaacattgc tggagcttgg gttactgcct gtgattactt cggcatttat cttgcagttg   6600
ttggctggtt ggaaagtttt caaagtaaac tttgatctgg ttagtgacag aatattgttc   6660
caaactttgc aaaagatcac ttcagtcgtt atcagcatcg tatatgctgt tcttctcaca   6720
ttttgtgact actttactcc aggtgtgtcc actgataacg tcttgtggtc ccaatttctg   6780
atcatcttac agatagtggt ggtcaacttc ttggttactc tactcgttga agtcattgac   6840
aaggattacg gattttcttc aggagctcta ttgttgcttg cggtttattc cgccaccaac   6900
ttcgtttttg gcacgattgg tcttagcacc gtcaacacct ccagatcgaa cgaatctatt   6960
ggtgctctga ttcaattatt ccgcaatttg agctctaaac caattggtgt tgccatatat   7020
gactccttct tcagagtaaa ccttcctaac ttgactcaat tttatctggg gattgccatt   7080
atttgtgttt gtctgttctt gaataatgca agatacgaag taccaattaa gccaaacaag   7140
gttcgtgcca tggcctcagc ttacccaatc aagctacttt tcaatggttc tttgccactt   7200
ctgtacacgt ggactgtgct gtacaacttg aaccttattg gttctttgt cttcaagctt   7260
accaactttt ctcttttagg gaacttcaaa gtggacccat cggcaacaa ctactacgaa   7320
attacatctg gactgctgta tttattgact cctactttca acgtcgaagc tggacttttta   7380
cccaatgttg ctaagccatt tgtttttcatt gccttctatg ttggtgttag cacttttcttt   7440
gctagatcgt ggtccaacat taacgggtcg tcaggcaagg acattgccaa gttttttcaag   7500
gctcaaggaa tctcattgtt aggaaaaaga gatgcctctg tgtctaaaga gtttaacacc   7560
ctagttcctg ttgcttctgc ctctggagct ttcctattgt cttttccagt tgccgtcgct   7620
gagtattgg gtggctctgg tgttccaacc tctatcggaa tcggtctttt gagtggtttg   7680
ttggcctgtg aaactgtttt gcaagaatgg acgagctgcc acagttcttc                7740
caatacttcc agacttctta ggtttagaaa tccttgaaga ctatccagac attcaccgc    7800
acctcaattt accttctaca tacatcacat attctataga ggagagttcc attgctcgta   7860
ctgaacccca caccactctt ctttatacccc tacaaactct tcgtccaact caatggcgtc   7920
attcgtgtcg gtatagacaa taatggtacc ccagtccatt tcaaagttgt cttttctgat   7980
atccatgatt aatttgggca ttatttgaag ttcgaactgt tttcctggca ctttagcttt   8040
```

```
gatgatcgtt tgatatattt catccttgga gttatacagt agtggctttc ctcccaggtg   8100
gtatcgtaaa acctgggaag gattgtgctc aagagccaac tccctttaca acctcactca   8160
agtccgttag agggcgcgcc gcacatgaag ctgtacatgg aaggcacggt gaataaccac   8220
cacttcaaat gcaccagcga gggtgagggt aaaccgtatg aaggcaccca aacgatgcgt   8280
atcaaagttg ttgagggtgg cccgttgccg tttgcgttgc acattttagc gacgagcttt   8340
atgtatggct ctcgtacgtt tatcaagtac ccgaagggta ttccggactt tttcaaacaa   8400
tcttttccag agggtttcac ctgggagcgc gtgactcgct acgaagatgg cggcgtcgtg   8460
accgcaacgc aggataccct cctggaagat ggctgcctgg tctaccacgt tcaggtccgt   8520
ggtgtcaatt tcccgagcaa tggtccggtt atgcagaaga aaaccctggg ttgggaaccg   8580
aacaccgaga tgttgtatcc tgcagatggt ggcctggaag gtcgcagcga catggcattg   8640
aaactggtcg gtggcggcca tctgagctgt agcttcgtga ccacgtatcg ttcgaagaaa   8700
acggtcggta acatcaaaat gccgggtatt cacgcgttgt accaccgtct ggtgcgcatt   8760
aaagaagccg acaaagagac ttacgtggag caacatgaag tagccgttgc gaaatttgct   8820
ggtttgggcg gtggtatgga cgaactgtac agttccttat catctggcga atcggaccca   8880
caagagcact gggttccgtt ttacattcca ggaagagttt cagtaatgtc ttgtttcttt   8940
tgttgcagtg gtgagccatt ttgacttcgt gaaagtttct ttagaatagt tgtttccaga   9000
ggccaaacat tccaccgta gtaaagtgca agcgtaggaa gaccaagact ggcataaatc   9060
aggtataagt gtcgagcact ggcaggtgat cttctgaaag tttctactag cagataagat   9120
ccagtagtca tgcatatggc aacaatgtac cgtgtggatc taagaacgcg tcctactaac   9180
cttcgcattc gttggtccag tttgttgtta tcgatcaacg tgacaaggtt gtcgattccg   9240
cgtaagcatg catacccaag gacgcctgtt gcaattccaa gtgagccagt tccaacaatc   9300
tttgtaatat tagagcactt cattgtgttg cgcttgaaga taaaatgcga acaaattaag   9360
agataatctc gaaaccgcga cttcaaacgc caatatgatg tgcggcacac aataagcgtt   9420
catatccgct gggtgacttt ctcgctttaa aaaattatcc gaaaaatttt ttgacggcta   9480
gctcagtcct aggtacgcta gcattaaaga ggagaaaatg actactcttg atgacacagc   9540
ctacagatat aggacatcag ttccgggtga cgcagaggct atcgaagcct tggacggttc   9600
attcactact gatacggtgt ttagagtcac cgctacaggt gatggcttca ccttgagaga   9660
ggttcctgta gacccaccct taacgaaagt tttccctgat gacgaatcgg atgacgagtc   9720
tgatgctggt gaggacggtg accctgattc cagaacattt gtcgcatacg gagatgatgg   9780
tgacctggct ggctttgttg tggtgtccta cagcggatgg aatcgtagac tcacagttga   9840
ggacatcgaa gttgcacctg aacatcgtgg tcacggtgtt ggtcgtgcac tgatgggact   9900
ggcaacagag tttgctagag aaagaggagc cggacatttg tggttagaag tgaccaatgt   9960
caacgctcct gctattcacg catataggcg aatgggtttc actttgtgcg gtcttgatac  10020
tgctttgtat gacggaactg cttcctgatgg tgaacaagct ctttacatga gtatgccatg  10080
tccatagcac gtccgacggc ggcccacggg tcccaggcct cggagatccg tccccctttt  10140
cctttgtcga tatcatgtaa ttagttatgt cacgcttaca ttcacgccct ccccccacat  10200
ccgctctaac cgaaaggaa ggagttagac aacctgaagt ctaggtccct atttatttt   10260
ttatagttat gttagtatta agaacgttat ttatatttca aattttctt tttttctgtt  10320
acagacgcgt gtacgcatgt aacattatac tgaaaaccctt gcttgagaag gttttgggac  10380
gctcgaaggc tttaatttgc aagctccgaa taacttcgta tagcatacat tataccttgt  10440
tattacagcg gccgcaaata tttatctga ttaataagat gatcttcttg agatcgtttt  10500
ggtctgcgcg taatctcttg ctctgaaaac gaaaaaaccg ccttgcaggg cggttttcg   10560
aaggttctct gagctaccaa ctctttgaac cgaggtaact ggcttggagg agcgcagtca  10620
ccaaaacttg tccttcagt ttagccttaa ccggcgcatg acttcaagac taactcctca  10680
aaatcaatta ccagtggctg ctgccagtgg tgcttttgca tgtcttttcc ggttggactc  10740
aagacgatag ttaccggata aggcgcagcg gtcggactga acgggggtt cgtgcataca  10800
gtccagcttg gagcgaactg cctacccgga actgagtgtc agcgtggaa tgagacaaac  10860
gcggccataa cagcggaatg acaccggtaa accgaaaggc aggaacagga gagcgcacga  10920
gggagccgcc aggggggaaac gcctggtatc tttatagtcc tgtcgggttt cgccaccact  10980
gatttgagcg tcagatttcg tgatgcttgt caggggggcg gagcctatgg aaaaacggct  11040
ttgccggcc cctctcactt ccctgttaag tatcttcctg gcatcttcca ggaaatctcc  11100
gccccgttcg taagccattt ccgctcgccg cagtcgaacg accgagcgta gcgagtcagt  11160
gagcgaggaa gcggaatata tcctgtatca catattctgc tgacgcaccg gtgcagcctt  11220
ttttctcctg ccacatgaag cacttcactg acccctcat cagtgccaac atagtaagcc  11280
agtatacact ccgctagcgc tgatgtccgg cggtgcgacg tc                     11322

SEQ ID NO: 97        moltype = DNA   length = 888
FEATURE              Location/Qualifiers
misc_feature         1..888
                     note = Description of Artificial Sequence: Synthetic
                     polynucleotide
source               1..888
                     mol_type = other DNA
                     organism = synthetic construct
SEQUENCE: 97
caactttctg ccgccaatct cctttccatt caaattctct acaacaaggc aggcttcgtc    60
cgttgatgtg aagtttgcaa aagccaaacc acgaaaaaca ccattgtcaa aatggtagtt   120
gaaggcataa ggcaaaggca agctaaactt tgtcataacg tctaaaagtt gctcttttt   180
tatggcaaaa gggatgttct ttatcacaat agcagtggga atgacatctt catcatcatt   240
cgtatcatca ataccatcga gttctgaatc caaaggtttc tgttgttggg ataaggcatc   300
agattctttg agcaggtcgt ccttggcgtc ctcctctaga tgaaatttgc catcgttagg   360
aggtgagtat tgggaaacgt tgacttgttg ctcaatccaa ggatcaacgt tgaccatcgg   420
attgccgttc tgaggagaca gccaggcatt ataccgtggt tgaccggcgt ttacgcgcag   480
aggattgttg ctggtgttgt tgacagaaga cgcatacccg gacgctgcgg atgacatcga   540
cgaaattgaa gggcgacgtt gcatacccat ttgttgctga tccaagaaac ttggtgtttc   600
agtcaattgt ctcaggtcca tattgatcaa tgtgttcaac tgtttcaatc tggttccgga   660
gggtggctat tacgacaagc tgtggctact atctaagtgg gagaagtaac ggaacacatt   720
gatgagacac aggaattaca gggcgtgcat ccaccaataa caattagtcg agatttcaac   780
caattacgta agcgctcaac cctttttccg aacacgtatc gagcaaagtc caggtgaaac   840
```

```
cttcatccat tatatccaaa gtcgaccgaa gctttaacaa catcccata              888

SEQ ID NO: 98           moltype = DNA   length = 953
FEATURE                 Location/Qualifiers
misc_feature            1..953
                        note = Description of Artificial Sequence: Synthetic
                         polynucleotide
source                  1..953
                        mol_type = other DNA
                        organism = synthetic construct
SEQUENCE: 98
agacaagtgg agagtggaca aattcttgat gttaattcgt aagatcctta acaaatcttt   60
agcaaaactg aaaagtgaag actacgatag ggatttactt gaaaaatata ttcaagtttt  120
gtcagaatac ccactccata ttaacgatat tattgtccct agaactatta cgtaccactt  180
gtgtgatatt tatactgatg agttggaaaa ggttatgttt agtgggcttc ctggatttga  240
agaagaagaa gattacgagg aagaagatga agtctcggct cctatcgaaa aaaaaaccag  300
agatactgat aattcagacg atgaggcctc tgataccgat ccagaaacga gtgacgaaga  360
agacgaaggt gagaatactg aaaacgagtc agaagaggaa ccgatcaaac tctctgcgga  420
agaagaaacg gctctgtgga aaacaaagat ggagattatc catgaaactc ctatcgacaa  480
attactctca cctttgtct cattgaagaa agatacctca aataaccat taaaattgaa    540
aatccaagaa gcagttcttg ctgatccaag actcggcaaa tggaaagtta aatcgtaccg  600
aaagcctaaa ccaaaaccaa aacctcttca ggtgctcaaa gaacagttat acgaacagat  660
caaatataaa aagggtaaag cagtcacagg tgaagacgac gatgaactca agacgaaga   720
cgaagatgac gatgacgagg tcatctcgga gagtgaagct gataactctg atgaagaaga  780
agatgaagaa tggaatggct ttggaactat ctagaataca tatgtaaaac catatcaggc  840
aataacaatt tctcgctatt ttgcatccca acacctcgac cgacgtgttc agttcgaccc  900
tttacctaca gtgtctttaa ctcccatttg gatctcctaa ataacctaca caa          953

SEQ ID NO: 99           moltype = DNA   length = 991
FEATURE                 Location/Qualifiers
misc_feature            1..991
                        note = Description of Artificial Sequence: Synthetic
                         polynucleotide
source                  1..991
                        mol_type = other DNA
                        organism = synthetic construct
SEQUENCE: 99
tctgaacggg tctttgagct gtctgtgtca tcaaacatat cttcatctgt agttgtattg   60
ttttcttta tcactaggag tccatccttc tggatggctg tcttgcactt atttagccac   120
tccaaaaatg ccgggtctgg gagatgaccg cagcaccatt gacaccatat cagagagtat  180
cgagactcct ctggtttcca gtcttgcatg ggaatttcat aaatgtctcc tatcttacct  240
tgttccatca gtgtttgtag ttccaccctc atctggtcga caaatggttt aactggttcc  300
aataaatcaa ccttatcaca aactttatgc agaaaattc ttgtcacgcg gccaataccg   360
gcaccaaagt ctataccata tttgattttg tcaggatcgt tagagaaacg actctttaac  420
tttcttaaaa aggtcatcga tccaacaaca tctgcttttg gaaccgaagt tgtctcaccg  480
tacccaccca aaactccgtc gacagatgct gggacgctgt tccagtatt cagggcatcg   540
tcatagttga tcaaactgtc cacctgttta gggtcatccc cattatgttc tgtcattgtg  600
gtaaaaatgg gatacagtga tatattgaag gggaatggtt ataagagcct acctgagaaa  660
taaaattatt atgcgccatc cgacatccag aaaaattgat gaaagattgg ctattgttga  720
cggttcttga tcccaaaaaa aaaaaaaaac aagaaatgct gccgtcctag ttttgcttca  780
aagaatgctt tcgtgctatg ccattcccaa cccaaagagc tgtcccatcc cattaagttg  840
tgctgactga ttatgttgca caatccagtg tcgtgattac ctccaacatc gcacgcgaat  900
ttcgccatgg ctgggaaacc caaattcttc ggtcgtccat caaactctga agtcatttca  960
acaccaaact caacagctat catagaaaaa t                                  991

SEQ ID NO: 100          moltype = DNA   length = 460
FEATURE                 Location/Qualifiers
misc_feature            1..460
                        note = Description of Artificial Sequence: Synthetic
                         polynucleotide
source                  1..460
                        mol_type = other DNA
                        organism = synthetic construct
SEQUENCE: 100
gacctatatt taaacaggtt tcatcatatc tgtactatat ttacaagtcc actgcgttta   60
ggtatatact aaagacattc aagaagcaca tccacaactt gtgcaagtcc tgtcaaatgt  120
actagatgct tttcagaaca tcctgcggtt tgaggagatt cctgaatttc ccagtcccaa  180
gtcttctct tgtagaggtc tttgagttct tgtgaatgct gaattggggt tcttacctca   240
atttctatta gtgggaaatg cttccccaca attatttgca atgggaatcc ggcaacttta  300
ctttgcttca acttatgtcc catactgaac tttccgtcac ggttgtcaac ttgaacgtcg  360
aatgagctca gtatttcggt gacagtgtct agattctttt tacttgatgt tttattcgaa  420
agtagcgtga tttgatatgg tgcgataatt tgtggccagg                        460

SEQ ID NO: 101          moltype = DNA   length = 492
FEATURE                 Location/Qualifiers
misc_feature            1..492
                        note = Description of Artificial Sequence: Synthetic
                         polynucleotide
source                  1..492
```

```
                    mol_type = other DNA
                    organism = synthetic construct
SEQUENCE: 101
aagtttaggt ttgaatacaa tgtgtatgct taattatatt cacttcgttt cattgatttt    60
tgctatcect gttgtgcgtt aatcatctct atcgtgatcc tctcaagttg cacctcaaat   120
agaagacaac ttatggaggt gtactaccca atatcagtct tgacgtttct agtttcgttg   180
tatgctgcat accaatttca gttcttccgt agtgttttga gcataggctt gtttacccgt   240
cttctttaca ctctgatatg agcacctat caaacctctt atcacagctg aaggagaag    300
gcggtggtgg ttcttctggt cagaatcggc ccagaactgt ggatcctgct gttgcaagat   360
tgaaagcaga aaggaagatg gaaagagaga agcaagctct taaagaggct cagcaagccc   420
aggaagctcg ggaaaggcga agaattagtc atgctaccca gataggttg agaccaacca    480
gtaaagctcc ca                                                       492

SEQ ID NO: 102          moltype = DNA  length = 371
FEATURE                 Location/Qualifiers
misc_feature            1..371
                    note = Description of Artificial Sequence: Synthetic
                     polynucleotide
source                  1..371
                    mol_type = other DNA
                    organism = synthetic construct
SEQUENCE: 102
gtttagaaat ccttgaagac tatccagaca ttcacccgca cctcaattta ccttctacat    60
acatcacata ttctatagag gagagttcca ttgctcgtac tgaacccac accactcttc   120
tttatacct acaaactctt cgtccaactc aatggcgtca ttcgtgtcgg tatagacaat    180
aatggtaccc cagtccattt caaagttgtc tttttcgata tccatgatta atttgggcat   240
tatttgaagt tcgaactgtt ttcctggcac tttagctttg atgatcgttt gatatatttc   300
atccttggag ttatacagta gtggctttcc tcccaggtgg tatcgtaaaa cctgggaagg   360
attgtgctca a                                                       371

SEQ ID NO: 103          moltype = DNA  length = 1487
FEATURE                 Location/Qualifiers
misc_feature            1..1487
                    note = Description of Artificial Sequence: Synthetic
                     polynucleotide
source                  1..1487
                    mol_type = other DNA
                    organism = synthetic construct
SEQUENCE: 103
ttcagtaatg tcttgtttct tttgttgcag tggtgagcca ttttgacttc gtgaaagttt    60
ctttagaata gttgtttcca gaggccaaac attccaccg tagtaaagtg caagcgtagg    120
aagaccaaga ctggcataaa tcaggtataa gtgtcgagca ctggcaggtg atcttctgaa   180
agtttctact agcagataag atccagtagt catgcatatg gcaacaatgt accgtgtgga   240
tctaagaacg cgtcctacta accttcgcat tcgttggtcc agtttgttgt tatcgatcaa   300
cgtgacaagg ttgtcgattc cgcgtaagca tgcatacca aggacgcctg ttgcaattcc    360
aagtgagcca gttccaacaa tctttgtaat attagagcac ttcattgtgt tgcgcttgaa   420
agtaaaatgc gaacaaatta agagataatc tcgaaaccgc gacttcaaac gccaatatga   480
tgtgcggcac acaataagcg ttcatatccg ctgggtgact ttctcgcttt aaaaaattat   540
ccgaaaaaat ttttgacggc tagctcagtc ctaggtacgc tagcattaaa gaggagaaaa   600
tgactactct tgatgacaca gcctacagat ataggacatc agttccgggt gacgcagagg   660
ctatcgaagc cttggacggt tcattcacta ctgatacgt gtttagagtc accgctacag    720
gtgatggctt caccttgaga gaggttcctg tagacccacc cttaacgaaa gttttccctg   780
atgacgaatc ggatgacgag tctgatgctg tgaggacgg tgaccctgat tccagaacat   840
ttgtcgcata cggagatgat ggtgacctgg ctggctttgt tgtggtgtcc tacagcggat   900
ggaatcgtag actcacagtt gaggacatcg aagttgcacc tgaacatcgt ggtcacgggh   960
ttggtcgtgc actgatggga ctggcaacag agtttgctag agaaagagga gccggacatt  1020
tgtggttaga agtgaccaat gtcaacgctc tgctattca cgcatatagg cgaatgggtt   1080
tcactttgtg cggtcttgat actgctttgt atgacggaac tgcttctgat ggtgaacaag   1140
ctcttttacat gagtatgcca tgtccatagc acgtccgacg gcggcccacg ggtcccaggc  1200
ctcggagatc cgtcccccctt ttcctttgtc gatatcatgt aattagttat gtcacgctta  1260
cattcacgcc ctccccccac atccgctcta accgaaaagg aaggagttag acaacctgaa   1320
gtctaggtcc ctatttattt ttttatagtt atgttagtat taagaacgtt atttatattt   1380
caaattttc ttttttttct gtacagacgc gtgtacgcat gtaacattat actgaaaacc    1440
ttgcttgaga aggttttggg acgctcgaag ctttaatttt gcaagct                1487

SEQ ID NO: 104          moltype = AA  length = 189
FEATURE                 Location/Qualifiers
VARIANT                 1..189
                    note = Description of Artificial Sequence: Synthetic
                     polypeptide
source                  1..189
                    mol_type = protein
                    organism = synthetic construct
SEQUENCE: 104
MTTLDDTAYR YRTSVPGDAE AIEALDGSFT TDTVFRVTAT GDGFTLREVP VDPPLTKVFP    60
DDESDDESDA GEDGDPDSRT FVAYGDDGDL AGFVVVSYSG WNRRLTVEDI EVAPEHRGHG   120
VGRALMGLAT EFARERGAGH LWLEVTNVNA PAIHAYRRMG FTLCGLDTAL YDGTASDGEQ   180
ALYMSMPCP                                                           189
```

```
SEQ ID NO: 105          moltype = DNA  length = 207
FEATURE                 Location/Qualifiers
misc_feature            1..207
                        note = Description of Artificial Sequence: Synthetic
                        polynucleotide
source                  1..207
                        mol_type = other DNA
                        organism = synthetic construct
SEQUENCE: 105
gctccagtca acactacaac agaagatgaa acggcacaaa ttccggctga agctgtcatc  60
ggttactcag atttagaagg ggatttcgat gttgctgttt tgccattttc caacagcaca  120
aataacgggt tattgtttat aaatactact attgccagca ttgctgctaa agaagaaggg  180
gtatctctcg agaaaagaga ggctgaa                                      207

SEQ ID NO: 106          moltype = AA  length = 69
FEATURE                 Location/Qualifiers
VARIANT                 1..69
                        note = Description of Artificial Sequence: Synthetic
                        polypeptide
source                  1..69
                        mol_type = protein
                        organism = synthetic construct
SEQUENCE: 106
APVNTTTEDE TAQIPAEAVI GYSDLEGDFD VAVLPFSNST NNGLLFINTT IASIAAKEEG  60
VSLEKREAE                                                          69

SEQ ID NO: 107          moltype = AA  length = 8
FEATURE                 Location/Qualifiers
source                  1..8
                        mol_type = protein
                        organism = synthetic construct
SEQUENCE: 107
HHHHHHHH                                                            8
```

The invention claimed is:

1. A *Pichia pastoris* microorganism, in which the activity of a SEC72 protein comprising a polypeptide sequence at least 95% identical to SEQ ID NO: 2 has been eliminated and wherein said microorganism expresses a recombinant silk-like protein comprising a secretion signal peptide derived from yeast.

2. The microorganism of claim 1, wherein said SEC72 protein comprises SEQ ID NO: 2.

3. The microorganism of claim 1, further comprising a recombinantly expressed SSH1 translocon complex.

4. The microorganism of claim 3, wherein said SSH1 translocon complex comprises a first polypeptide sequence at least 95% identical to SEQ ID NO: 4, a second polypeptide sequence at least 95% identical to SEQ ID NO: 6, and a third polypeptide sequence at least 95% identical to SEQ ID NO: 8.

5. The microorganism of claim 3, wherein said SSH1 translocon complex comprises a first polypeptide comprising SEQ ID NO: 4, a second polypeptide comprising SEQ ID NO: 6, and a third polypeptide comprising SEQ ID NO: 8.

6. A method of producing a recombinant protein, comprising:
culturing the microorganism of claim 3 in a culture medium under conditions suitable for expression of the recombinantly expressed protein; and
isolating the recombinant protein from the microorganism or the culture medium.

7. The microorganism of claim 1, further comprising a recombinantly expressed translocon complex.

8. The microorganism of claim 7, wherein said translocon complex is expressed from a recombinant SSH1 gene, a recombinant SSS1 gene, and a recombinant SBH2 gene.

9. The microorganism of claim 8, wherein said SSH1 gene comprises SEQ ID NO: 3.

10. The microorganism of claim 8, wherein said SSH1 gene comprises a polynucleotide sequence at least 95% identical to SEQ ID NO: 3, wherein said SSS1 gene comprises a polynucleotide sequence at least 95% identical to SEQ ID NO: 5, or wherein said SBH2 gene comprises a polynucleotide sequence at least 95% identical to SEQ ID NO: 7.

11. The microorganism of claim 7, wherein said translocon complex comprises an SSH1 protein comprising a polypeptide sequence at least 95% identical to SEQ ID NO: 4, an SSS1 protein comprising a polypeptide sequence at least 95% identical to SEQ ID NO: 6, and an SBH2 protein comprises a polypeptide sequence at least 95% identical to SEQ ID NO: 8.

12. The microorganism of claim 1, wherein activity of a YPS1-1 protease and a YPS1-2 protease have been attenuated or eliminated.

13. The microorganism of claim 12, wherein said YPS1-1 protease comprises a polypeptide sequence at least 95% identical to SEQ ID NO: 10 or wherein said YPS1-2 protease comprises a polypeptide sequence at least 95% identical to SEQ ID NO: 12.

14. The microorganism of claim 1, wherein said secretion signal peptide is selected from the group consisting of: a PEP4 signal sequence, a CPY +4 signal sequence, a DAP2 signal sequence, and a MFα1 signal sequence.

15. The microorganism of claim 1, wherein said secretion signal peptide is selected from the group consisting of: SEQ ID NO: 84, SEQ ID NO: 86, SEQ ID NO: 88, and SEQ ID NO: 90.

16. A *Pichia pastoris* microorganism, in which the activity of a SEC72 has been eliminated or a sec72 gene has been deleted, and wherein said microorganism expresses a recombinant protein, wherein said recombinant protein comprises a silk-like polypeptide or comprises at least one block polypeptide sequence from a silk, and wherein said silk-like polypeptide comprises one or more repeat sequences {GGY-[GPG-X$_1$]$_{n1}$-GPS-(A)$_{n2}$}$_{n3}$, wherein X1=SGGQQ or GAGQQ or GQGPY or AGQQ or SQ;

n1 is from 4 to 8;

n2 is from 6 to 20; and n3 is from 2 to 20.

17. The microorganism of claim 16, wherein said silk-like polypeptide comprises a polypeptide sequence encoded by SEQ ID NO: 21.

18. A *Pichia pastoris* microorganism, wherein the activity of SEC72 of said microorganism has been eliminated or an sec72 gene comprising SEQ ID NO: 1 has been knocked out, wherein the microorganism comprises a recombinantly expressed SSH1 gene comprising SEQ ID NO: 3, a recombinantly expressed SSS1 gene comprising SEQ ID NO: 5, and a recombinantly expressed SBH2 gene comprising SEQ ID NO: 7, and wherein said microorganism comprises a silk-like polypeptide comprising a polypeptide sequence encoded by SEQ ID NO: 21.

19. A method of modifying *Pichia pastoris* microorganism to improve the secretion of a recombinantly expressed protein, said method comprising knocking out a gene encoding an SEC72 protein, wherein said microorganism expresses a recombinant silk-like protein comprising a secretion signal peptide derived from yeast.

20. The method of claim 19, further comprising transforming said *Pichia pastoris* with a vector comprising genes encoding a recombinantly expressed SSH1 translocon complex.

* * * * *